(12) United States Patent
Seo et al.

(10) Patent No.: US 10,636,976 B2
(45) Date of Patent: Apr. 28, 2020

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Satoshi Seo, Kanagawa (JP); Tsunenori Suzuki, Kanagawa (JP); Tomohiro Kubota, Kanagawa (JP); Naoaki Hashimoto, Kanagawa (JP); Yusuke Takita, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 129 days.

(21) Appl. No.: 15/440,270

(22) Filed: Feb. 23, 2017

(65) Prior Publication Data
US 2017/0250346 A1   Aug. 31, 2017

(30) Foreign Application Priority Data

Feb. 26, 2016 (JP) .................................. 2016-035629

(51) Int. Cl.
*H01L 51/50* (2006.01)
*H01L 51/00* (2006.01)
(Continued)

(52) U.S. Cl.
CPC ........ *H01L 51/0052* (2013.01); *C07D 209/80* (2013.01); *C07D 209/86* (2013.01);
(Continued)

(58) Field of Classification Search
None
See application file for complete search history.

(56) References Cited

U.S. PATENT DOCUMENTS 5,811,834 A   9/1998 Tamano et al.
6,482,986 B1  11/2002 Boigegrain et al.
(Continued)

FOREIGN PATENT DOCUMENTS

CN   101200634 A   6/2008
JP   11-144876 A   5/1999
(Continued)

OTHER PUBLICATIONS

Benaglia.M et al., "Synthesis of Pyridylstannanes From Halopyridines and Hexamethyldistannane With Catalytic Palladium", Tetrahedron Letters, 1997, vol. 38, No. 27, pp. 4737-4740.
(Continued)

*Primary Examiner* — Gregory D Clark
(74) *Attorney, Agent, or Firm* — Fish & Richardson P.C.

(57) ABSTRACT

A novel compound in which a delayed fluorescence component due to TTA accounts for a high proportion of emissive components is provided. The organic compound includes an anthracene skeleton, an arylene group, and a substituted or unsubstituted heterocyclic group including a carbazole skeleton. The anthracene skeleton and the substituted or unsubstituted heterocyclic group including the carbazole skeleton are bonded to each other through the arylene group. The anthracene skeleton includes an aryl group at the 2-position or the 3-position.

40 Claims, 55 Drawing Sheets

(51) Int. Cl.
*C07D 209/86* (2006.01)
*C07D 209/80* (2006.01)
*C09K 11/06* (2006.01)

(52) U.S. Cl.
CPC .......... *C09K 11/06* (2013.01); *H01L 51/0072* (2013.01); *C09K 2211/1007* (2013.01); *C09K 2211/1011* (2013.01); *C09K 2211/1029* (2013.01)

(56) References Cited

U.S. PATENT DOCUMENTS

| | | | |
|---|---|---|---|
| 6,565,996 | B2 | 5/2003 | Hatwar et al. |
| 6,617,051 | B1 | 9/2003 | Higashi et al. |
| 6,661,023 | B2 | 12/2003 | Hoag et al. |
| 6,713,566 | B1 | 3/2004 | Marcuccio et al. |
| 6,815,094 | B2 | 11/2004 | Lee et al. |
| 6,984,462 | B2 | 1/2006 | Kim et al. |
| 7,132,456 | B2 | 11/2006 | Gillig et al. |
| 7,161,185 | B2 | 1/2007 | Yamazaki et al. |
| 7,173,373 | B2 | 2/2007 | Yamada et al. |
| 7,196,466 | B2 | 3/2007 | Hieda et al. |
| 7,252,894 | B2 | 8/2007 | Yu et al. |
| 7,270,893 | B2 | 9/2007 | Fukuda et al. |
| 7,387,845 | B2 | 6/2008 | Saitoh et al. |
| 7,541,097 | B2 | 6/2009 | Seo et al. |
| 7,597,602 | B2 | 10/2009 | Yamada et al. |
| 7,629,060 | B2 | 12/2009 | Oshiyama et al. |
| 7,649,197 | B2 | 1/2010 | Iwaki et al. |
| 7,651,787 | B2 | 1/2010 | Seo et al. |
| 7,704,912 | B2 | 4/2010 | Reets et al. |
| 7,723,722 | B2 | 5/2010 | Kawakami et al. |
| 7,745,988 | B2 | 6/2010 | Sasaki et al. |
| 7,790,892 | B2 | 9/2010 | Ikeda et al. |
| 7,906,224 | B2 | 3/2011 | Taka et al. |
| 7,919,773 | B2 | 4/2011 | Kawakami et al. |
| 8,084,146 | B2 | 12/2011 | Murase et al. |
| 8,183,793 | B2 | 5/2012 | Egawa et al. |
| 8,324,403 | B2 | 12/2012 | Yabe et al. |
| 8,420,227 | B2 | 4/2013 | Iwaki et al. |
| 8,986,857 | B2 | 3/2015 | Suzuki et al. |
| 2001/0052751 | A1 | 12/2001 | Wakimoto et al. |
| 2003/0068524 | A1 | 4/2003 | Hatwar |
| 2003/0186077 | A1 | 10/2003 | Chen |
| 2003/0205696 | A1 | 11/2003 | Thoms et al. |
| 2004/0086745 | A1 | 5/2004 | Iwakuma et al. |
| 2004/0146746 | A1 | 7/2004 | Lee et al. |
| 2004/0161632 | A1 | 8/2004 | Seo et al. |
| 2004/0161633 | A1 | 8/2004 | Seo et al. |
| 2004/0170863 | A1 | 9/2004 | Kim et al. |
| 2004/0263069 | A1 | 12/2004 | Yamazaki et al. |
| 2005/0031898 | A1 | 2/2005 | Li et al. |
| 2005/0058852 | A1 | 3/2005 | Tyan et al. |
| 2005/0084711 | A1 | 4/2005 | Sasaki et al. |
| 2005/0214565 | A1 | 9/2005 | Ikeda et al. |
| 2005/0244670 | A1 | 11/2005 | Saitoh et al. |
| 2006/0055305 | A1 | 3/2006 | Funahashi et al. |
| 2006/0068221 | A1 | 3/2006 | Saitoh et al. |
| 2006/0115680 | A1 | 6/2006 | Hwang et al. |
| 2006/0124924 | A1* | 6/2006 | Suh .................. H01L 51/002 257/40 |
| 2007/0049760 | A1 | 3/2007 | Kawakami et al. |
| 2007/0075632 | A1 | 4/2007 | Kawakami et al. |
| 2007/0106103 | A1 | 5/2007 | Ikeda et al. |
| 2007/0215889 | A1 | 9/2007 | Kawakami et al. |
| 2007/0247063 | A1* | 10/2007 | Murase ................ C07D 209/86 313/504 |
| 2008/0107918 | A1 | 5/2008 | Egawa et al. |
| 2008/0122344 | A1 | 5/2008 | Shin et al. |
| 2009/0102360 | A1 | 4/2009 | Kawakami et al. |
| 2010/0039355 | A1* | 2/2010 | Park .................. H04R 1/028 345/76 |
| 2010/0069647 | A1 | 3/2010 | Suzuki et al. |
| 2010/0076201 | A1 | 3/2010 | Suzuki et al. |
| 2010/0084645 | A1 | 4/2010 | Iwaki et al. |
| 2010/0200847 | A1 | 8/2010 | Kawakami et al. |
| 2010/0308727 | A1* | 12/2010 | Verjans ................. G09G 3/14 315/51 |
| 2012/0138907 | A1 | 6/2012 | Murase et al. |

FOREIGN PATENT DOCUMENTS

| | | |
|---|---|---|
| JP | 2003-031371 A | 1/2003 |
| JP | 2003-167550 A | 6/2003 |
| JP | 2003-229273 A | 8/2003 |
| JP | 2003-238534 A | 8/2003 |
| JP | 2004-087396 A | 3/2004 |
| JP | 2004-091334 A | 3/2004 |
| JP | 2004-311415 A | 11/2004 |
| JP | 2007-131722 A | 5/2007 |
| WO | WO-2001/023353 | 4/2001 |
| WO | WO-2010/107244 | 9/2010 |
| WO | WO-2011/010842 | 1/2011 |

OTHER PUBLICATIONS

Li.Z et al., "Synthesis and Functional Properties of End-Dendronized Oligo(9,9-diphenyl)fluorenes", Organic Letters, Mar. 9, 2006, vol. 8, No. 7, pp. 1499-1502.

Grigalevicius.S et al., "Well defined carbazol-3,9-diyl based oligomers with diphenylamino end-cap as novel amorphous molecular materials for optoelectronics", J. Photochem. Photobiol.A: Chem. (Journal of Photochemistry and Photobiology A: Chemistry), 2005, vol. 174, No. 2, pp. 125-129.

Li.J et al., "CuI/DABCO-Catalyzed Cross-Coupling Reactions of Aryl Halides with Arylboronic Acids", Eur. J. Org. Chem(European Journal of Organic Chemistry), 2006, pp. 2063-2066.

Kim.S et al., "Synthesis and Hole-Transporting Properties of Phenyl-Carbazyl Derivatives", Mol. Cryst. (Molecular Crystals and Liquid Crystals), 2008, vol. 491, pp. 133-144, Taylor & Francis.

Promarak.V et al., "Synthesis and Properties of Stable Amorphous Hole-Transporting Molecules for Electroluminescent Devices", Tetrahedron Letters, 2006, vol. 47, No. 50, pp. 8949-8952.

Grisorio.R et al., "Novel Bifluorene Based Conjugated Systems: Synthesis and Properties", Tetrahedron, 2006, vol. 62, pp. 627-634.

Chen.Y et al., "High Triplet Energy Polymer as Host for Electrophosphorescence with High Efficiency", J. Am. Chem. Soc. (Journal of the American Chemical Society), 2006, vol. 128, No. 26, pp. 8549-8558.

Kurti L et al., "Suzuki Cross-Coupling", Strategic Applications of Named Reactions in Organic Synthesis, Mar. 4, 2005, p. 448.

Pine.S, "20-4 Applications and Examples", Organic Chemistry, 1987, pp. 744-746.

Carey.F et al., "Advanced Organic Chemistry", Springer, p. 731.

Goldsmith.C et al., "C—H Bond Activation by a Ferric Methoxide Complex: Modeling the Rate-Determining Step in the Mechanism of Lipdxygenase", vol. 124, No. 1, pp. 83-96 dated in 2002.

Onishi.T et al., "(2) A Method of Measuring an Energy Level" in "High Molecular EL Materials—Development of Light-Emitting High Molecular Compounds" pp. 64-67 dated on Dec. 25, 2004 published by Kyoritsu Shuppan.

Zander.M et al. "Note on the Dehydration of Di-β-naphthylamine and Di-β-anthrylamine with Copper Powder", Chemische Berichte, vol. 97, No. 1, pp. 304-306 dated in 1964.

Suzuki.T et al., "Highly efficient long-life blue fluorescent organic light-emitting diode exhibiting triplet-triplet annihilation effects enhanced by a novel hole-transporting material", Jpn. J. Appl. Phys.(Japanese Journal of Applied Physics), 2014, vol. 53, pp. 052102-1-052102-6.

* cited by examiner

FIG. 15B1

FIG. 15B2

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organic compound. One embodiment of the present invention relates to a light-emitting element from which light emission can be obtained by application of an electric field between a pair of electrodes between which a light-emitting layer is provided, and a light-emitting device, an electronic device, and a lighting device including the light-emitting element. Note that one embodiment of the present invention is not limited to the above technical field. The technical field of one embodiment of the invention disclosed in this specification and the like relates to an object, a method, or a manufacturing method. Furthermore, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a power storage device, a memory device, a method for driving any of them, and a method for manufacturing any of them.

2. Description of the Related Art

In recent years, research and development of light-emitting elements using electroluminescence (EL) have been actively conducted. In a basic structure of such a light-emitting element, a layer containing a light-emitting substance (an EL layer) is interposed between a pair of electrodes. By applying a voltage between the pair of electrodes of this element, light emission from the light-emitting substance can be obtained.

Since the above light-emitting element is a self-luminous type, a display device using this light-emitting element has advantages such as high visibility, no necessity of a backlight, and low power consumption. Furthermore, such a light-emitting element also has advantages in that the element can be formed to be thin and lightweight, and that response time is high.

It is said that the light emission mechanism of a light-emitting element is as follows: when a voltage is applied between a pair of electrodes with an EL layer including a light-emitting substance provided therebetween, electrons injected from a cathode and holes injected from an anode recombine in the light emission center of the EL layer to form molecular excitons, and energy is released and light is emitted when the molecular excitons relax to the ground state.

The excited states of an organic compound in which molecular excitons are formed include a singlet excited state (S*) and a triplet excited state (T*), and light emission from the singlet excited state is referred to as fluorescence, and light emission from the triplet excited state is referred to as phosphorescence. The statistical generation ratio thereof in the light-emitting element is considered to be S*:T*=1:3. In other words, a light-emitting element containing a compound emitting phosphorescence has higher emission efficiency than a light-emitting element containing a compound emitting fluorescence. Therefore, light-emitting elements containing phosphorescent compounds capable of converting the triplet excited state into light emission have been actively developed in recent years.

Among light-emitting elements containing phosphorescent compounds, in particular, a light-emitting element that emits blue light has not yet been put into practical use because it is difficult to develop a stable compound having a high triplet excited energy level. For this reason, as a light-emitting element that emits blue light, a light-emitting element containing a more stable fluorescent compound has been developed and high efficiency of a light-emitting element containing a fluorescent compound (fluorescent light-emitting element) has been required.

In the light-emitting element containing a fluorescent compound, triplet-triplet annihilation (TTA) is known as a light emission mechanism capable of converting part of a triplet excited state into light emission. The term TTA refers to a process in which, when two triplet excitons approach each other, excited energy and spin angular momentum are exchanged and transferred to form singlet excitons.

As a compound in which TTA occurs, a compound including an anthracene skeleton is known. Non-Patent Document 1 discloses that the use of a compound including an anthracene skeleton as a host material achieves high external quantum efficiency in a light-emitting element that emits blue light. It also discloses that the proportion of the delayed fluorescence component due to TTA to the total light emitted from the light-emitting element using a compound including an anthracene skeleton is approximately 10%.

REFERENCE

Non-Patent Document

[Non-Patent Document 1]
Tsunenori Suzuki et al., Japanese Journal of Applied Physics, Vol. 53, 052102 (2014)

SUMMARY OF THE INVENTION

Thus, what is important in increasing the emission efficiency of a light-emitting element including a fluorescent compound is to convert energy of triplet excitons, which do not contribute to light emission, into energy of singlet excitons, which contribute to light emission, by TTA. In a light-emitting element in which such energy conversion is performed efficiently, a delayed fluorescence component due to TTA accounts for a high proportion of emissive components. In view of the above, an object of one embodiment of the present invention is to provide a novel compound in which a delayed fluorescence component due to TTA accounts for a high proportion of emissive components. Another object of one embodiment of the present invention is to provide a light-emitting element in which a delayed fluorescence component due to TTA accounts for a high proportion of emissive components.

As compared with a light-emitting element including a phosphorescent compound, a light-emitting element including a fluorescent compound requires a larger amount of current to emit light with the same luminance. Thus, a decrease in drive voltage is important in reducing power consumption. Therefore, another object of one embodiment of the present invention is to provide a light-emitting element with low drive voltage. Since a light-emitting element is likely to deteriorate when a large amount of current flows, another object is to extend lifetime.

Another object of one embodiment of the present invention is to provide a novel compound. Another object of one embodiment of the present invention is to provide a light-emitting element including a novel compound. Another object of one embodiment of the present invention is to provide a light-emitting device with high emission efficiency, low power consumption, and long lifetime.

Note that the description of the object does not disturb the existence of other objects. In one embodiment of the present invention, there is no need to achieve all the objects. Other objects will be apparent from and can be derived from the description of the specification, the drawings, the claims, and the like.

One embodiment of the present invention is an organic compound including an anthracene skeleton, an arylene group, and a substituted or unsubstituted heterocyclic group including a carbazole skeleton. The anthracene skeleton and the substituted or unsubstituted heterocyclic group including the carbazole skeleton are bonded to each other through the arylene group. The anthracene skeleton includes an aryl group at the 2-position or the 3-position.

Another embodiment of the present invention is an organic compound represented by the following general formula (G1).

[Chemical formula 1]

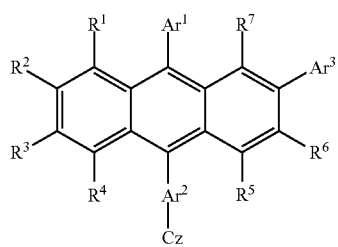

(G1)

In the general formula (G1), $Ar^1$ and $Ar^3$ each independently represent a substituted or unsubstituted aryl group having 6 to 30 carbon atoms. In addition, $Ar^2$ represents a substituted or unsubstituted arylene group having 6 to 14 carbon atoms. Furthermore, Cz represents a substituted or unsubstituted heterocyclic group including a carbazole skeleton, and the carbazole skeleton is directly bonded to the $Ar^2$. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms.

Another embodiment of the present invention is an organic compound represented by the following general formula (G2).

[Chemical formula 2]

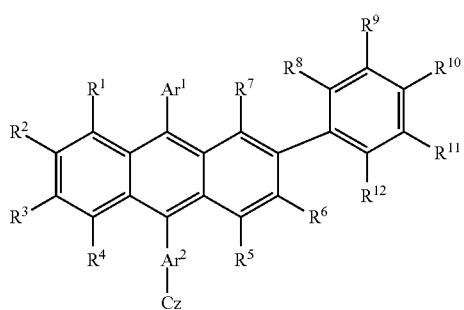

(G2)

In the general formula (G2), $Ar^1$ represents a substituted or unsubstituted aryl group having 6 to 30 carbon atoms. In addition, $Ar^2$ represents a substituted or unsubstituted arylene group having 6 to 14 carbon atoms. Furthermore, Cz represents a substituted or unsubstituted heterocyclic group including a carbazole skeleton, and the carbazole skeleton is directly bonded to the $Ar^2$. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{12}$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{12}$ may be bonded to each other to form a ring.

In any of the above structures, the $Ar^2$ represents a substituted or unsubstituted phenylene group.

Another embodiment of the present invention is an organic compound represented by the following general formula (G3).

[Chemical formula 3]

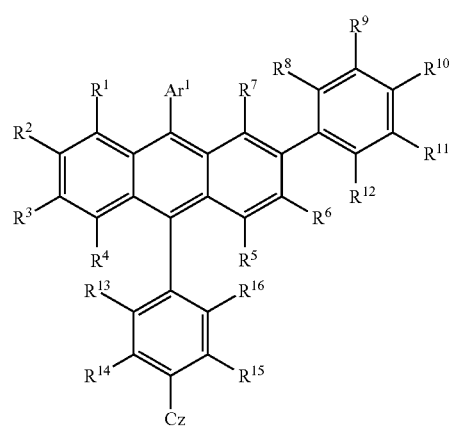

(G3)

In the general formula (G3), $Ar^1$ represents a substituted or unsubstituted aryl group having 6 to 30 carbon atoms. Furthermore, Cz represents a substituted or unsubstituted heterocyclic group including a carbazole skeleton. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{16}$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{16}$ may be bonded to each other to form a ring.

Another embodiment of the present invention is an organic compound represented by the following general formula (G4).

[Chemical formula 4]

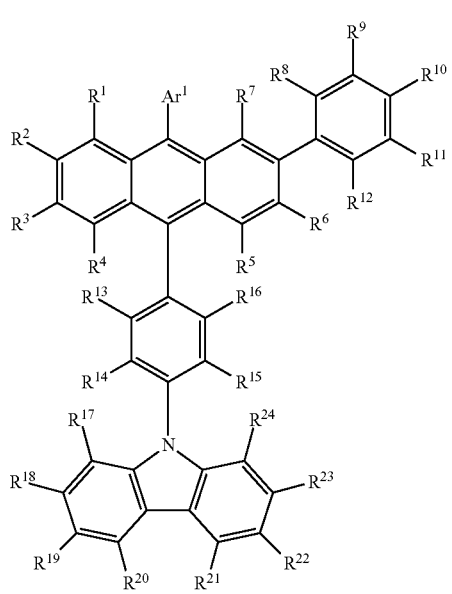

(G4)

[Chemical formula 5]

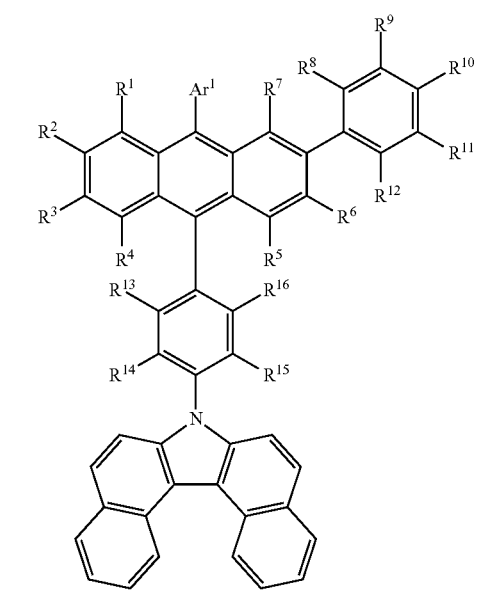

(G5)

In the general formula (G4), $Ar^1$ represents a substituted or unsubstituted aryl group having 6 to 30 carbon atoms. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{24}$ each independently represent any of hydrogen, a substituted or unsubstituted alkyl group having 1 to 6 carbon atoms, an alkoxy group having 1 to 6 carbon atoms, a hydroxyl group, a sulfanyl group, a substituted or unsubstituted arylamino group having 6 to 12 carbon atoms, a vinyl group, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{24}$ may be bonded to each other to form a ring.

Another embodiment of the present invention is an organic compound represented by the following general formula (G5).

In the general formula (G5), $Ar^1$ represents a substituted or unsubstituted aryl group having 6 to 30 carbon atoms. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{16}$ each independently represent any of hydrogen, an alkyl group having 1 to 6 carbon atoms, an alkoxy group having 1 to 6 carbon atoms, a hydroxyl group, a sulfanyl group, a substituted or unsubstituted arylamino group having 6 to 12 carbon atoms, a vinyl group, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{16}$ may be bonded to each other to form a ring.

Another embodiment of the present invention is an organic compound represented by the following structural formula (100).

[Chemical formula 6]

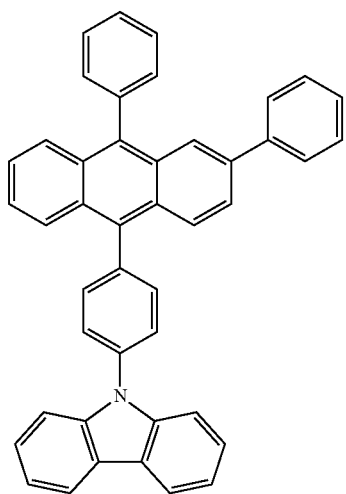

(100)

Another embodiment of the present invention is an organic compound represented by the following structural formula (200).

[Chemical formula 7]

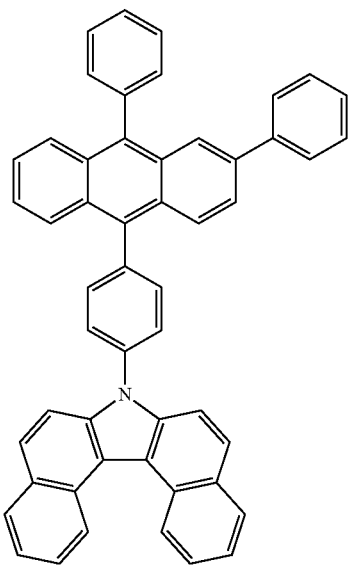

(200)

The organic compound according to any one of the above-described embodiments of the present invention includes an anthracene skeleton, an arylene group, and a substituted or unsubstituted heterocyclic group including a carbazole skeleton. The anthracene skeleton and the substituted or unsubstituted heterocyclic group including the carbazole skeleton are bonded to each other through the arylene group. The anthracene skeleton includes an aryl group at the 2-position or the 3-position. This compound in which the heterocyclic group including the carbazole skeleton is bonded to the 9-position or the 10-position of the anthracene skeleton through the arylene group and the anthracene skeleton includes the aryl group at the 2-position or the 3-position can reduce drive voltage and improve reliability of a light-emitting element. Such effects can be obtained only when both the heterocyclic group and the aryl group are included. In addition, a light-emitting element in which a delayed fluorescence component due to TTA accounts for a high proportion and emission efficiency is high can be obtained with such a compound.

The heterocyclic group is bonded to the 9-position or the 10-position of the anthracene skeleton through the arylene group, depending on the kind of a substituent included in the compound. In the case where the heterocyclic group is bonded to the 9-position of the anthracene skeleton through the arylene group, the aryl group is bonded to the 3-position of the anthracene skeleton. In the case where the heterocyclic group is bonded to the 10-position of the anthracene skeleton through the arylene group, the aryl group is bonded to the 2-position of the anthracene skeleton.

Another embodiment of the present invention is a light-emitting element including an EL layer between a pair of electrodes. The EL layer includes a light-emitting layer. The light-emitting layer includes at least one of the above-described organic compounds.

One embodiment of the present invention includes, in its scope, not only a light-emitting device including the light-emitting element but also a lighting device including the light-emitting device. Thus, the light-emitting device in this specification refers to an image display device and a light source (e.g., a lighting device). In addition, the light-emitting device refers to all of the following modules: a module in which a connector, for example, a flexible printed circuit (FPC) or a tape carrier package (TCP) is provided to a light-emitting device; a module provided with a printed wiring board at the end of a TCP; and a module where an integrated circuit (IC) is directly mounted on a light-emitting element by a chip-on-glass (COG) method.

According to one embodiment of the present invention, a novel compound in which a delayed fluorescence component due to TTA accounts for a high proportion of emissive components can be provided. According to one embodiment of the present invention, a light-emitting element in which a delayed fluorescence component due to TTA accounts for a high proportion of emissive components can be provided. According to one embodiment of the present invention, a novel compound can be provided. According to one embodiment of the present invention, a light-emitting element including a novel compound can be provided. According to one embodiment of the present invention, a novel light-emitting device with high emission efficiency and low power consumption can be provided.

BRIEF DESCRIPTION OF THE DRAWINGS

FIGS. 15A, 15B1, and 15B2 are block diagrams of a display device.

DETAILED DESCRIPTION OF THE INVENTION

Figure 1A:
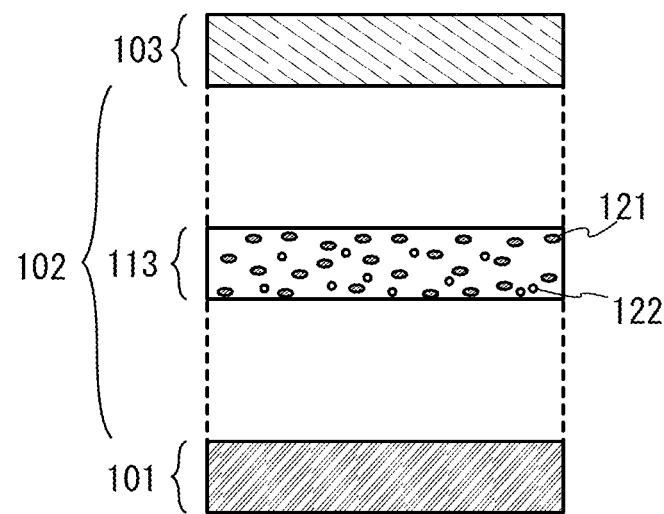
FIGS. 1A and 1B illustrate structures of light-emitting elements.

Embodiments of the present invention will be described in detail below with reference to the drawings. However, the present invention is not limited to the following description, and the mode and details can be variously changed unless departing from the scope and spirit of the present invention. Thus, the present invention should not be construed as being limited to the description in the following embodiments.

Note that the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

Embodiment 1

In this embodiment, organic compounds of embodiments of the present invention will be described.

An organic compound described in this embodiment includes an anthracene skeleton, an arylene group, and a substituted or unsubstituted heterocyclic group including a carbazole skeleton. The anthracene skeleton and the substituted or unsubstituted heterocyclic group including the carbazole skeleton are bonded to each other through the arylene group. The anthracene skeleton includes an aryl group at the 2-position or the 3-position.

The organic compound described in this embodiment is an organic compound having a structure represented by the following general formula (G1).

[Chemical formula 8]

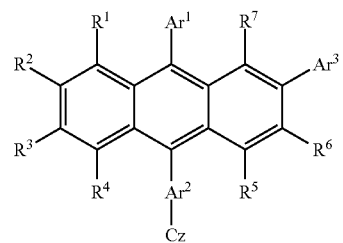

(G1)

In the general formula (G1), $Ar^1$ and $Ar^3$ each independently represent a substituted or unsubstituted aryl group having 6 to 30 carbon atoms. In addition, $Ar^2$ represents a substituted or unsubstituted arylene group having 6 to 14 carbon atoms. Furthermore, Cz represents a substituted or unsubstituted heterocyclic group including a carbazole skeleton, and the carbazole skeleton is directly bonded to the $Ar^2$. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms.

The organic compound described in this embodiment is an organic compound having a structure represented by the following general formula (G2).

[Chemical formula 9]

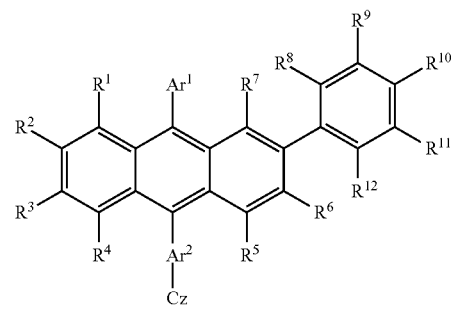

(G2)

In the general formula (G2), $Ar^1$ represents a substituted or unsubstituted aryl group having 6 to 30 carbon atoms. In addition, $Ar^2$ represents a substituted or unsubstituted arylene group having 6 to 14 carbon atoms. Furthermore, Cz represents a substituted or unsubstituted heterocyclic group including a carbazole skeleton, and the carbazole skeleton is directly bonded to the $Ar^2$. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{12}$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{12}$ may be bonded to each other to form a ring.

The organic compound described in this embodiment is an organic compound having a structure represented by the following general formula (G3).

[Chemical formula 10]

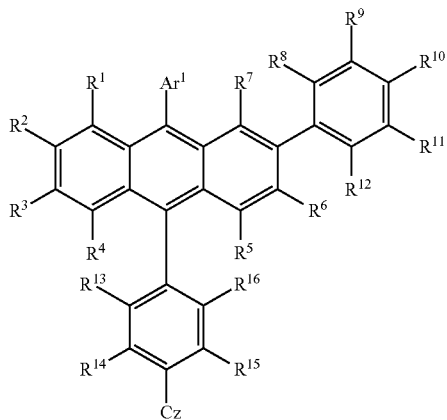

(G3)

In the general formula (G3), Ar¹ represents a substituted or unsubstituted aryl group having 6 to 30 carbon atoms. Furthermore, Cz represents a substituted or unsubstituted heterocyclic group including a carbazole skeleton. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{16}$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{16}$ may be bonded to each other to form a ring.

The organic compound described in this embodiment is an organic compound having a structure represented by the following general formula (G4).

[Chemical formula 11]

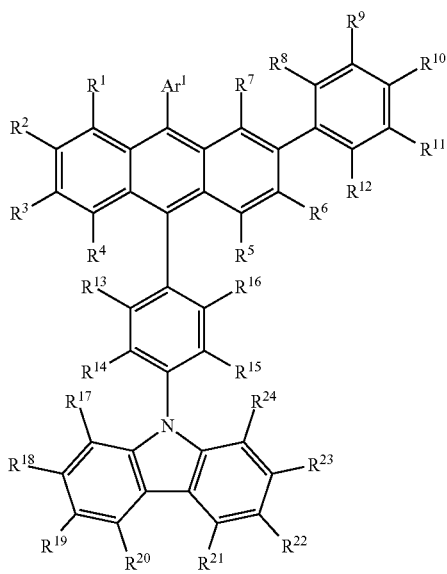

(G4)

In the general formula (G4), Ar¹ represents a substituted or unsubstituted aryl group having 6 to 30 carbon atoms. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{24}$ each independently represent any of hydrogen, a substituted or unsubstituted alkyl group having 1 to 6 carbon atoms, an alkoxy group having 1 to 6 carbon atoms, a hydroxyl group, a sulfanyl group, a substituted or unsubstituted arylamino group having 6 to 12 carbon atoms, a vinyl group, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{24}$ may be bonded to each other to form a ring.

The organic compound described in this embodiment is an organic compound having a structure represented by the following general formula (G5).

[Chemical formula 12]

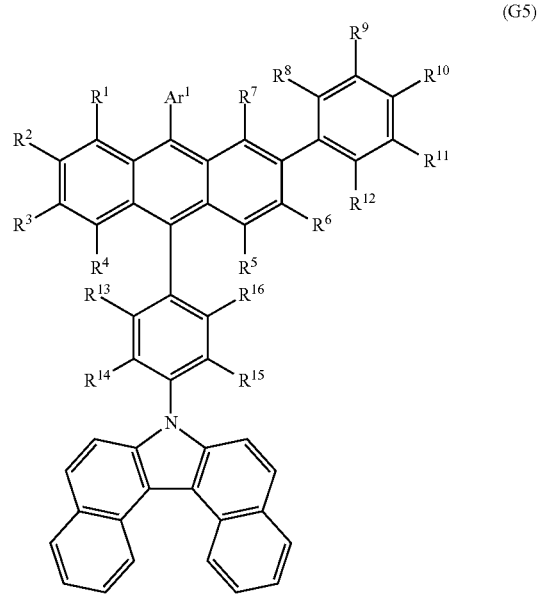

(G5)

In the general formula (G5), Ar¹ represents a substituted or unsubstituted aryl group having 6 to 30 carbon atoms. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms. Moreover, $R^8$ to $R^{16}$ each independently represent any of hydrogen, an alkyl group having 1 to 6 carbon atoms, an alkoxy group having 1 to 6 carbon atoms, a hydroxyl group, a sulfanyl group, a substituted or unsubstituted arylamino group having 6 to 12 carbon atoms, a vinyl group, a substituted or unsubstituted aryl group having 6 to 13 carbon atoms, and a substituted or unsubstituted heteroaryl group having 3 to 12 carbon atoms. Note that any adjacent substituents among the $R^8$ to the $R^{16}$ may be bonded to each other to form a ring.

Note that in any of the above general formulae (G1) to (G5), in the case where any of the substituted or unsubstituted aryl group having 6 to 30 carbon atoms, the substituted or unsubstituted arylene group having 6 to 14 carbon atoms, the substituted or unsubstituted heterocyclic group, the substituted or unsubstituted alkyl group having 1 to 6 carbon atoms, the substituted or unsubstituted aryl group having 6 to 13 carbon atoms, the substituted or unsubstituted aryl group having 6 to 14 carbon atoms, and the substituted or unsubstituted heteroaryl group having 3 to 12 carbon atoms has a substituent, examples of the substituent include an alkyl group having 1 to 6 carbon atoms, e.g., a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, e.g., a cyclopentyl group, a cyclohexyl group, a cycloheptyl group, a 1-norbornyl group, or a 2-norbornyl group; and an aryl group having 6 to 12 carbon atoms, e.g., a phenyl group or a biphenyl group.

Specific examples of the substituted or unsubstituted aryl group having 6 to 30 carbon atoms in any of the above general formulae (G1) to (G5) include a phenyl group, a naphthyl group (a 1-naphthyl group and a 2-naphthyl group), a tolyl group (an o-tolyl group, an m-tolyl group, and a p-tolyl group), a biphenyl group (a biphenyl-2-yl group, a biphenyl-3-yl group, and a biphenyl-4-yl group), a xylyl group, a pentalenyl group, an indenyl group, a fluorenyl group, an anthranil group, a terphenyl group, a phenanthryl group, a quaterphenyl group, a spirofluorenyl group, a phenylanthranyl group, and a diphenylanthranyl group.

Specific examples of the substituted or unsubstituted arylene group having 6 to 14 carbon atoms in any of the above general formulae (G1) to (G5) includes a phenylene group, a toluenediyl group, a naphthylene group, a biphenyldiyl group, a xylenediyl group, a pentalenediyl group, an indenediyl group, a fluorenediyl group, and an anthracenediyl group.

Specific examples of the substituted or unsubstituted heterocyclic group in any of the above general formulae (G1) to (G5) include a carbazolyl group, a phenylcarbazolyl group (a 1-phenylcarbazolyl group, a 2-phenylcarbazolyl group, a 3-phenylcarbazolyl group, and a 4-phenylcarbazolyl group), a diphenylcarbazolyl group (a 1,8-diphenylcarbazolyl group, a 2,7-diphenylcarbazolyl group, a 3,6-diphenylcarbazolyl group, and a 4,5-diphenylcarbazolyl group), a benzocarbazolyl group (an [a]benzocarbazolyl group, a [b]benzocarbazolyl group, a [c]benzocarbazolyl group, and a [d]benzocarbazolyl group), a dibenzocarbazolyl group (an [a,c]dibenzocarbazolyl group, an [a,g]dibenzocarbazolyl group, an [a,h]dibenzocarbazolyl group, an [a,i]dibenzocarbazolyl group, a [b,g]dibenzocarbazolyl group, a [b,h]dibenzocarbazolyl group, and a [b,i]dibenzocarbazolyl group), and a tribenzocarbazolyl group.

Specific examples of the substituted or unsubstituted alkyl group having 1 to 6 carbon atoms in any of the above general formulae (G1) to (G5) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and a trifluoromethyl group.

Specific examples of the substituted or unsubstituted aryl group having 6 to 13 carbon atoms and the substituted or unsubstituted aryl group having 6 to 14 carbon atoms in any of the above general formulae (G1) to (G5) include a phenyl group, a tolyl group (an o-tolyl group, an m-tolyl group, and a p-tolyl group), a naphthyl group (a 1-naphthyl group and a 2-naphthyl group), a biphenyl group (a biphenyl-2-yl group, a biphenyl-3-yl group, and a biphenyl-4-yl group), a xylyl group, a pentalenyl group, an indenyl group, a fluorenyl group, and a phenanthryl group. Note that the above substituents may be bonded to each other to form a ring. In such a case, for example, a spirofluorene skeleton is formed in such a manner that carbon at the 9-position of a fluorenyl group has two phenyl groups as substituents and these phenyl groups are bonded to each other.

Specific examples of the substituted or unsubstituted heteroaryl group having 3 to 12 carbon atoms in any of the above general formulae (G1) to (G5) include an imidazolyl group, a pyrazolyl group, a pyridyl group, a pyridazinyl group, a pyrimidyl group, an indolyl group, a triazinyl group, a benzimidazolyl group, and a quinolyl group.

The organic compound of one embodiment of the present invention in any of the above general formulae (G1) to (G5) includes an anthracene skeleton, an arylene group, and a substituted or unsubstituted heterocyclic group including a carbazole skeleton. The anthracene skeleton and the substituted or unsubstituted heterocyclic group including the carbazole skeleton are bonded to each other through the arylene group. The anthracene skeleton includes an aryl group at the 2-position or the 3-position. This compound in which the heterocyclic group including the carbazole skeleton is bonded to the 9-position or the 10-position of the anthracene skeleton through the arylene group and the anthracene skeleton includes the aryl group at the 2-position or the 3-position can reduce drive voltage and improve reliability of a light-emitting element. Such effects can be obtained only when both the heterocyclic group and the aryl group are included. In addition, a light-emitting element in which a delayed fluorescence component due to TTA accounts for a high proportion and emission efficiency is high can be obtained with such a compound.

For example, 9-[4-(10-phenyl-9-anthracenyl)phenyl]-9H-carbazole (abbreviation: CzPA) is known as a compound in which a heterocyclic group including a carbazole skeleton is bonded to the 9-position or the 10-position of an anthracene skeleton through an arylene group and an aryl group is bonded to neither the 2-position nor the 3-position of the anthracene skeleton. CzPA is obtained by introducing carbazole so as to bond to 9,10-diphenylanthracene (abbreviation: DPAnth); the introduction of carbazole enables the film quality of CzPA to be stable and facilitates the entrance of carriers. In fact, DPAnth has a HOMO level of −5.84 eV and a LUMO level of −2.70 eV, whereas CzPA has a HOMO level of −5.79 eV and a LUMO level of −2.73 eV. This indicates that both holes and electrons can enter CzPA slightly more easily. Accordingly, a light-emitting element including CzPA as a host can drive at relatively low voltage. Unfortunately, however, lifetime of the light-emitting element including CzPA as a host is not sufficiently long.

For example, 2,9,10-triphenylanthracene (abbreviation: 2PPA) is known as a compound which includes an aryl group at the 2-position or the 3-position of an anthracene skeleton but does not include a heterocyclic group including a carbazole skeleton. The HOMO level of 2PPA is −5.81 eV and the LUMO level thereof is −2.77 eV, which indicates that holes are slightly less likely to enter 2PPA than to enter CzPA but electrons are rather more likely to enter 2PPA than to enter CzPA. Since the energy gap between the HOMO level and the LUMO level of 2PPA is substantially the same as that of CzPA, a light-emitting element including 2PPA as a host is expected to operate at substantially the same voltage as that of a light-emitting element including CzPA.

However, the actual operation voltage of the light-emitting element including 2PPA is far higher than that of the light-emitting element including CzPA. The result of the current-voltage characteristics suggests that the high operation voltage of the light-emitting element including 2PPA is not due to the energy gap between the HOMO level and the LUMO level but due to less likelihood of entrance of carriers (holes in particular) under the influence of morphology or the like. Furthermore, the light-emitting element including 2PPA has extremely unfavorable lifetime. That is, because of the short lifetime and the decrease in carrier injection property due to morphology or the like, there seems to be no advantage in introducing an aryl group so as to bond to the 2-position or the 3-position of an anthracene skeleton.

However, surprisingly, the present inventors have found that a coexistence of a structure in which a heterocyclic group including a carbazole skeleton is bonded to the 9-position or the 10-position of an anthracene skeleton through an arylene group with a structure in which the anthracene skeleton includes an aryl group at the 2-position or the 3-position not only reduces the drive voltage but also extends lifetime significantly. For example, 9-[4-(3,10-diphenylanthracen-9-yl)phenyl]-9H-carbazole (abbreviation: 2Ph-CzPA) in which a phenyl group is introduced so as to bond to the 3-position of an anthracene skeleton of CzPA can operate at a voltage lower than the operation voltage of CzPA. The HOMO level of 2Ph-CzPA is −5.77 eV and the LUMO level thereof is −2.80 eV. A slightly narrower HOMO-LUMO gap of 2Ph-CzPA is one factor of low drive voltage. This physical property can be obtained only when a structure in which a heterocyclic group including a carbazole skeleton is bonded to the 9-position or the 10-position of an anthracene skeleton through an arylene group and a structure in which the anthracene skeleton includes an aryl group at the 2-position or the 3-position coexist. Not surprisingly, a problem of morphology does not arise. It is more notable that 2Ph-CzPA has much longer lifetime than CzPA or 2PPA. That is, in terms of long lifetime, a structure in which a heterocyclic group including a carbazole skeleton is bonded to the 9-position or the 10-position of an anthracene skeleton through an arylene group and a structure in which the anthracene skeleton includes an aryl group at the 2-position or the 3-position cannot be separated.

In addition, the emission efficiency of 2Ph-CzPA is as high as that of CzPA. The high emission efficiency results from a high proportion of a delayed fluorescence component due to TTA. That is, in a compound of one embodiment of the present invention, an aryl group introduced so as to bond to the 2-position or the 3-position of an anthracene skeleton does not hinder at least TTA. On the contrary, the aryl group contributes to an increase in probability of transition from T1 to Tn, which can be advantageous to TTA (to be described in the following example).

The above effects can also be obtained in the case where the carbazole skeleton includes a condensed ring. Thus, a carbazole skeleton is necessary to obtain the above effects, but the carbazole skeleton does not necessarily have a monocyclic structure.

Note that the HOMO levels and LUMO levels are estimated by cyclic voltammetry measurement.

Next, specific structural formulae of the above-described organic compounds of embodiments of the present invention are shown below. Note that the present invention is not limited to these formulae.

[Chemical formulae 13]

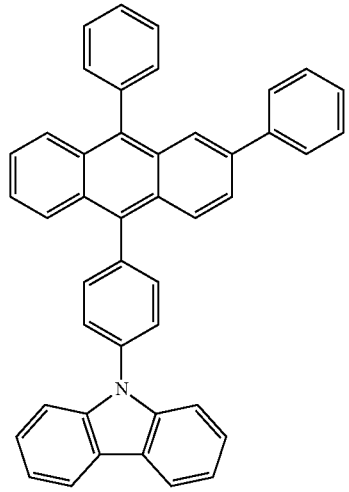

(100)

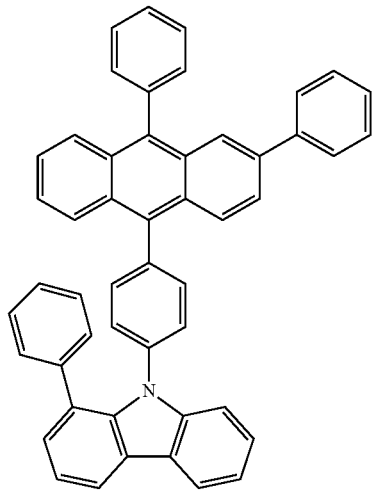

(101)

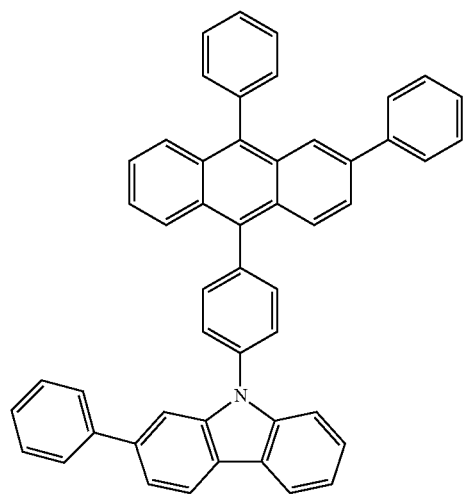

(102)

(103)
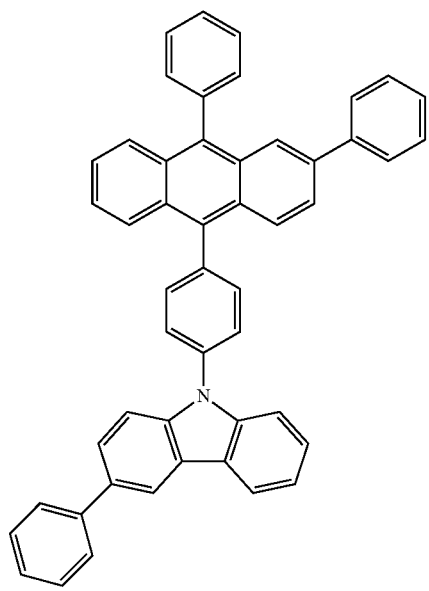
(104)
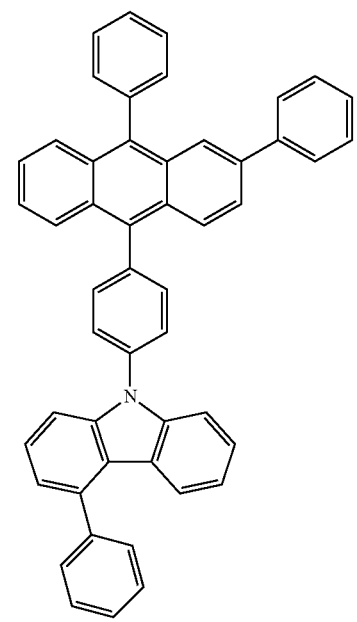
(105)
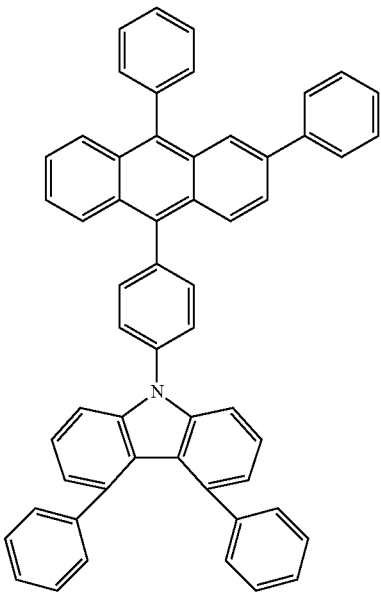
(106)
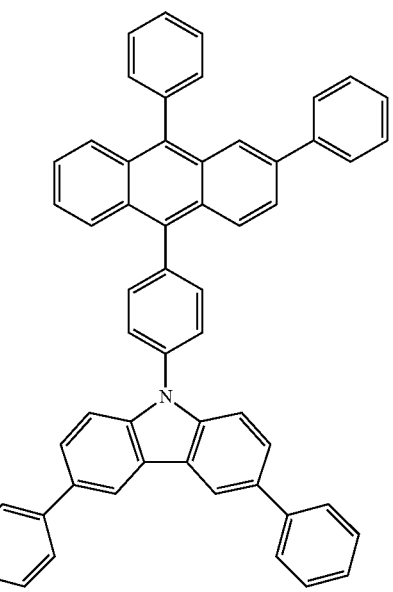
(107)
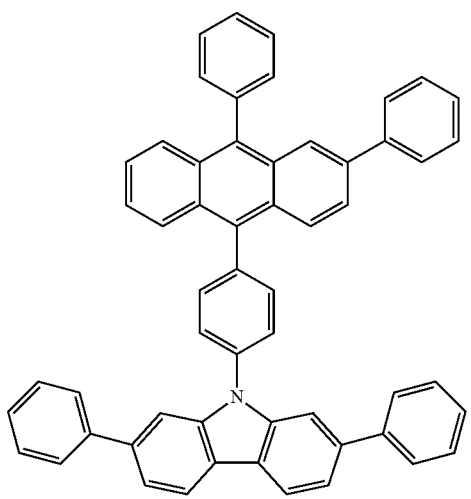

(108)
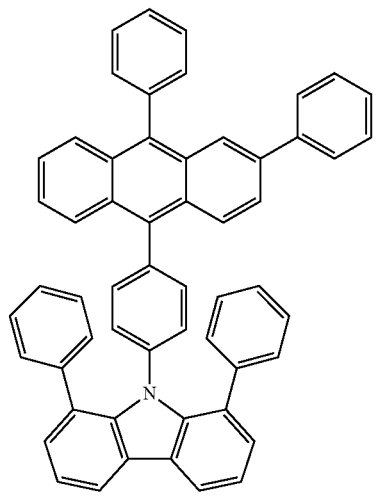
[Chemical formulae 14]
(109)
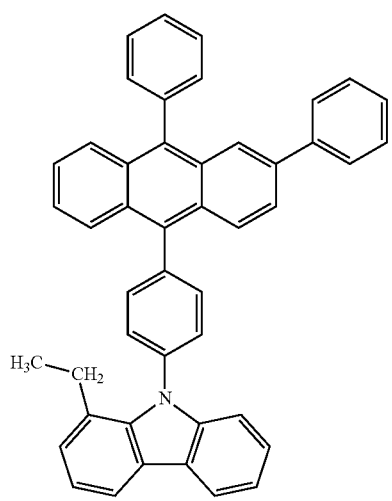
(110)
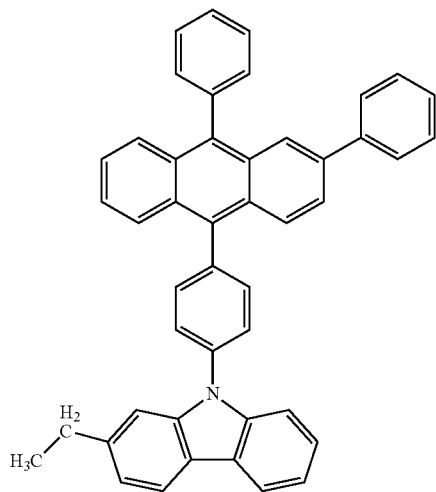
(111)
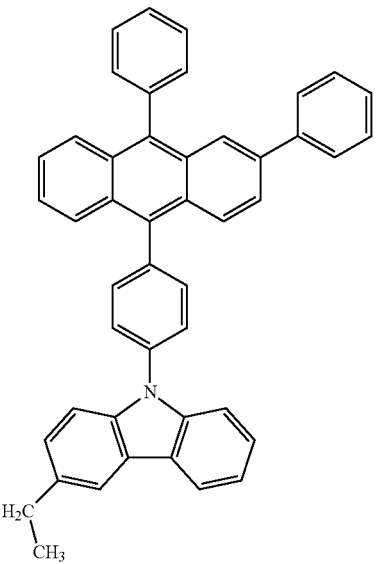
(112)
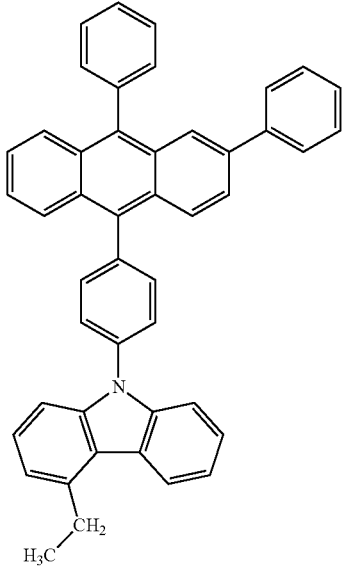

(113)
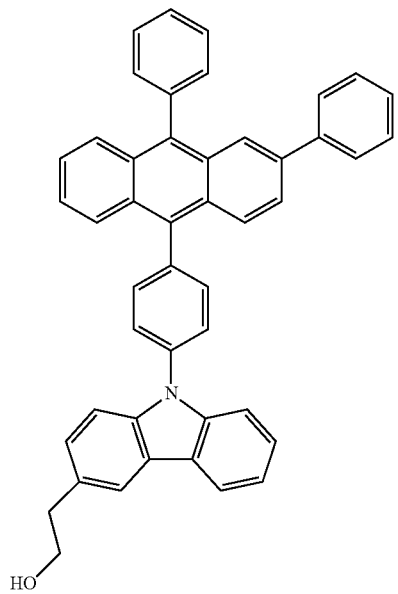
(114)
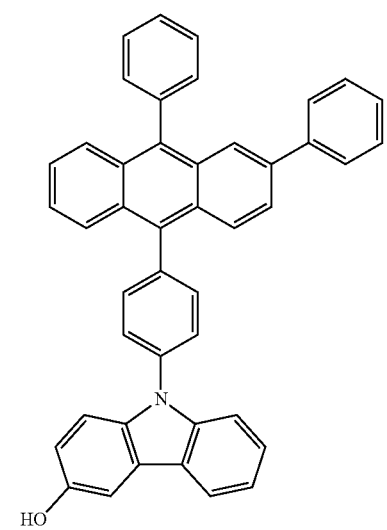
(115)
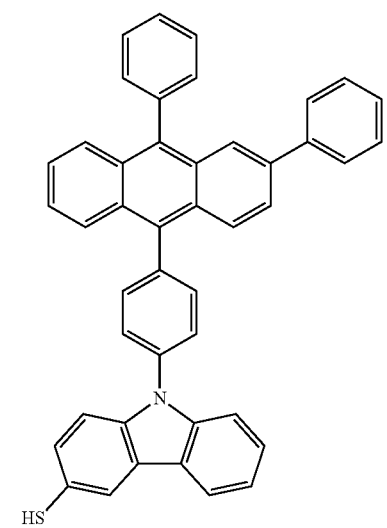
(116)
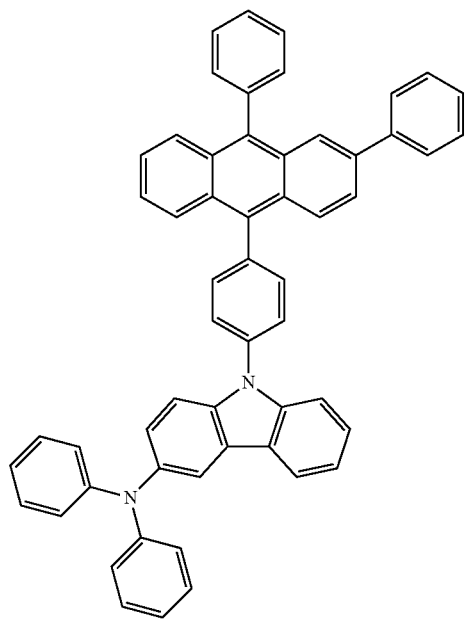
(117)
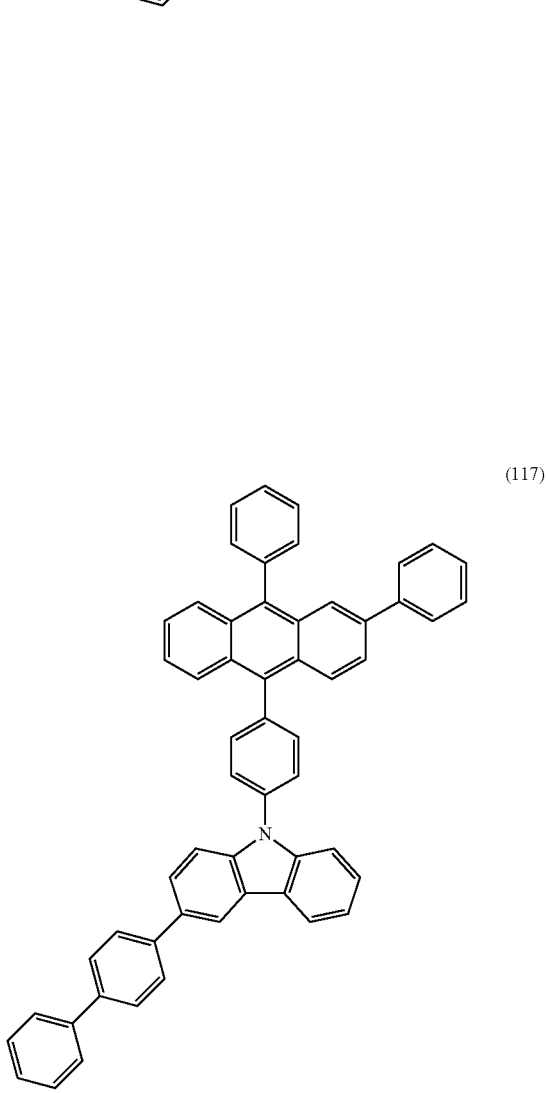

[Chemical formulae 15]
(118)
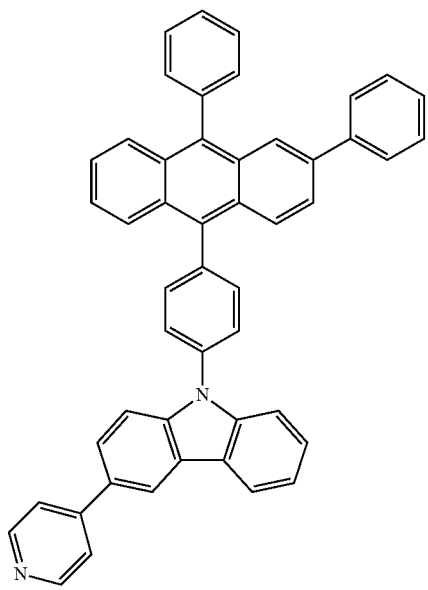
(119)
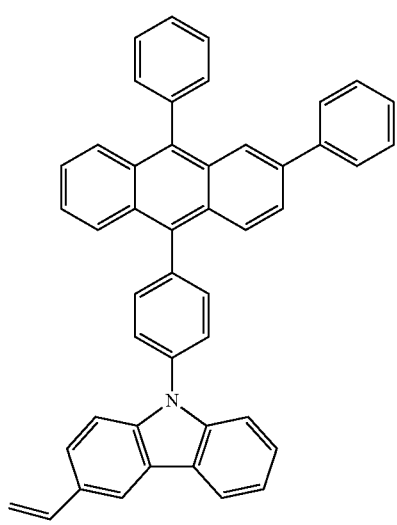
(120)
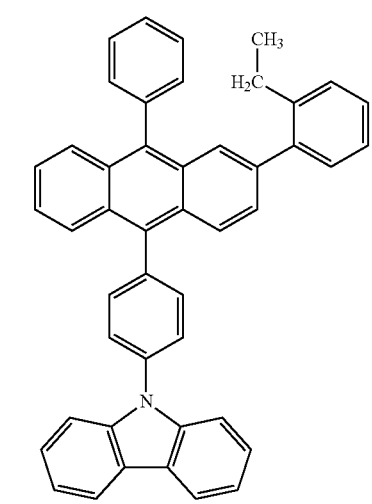
(121)
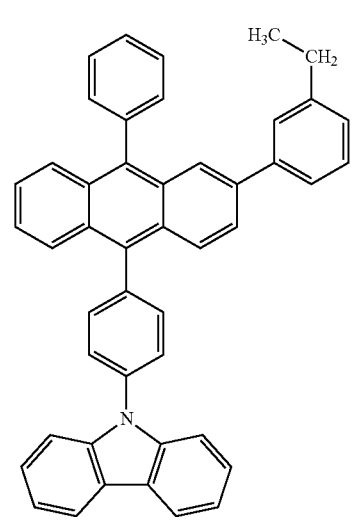
(122)
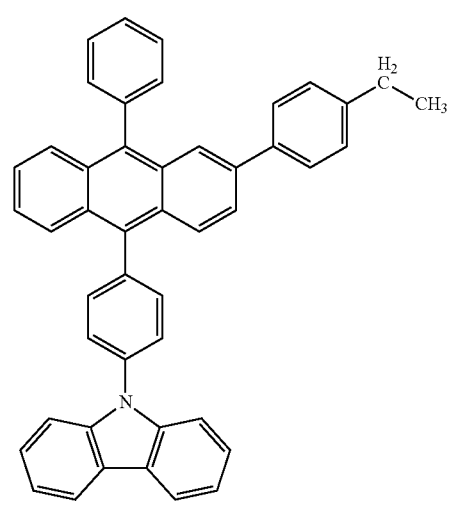
(123)
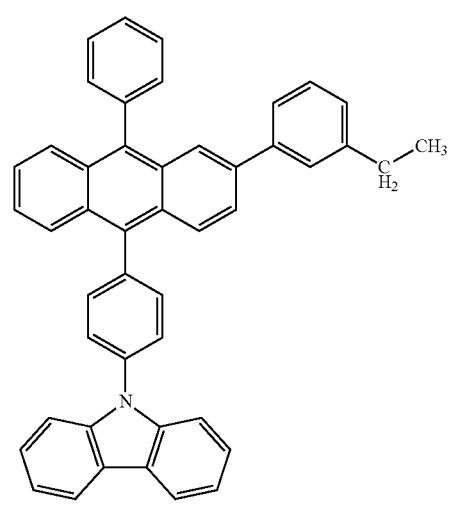

(124) 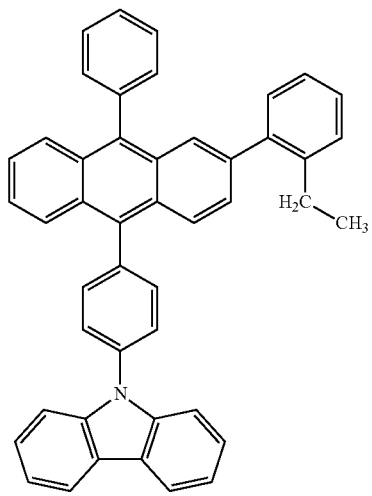
(125) 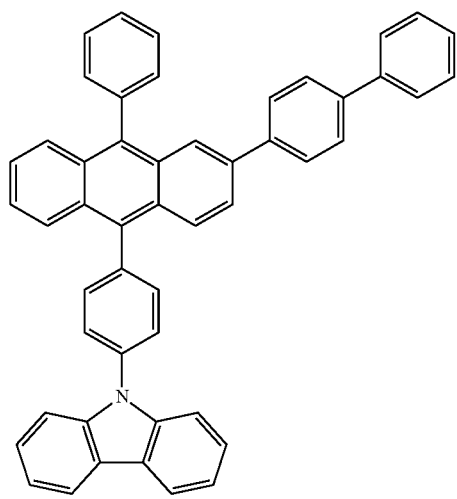
(126) 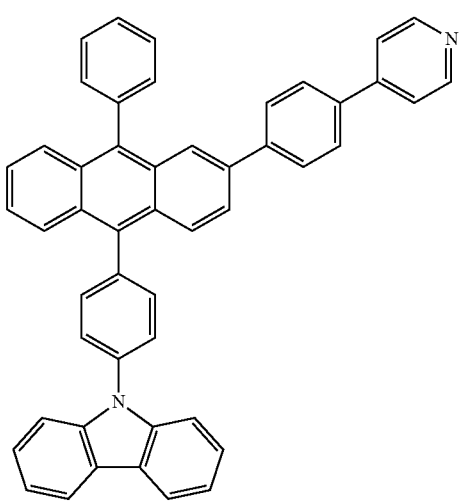
[Chemical formulae 16]
(127) 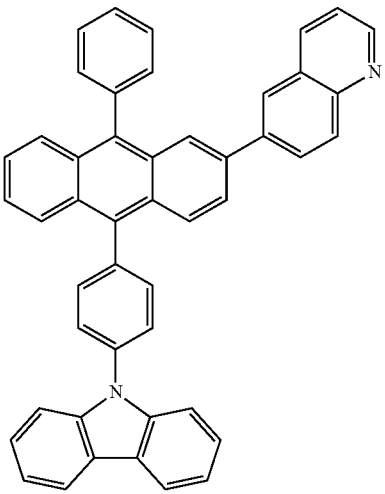
(128) 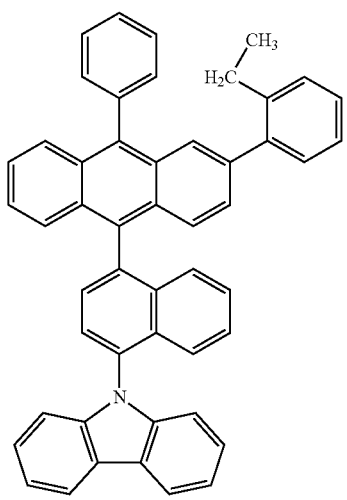
(129) 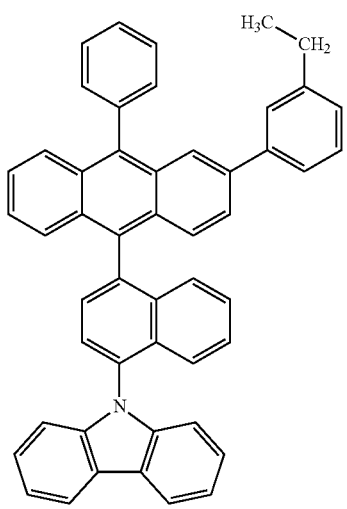

(130) 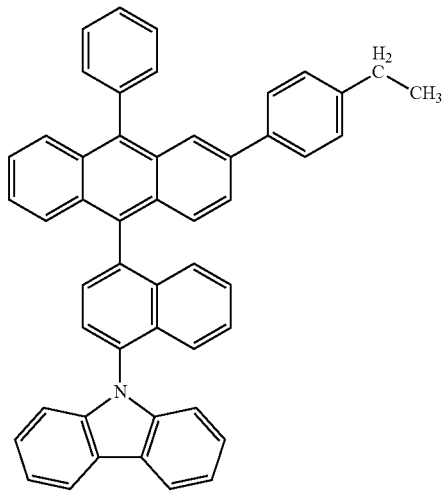
(131) 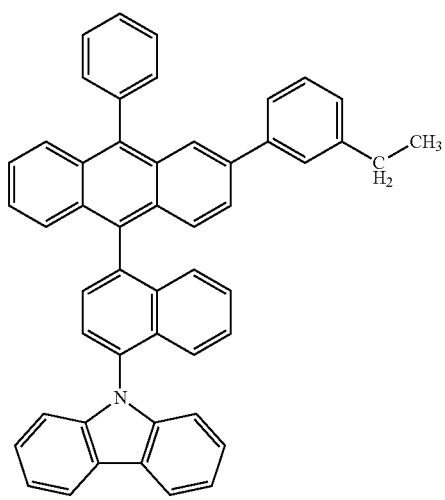
(132) 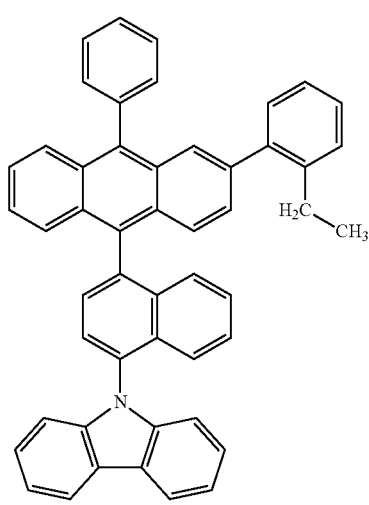
(133) 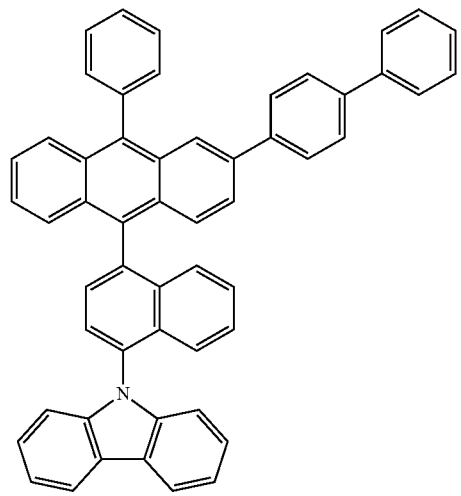
(134) 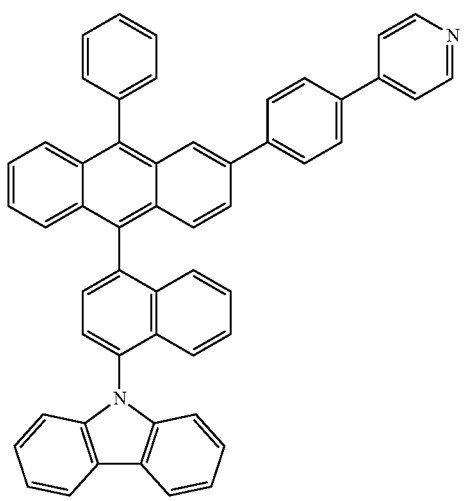
(135) 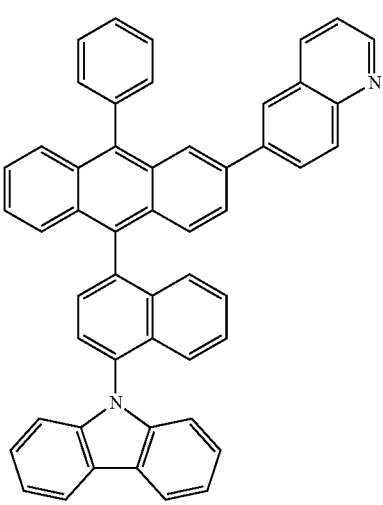

[Chemical formulae 17]
(136)
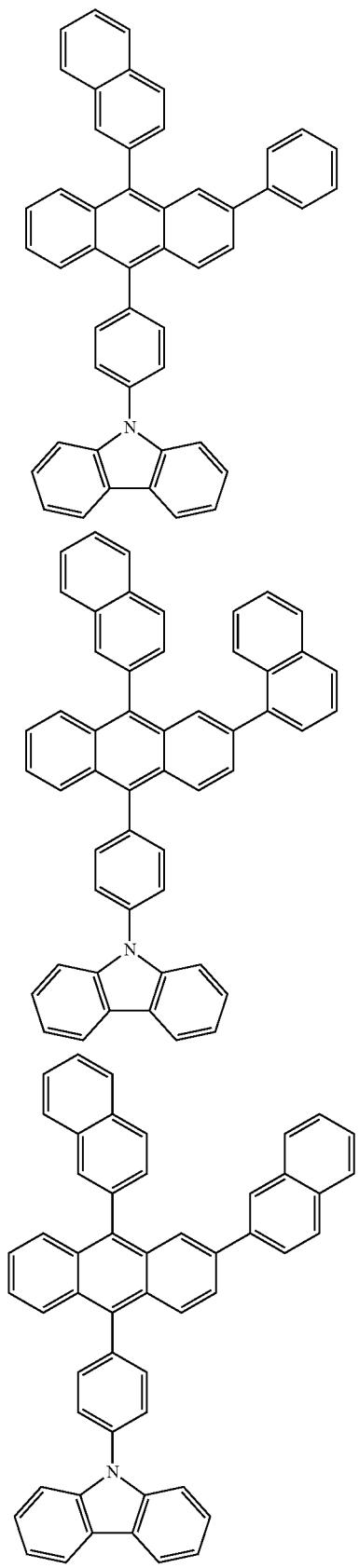
(137)
(138)
(139)
(140)

(141)
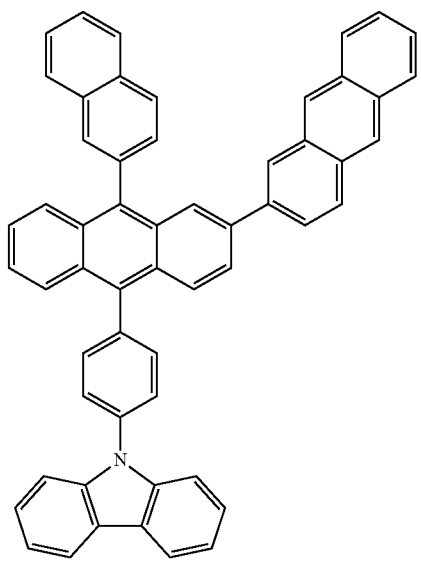
(143)
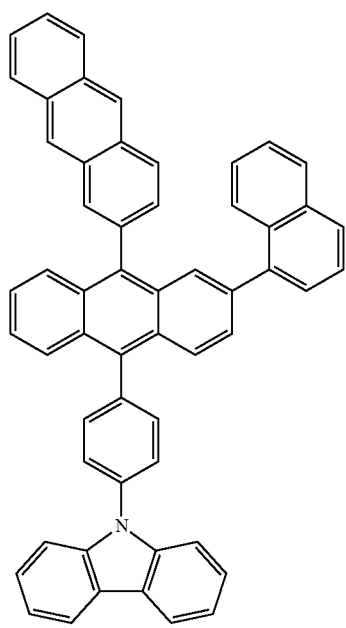
(142)
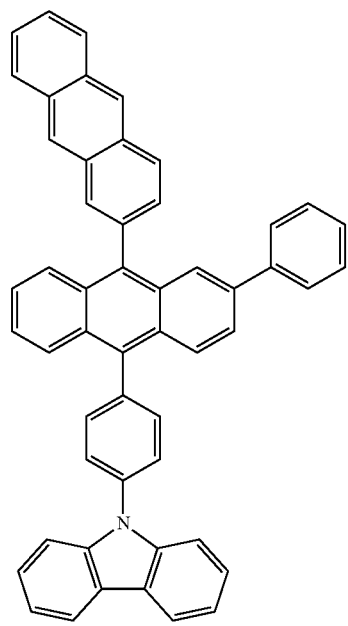
(144)
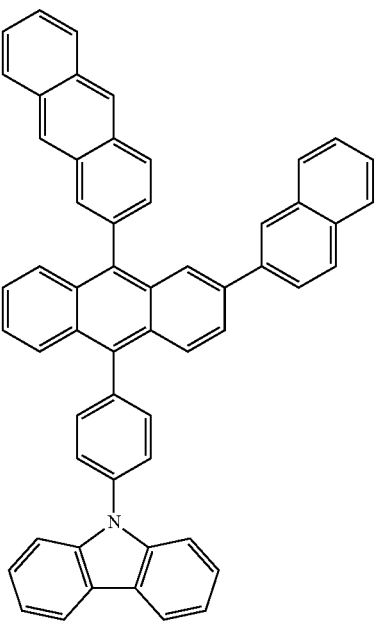

[Chemical formulae 18]
(145)
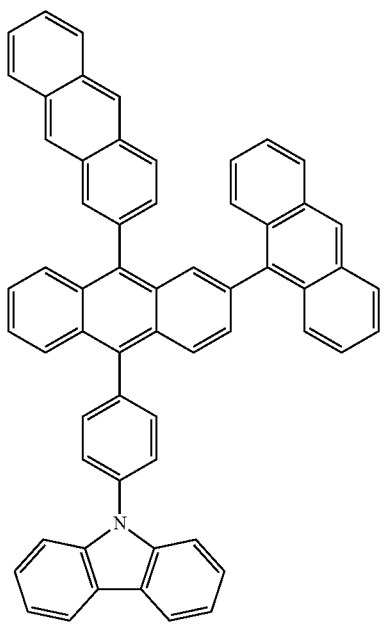
(146)
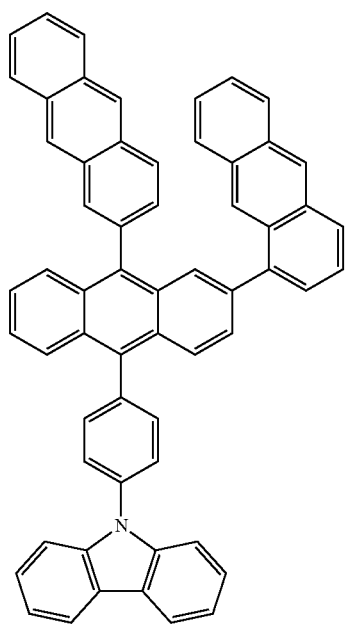
(147)
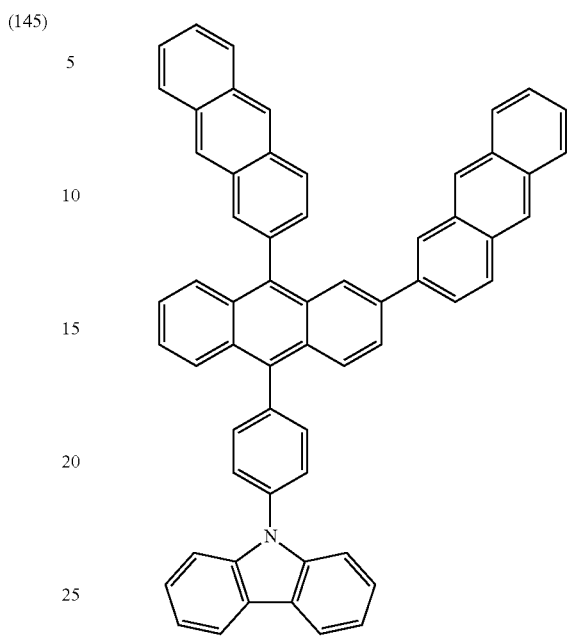
(148)
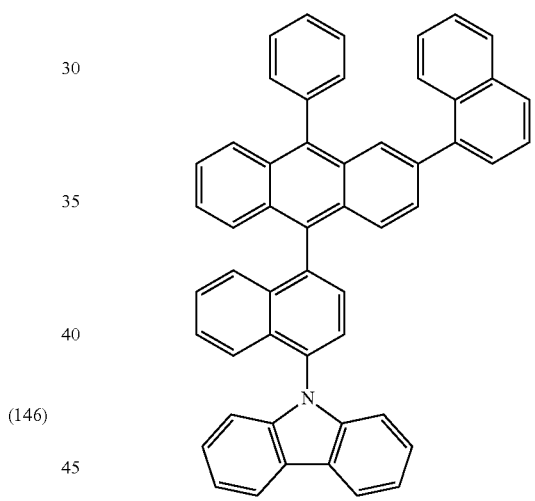
(149)
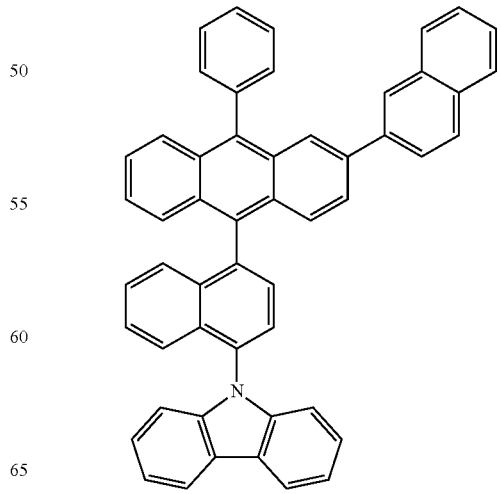

(150)
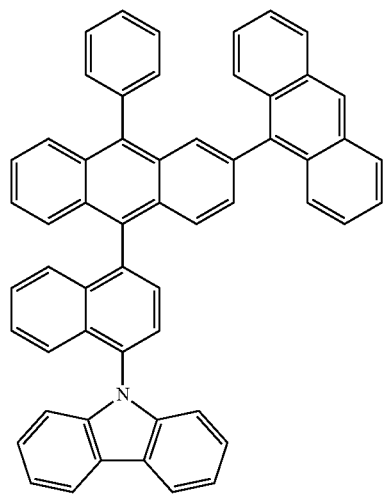
(151)
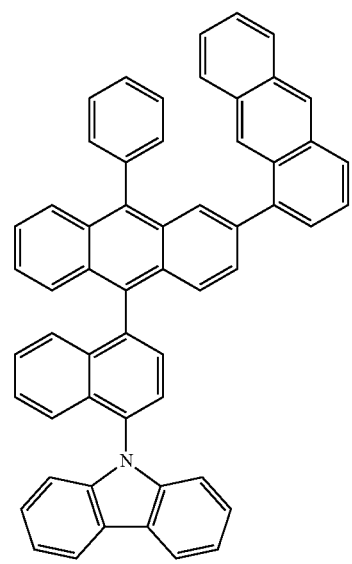
(152)
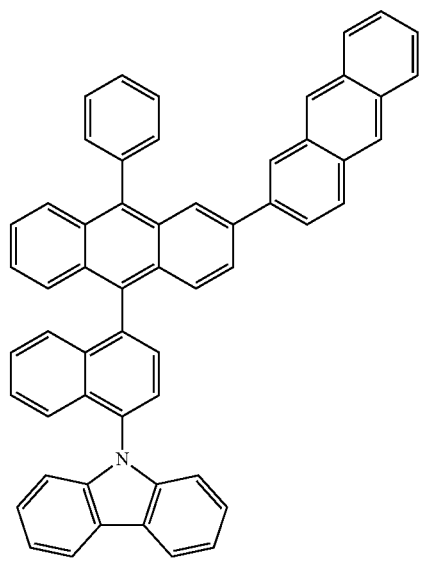
(153)
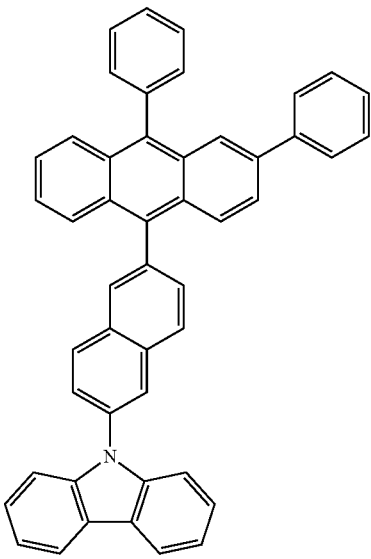
[Chemical formulae 19]
(154)
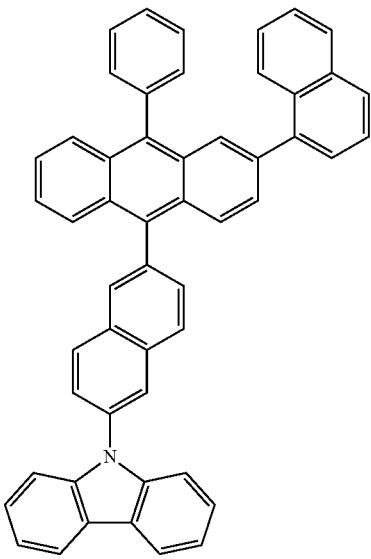

(155)
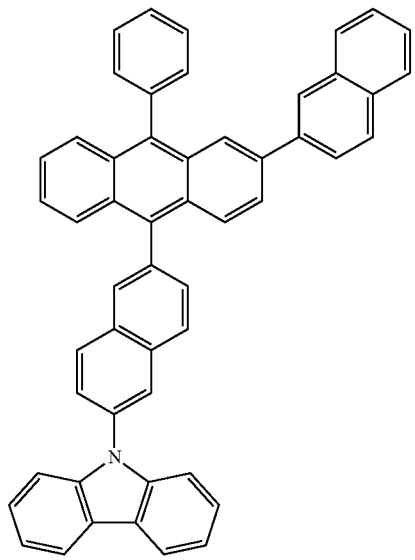
(156)
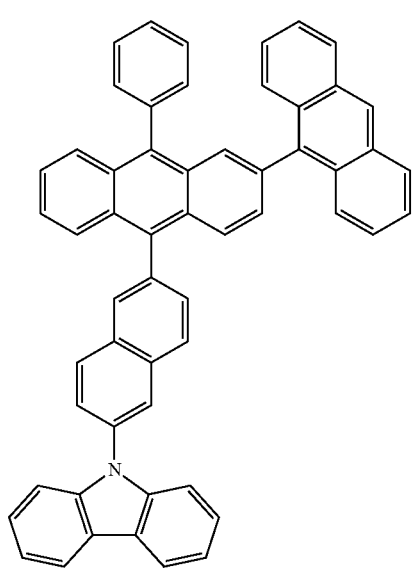
(157)
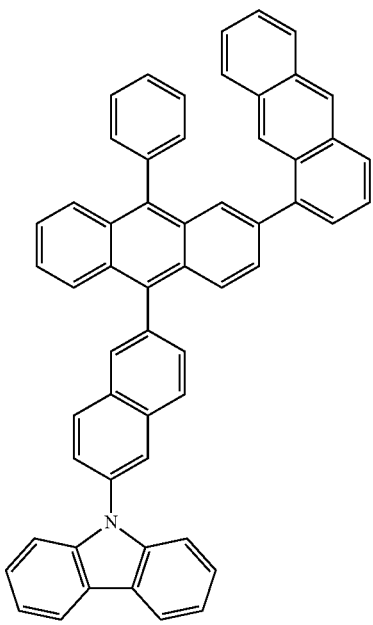
(158)
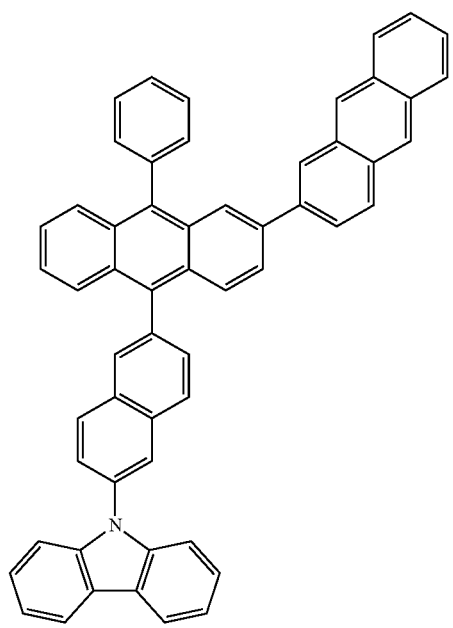

(159)
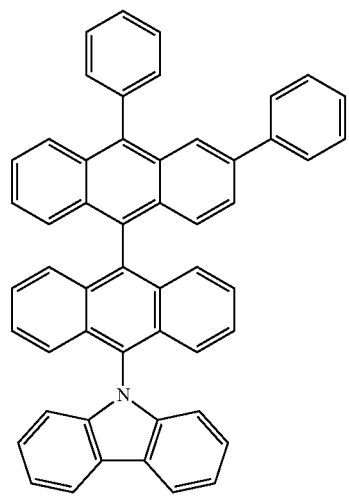
(160)
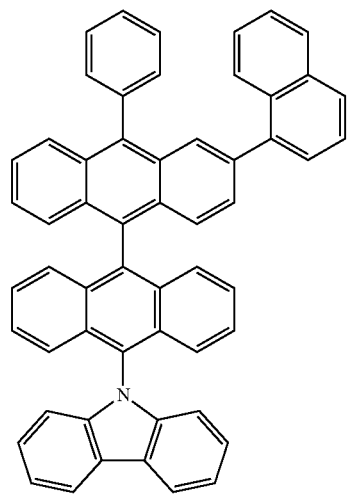
(161)
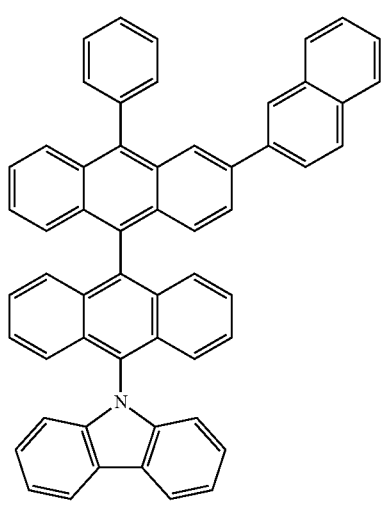
(162)
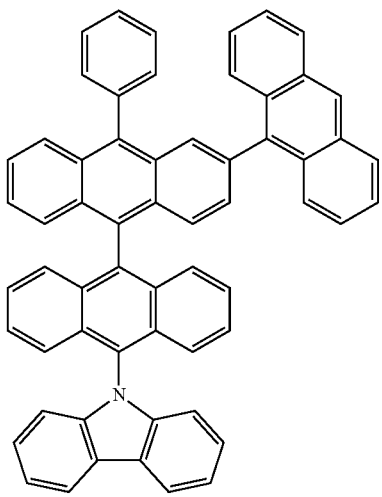
[Chemical formulae 20]
(163)
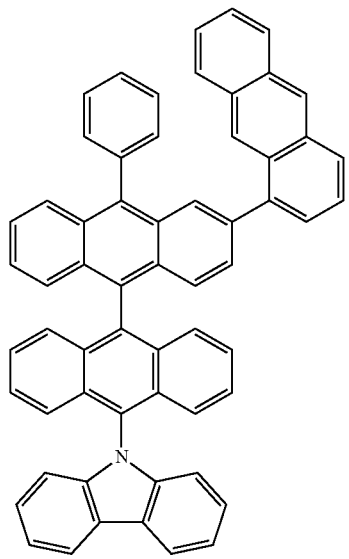
(164)
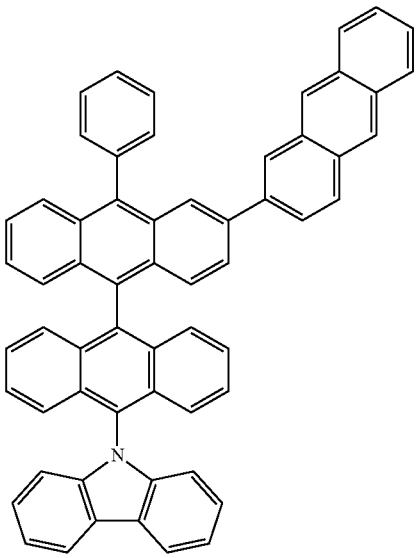

(165)
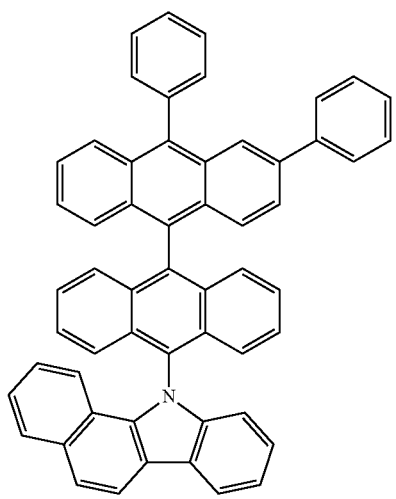
(168)
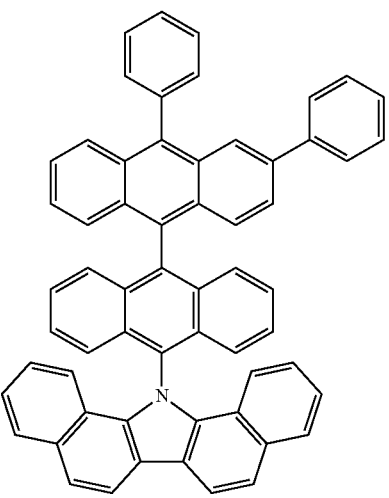
(166)
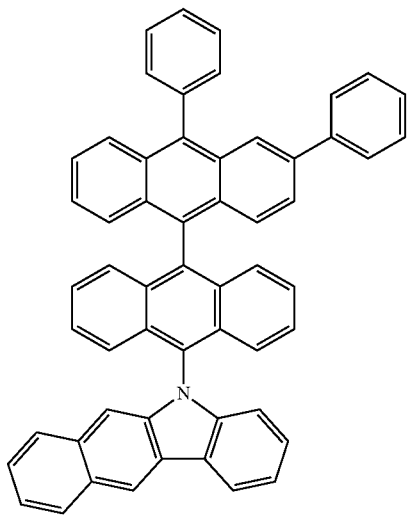
(169)
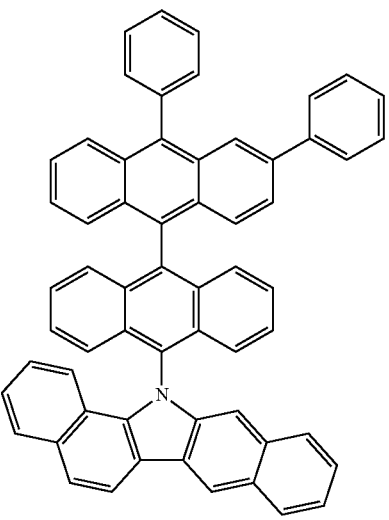
(167)
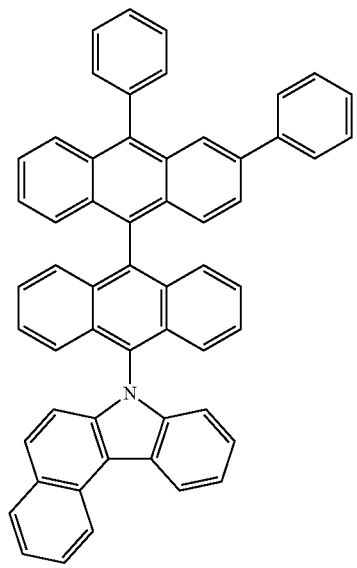
(170)
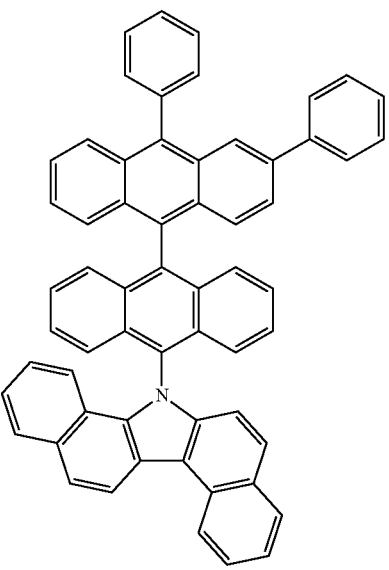

[Chemical formulae 21]
(171) 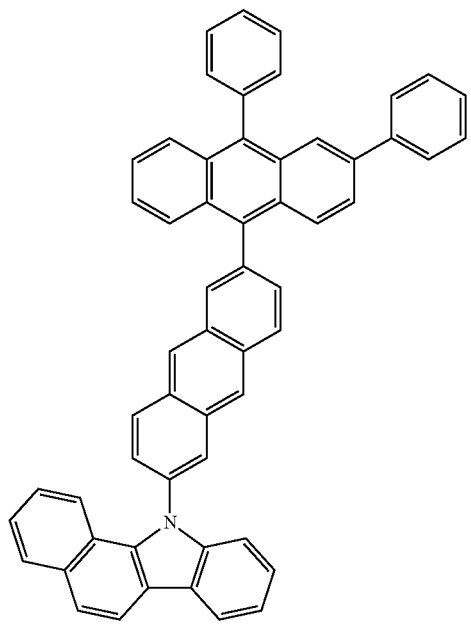
(172) 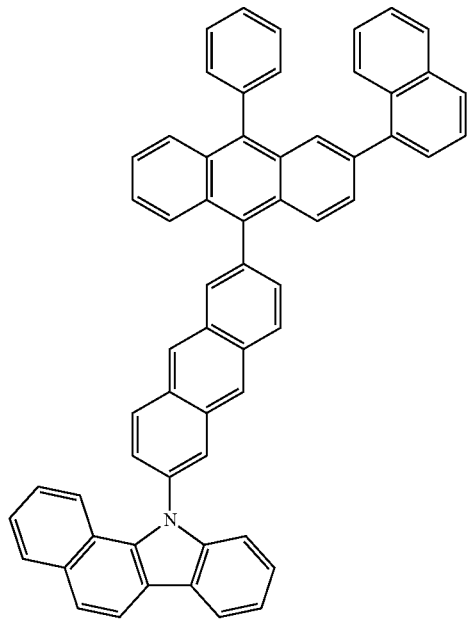
(173) 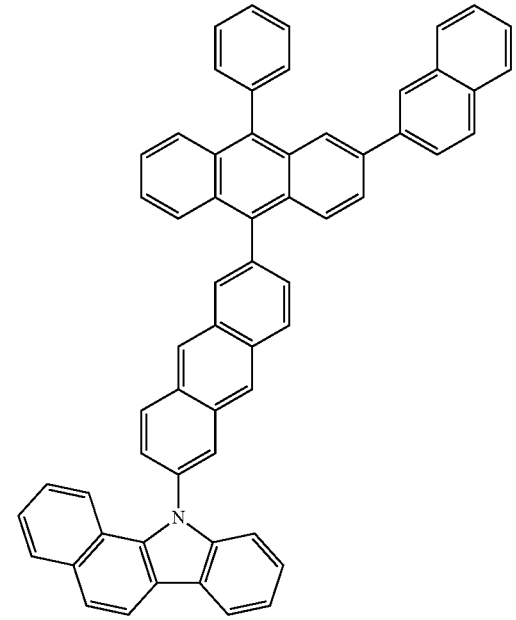
(174) 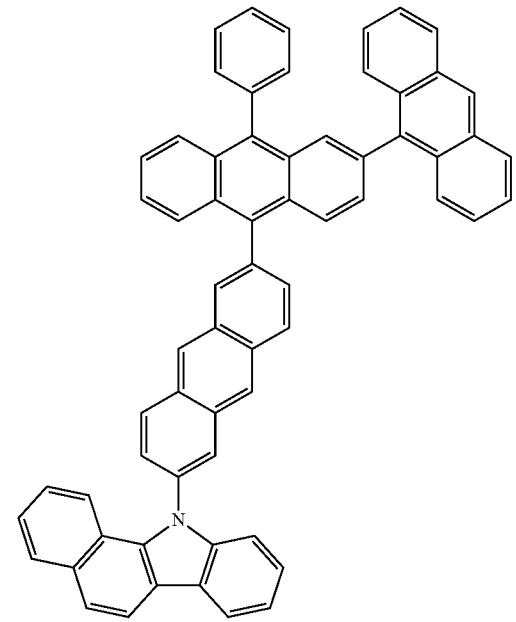

(175)
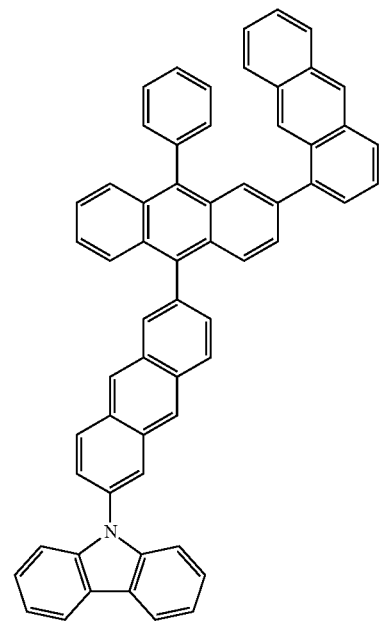
(176)
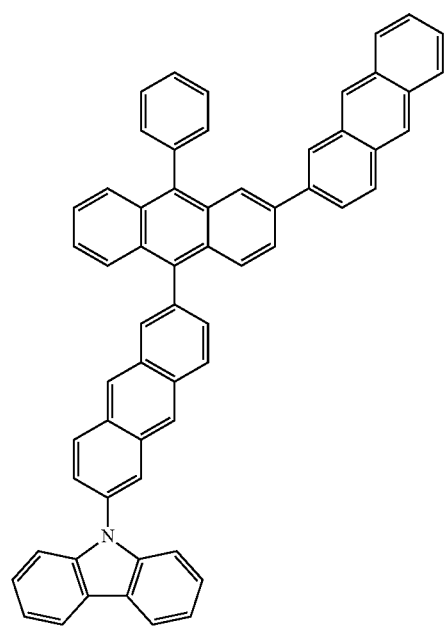
(177)
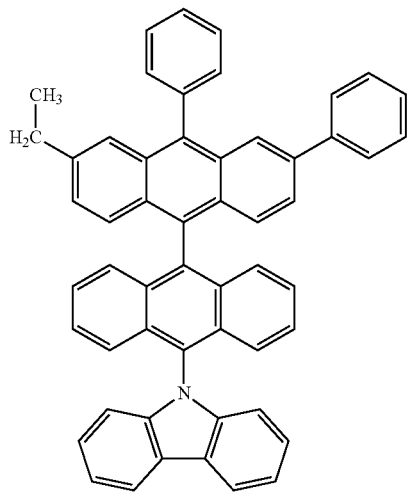
(178)
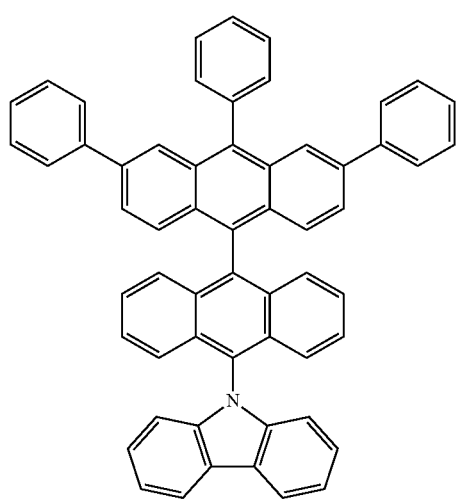
(179)
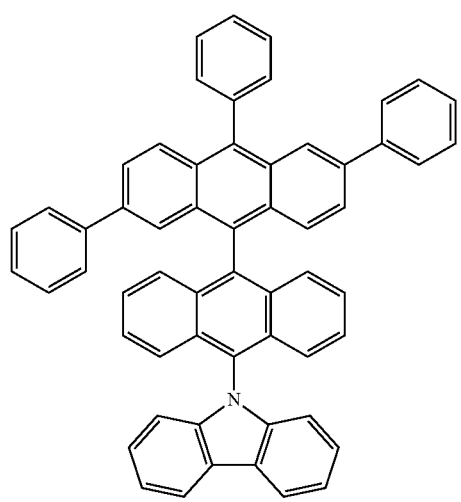

(180)
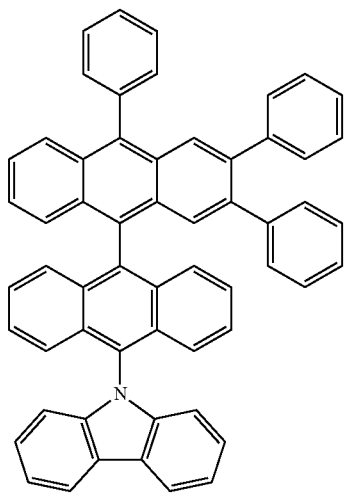
[Chemical formulae 22]
(181)
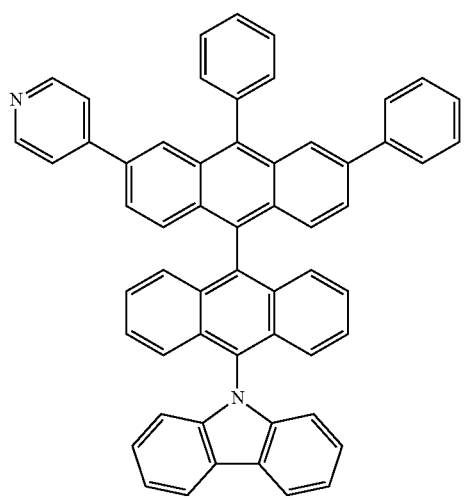
(182)
(183)
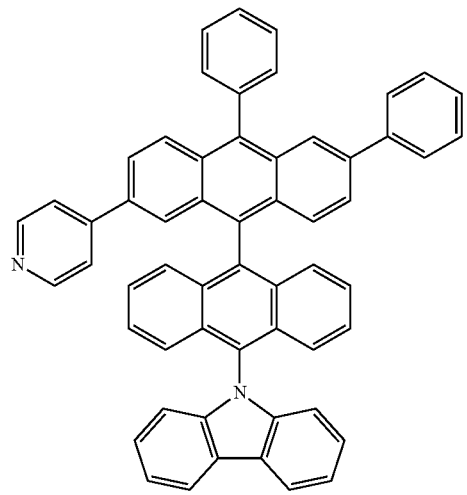
(184)
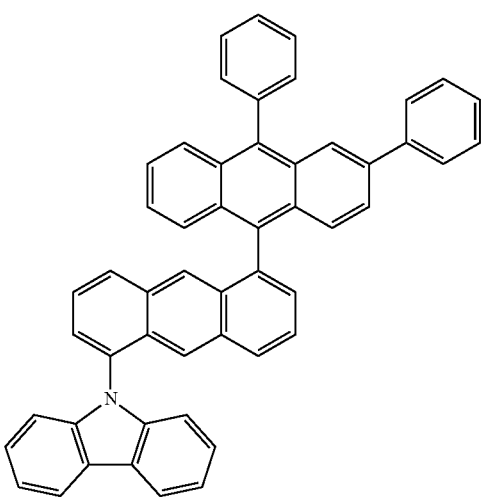
(185)
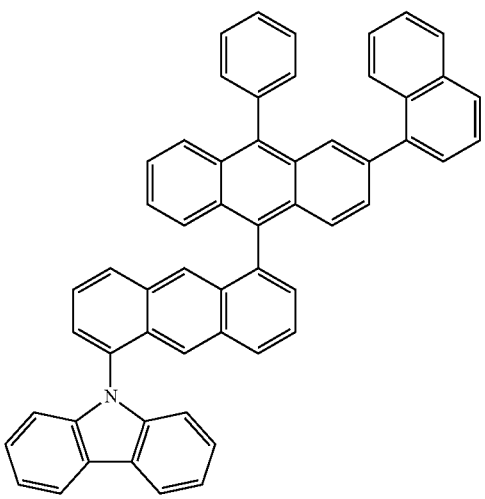

51
-continued
(186)
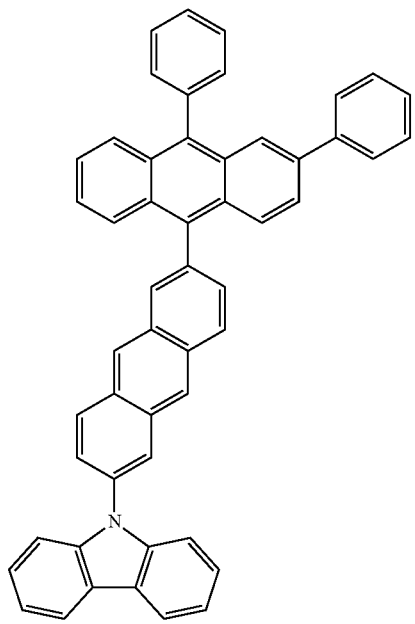
(200)
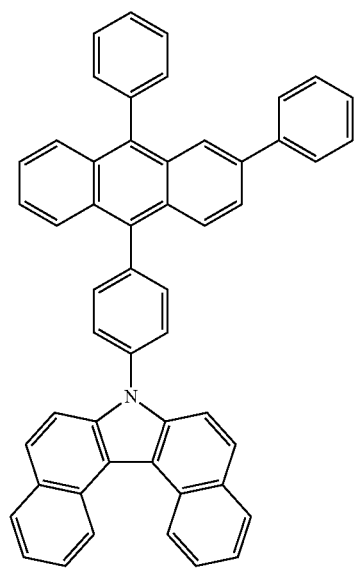
[Chemical formulae 23]
52
-continued
(201)
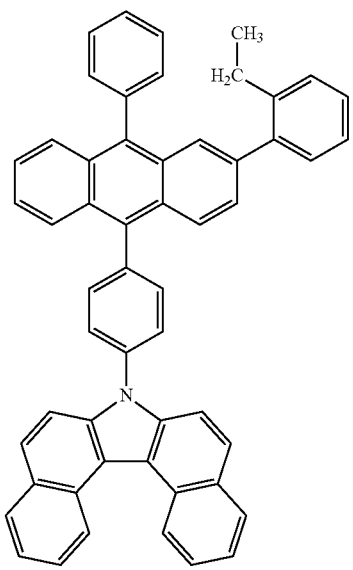
(202)
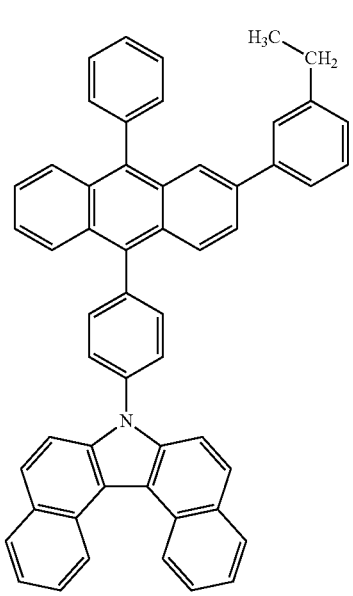

53
-continued
(203)
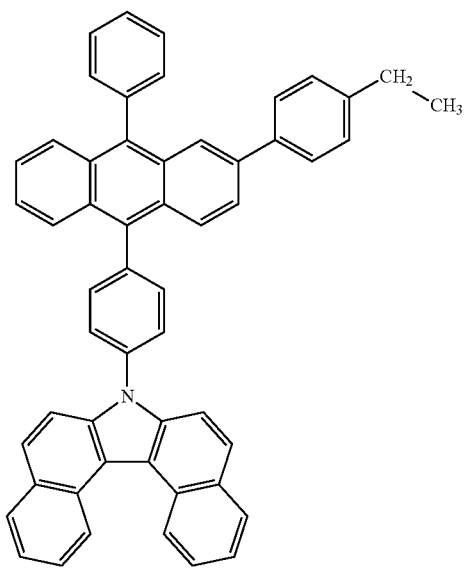
(204)
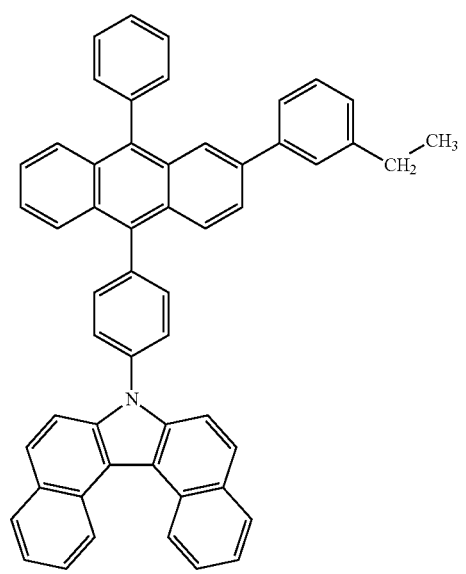
54
-continued
(205)
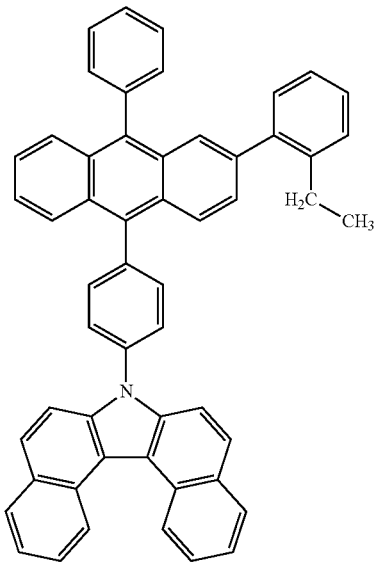
(206)
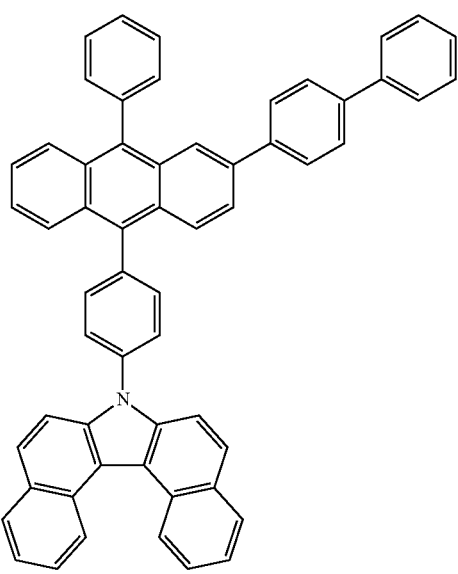

[Chemical formulae 24]
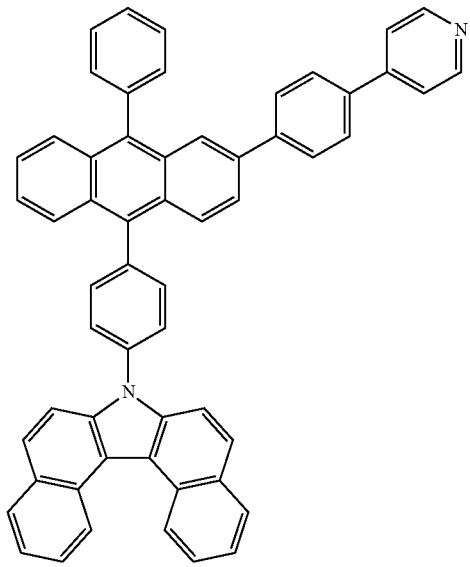
(207)
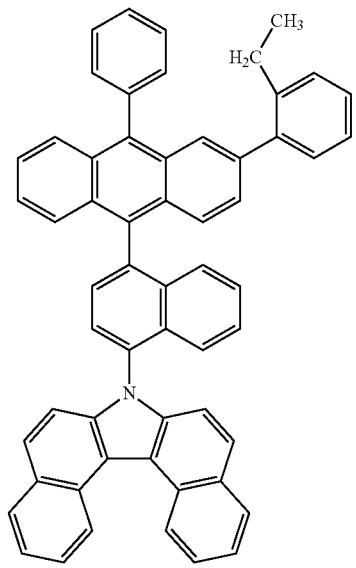
(209)
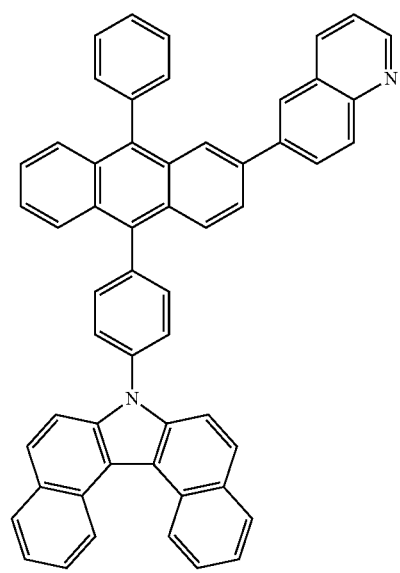
(208)
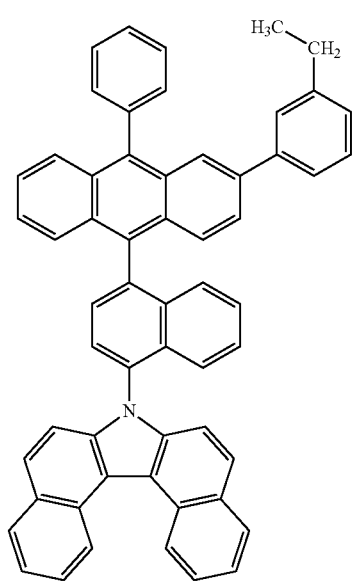
(210)

(211)
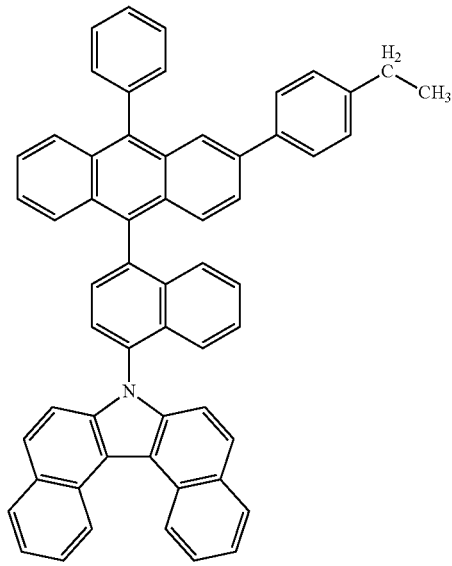
(213)
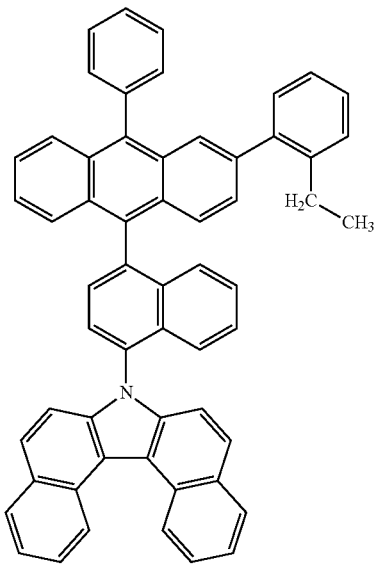
(212)
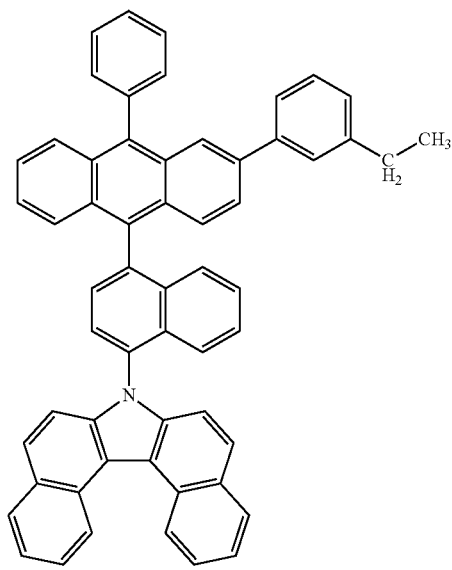
(214)
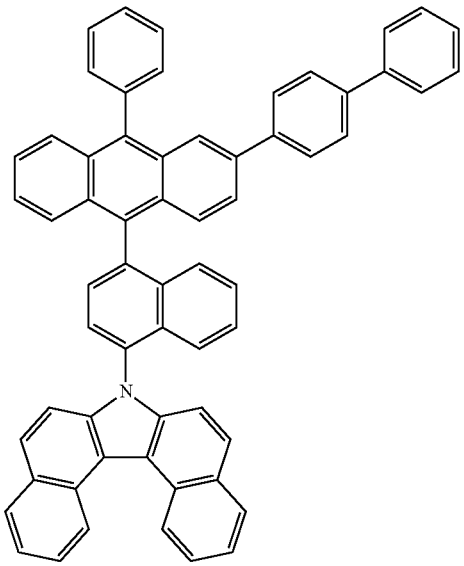

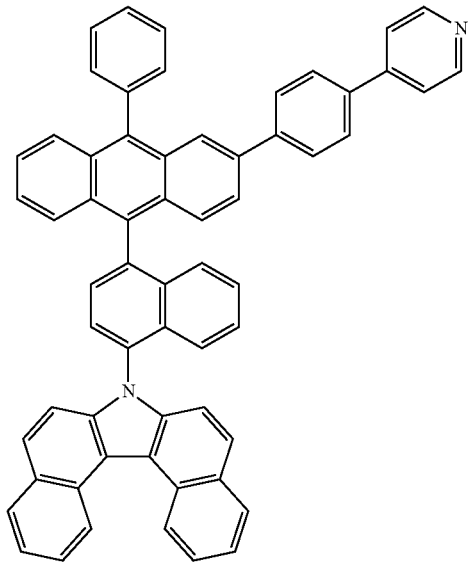 (215)
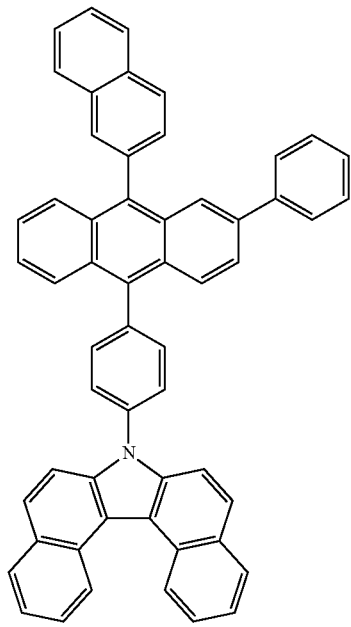 (217)
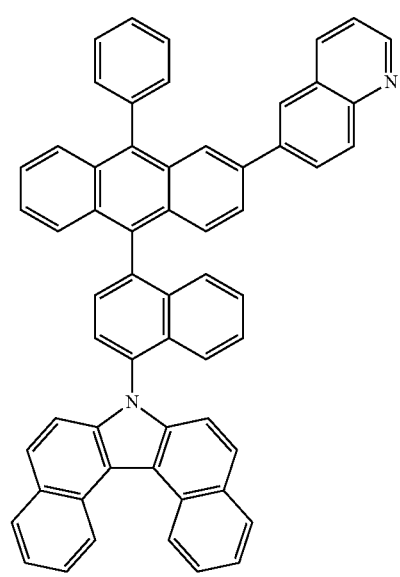 (216)
[Chemical formulae 25]
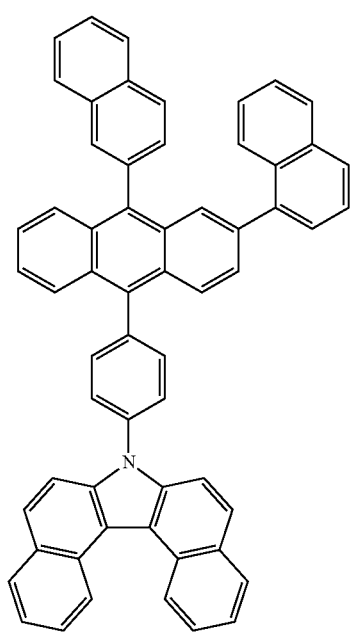 (218)

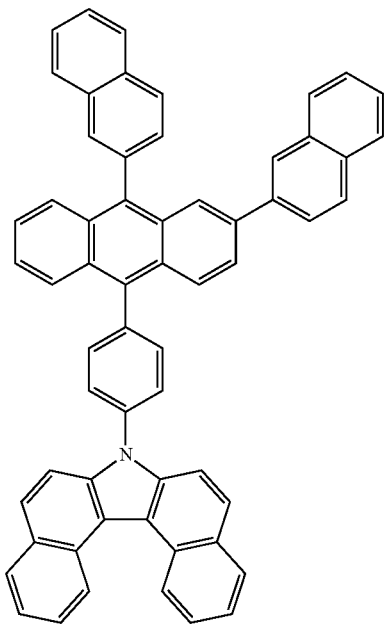
(219)
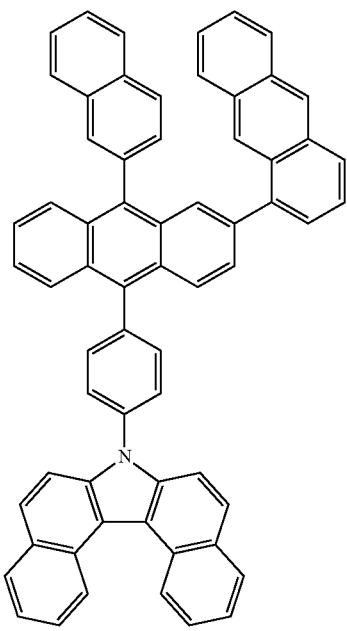
(221)
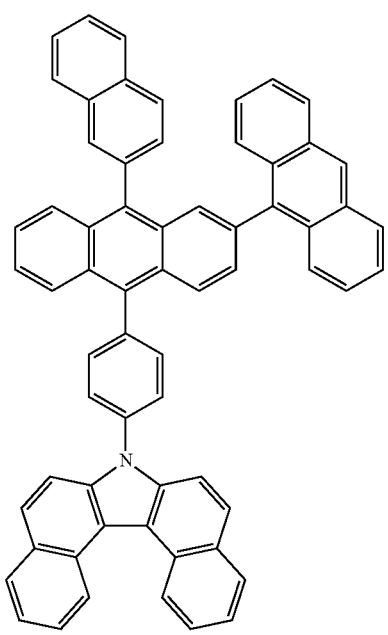
(220)
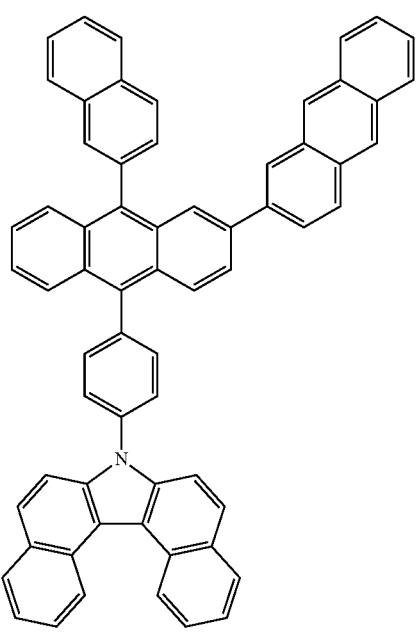
(222)

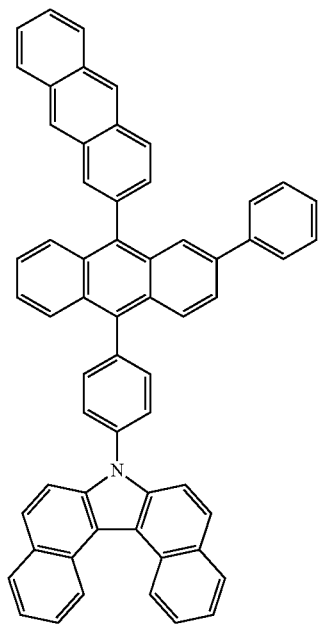
(223)
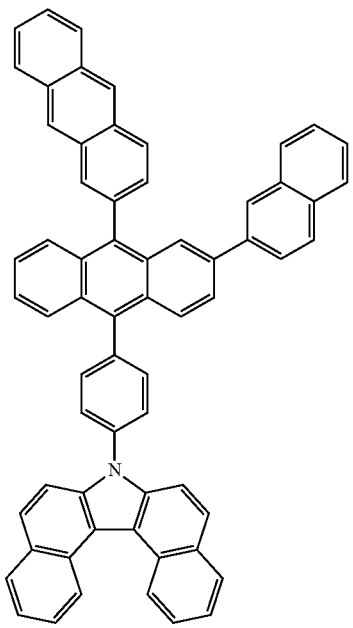
(225)
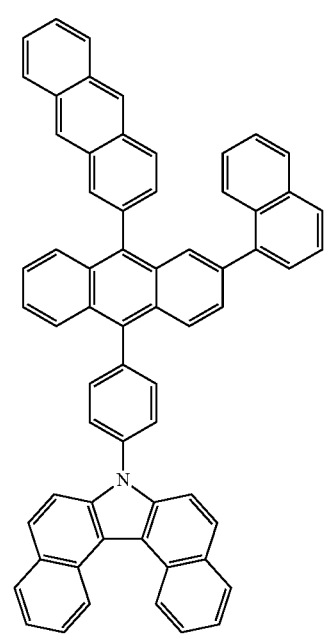
(224)
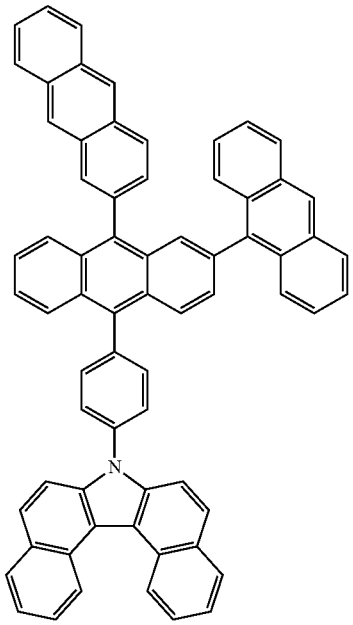
(226)

[Chemical formulae 26]
(227)
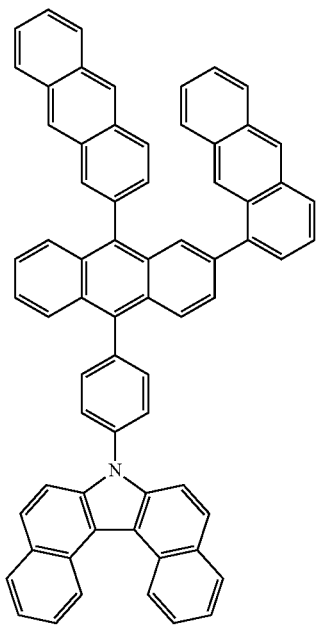
(228)
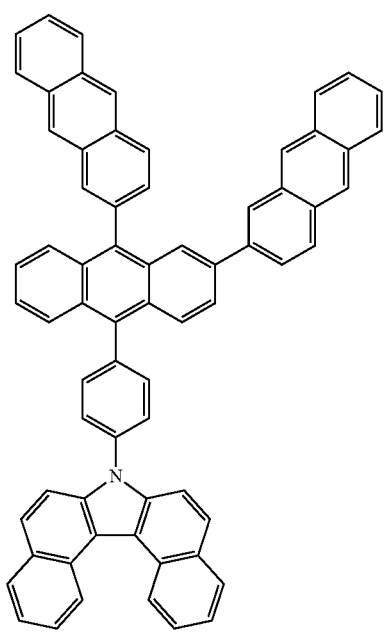
(229)
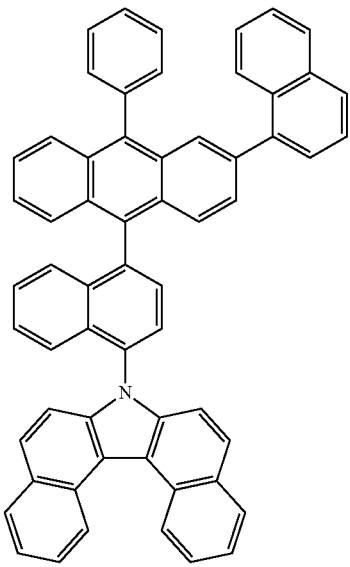
(230)
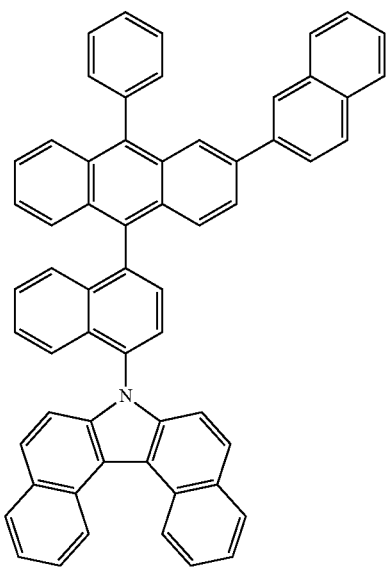

(231)
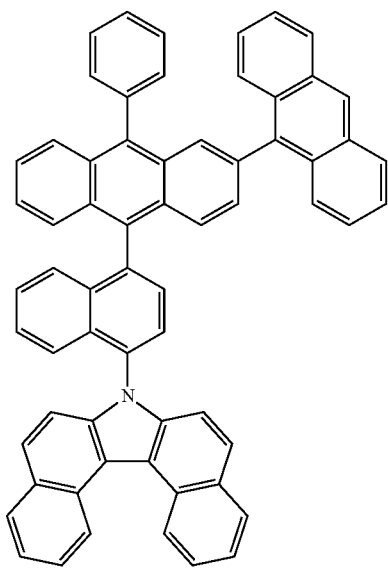
(232)
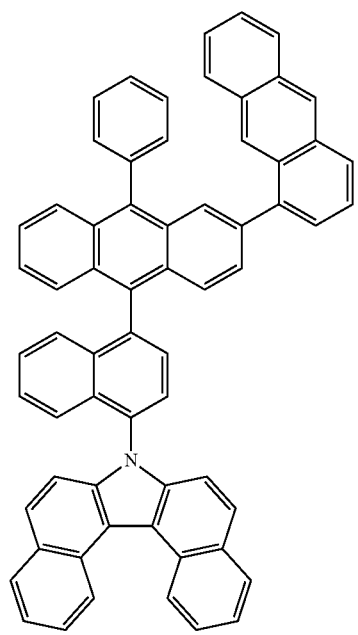
(233)
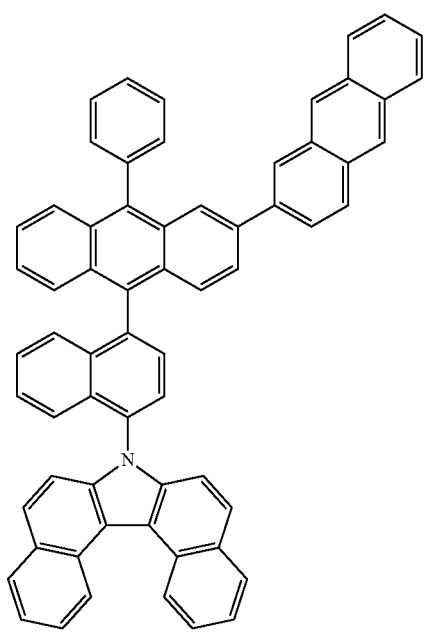
(234)
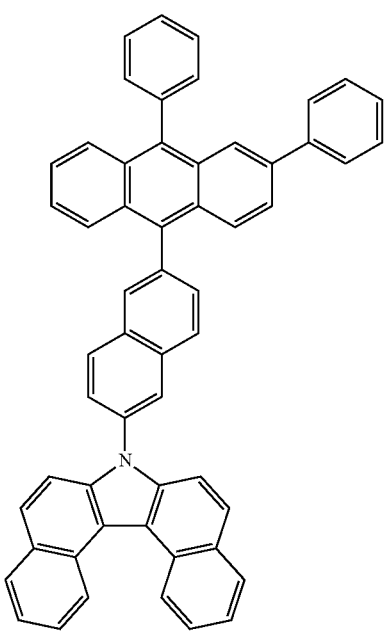

(235)
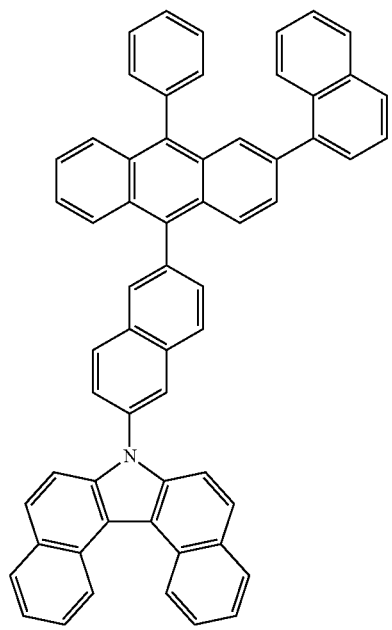
(237)
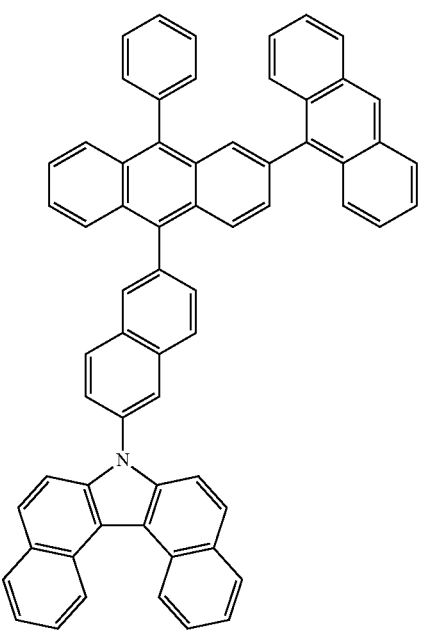
[Chemcial formulae 27]
(236)
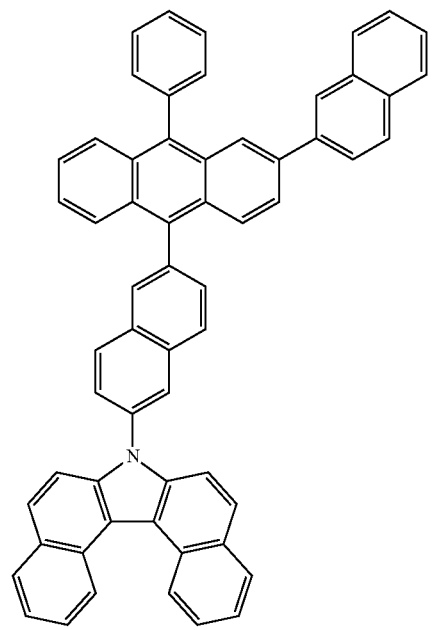
(238)
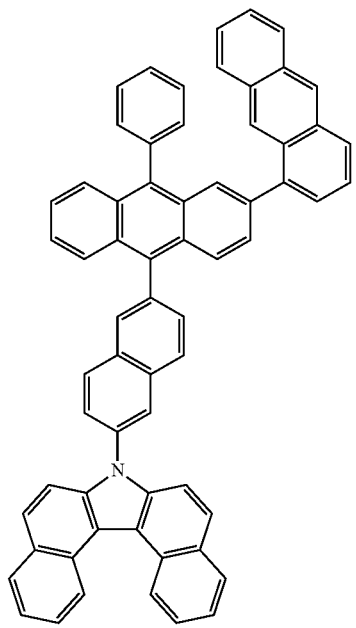

(239)
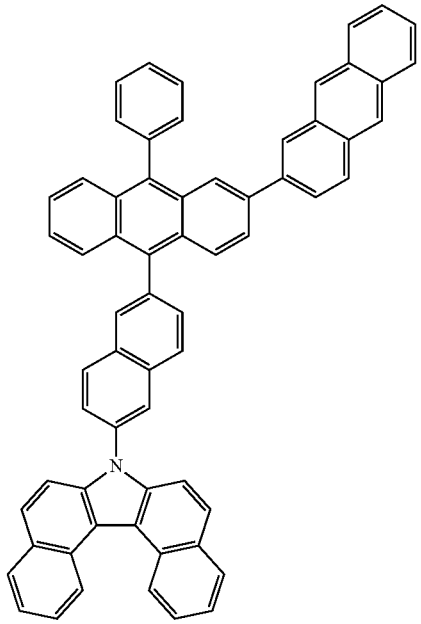
(240)
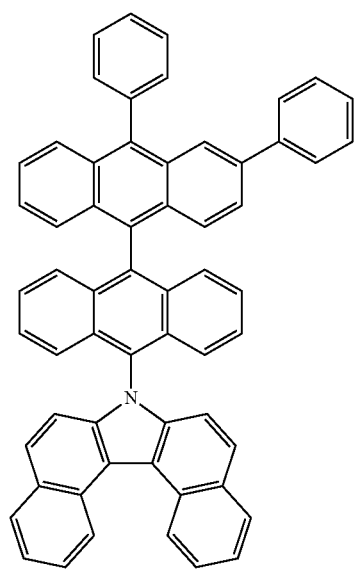
(241)
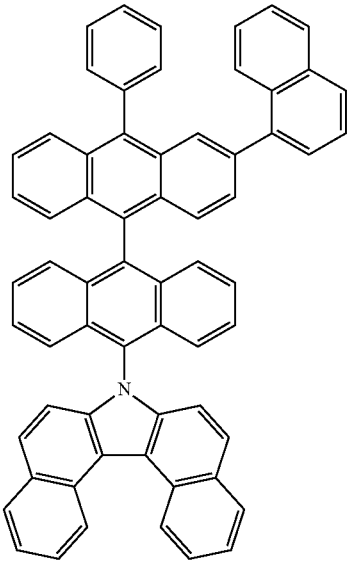
(242)
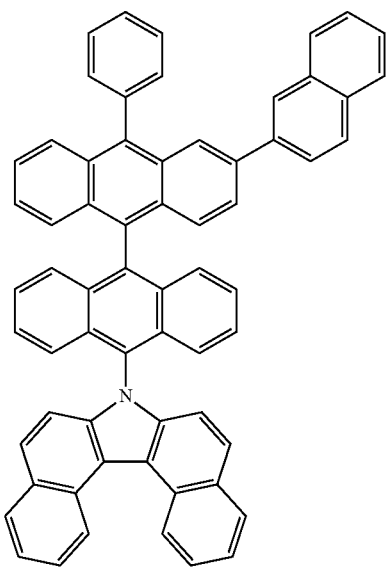

-continued
(243)
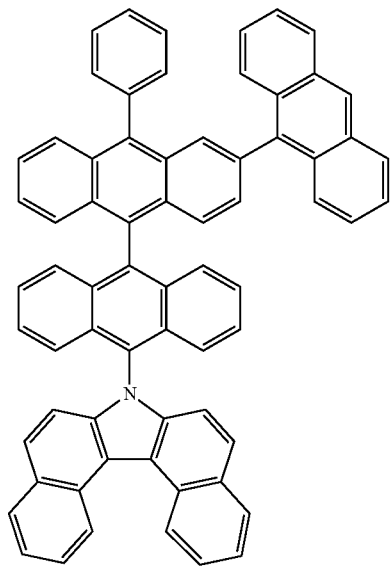
(244)
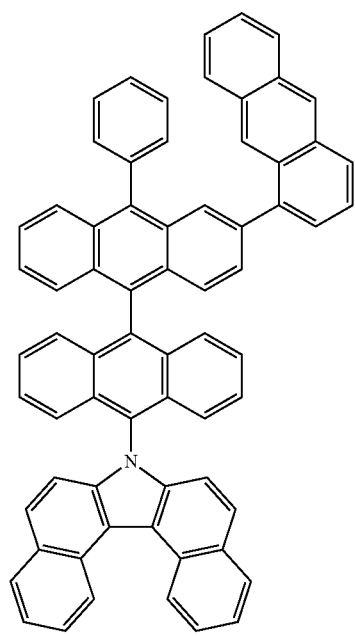
-continued
[Chemical formulae 28]
(245)
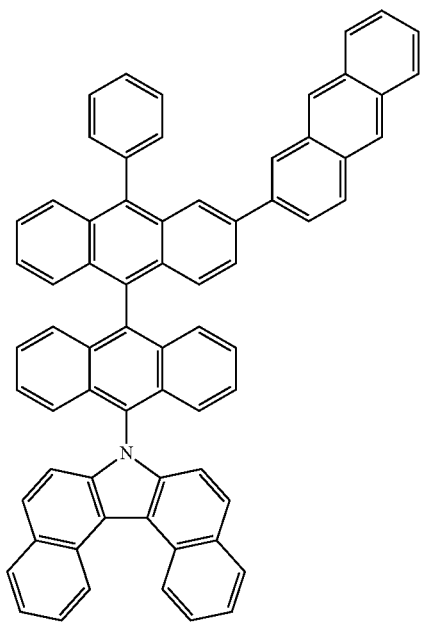
(246)
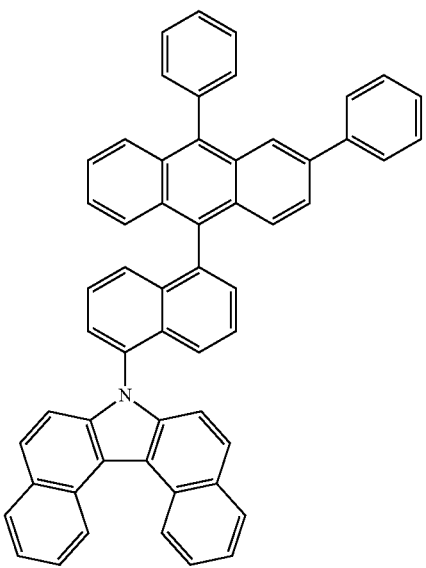

(247)
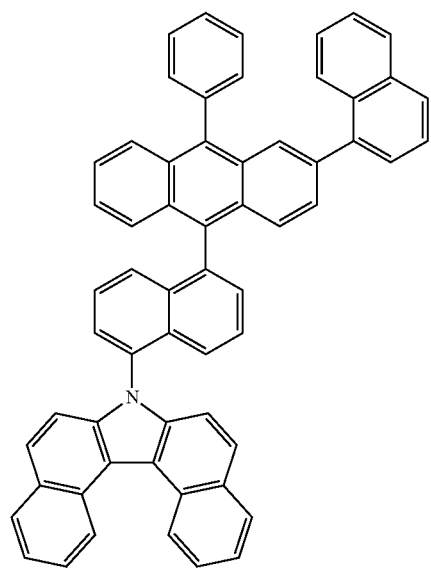
(248)
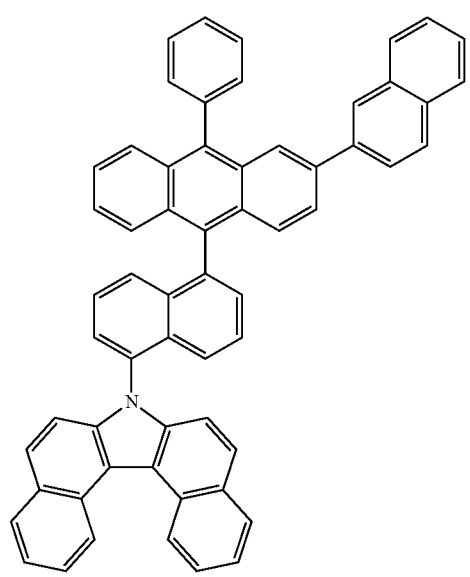
(249)
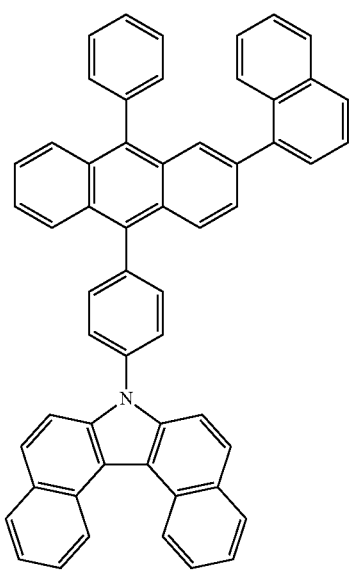
(250)
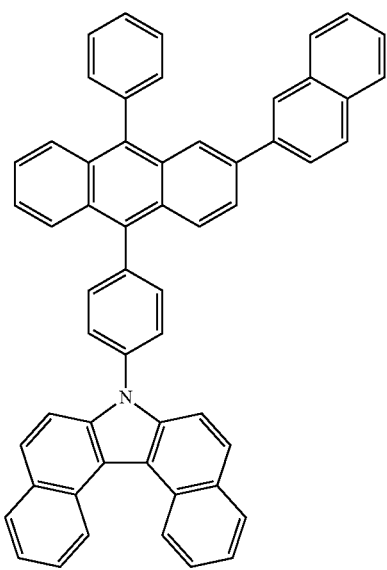

(251)
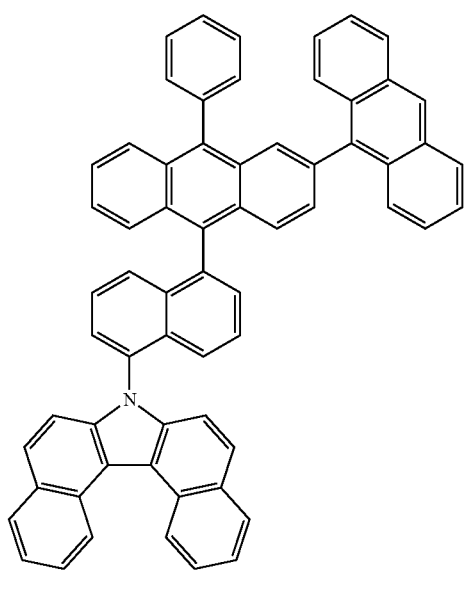
(253)
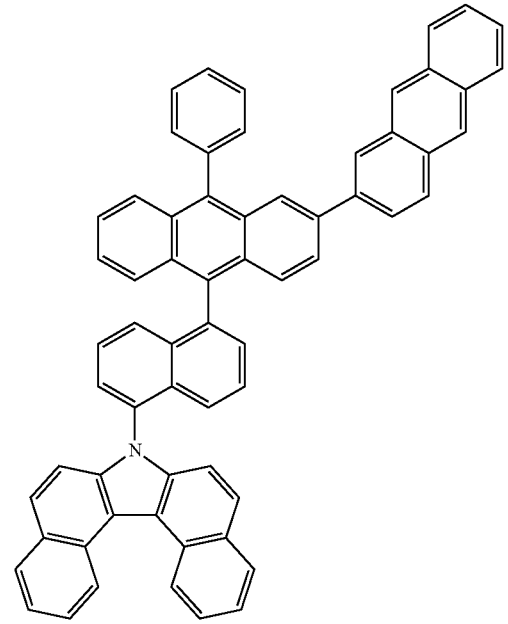
(252)
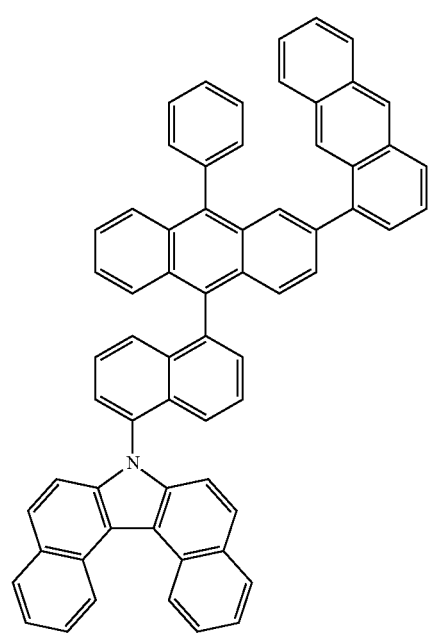
[Chemical formulae 29]
(254)
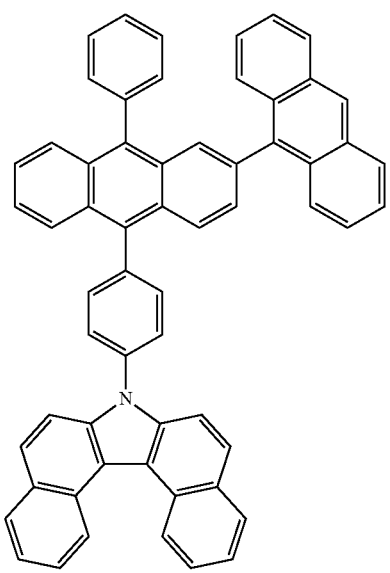

79
-continued
(255)
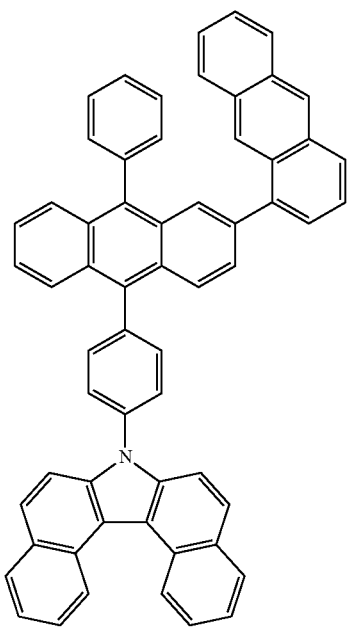
80
-continued
(257)
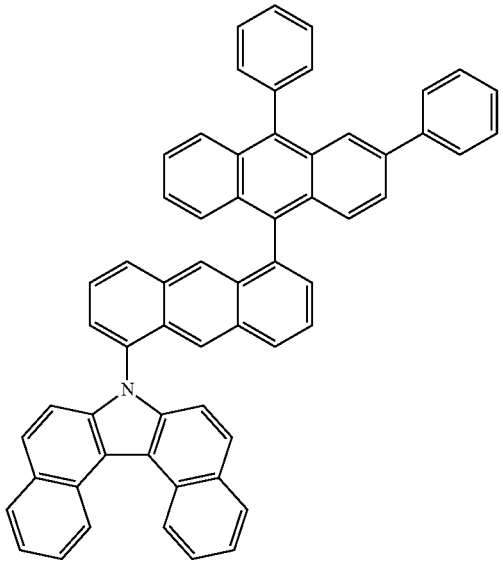
(256)
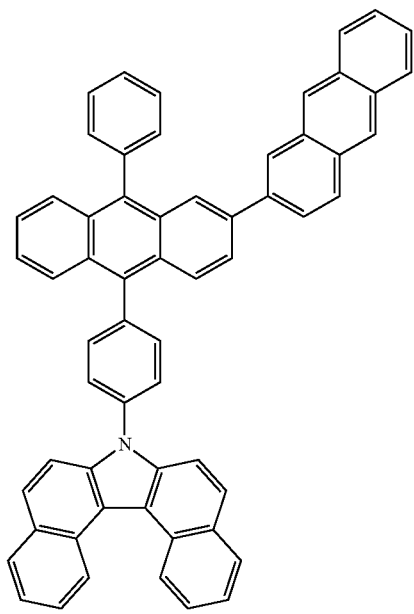
(258)
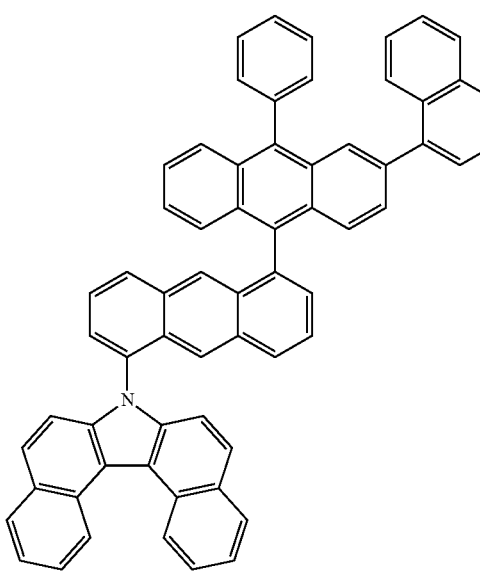

(259)
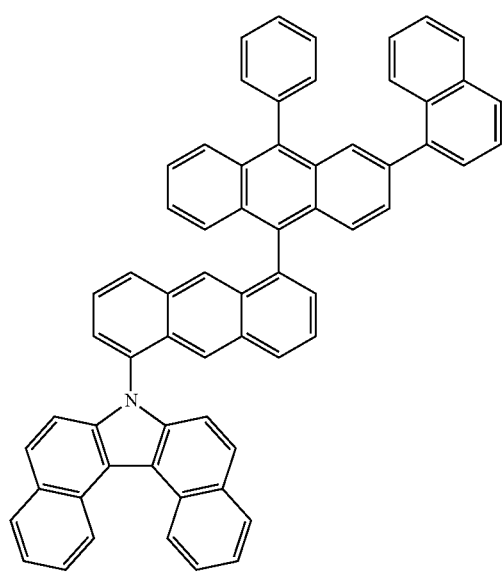
(261)
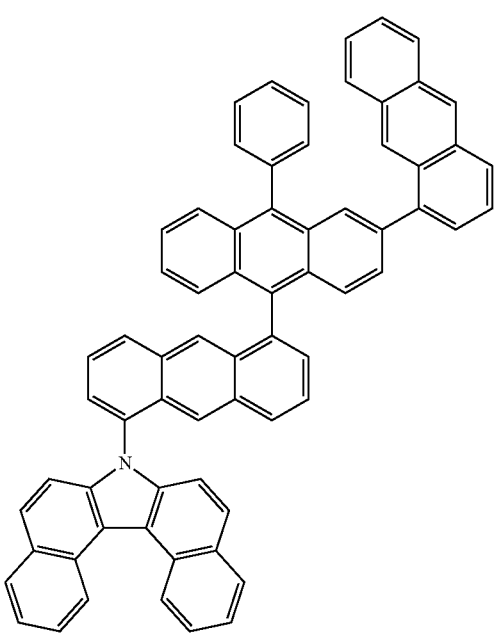
(260)
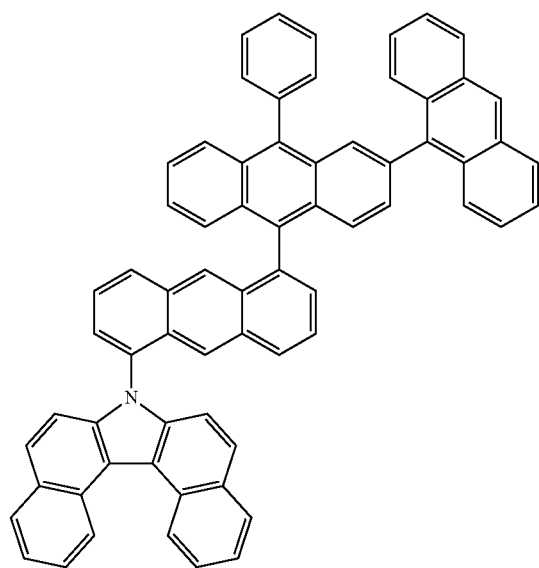
(262)
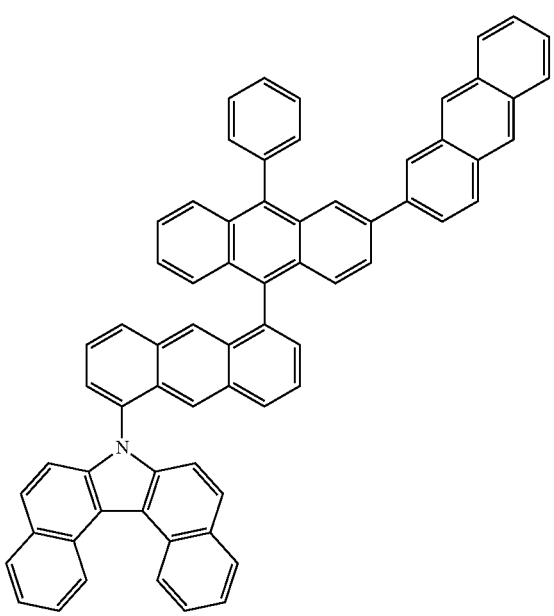

[Chemical formulae 30]
(263)
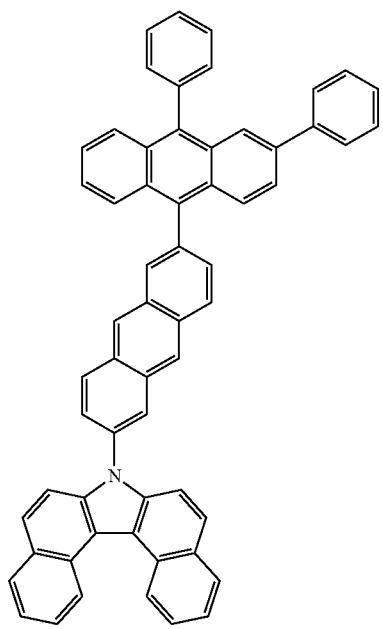
(264)
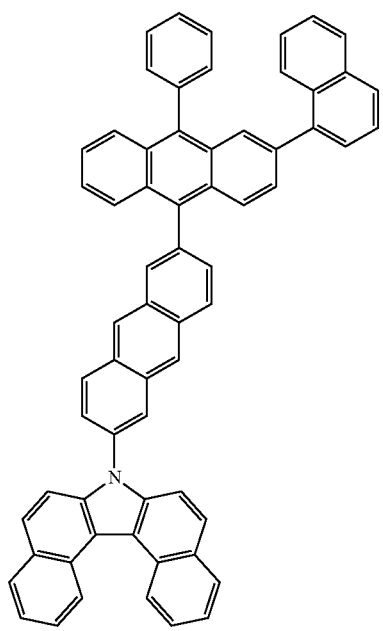
(265)
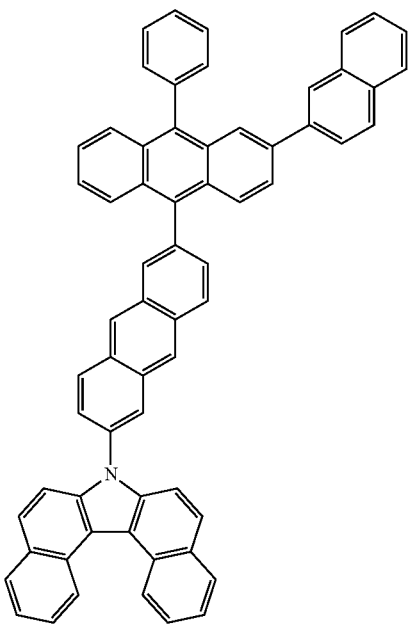
(266)

-continued (267)

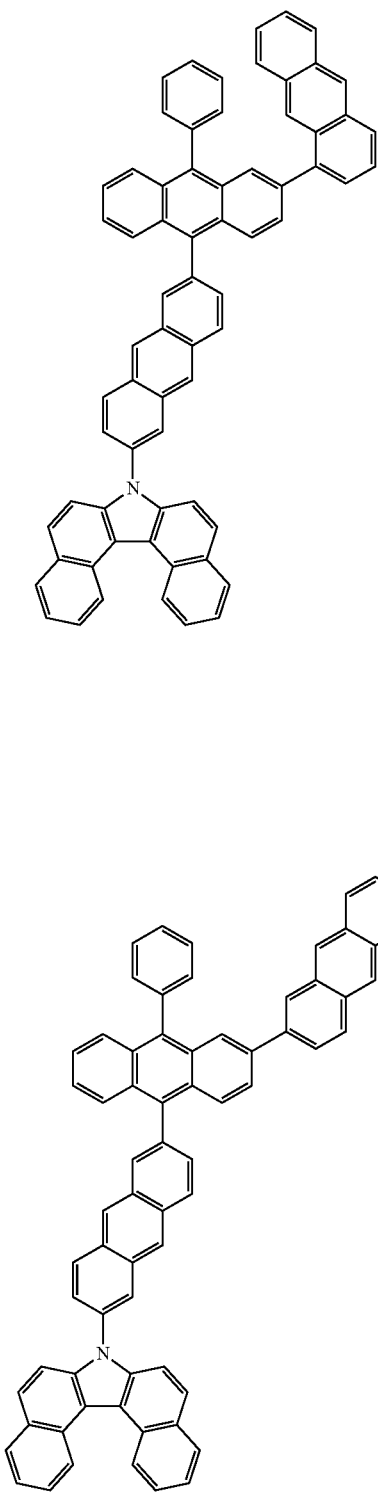

(268)

[Chemical formula 31]

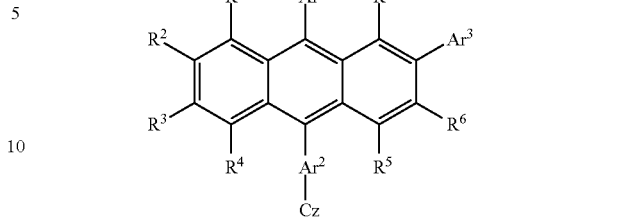

As shown in the following synthesis scheme (A), a halide of an anthracene derivative (a1) and a heterocyclic compound including a carbazole skeleton (a2) are subjected to coupling using a metal catalyst, a metal, or a metal compound in the presence of a base, so that the organic compound represented by the general formula (G1), which is one embodiment of the present invention, can be obtained.

[Chemical formula 32]

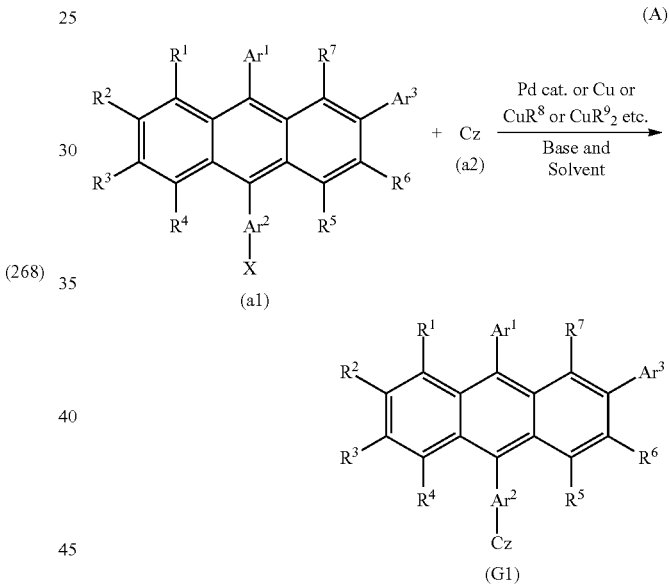

In the synthesis scheme (A), $Ar^1$ and $Ar^3$ each independently represent a substituted or unsubstituted aryl group having 6 to 30 carbon atoms. In addition, Are represents a substituted or unsubstituted arylene group having 6 to 14 carbon atoms. Furthermore, Cz represents a substituted or unsubstituted heterocyclic group including a carbazole skeleton, and the carbazole skeleton is directly bonded to the Are. Note that $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms.

Next, an example of a method for synthesizing the organic compound of one embodiment of the present invention is described.

An example of a method for synthesizing a dibenzo organic compound represented by the following general formula (G1), which is one embodiment of the present invention, is described below.

In the case where a Buchwald-Hartwig reaction is caused in the synthesis scheme (A), X represents a halogen or a triflate group. As the halogen, iodine, bromine, or chlorine is preferable. In this reaction, a palladium catalyst including a palladium complex or a palladium compound such as bis (dibenzylideneacetone)palladium(0) or allylpalladium(II) chloride and a ligand that coordinates to the palladium complex or the palladium compound, such as tri(tert-butyl)

phosphine, di-tert-butyl(1-methyl-2,2-diphenylcyclopropyl) phosphine, or tricyclohexylphosphine, is used. Examples of the base include organic bases such as sodium tert-butoxide, inorganic bases such as a potassium carbonate, and the like. In the case where a solvent is used, toluene, xylene, 1,3,5-trimethylbenzene (mesitylene), benzene, tetrahydrofuran, or the like can be used.

In the case where an Ullmann reaction is caused in the synthesis scheme (A), X represents a halogen. As the halogen, iodine, bromine, or chlorine is preferable. As a catalyst, copper or a copper compound is used. In the case where a copper compound is used as the catalyst, $R^8$ and $R^9$ in the synthesis scheme (A) individually represent a halogen, an acetyl group, or the like. As the halogen, chlorine, bromine, or iodine can be used. Note that copper(I) iodide where $R^8$ is iodine or copper(II) acetate where $R^9$ is an acetyl group is preferably used. As the base which is used, an inorganic base such as potassium carbonate can be given. As a solvent, 1,3-dimethyl-3,4,5,6-tetrahydro-2(1H)-pyrimidinone (DMPU), toluene, xylene, 1,3,5-trimethylbenzene (mesitylene), benzene, or the like can be employed. However, the solvent is not limited thereto. In the Ullmann reaction, when the reaction temperature is 100° C. or higher, an objective substance can be obtained in a shorter time in a higher yield; therefore, it is preferable to use DMPU or 1,3,5-trimethylbenzene each having a high boiling point. In addition, since the reaction temperature is further preferably 150° C. or higher, DMPU is more preferably used.

In the above manner, the organic compound represented by the general formula (G1) can be synthesized.

Note that the organic compound described in this embodiment can be used in combination with any of the structures described in the other embodiments as appropriate.

Embodiment 2

In this embodiment, a light-emitting element of one embodiment of the present invention is described with reference to FIGS. 1A and 1B.

Figure 1B:
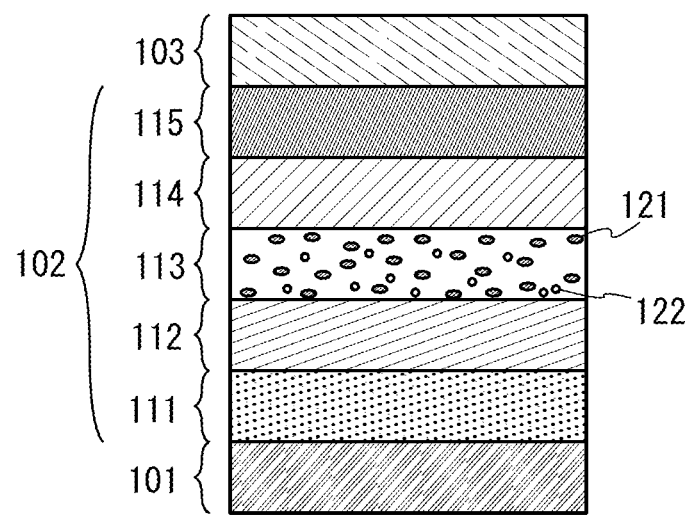

As shown in FIG. 1A, a light-emitting element in this embodiment has a structure in which an EL layer 102 including a light-emitting layer 113 is provided between a pair of electrodes (a first electrode (anode) 101 and a second electrode (cathode) 103). The light-emitting layer 113 includes a host material 121 and a guest material 122. As shown in FIG. 1B, the EL layer 102 includes, in addition to the light-emitting layer 113, a hole-transport layer 112, a hole-injection layer 111, an electron-transport layer 114, an electron-injection layer 115, and the like.

By application of a voltage to such a light-emitting element, holes injected from the first electrode 101 side and electrons injected from the second electrode 103 side are recombined in the light-emitting layer 113 to form an exciton. Through conversion from the triplet exciton to the singlet exciton due to TTA and transfer of energy from the exciton, the guest material 122 contained in the light-emitting layer 113 emits light.

The hole-injection layer 111 included in the EL layer 102 contains a substance having a high hole-transport property and an acceptor substance. When electrons are extracted from the substance having a high hole-transport property with the acceptor substance, holes are generated. Thus, holes are injected from the hole-injection layer 111 into the light-emitting layer 113 through the hole-transport layer 112.

In the layer containing a substance having a high hole-transport property and an acceptor substance, electrons are extracted from the substance having a high hole-transport property with the acceptor substance. Therefore, the layer can be regarded as a layer where electrons are generated through the extraction. That is, by providing the layer on the cathode side, electrons can be injected to the light-emitting layer 113 through the electron-transport layer 114. The layer having a function of generating electric charge such as holes and electrons in this manner is what is called a charge generation layer and can be provided in the light-emitting element of one embodiment of the present invention as appropriate, as a functional layer of the light-emitting element.

A specific example in which the light-emitting element described in this embodiment is fabricated is described below.

For the first electrode (anode) 101 and the second electrode (cathode) 103, a metal, an alloy, an electrically conductive compound, a mixture thereof, and the like can be used. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

Examples of the substance having a high hole-transport property and used for the hole-injection layer 111 and the hole-transport layer 112 (including the above-described charge generation layer) include 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 4-phenyl-4'-(9-phenyl-9H-carbazol-3-yl)triphenylamine (abbreviation: PCBA1BP), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), 3,3'-bis(9-phenyl-9H-carbazole) (abbreviation: PCCP), N-[4-(9H-carbazol-9-yl)phenyl]-N-(4-phenyl)phenylaniline (abbreviation: YGA1BP), 1,3,5-tri(dibenzothiophen-4-yl)-benzene (abbreviation: DBT3P-II), 4,4',4"-(benzene-1,3,5-triyl)tri(dibenzofuran) (abbreviation: DBF3P-II), 4-phenyl-4'-(9-phenylfluoren-9-yl)triphenylamine (abbreviation: BPAFLP), 4-[3-(triphenylen-2-yl)phenyl]dibenzothiophene (abbreviation: mDBTPTp-II), 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). Other examples include carbazole compounds such as 4,4'-di(N- carbazolyl)biphenyl (abbreviation: CBP) and 1,3,5-tris[4-(N-carbazolyl)phenyl]benzene (abbreviation: TCPB); amine compounds; dibenzothiophene compounds; dibenzofuran compounds; fluorene compounds; triphenylene compounds; and phenanthrene compounds. The substances listed here are mainly ones that have a hole mobility of $1 \times 10^{-6}$ cm$^2$/Vs or higher. Note that any substance other than the substances listed here may be used as long as the hole-transport property is higher than the electron-transport property. Note that a material of the hole-transport layer in the light-emitting element which is one embodiment of the present invention is preferably selected from these materials so that the above-described relation of the T1 levels regarding energy is satisfied between the hole-transport layer 112, the host material of the light-emitting layer 113, and the guest material of the light-emitting layer 113.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 (including the above-described charge generation layer), a transition metal oxide and an oxide of a metal belonging to any of Groups 4 to 8 of the periodic table can be given. Specifically, molybdenum oxide is particularly preferable.

The light-emitting layer 113 includes the host material 121 and the guest material 122. The T1 level of the host material 121 is preferably lower than the T1 level of the guest material 122.

It is particularly preferable to use, as the host material 121, any of the organic compounds described in Embodiment 1, which are embodiments of the present invention. In addition, preferable examples of the host material 121 include 3-[4-(1-naphthyl)-phenyl]-9-phenyl-9H-carbazole (abbreviation: PCPN), and anthracene compounds such as 9-phenyl-3-[4-(10-phenyl-9-anthryl)phenyl]-9H-carbazole (abbreviation: PCzPA), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). The anthracene compound is preferable because of its high S1 level and low T1 level.

Preferable examples of the guest material include pyrene compounds such as N,N'-bis(3-methylphenyl)-N,N-bis[3-(9-phenyl-9H-fluoren-9-yl)phenyl]-pyrene-1,6-diamine (abbreviation: 1,6mMemFLPAPrn), N,N-diphenyl-N,N-bis[4-(9-phenyl-9H-fluoren-9-yl)phenyl]pyrene-1,6-diamine (abbreviation: 1,6FLPAPrn), N,N-bis(dibenzofuran-2-yl)-N,N-diphenylpyrene-1,6-diamine (abbreviation: 1,6FrAPrn), and N,N-bis(dibenzothiophen-2-yl)-N,N'-diphenylpyrene-1,6-diamine (abbreviation: 1,6ThAPrn); anthracene compounds; triphenylene compounds; fluorene compounds; carbazole compounds; dibenzothiophene compounds; dibenzofuran compounds; dibenzoquinoxaline compounds; quinoxaline compounds; pyridine compounds; pyrimidine compounds; phenanthrene compounds; and naphthalene compounds. In particular, the pyrene compound is preferable because of its high luminescence quantum yield.

The electron-transport layer 114 contains a substance having a high electron-transport property. For the electron-transport layer 114, a metal complex such as tris(8-quinolinolato)aluminum(III) (abbreviation: Alq$_3$), tris(4-methyl-8-quinolinolato)aluminum(III) (abbreviation: Almq$_3$), bis(10-hydroxybenzo[h]quinolinato)beryllium(II) (abbreviation: BeBq$_2$), BAlq, Zn(BOX)$_2$, or bis[2-(2-hydroxyphenyenzothiazolato]zinc(II) (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances listed here are mainly ones that have an electron mobility of $1 \times 10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, and a stacked layer in which two or more layers containing any of the above-described substances are stacked may be used.

The electron-injection layer 115 contains a substance having a high electron-injection property. For the electron-injection layer 115, an alkali metal, an alkaline earth metal, magnesium (Mg), or a compound of any of the above metals such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. Further alternatively, the above-described substances for forming the electron-transport layer 114 can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the above-described substances for forming the electron-transport layer 114 (e.g., a metal complex and a heteroaromatic compound) or the like can be used. As the electron donor, a substance showing an electron-donating property with respect to the organic compound may be used. Preferable examples are an alkali metal, an alkaline earth metal, and a rare earth metal. Specifically, magnesium and the like can be used as well as lithium, cesium, calcium, erbium, and ytterbium. Furthermore, an alkali metal oxide and an alkaline earth metal oxide are preferable, and a lithium oxide, a calcium oxide, a barium oxide, and the like can be given. Alternatively, Lewis base such as magnesium oxide can be used. Further alternatively, an organic compound such as tetrathiafulvalene (abbreviation: TTF) can be used.

Note that each of the hole-injection layer 111, the hole-transport layer 112, the light-emitting layer 113, the electron-transport layer 114, and the electron-injection layer 115 (including the above-described charge generation layer)

described above can be formed by, for example, an evaporation method (e.g., a vacuum evaporation method), an ink-jet method, or a coating method.

Light emission obtained in the light-emitting layer 113 of the above-described light-emitting element is extracted to the outside through either the first electrode 101 or the second electrode 103 or both. Thus, one or both of the first electrode 101 and the second electrode 103 are electrodes having light-transmitting properties.

The above-described light-emitting element is a fluorescent light-emitting element utilizing fluorescence from the light-emitting layer 113. In the case where such a fluorescent light-emitting element emits light using a singlet exciton generated by triplet-triplet annihilation (TTA) from a triplet exciton which generally makes no contribution to light emission, the fluorescent light-emitting element can have higher efficiency than a conventional fluorescent light-emitting element.

Furthermore, as a light-emitting device including the above light-emitting element, a passive matrix type light-emitting device and an active matrix type light-emitting device can be manufactured. It is also possible to manufacture a light-emitting device with a microcavity structure including a light-emitting element which is a different light-emitting element from the above light-emitting element. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Furthermore, a driver circuit formed over a TFT substrate may be formed of both an n-type TFT and a p-type TFT or only either an n-type TFT or a p-type TFT. In addition, the crystallinity of a semiconductor film used for the TFT is not particularly limited. For example, an amorphous semiconductor film or a crystalline semiconductor film may be used. Examples of a semiconductor material include Group 14 semiconductors (e.g., silicon and germanium), compound semiconductors (including oxide semiconductors), and organic semiconductors.

The structure described in this embodiment can be used in appropriate combination with the structure described in any of the other embodiments.

Embodiment 3

In this embodiment, a light-emitting element (hereinafter referred to as a tandem light-emitting element) which is one embodiment of the present invention and includes a plurality of EL layers will be described.

Figure 2A:
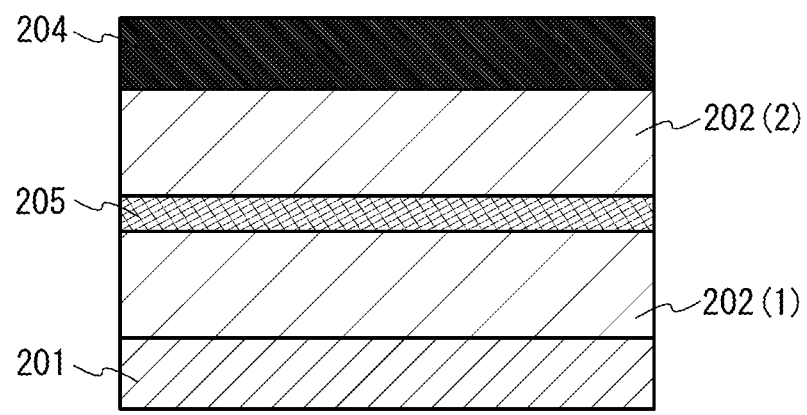
FIGS. 2A and 2B illustrate structures of light-emitting elements.

A light-emitting element described in this embodiment is a tandem light-emitting element including, between a pair of electrodes (a first electrode 201 and a second electrode 204), a plurality of EL layers (a first EL layer 202(1) and a second EL layer 202(2)) and a charge-generation layer 205 provided therebetween, as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to that described in Embodiment 2. In other words, the structures of the first EL layer 202(1) and the second EL layer 202(2) may be the same or different from each other. When the structures are the same, Embodiment 2 can be referred to.

The charge-generation layer 205 provided between the plurality of EL layers (the first EL layer 202(1) and the second EL layer 202(2)) has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, the substances having a high hole-transport property which are given in Embodiment 2 as the substances used for the hole-injection layer 111 and the hole-transport layer 112 can be used. For example, an aromatic amine compound such as NPB, TPD, TDATA, MTDATA, or BSPB, or the like can be used. The substances listed here are mainly ones that have a hole mobility of $1\times10^{-6}$ cm$^2$/Vs or higher. However, substances other than the above substances may be used as long as they are organic compounds in which a hole-transport property is higher than an electron-transport property.

Furthermore, as the electron acceptor, 7,7,8,8-tetracyano-2,3,5,6-tetrafluoroquinodimethane (abbreviation: F4-TCNQ), chloranil, and the like can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air, has a low hygroscopic property, and is easy to handle.

In the case of the structure in which an electron donor is added to an organic compound having a high electron-transport property, as the organic compound having a high electron-transport property, the substances having a high electron-transport property which are given in Embodiment 2 as the substances used for the electron-transport layer 114 can be used. For example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Further alternatively, other than such metal complexes, PBD, OXD-7, TAZ, BPhen, BCP, or the like can be used. The substances listed here are mainly ones that have an electron mobility of $1\times10^{-6}$ cm$^2$/Vs or higher.

Note that any substance other than the above substances may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers. The charge-generation layer 205 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like.

Figure 2B:
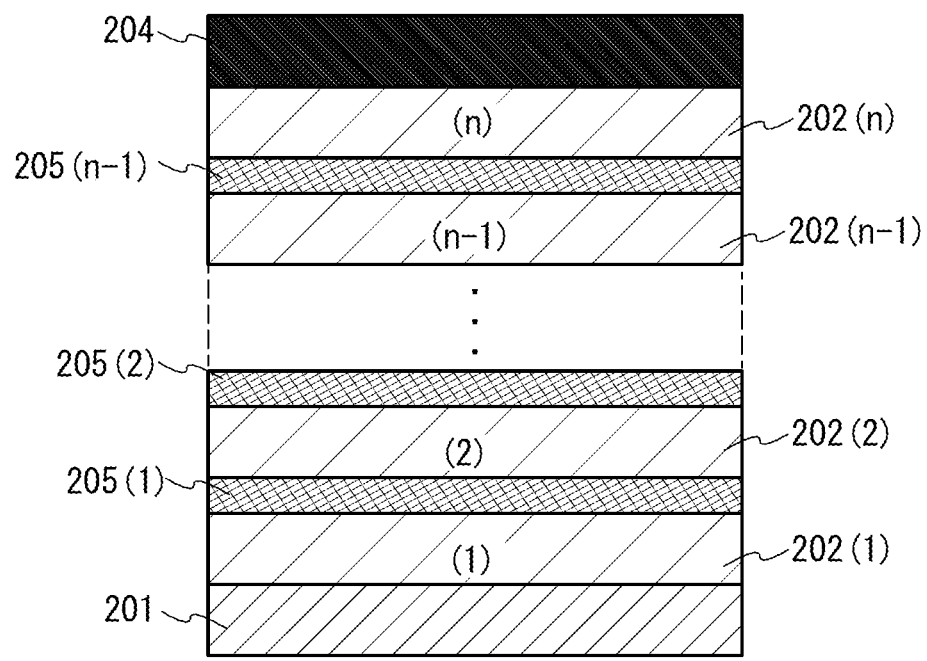

Although the light-emitting element including two EL layers is described in this embodiment, the present invention can be similarly applied to a light-emitting element in which n EL layers (202(1) to 202(*n*)) (n is three or more) are stacked as illustrated in FIG. 2B. In the case where a plurality of EL layers are included between a pair of electrodes as in the light-emitting element according to this embodiment, by providing charge-generation layers (205(1) to 205(*n*−1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, mixing light of complementary colors allows white light emission to be obtained. Specifically, a combination in which blue light emission is obtained from the first EL layer and yellow or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

In this embodiment, a light-emitting device of one embodiment of the present invention is described.

The light-emitting device may be either a passive matrix light-emitting device or an active matrix light-emitting device. Any of the light-emitting elements described in other embodiments can be used for the light-emitting device described in this embodiment.

In this embodiment, first, an active matrix light-emitting device is described with reference to FIGS. 3A to 3C.

Figure 3A:
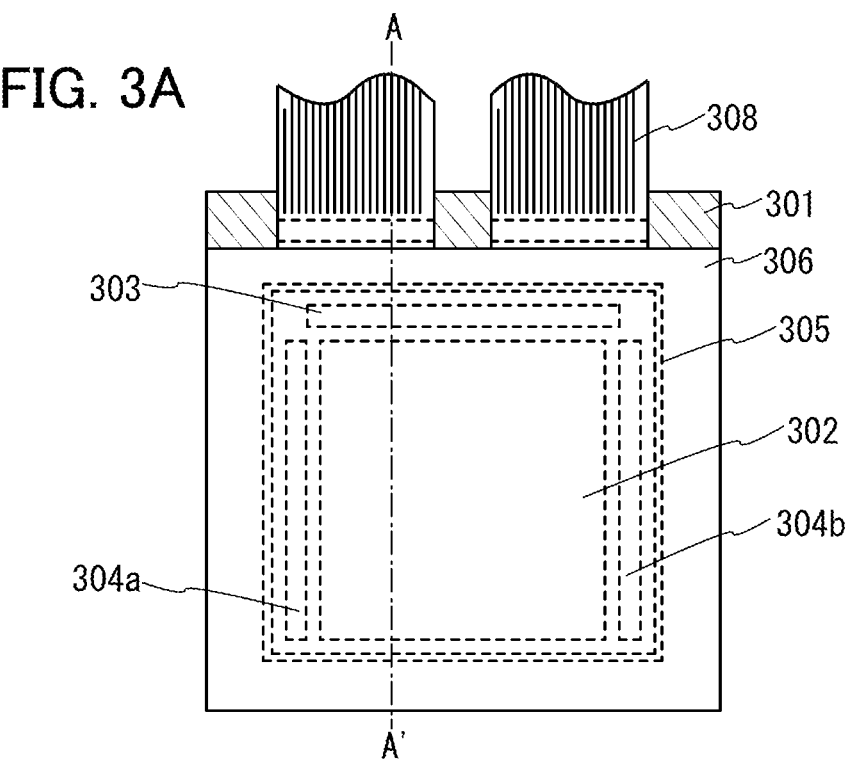
FIGS. 3A to 3C illustrate light-emitting devices.
Figure 3B:
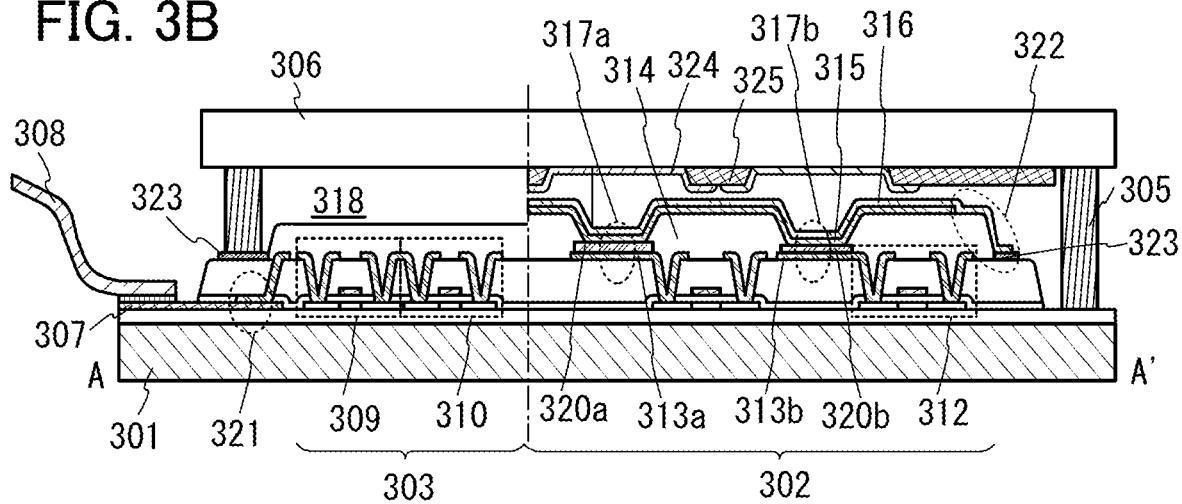

Note that FIG. 3A is a top view illustrating a light-emitting device and FIG. 3B is a cross-sectional view taken along the chain line A-A' in FIG. 3A. The light-emitting device according to this embodiment includes a pixel portion 302 provided over an element substrate 301, a driver circuit portion (a source line driver circuit) 303, and driver circuit portions (gate line driver circuits) 304*a* and 304*b*. The pixel portion 302, the driver circuit portion 303, and the driver circuit portions 304*a* and 304*b* are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, or a reset signal) or a potential from the outside is transmitted to the driver circuit portion 303 and the driver circuit portions 304*a* and 304*b*, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portions and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a switching FET (not shown) and a current control FET 312, and a wiring of the current control FET 312 (a source electrode or a drain electrode) is electrically connected to first electrodes (anodes) (313*a* and 313*b*) of light-emitting elements 317*a* and 317*b*. Although the pixel portion 302 includes two FETs (the switching FET and the current control FET 312) in this embodiment, one embodiment of the present invention is not limited thereto. The pixel portion 302 may include, for example, three or more FETs and a capacitor in combination.

As the FETs 309, 310, and 312, for example, a staggered transistor or an inverted staggered transistor can be used. Examples of a semiconductor material that can be used for the FETs 309, 310, and 312 include Group 13 semiconductors, Group 14 semiconductors (e.g., silicon), compound semiconductors, oxide semiconductors, and organic semiconductors. In addition, there is no particular limitation on the crystallinity of the semiconductor material, and an amorphous semiconductor or a crystalline semiconductor can be used. In particular, an oxide semiconductor is preferably used for the FETs 309, 310, and 312. Examples of the oxide semiconductor are In—Ga oxides, In-M-Zn oxides (M is Al, Ga, Y, Zr, La, Ce, Hf, or Nd), and the like. For example, an oxide semiconductor that has an energy gap of 2 eV or more, preferably 2.5 eV or more, further preferably 3 eV or more is used for the FETs 309, 310, and 312, so that the off-state current of the transistors can be reduced.

In addition, conductive films (320a and 320b) for optical adjustment are stacked over the first electrodes 313a and 313b. For example, as illustrated in FIG. 3B, in the case where the wavelengths of light extracted from the light-emitting elements 317a and 317b are different from each other, the thicknesses of the conductive films 320a and 320b are different from each other. In addition, an insulator 314 is formed to cover end portions of the first electrodes (313a and 313b). In this embodiment, the insulator 314 is formed using a positive photosensitive acrylic resin. The first electrodes (313a and 313b) are used as anodes in this embodiment.

The insulator 314 preferably has a surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material for the insulator 314 is not limited to an organic compound and an inorganic compound such as silicon oxide, silicon oxynitride, or silicon nitride can also be used.

An EL layer 315 and a second electrode 316 are stacked over the first electrodes (313a and 313b). In the EL layer 315, at least a light-emitting layer is provided. In the light-emitting elements (317a and 317b) including the first electrodes (313a and 313b), the EL layer 315, and the second electrode 316, an end portion of the EL layer 315 is covered with the second electrode 316. The structure of the EL layer 315 may be the same as or different from the single-layer structure and the stacked-layer structure described in Embodiments 2 and 3. Furthermore, the structure may differ between the light-emitting elements.

For the first electrodes (313a and 313b), the EL layer 315, and the second electrode 316, any of the materials given in Embodiment 2 can be used. The first electrodes (313a and 313b) of the light-emitting elements (317a and 317b) are electrically connected to the lead wiring 307 in a region 321, so that an external signal is input through the FPC 308. The second electrode 316 in the light-emitting elements (317a and 317b) is electrically connected to a lead wiring 323 in a region 322, so that an external signal is input through the FPC 308 that is not illustrated in the figure.

Although the cross-sectional view in FIG. 3B illustrates only the two light-emitting elements (317a and 317b), a plurality of light-emitting elements are arranged in a matrix in the pixel portion 302. Specifically, in the pixel portion 302, light-emitting elements that emit light of two kinds of colors (e.g., B and Y), light-emitting elements that emit light of three kinds of colors (e.g., R, G, and B), light-emitting elements that emit light of four kinds of colors (e.g., (R, G, B, and Y) or (R, G, B, and W)), or the like are formed so that a light-emitting device capable of full color display can be obtained. In such cases, full color display may be achieved as follows: materials different according to the emission colors or the like of the light-emitting elements are used to form light-emitting layers (so-called separate coloring formation); alternatively, the plurality of light-emitting elements share one light-emitting layer formed using the same material and further include color filters. Thus, the light-emitting elements that emit light of a plurality of kinds of colors are used in combination, so that effects such as an improvement in color purity and a reduction in power consumption can be achieved. Furthermore, the light-emitting device may have improved emission efficiency and reduced power consumption by combination with quantum dots.

The sealing substrate 306 is attached to the element substrate 301 with the sealant 305, whereby the light-emitting elements (317a and 317b) are provided in a space 318 surrounded by the element substrate 301, the sealing substrate 306, and the sealant 305.

The sealing substrate 306 is provided with coloring layers (color filters) 324, and a black layer (black matrix) 325 is provided between adjacent coloring layers. Note that one or both of the adjacent coloring layers (color filters) 324 may be provided so as to partly overlap with the black layer (black matrix) 325. Light emission obtained from the light-emitting elements 317a and 317b is extracted through the coloring layers (color filters) 324.

Note that the space 318 may be filled with an inert gas (such as nitrogen or argon) or the sealant 305. In the case where the sealant is applied for attachment of the substrates, one or more of UV treatment, heat treatment, and the like are preferably performed.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, an acrylic resin, or the like can be used. In the case where glass frit is used as the sealant, the element substrate 301 and the sealing substrate 306 are preferably glass substrates for high adhesion.

Figure 3C:
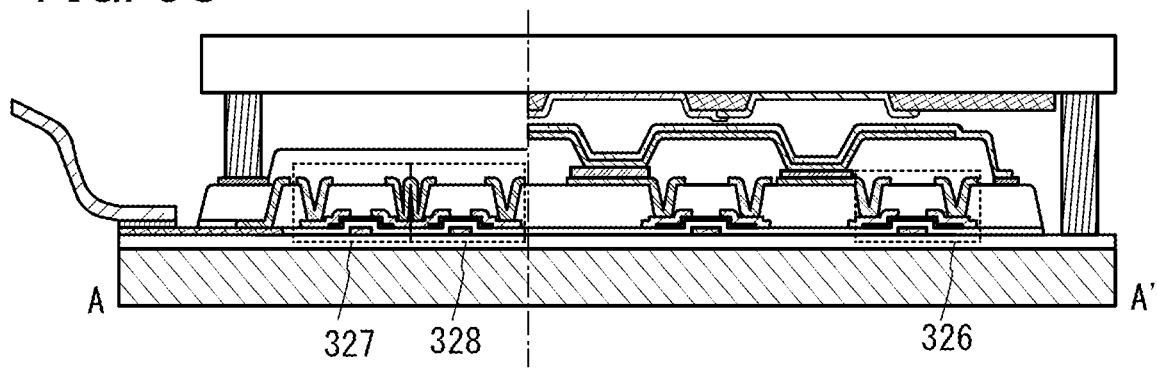

Structures of the FETs electrically connected to the light-emitting elements may be different from those in FIG. 3B in the position of a gate electrode; that is, the structures may be the same as those of an FET 326, an FET 327, and an FET 328, as illustrated in FIG. 3C. The coloring layer (color filter) 324 with which the sealing substrate 306 is provided may be provided as illustrated in FIG. 3C such that, at a position where the coloring layer (color filter) 324 overlaps with the black layer (black matrix) 325, the coloring layer (color filter) 324 further overlaps with an adjacent coloring layer (color filter) 324.

As described above, the active matrix light-emitting device can be obtained.

The light-emitting device of one embodiment of the present invention may be of the passive matrix type, instead of the active matrix type described above.

Figure 4A:
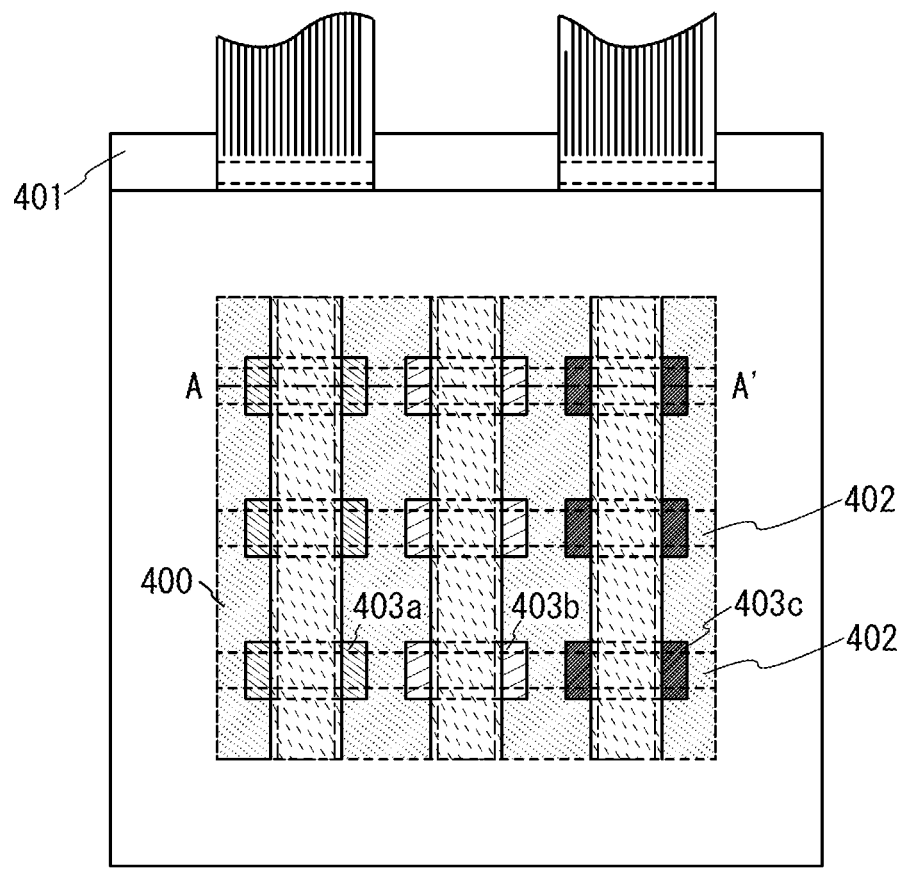
FIGS. 4A and 4B illustrate a light-emitting device.
Figure 4B:
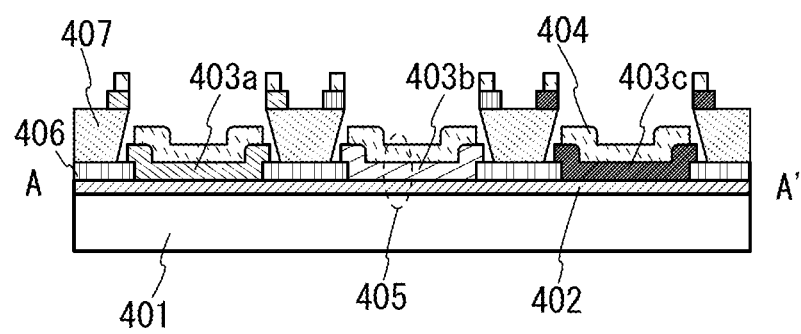

FIGS. 4A and 4B illustrate a passive matrix light-emitting device. FIG. 4A is a top view of the passive matrix light-emitting device, and FIG. 4B is a cross-sectional view of a pixel portion 400.

As illustrated in FIGS. 4A and 4B, light-emitting elements 405 including a first electrode 402, EL layers (403a, 403b, and 403c), and second electrodes 404 are formed over a substrate 401. Note that the first electrode 402 has an island-like shape, and a plurality of the first electrodes 402 are formed in one direction (the lateral direction in FIG. 4A) to form a striped pattern. An insulating film 406 is formed over part of the first electrode 402. A partition 407 formed using an insulating material is provided over the insulating film 406. The sidewalls of the partition 407 slope so that the distance between one sidewall and the other sidewall gradually decreases toward the surface of the substrate as illustrated in FIG. 4B.

Since the insulating film 406 includes openings over the part of the first electrode 402, the EL layers (403a, 403b, and 403c) and second electrodes 404 which are divided as desired can be formed over the first electrode 402. In the example in FIGS. 4A and 4B, a mask such as a metal mask and the partition 407 over the insulating film 406 are employed to form the EL layers (403a, 403b, and 403c) and the second electrodes 404. In this example, the EL layer 403a, the EL layer 403b, and the EL layer 403c emit light of different colors (e.g., red, green, blue, yellow, orange, and white).

After the formation of the EL layers (403a, 403b, and 403c), the second electrodes 404 are formed. Thus, the second electrodes 404 are formed over the EL layers (403a, 403b, and 403c) without contact with the first electrode 402.

Note that sealing can be performed by a method similar to that used for the active matrix light-emitting device, and description thereof is not made.

As described above, the passive matrix light-emitting device can be obtained.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As examples of a glass substrate, a barium borosilicate glass substrate, an aluminoborosilicate glass substrate, a soda lime glass substrate, and the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current supply capability. A circuit using such transistors achieves lower power consumption of the circuit or higher integration of the circuit.

Alternatively, a flexible substrate may be used as the substrate, and a transistor or a light-emitting element may be provided directly on the flexible substrate. Still alternatively, a separation layer may be provided between the substrate and the transistor or the light-emitting element. The separation layer can be used when part or the whole of a semiconductor device formed over the separation layer is separated from the substrate and transferred onto another substrate. In such a case, the transistor or the light-emitting element can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred are, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, a rubber substrate, and the like. When such a substrate is used, a transistor with excellent characteristics or a transistor with low power consumption can be formed, a device with high durability or high heat resistance can be provided, or a reduction in weight or thickness can be achieved.

Note that the structure described in this embodiment can be combined as appropriate with any of the structures described in other embodiments.

Embodiment 5

In this embodiment, examples of a variety of electronic devices and an automobile manufactured using a light-emitting device of one embodiment of the present invention are described.

Examples of the electronic device including the light-emitting device are television devices (also referred to as TV or television receivers), monitors for computers and the like, cameras such as digital cameras and digital video cameras, digital photo frames, cellular phones (also referred to as mobile phones or portable telephone devices), portable game consoles, portable information terminals, audio playback devices, large game machines such as pachinko machines, and the like. Specific examples of the electronic devices are illustrated in FIGS. 5A, 5B, 5C, 5D, 5D'-1, and 5D'-2 and FIGS. 6A to 6C.

Figure 5A:
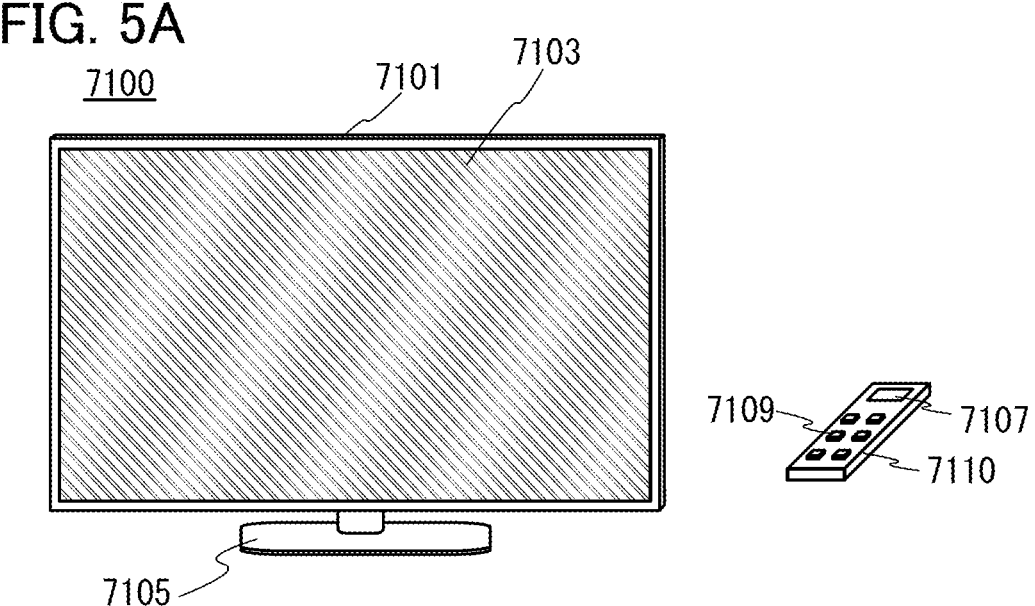
FIGS. 5A, 5B, 5C, 5D, 5D'-1, and 5D'-2 illustrate electronic devices.

FIG. 5A illustrates an example of a television device. In the television device 7100, a display portion 7103 is incorporated in a housing 7101. The display portion 7103 can display images and may be a touch panel (an input/output device) including a touch sensor (an input device). Note that the light-emitting device of one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 5B:
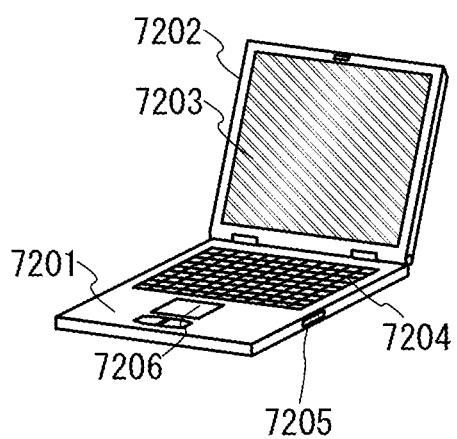

FIG. 5B illustrates a computer, which includes a main body 7201, a housing 7202, a display portion 7203, a keyboard 7204, an external connection port 7205, a pointing device 7206, and the like. Note that this computer can be manufactured using the light-emitting device of one embodiment of the present invention for the display portion 7203. The display portion 7203 may be a touch panel (an input/output device) including a touch sensor (an input device).

Figure 5C:
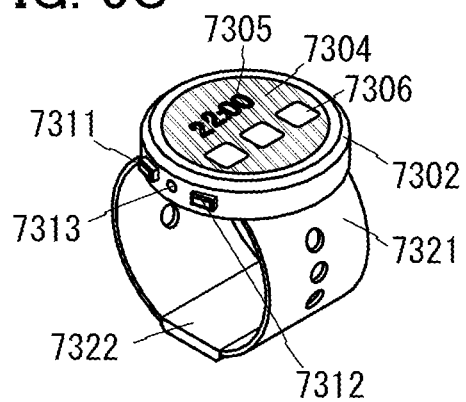

FIG. 5C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (an input/output device) including a touch sensor (an input device).

The smart watch illustrated in FIG. 5C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

Figure 5D:
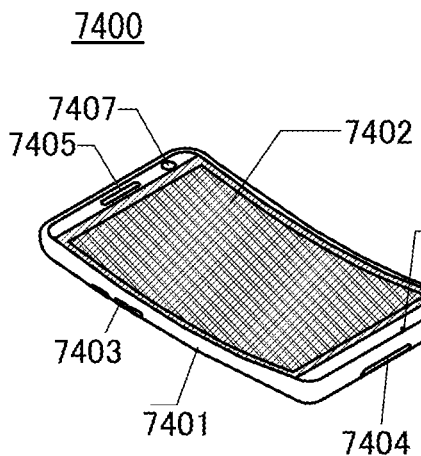
Figure 5D:
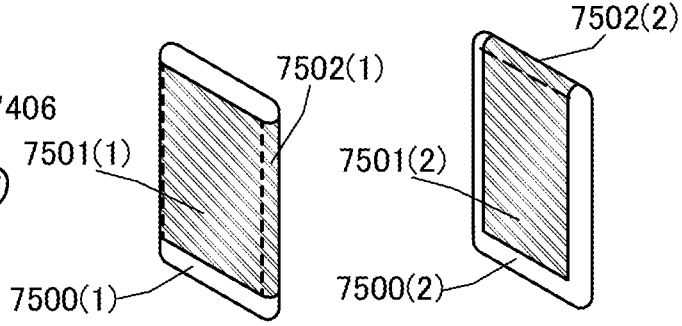

FIGS. 5D, 5D'-1, and 5D'-2 illustrate an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming the light-emitting element of one embodiment of the present invention over a flexible substrate, the light-emitting device can be used for the display portion 7402 having a curved surface as illustrated in FIG. 5D.

When the display portion 7402 of the cellular phone 7400 illustrated in FIG. 5D is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or composing e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope sensor or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 5D'-1 or FIG. 5D'-2, which is another structure of the cellular phone (e.g., a smartphone).

Note that in the case of the structure illustrated in FIG. 5D'-1 or FIG. 5D'-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in the user's breast pocket.

Figure 6A:
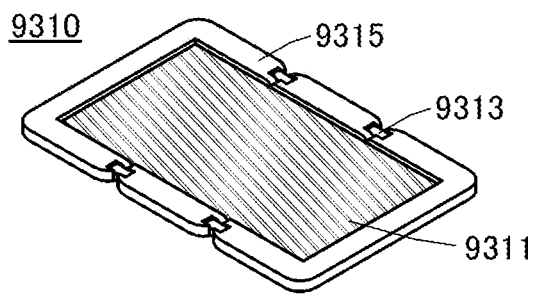
FIGS. 6A to 6C illustrate an electronic device.
Figure 6B:
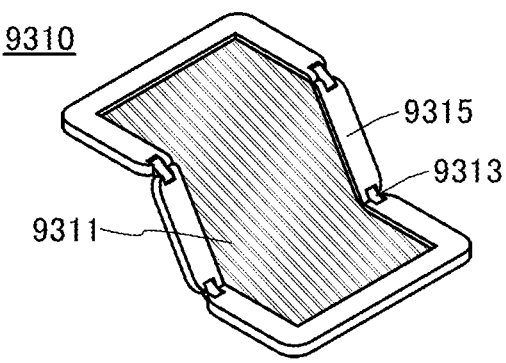
Figure 6C:
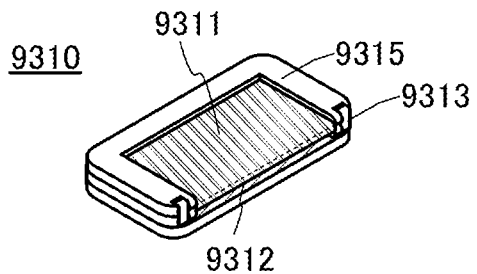

Another electronic device including a light-emitting device is a foldable portable information terminal illustrated in FIGS. 6A to 6C. FIG. 6A illustrates a portable information terminal 9310 which is opened. FIG. 6B illustrates the portable information terminal 9310 which is being opened or being folded. FIG. 6C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application can be smoothly performed.

Figure 7A:
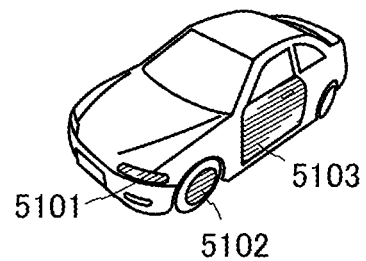
FIGS. 7A and 7B illustrate an automobile.
Figure 7B:
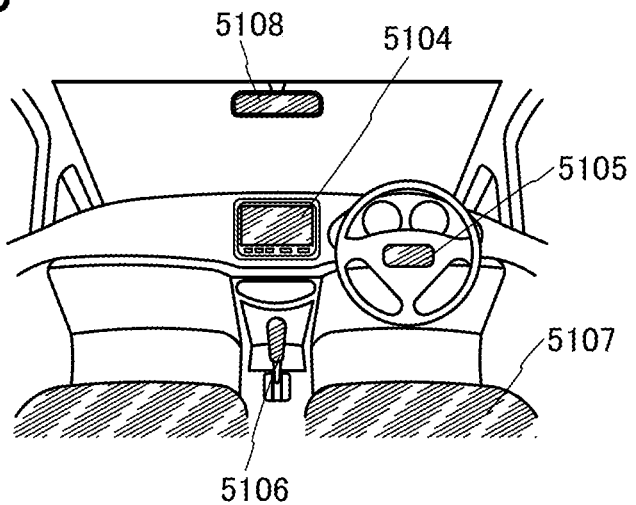

FIGS. 7A and 7B illustrate an automobile including a light-emitting device. The light-emitting device can be incorporated in the automobile, and specifically, can be included in lights 5101 (including lights of the rear part of the car), a wheel 5102 of a tire, a part or whole of a door 5103, or the like on the outer side of the automobile which is illustrated in FIG. 7A. The light-emitting device can also be included in a display portion 5104, a steering wheel 5105, a gear lever 5106, a seat 5107, an inner rearview mirror 5108, or the like on the inner side of the automobile which is illustrated in FIG. 7B, or in a part of a glass window.

As described above, the electronic devices and automobiles can be obtained using the light-emitting device of one embodiment of the present invention. Note that the light-emitting device can be used for electronic devices and automobiles in a variety of fields without being limited to the electronic devices described in this embodiment.

Note that the structure described in this embodiment can be combined as appropriate with any of the structures described in other embodiments.

Embodiment 6

In this embodiment, a structure of a lighting device fabricated using the light-emitting element of one embodiment of the present invention is described with reference to FIGS. 8A to 8D.

Figure 8A:
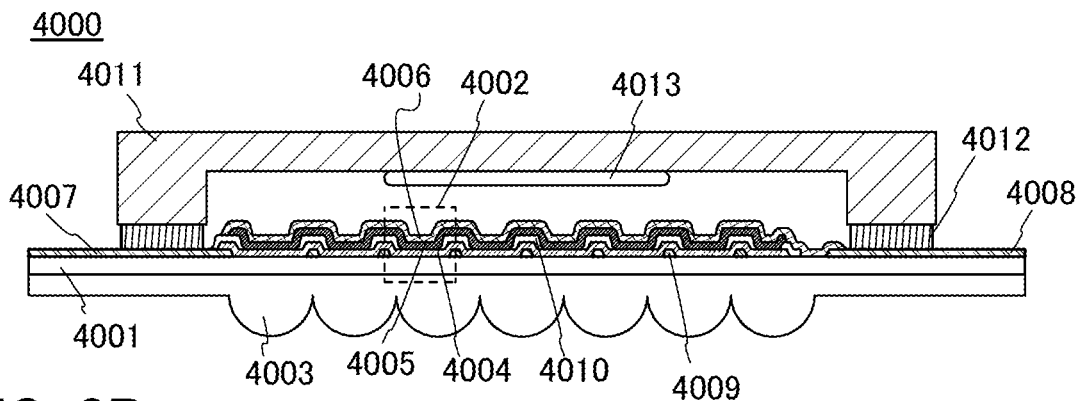
FIGS. 8A to 8D illustrate lighting devices.
Figure 8B:
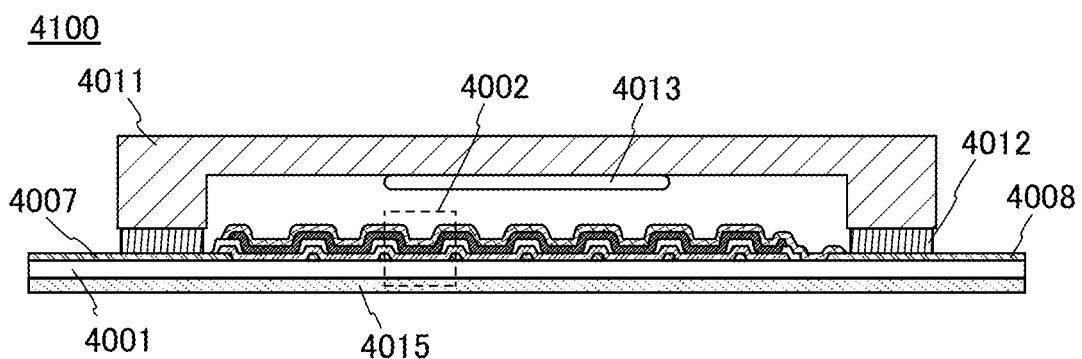
Figure 8C:
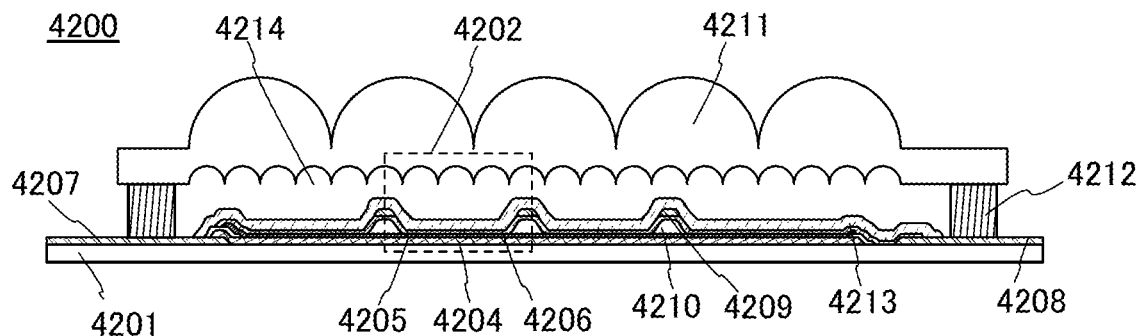
Figure 8D:
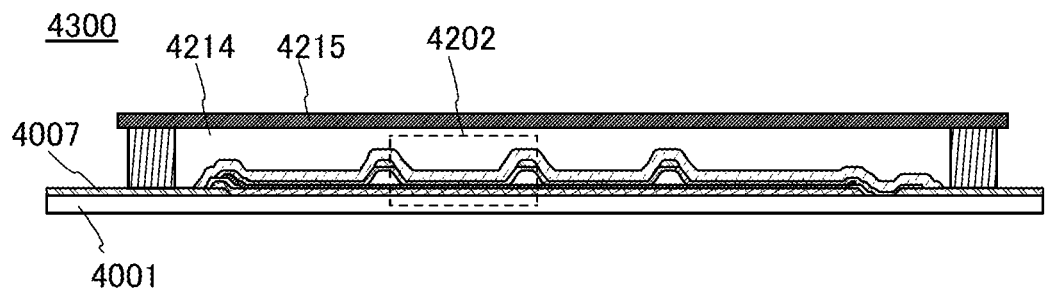

FIGS. 8A to 8D are examples of cross-sectional views of lighting devices. FIGS. 8A and 8B illustrate bottom-emission lighting devices in which light is extracted from the substrate side, and FIGS. 8C and 8D illustrate top-emission lighting devices in which light is extracted from the sealing substrate side.

A lighting device 4000 illustrated in FIG. 8A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 8A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 8B.

A lighting device 4200 illustrated in FIG. 8C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other by a sealant 4212. A barrier film 4213 and a planarization film 4214 may be provided between the sealing substrate 4211 and the light-emitting element 4202. The sealing substrate 4211 has the unevenness illustrated in FIG. 8C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 8D.

Note that the EL layers 4005 and 4205 in this embodiment can include the organometallic complex of one embodiment of the present invention. In that case, a lighting device with low power consumption can be provided.

Note that the structure described in this embodiment can be combined as appropriate with any of the structures described in the other embodiments.

Embodiment 7

In this embodiment, examples of a lighting device to which the light-emitting device of one embodiment of the present invention is applied are described with reference to FIG. 9.

Figure 9:
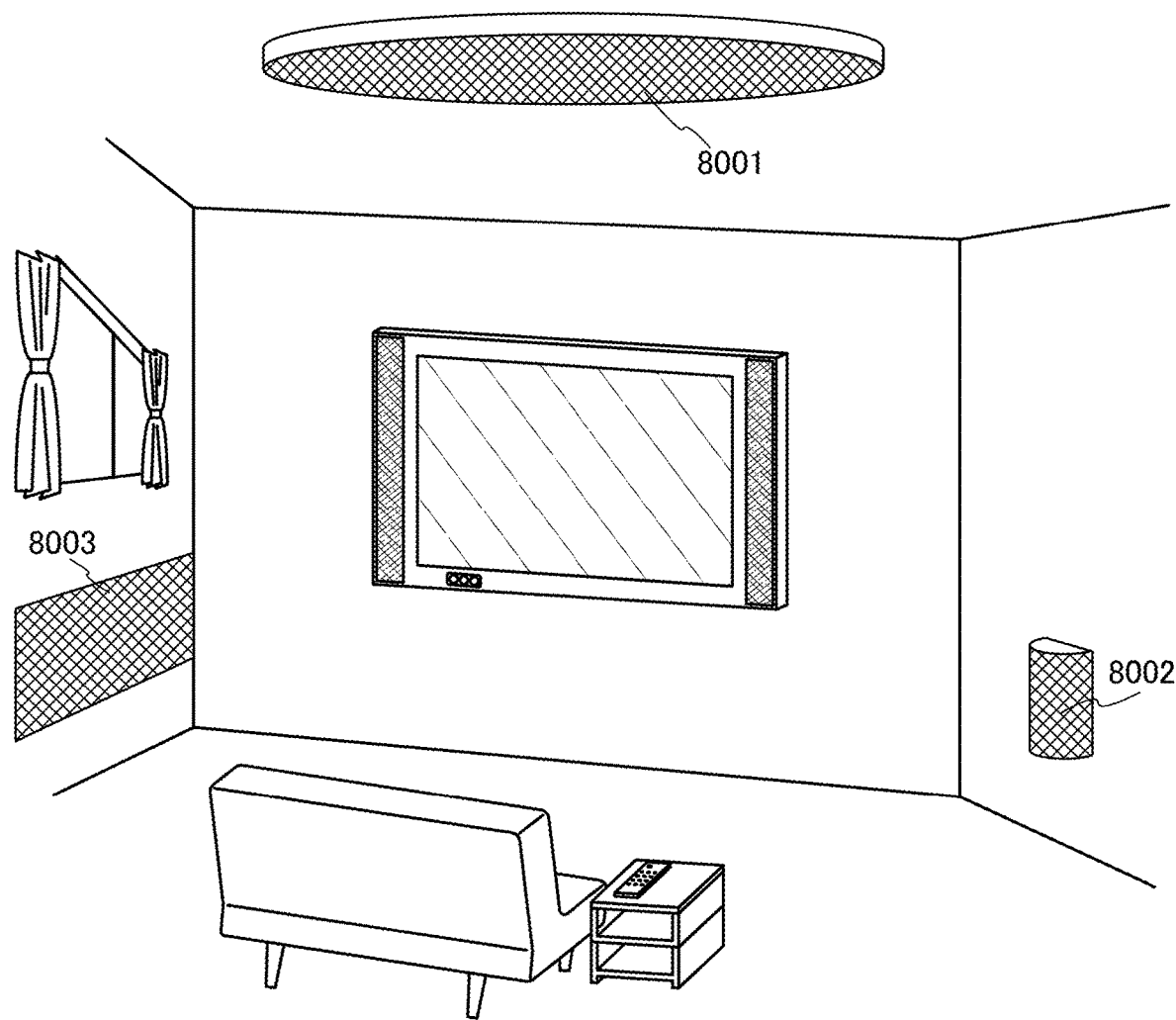
FIG. 9 illustrates lighting devices.

FIG. 9 illustrates an example in which the light-emitting device is used as an indoor lighting device 8001. Since the light-emitting device can have a large area, it can be used for a lighting device having a large area. In addition, with the use of a housing with a curved surface, a lighting device 8002 in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a lighting device 8003.

Besides the above examples, when the light-emitting device is used as part of furniture in a room, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in the other embodiments.

Embodiment 8

In this embodiment, touch panels including the light-emitting element of one embodiment of the present invention or the light-emitting device of one embodiment of the present invention are described with reference to FIGS. 10A and 10B, FIGS. 11A and 11B, FIGS. 12A and 12B, FIGS. 13A and 13B, and FIG. 14.

Figure 10A:
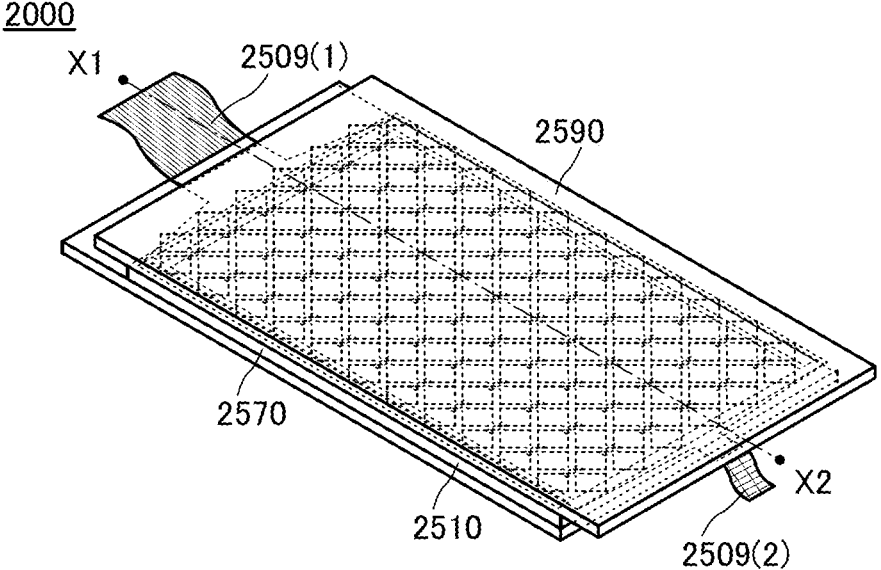
FIGS. 10A and 10B illustrate an example of a touch panel.
Figure 10B:
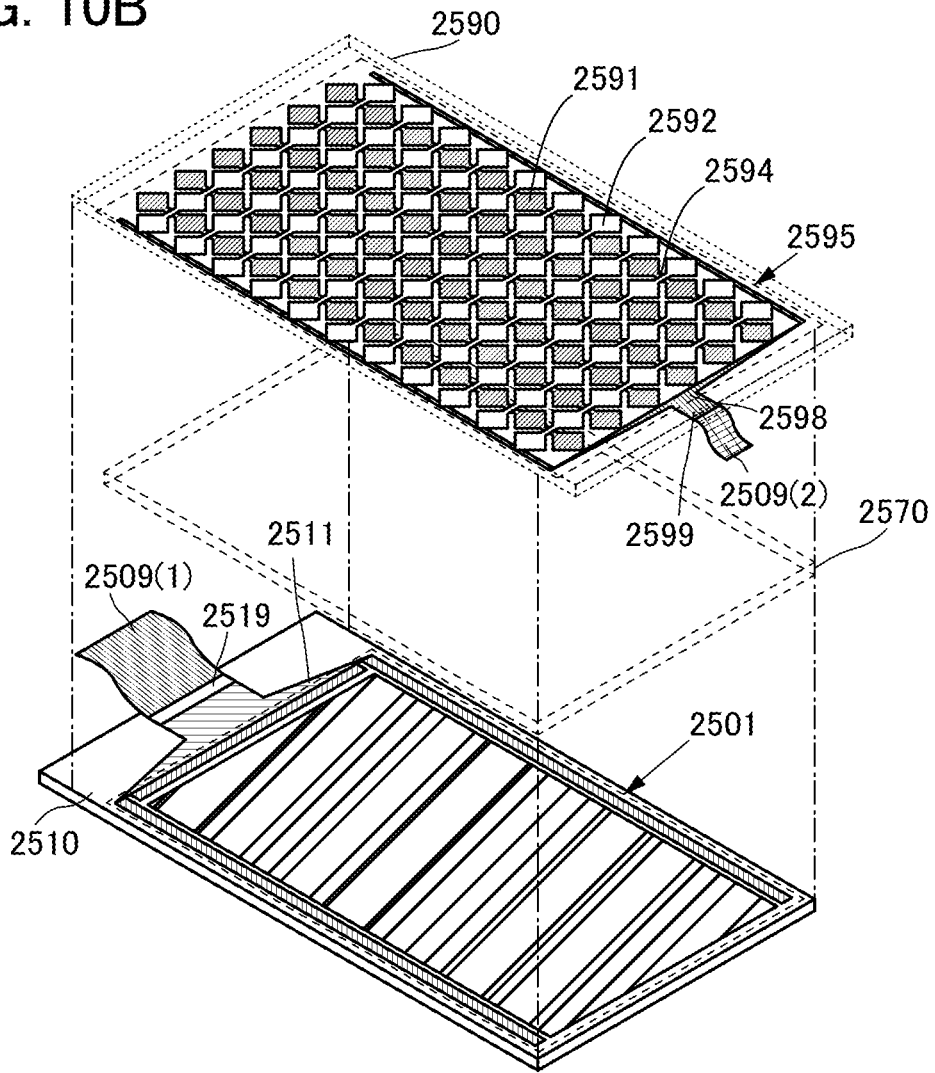

FIGS. 10A and 10B are perspective views of a touch panel 2000. Note that FIGS. 10A and 10B illustrate typical components of the touch panel 2000 for simplicity.

The touch panel 2000 includes a display panel 2501 and a touch sensor 2595 (see FIG. 10B). Furthermore, the touch panel 2000 includes substrates 2510, 2570, and 2590.

The display panel 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 10B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive touch sensor is preferable because multiple points can be sensed simultaneously.

First, an example of using a projected capacitive touch sensor is described with reference to FIG. 10B. Note that in the case of a projected capacitive touch sensor, a variety of sensors that can sense the approach or contact of an object such as a finger can be used.

The projected capacitive touch sensor 2595 includes electrodes 2591 and 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction, as illustrated in FIGS. 10A and 10B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, unevenness in the luminance of light passing through the touch sensor 2595 can be reduced.

Note that the shapes of the electrodes 2591 and 2592 are not limited to the above-described shapes and can be any of a variety of shapes. For example, the plurality of electrodes 2591 may be provided so that a space between the electrodes 2591 are reduced as much as possible, and the plurality of electrodes 2592 may be provided with an insulating layer sandwiched between the electrodes 2591 and 2592. In that case, it is preferable to provide, between two adjacent electrodes 2592, a dummy electrode which is electrically insulated from these electrodes because the area of a region having a different transmittance can be reduced.

Figure 11A:
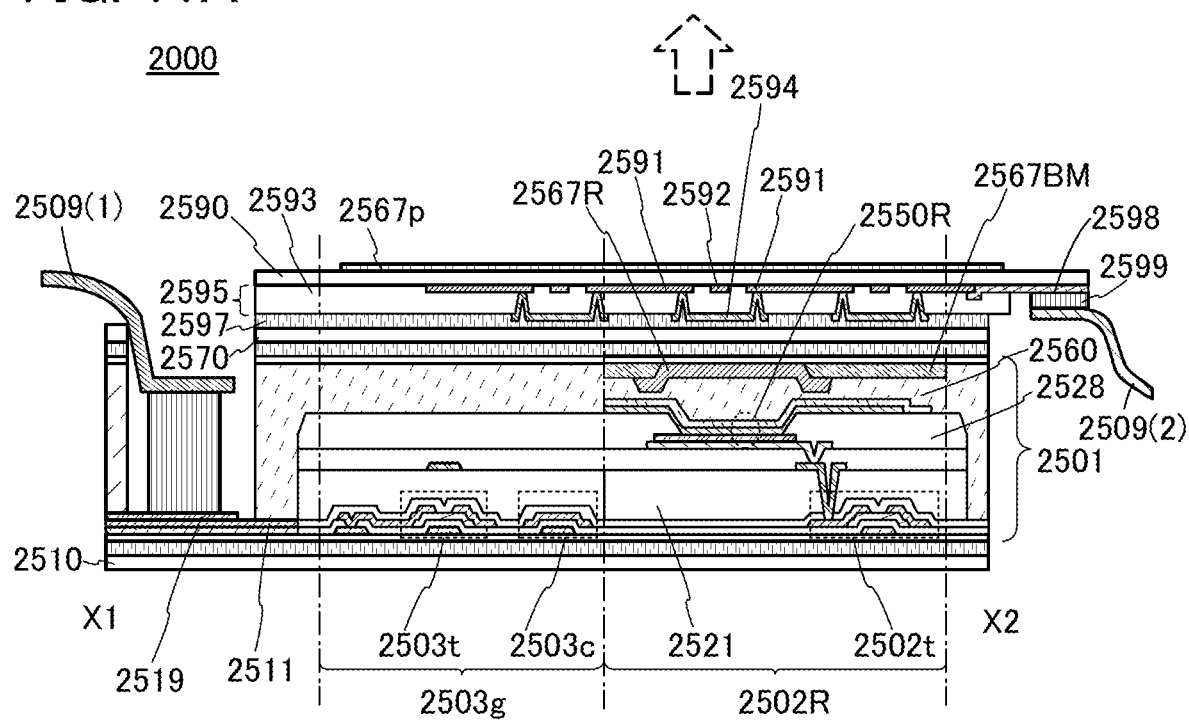
FIGS. 11A and 11B illustrate an example of a touch panel.
Figure 11B:
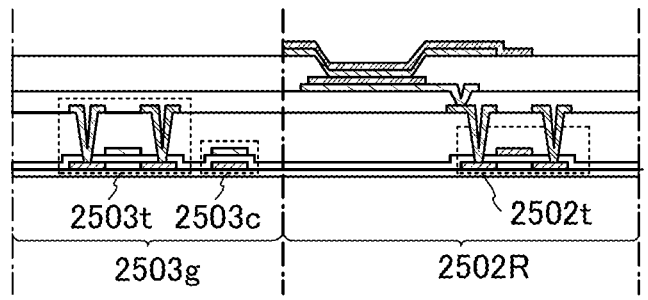

Next, the touch panel 2000 is described in detail with reference to FIGS. 11A and 11B. FIGS. 11A and 11B are cross-sectional views taken along the dashed-dotted line X1-X2 in FIG. 10A.

The touch panel 2000 includes the touch sensor 2595 and the display panel 2501.

The touch sensor 2595 includes the electrodes 2591 and 2592 that are provided in a staggered arrangement and in contact with the substrate 2590, an insulating layer 2593 covering the electrodes 2591 and 2592, and the wiring 2594 that electrically connects the adjacent electrodes 2591 to each other. Between the adjacent electrodes 2591, the electrode 2592 is provided.

The electrodes 2591 and 2592 can be formed using a light-transmitting conductive material. As a light-transmitting conductive material, a conductive oxide such as indium oxide, indium tin oxide, indium zinc oxide, zinc oxide, or zinc oxide to which gallium is added can be used. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and 2592 can be formed by depositing a light-transmitting conductive material on the substrate 2590 by a sputtering method and then removing an unneeded portion by any of various patterning techniques such as photolithography.

Examples of a material for the insulating layer 2593 are a resin such as an acrylic resin or an epoxy resin, a resin having a siloxane bond, and an inorganic insulating material such as silicon oxide, silicon oxynitride, or aluminum oxide.

The adjacent electrodes 2591 are electrically connected to each other with the wiring 2594 formed in part of the insulating layer 2593. Note that a material for the wiring 2594 preferably has higher conductivity than materials for the electrodes 2591 and 2592 to reduce electrical resistance.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as illustrated in FIG. 11A may be provided over the surface of the display panel 2501 that is in contact with the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display panel 2501 in FIG. 11A includes, between the substrate 2510 and the substrate 2570, a plurality of pixels arranged in a matrix and a driver circuit. Each pixel includes a light-emitting element and a pixel circuit driving the light-emitting element.

In FIG. 11A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 covers unevenness caused by the transistor and the like that have been already formed to provide a flat surface. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

The scan line driver circuit 2503g includes a transistor 2503t and a capacitor 2503c. Note that the driver circuit and the pixel circuits can be formed in the same process over the same substrate. Thus, in a manner similar to that of the transistor 2502t in the pixel circuit, the transistor 2503t in the driver circuit (scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 illustrated in FIG. 11A includes a bottom-gate transistor is described, the structure of the transistor is not limited thereto, and any of transistors with various structures can be used. In each of the transistors 2502t and 2503t illustrated in FIG. 11A, a semiconductor layer containing an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 11B illustrates the structure of the display panel 2501 that includes a top-gate transistor instead of the bottom-gate transistor illustrated in FIG. 11A. The kind of the semiconductor layer that can be used for the channel region does not depend on the structure of the transistor.

In the touch panel 2000 illustrated in FIG. 11A, an anti-reflection layer 2567p overlapping with at least the pixel is preferably provided on a surface of the touch panel on the side from which light from the pixel is extracted, as illustrated in FIG. 11A. As the anti-reflection layer 2567p, a circular polarizing plate or the like can be used.

For the substrates 2510, 2570, and 2590 in FIG. 11A, for example, a flexible material having a vapor permeability of $1\times10^{-5}$ g/(m²·day) or lower, preferably $1\times10^{-6}$ g/(m²·day) or lower, can be favorably used. Alternatively, it is preferable to use the materials that make these substrates have substantially the same coefficient of thermal expansion. For example, the coefficients of linear expansion of the materials are $1\times10^{-3}$/K or lower, preferably $5\times10^{-5}$/K or lower, and further preferably $1\times10^{-5}$/K or lower.

Next, a touch panel 2000' having a structure different from that of the touch panel 2000 illustrated in FIGS. 11A and 11B is described with reference to FIGS. 12A and 12B. It can be used as a touch panel as well as the touch panel 2000.

Figure 12A:
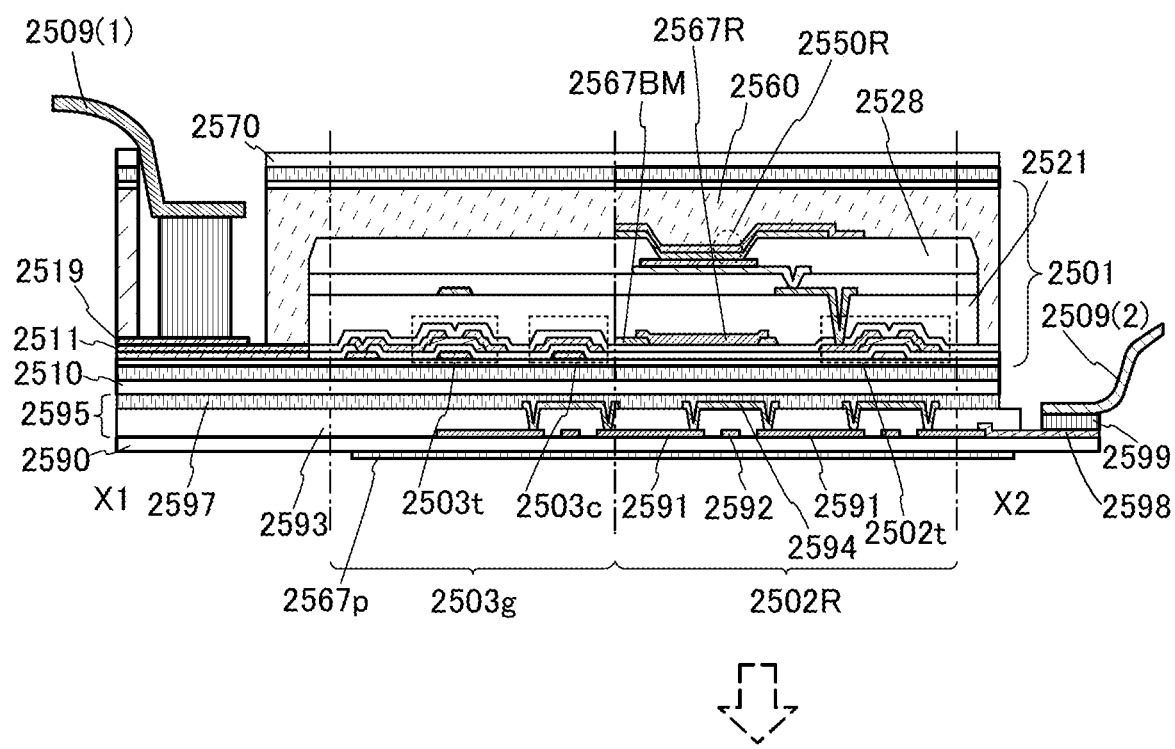
FIGS. 12A and 12B illustrate an example of a touch panel.
Figure 12B:
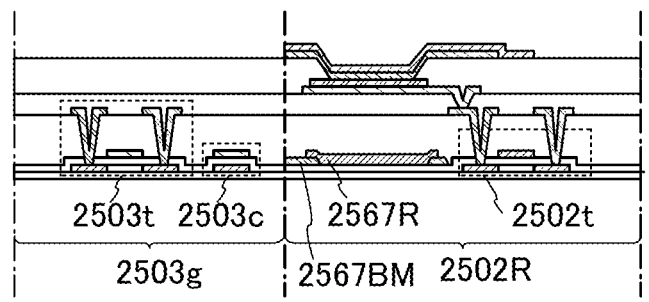

FIGS. 12A and 12B are cross-sectional views of the touch panel 2000'. In the touch panel 2000' illustrated in FIGS. 12A and 12B, the position of the touch sensor 2595 relative to the display panel 2501 is different from that in the touch panel 2000 illustrated in FIGS. 11A and 11B. Only different structures are described below, and the above description of the touch panel 2000 can be referred to for the other similar structures.

The coloring layer 2567R overlaps with the light-emitting element 2550R. Light from the light-emitting element 2550R illustrated in FIG. 12A is emitted to the side where the transistor 2502t is provided. That is, (part of) light emitted from the light-emitting element 2550R passes through the coloring layer 2567R and is extracted in the direction indicated by an arrow in FIG. 12A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 12A).

The adhesive layer 2597 is in contact with the substrate 2510 of the display panel 2501 and attaches the display panel 2501 and the touch sensor 2595 to each other in the structure illustrated in FIG. 12A. The substrate 2510 is not necessarily provided between the display panel 2501 and the touch sensor 2595 that are attached to each other by the adhesive layer 2597.

As in the touch panel 2000, transistors with a variety of structures can be used for the display panel 2501 in the touch panel 2000'. Although a bottom-gate transistor is used in FIG. 12A, a top-gate transistor may be used as illustrated in FIG. 12B.

An example of a driving method of the touch panel is described with reference to FIGS. 13A and 13B.

Figure 13A:
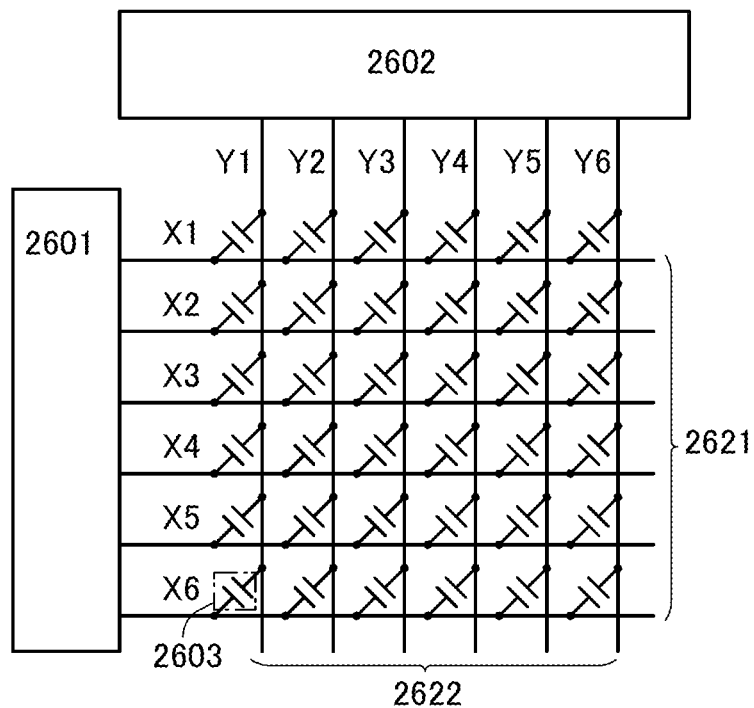
FIGS. 13A and 13B are a block diagram and a timing chart of a touch sensor.

FIG. 13A is a block diagram illustrating the structure of a mutual capacitive touch sensor. FIG. 13A illustrates a pulse voltage output circuit 2601 and a current sensing circuit 2602. Note that in the example of FIG. 13A, six wirings X1-X6 represent electrodes 2621 to which a pulse voltage is supplied, and six wirings Y1-Y6 represent electrodes 2622 that sense a change in current. FIG. 13A also illustrates a capacitor 2603 which is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 13B:
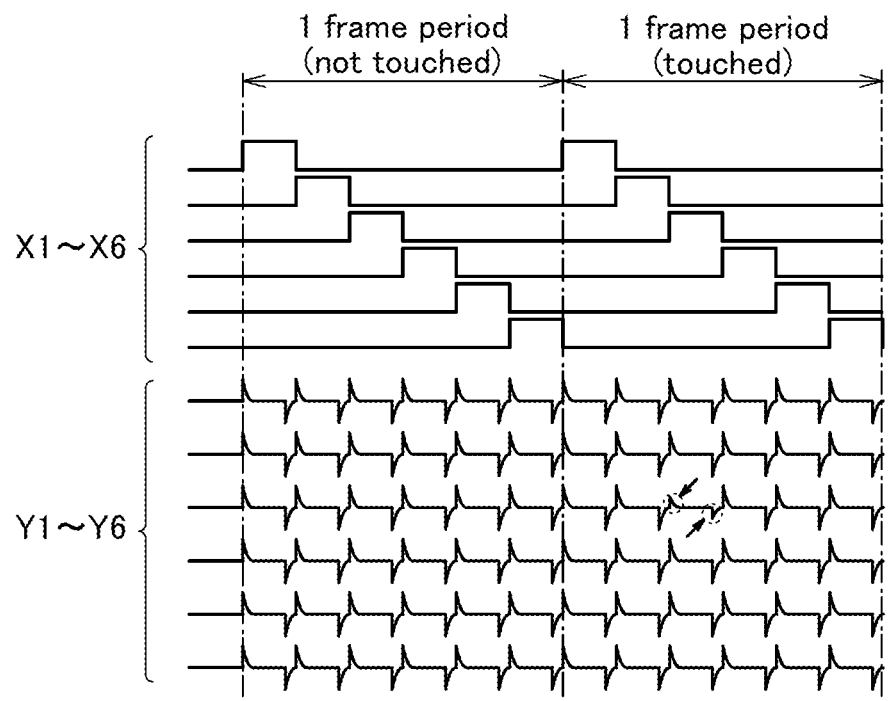

FIG. 13B is a timing chart showing input and output waveforms in the mutual capacitive touch sensor illustrated in FIG. 13A. In FIG. 13B, sensing of a sensing target is performed in all the rows and columns in one frame period. FIG. 13B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6. The current value is decreased at the point of approach or contact of a sensing target and accordingly the waveform of the voltage value changes. By sensing a change in mutual capacitance in this manner, the approach or contact of a sensing target can be sensed.

Figure 14:
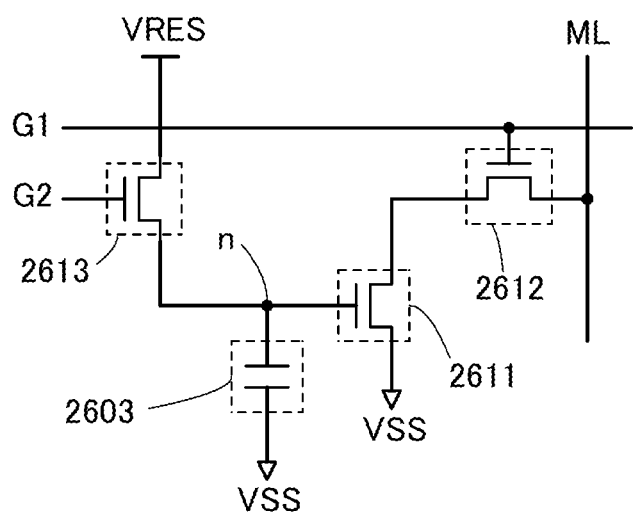
FIG. 14 is a circuit diagram of a touch sensor.

Although FIG. 13A illustrates a passive touch sensor in which only the capacitor 2603 is provided at the intersection of wirings as a touch sensor, an active touch sensor including a transistor and a capacitor may be used. FIG. 14 illustrates a sensor circuit included in an active touch sensor.

The sensor circuit illustrated in FIG. 14 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 14 is described. First, a potential for turning on the transistor 2613 is supplied as the signal G2, and a potential with respect to the voltage VRES is thus applied to a node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger; accordingly, the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613, so that the potential of the node n can be held for a long time and the frequency of operation of resupplying VRES to the node n (refresh operation) can be reduced.

Note that the structure described in this embodiment can be used in appropriate combination with any of the structures described in other embodiments.

Embodiment 9

In this embodiment, as a display device including any of the light-emitting elements which are embodiments of the present invention, a display device which includes a reflective liquid crystal element and a light-emitting element and is capable of performing display both in a transmissive mode and a reflective mode is described with reference to FIGS. 15A, 15B1, and 15B2, FIG. 16, and FIG. 17. Such a display device can also be referred to as an emissive OLED and reflective LC hybrid display (ER-hybrid display).

The display device described in this embodiment can be driven with extremely low power consumption for display using the reflective mode in a bright place such as outdoors. Meanwhile, in a dark place such as indoors or at night, an image can be displayed at an optimal luminance with the use of the transmissive mode. Thus, by combination of these modes, the display device can display an image with lower power consumption and a higher contrast compared to a conventional display panel.

As an example of the display device of this embodiment, description is made on a display device in which a liquid crystal element provided with a reflective electrode and a light-emitting element are stacked and an opening of the reflective electrode is provided in a position overlapping with the light-emitting element. Visible light is reflected by the reflective electrode in the reflective mode and light emitted from the light-emitting element is emitted through the opening of the reflective electrode in the transmissive mode. Note that transistors used for driving these elements (the liquid crystal element and the light-emitting element) are preferably formed on the same plane. It is preferable that the liquid crystal element and the light-emitting element be stacked through an insulating layer.

Figure 15A:
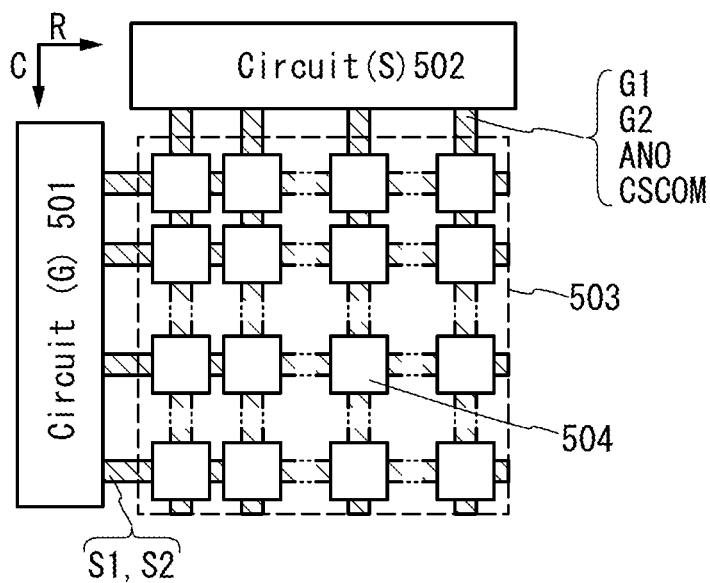
Figure 15A:
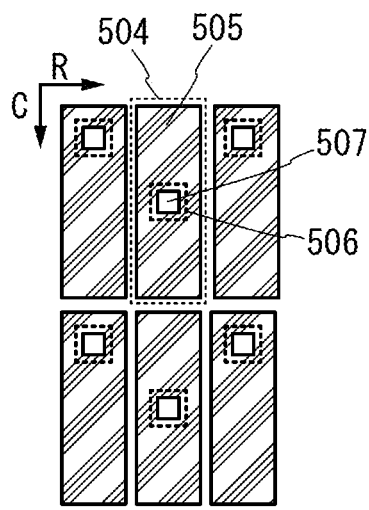
Figure 15A:
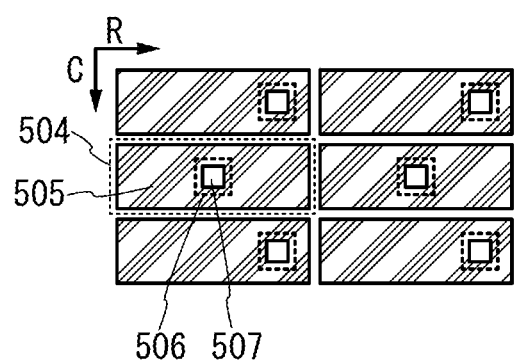

FIG. 15A is a block diagram illustrating a display device described in this embodiment. A display device 500 includes a circuit (G) 501, a circuit (S) 502, and a display portion 503. In the display portion 503, a plurality of pixels 504 are arranged in an R direction and a C direction in a matrix. A plurality of wirings G1, wirings G2, wirings ANO, and wirings CSCOM are electrically connected to the circuit (G) 501. These wirings are also electrically connected to the plurality of pixels 504 arranged in the R direction. A plurality of wirings S1 and wirings S2 are electrically connected to the circuit (S) 502, and these wirings are also electrically connected to the plurality of pixels 504 arranged in the C direction.

Each of the plurality of pixels 504 includes a liquid crystal element and a light-emitting element. The liquid crystal element and the light-emitting element include portions overlapping with each other.

FIG. 15B1 shows the shape of a conductive film 505 serving as a reflective electrode of the liquid crystal element included in the pixel 504. Note that an opening 507 is provided in a position 506 which is part of the conductive film 505 and which overlaps with the light-emitting element. That is, light emitted from the light-emitting element is emitted through the opening 507.

The pixels 504 in FIG. 15B1 are arranged such that adjacent pixels 504 in the R direction exhibit different colors. Furthermore, the openings 507 are provided so as not to be arranged in a line in the R direction. Such arrangement has an effect of suppressing crosstalk between the light-emitting elements of adjacent pixels 504. Furthermore, there is an advantage that element formation is facilitated.

The opening 507 can have a polygonal shape, a quadrangular shape, an elliptical shape, a circular shape, a cross shape, a stripe shape, or a slit-like shape, for example.

FIG. 15B2 illustrates another example of the arrangement of the conductive films 505.

The ratio of the opening 507 to the total area of the conductive film 505 (excluding the opening 507) affects the display of the display device. That is, a problem is caused in that as the area of the opening 507 is larger, the display using the liquid crystal element becomes darker; in contrast, as the area of the opening 507 is smaller, the display using the light-emitting element becomes darker. Furthermore, in addition to the problem of the ratio of the opening, a small area of the opening 507 itself also causes a problem in that extraction efficiency of light emitted from the light-emitting element is decreased. The ratio of opening 507 to the total area of the conductive film 505 (other than the opening 507) is preferably 5% or more and 60% or less for maintaining display quality at the time of combination of the liquid crystal element and the light-emitting element.

Figure 16:
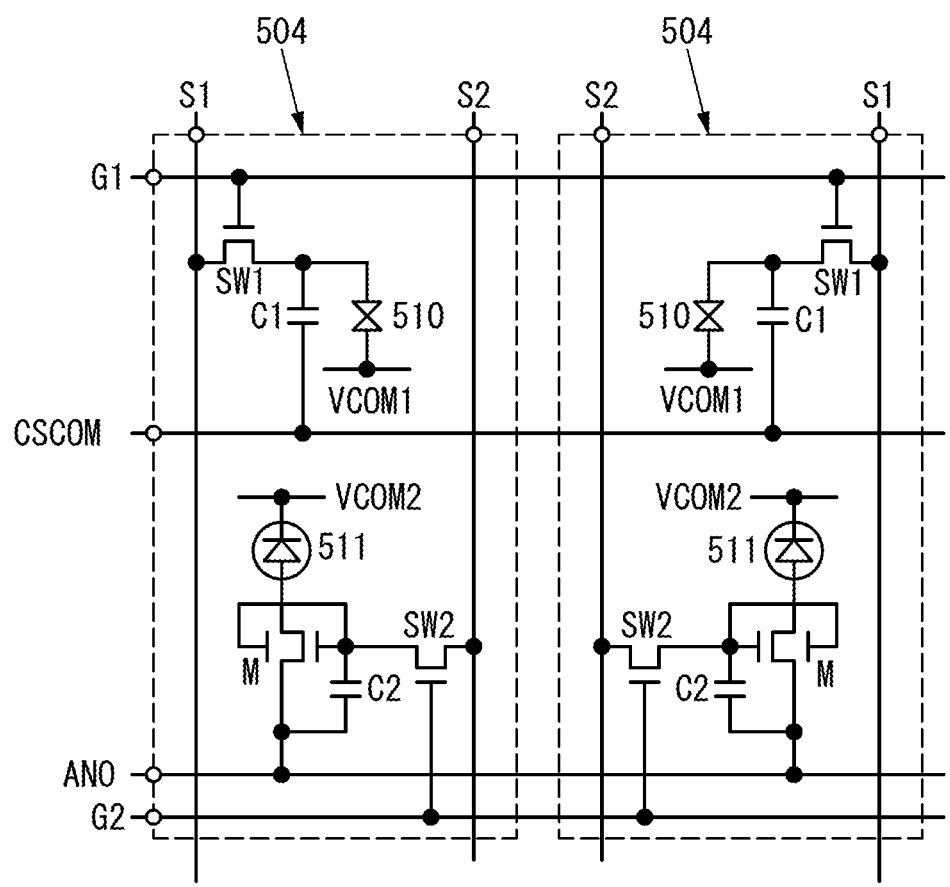
FIG. 16 illustrates a circuit configuration of a display device.

Next, an example of a circuit configuration of the pixel 504 is described with reference to FIG. 16. FIG. 16 shows two adjacent pixels 504.

The pixel 504 includes a transistor SW1, a capacitor C1, a liquid crystal element 510, a transistor SW2, a transistor M, a capacitor C2, a light-emitting element 511, and the like. Note that these components are electrically connected to any of the wiring G1, the wiring G2, the wiring ANO, the wiring CSCOM, the wiring S1, and the wiring S2 in the pixel 504. The liquid crystal element 510 and the light-emitting element 511 are electrically connected to a wiring VCOM1 and a wiring VCOM2, respectively.

A gate of the transistor SW1 is connected to the wiring G1. One of a source and a drain of the transistor SW1 is connected to the wiring S1, and the other of the source and the drain is connected to one electrode of the capacitor C1 and one electrode of the liquid crystal element 510. The other electrode of the capacitor C1 is connected to the wiring CSCOM. The other electrode of the liquid crystal element 510 is connected to the wiring VCOM1.

A gate of the transistor SW2 is connected to the wiring G2. One of a source and a drain of the transistor SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 511. Furthermore, the other electrode of the light-emitting element 511 is connected to the wiring VCOM2.

Note that the transistor M includes two gates between which a semiconductor is provided and which are electrically connected to each other. With such a structure, the amount of current flowing through the transistor M can be increased.

The on/off state of the transistor SW1 is controlled by a signal from the wiring G1. A predetermined potential is supplied from the wiring VCOM1. Furthermore, orientation of liquid crystals of the liquid crystal element 510 can be controlled by a signal from the wiring S1. A predetermined potential is supplied from the wiring CSCOM.

The on/off state of the transistor SW2 is controlled by a signal from the wiring G2. By the difference between the potentials applied from the wiring VCOM2 and the wiring ANO, the light-emitting element 511 can emit light. Furthermore, the on/off state of the transistor M is controlled by a signal from the wiring S2.

Accordingly, in the structure of this embodiment, in the case of the reflective mode, the liquid crystal element 510 is controlled by the signals supplied from the wiring G1 and the wiring S1 and optical modulation is utilized, whereby display can be performed. In the case of the transmissive mode, the light-emitting element 511 can emit light when the signals are supplied from the wiring G2 and the wiring S2. In the case where both modes are performed at the same time, desired driving can be performed on the basis of the signals from the wiring G1, the wiring G2, the wiring S1, and the wiring S2.

Figure 17:
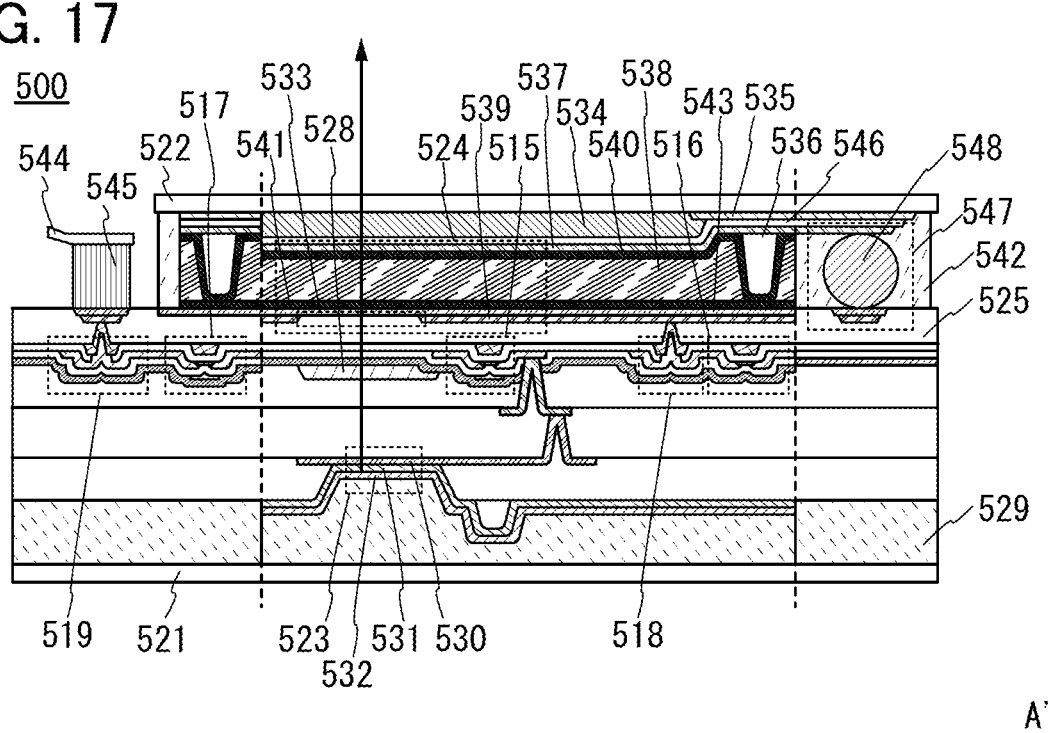
FIG. 17 illustrates a cross-sectional structure of a display device.

Next, specific description is given with reference to FIG. 17, a schematic cross-sectional view of the display device 500 described in this embodiment.

The display device 500 includes a light-emitting element 523 and a liquid crystal element 524 between substrates 521 and 522. Note that the light-emitting element 523 and the liquid crystal element 524 are formed with an insulating layer 525 positioned therebetween. That is, the light-emitting element 523 is positioned between the substrate 521 and the insulating layer 525, and the liquid crystal element 524 is positioned between the substrate 522 and the insulating layer 525.

A transistor 515, a transistor 516, a transistor 517, a coloring layer 528, and the like are provided between the insulating layer 525 and the light-emitting element 523.

A bonding layer 529 is provided between the substrate 521 and the light-emitting element 523. The light-emitting element 523 includes a conductive layer 530 serving as one electrode, an EL layer 531, and a conductive layer 532 serving as the other electrode which are stacked in this order over the insulating layer 525. In the light-emitting element 523 that is a bottom emission light-emitting element, the conductive layer 532 and the conductive layer 530 contain a material that reflects visible light and a material that transmits visible light, respectively. Light emitted from the light-emitting element 523 is transmitted through the coloring layer 528 and the insulating layer 525 and then transmitted through the liquid crystal element 524 via an opening 533, thereby being emitted to the outside of the substrate 522.

In addition to the liquid crystal element 524, a coloring layer 534, a light-blocking layer 535, an insulating layer 546, a structure 536, and the like are provided between the insulating layer 525 and the substrate 522. The liquid crystal element 524 includes a conductive layer 537 serving as one electrode, a liquid crystal 538, a conductive layer 539 serving as the other electrode, alignment films 540 and 541, and the like. Note that the liquid crystal element 524 is a reflective liquid crystal element and the conductive layer 539 serves as a reflective electrode; thus, the conductive layer 539 is formed using a material with high reflectivity. Furthermore, the conductive layer 537 serves as a transparent electrode, and thus is formed using a material that transmits visible light. Alignment films 540 and 541 may be provided on the conductive layers 537 and 539 and in contact with the liquid crystal 538. The insulating layer 546 is provided so as to cover the coloring layer 534 and the light-blocking layer 535 and serves as an overcoat. Note that the alignment films 540 and 541 are not necessarily provided.

The opening 533 is provided in part of the conductive layer 539. A conductive layer 543 is provided in contact with the conductive layer 539. Since the conductive layer 543 has a light-transmitting property, a material transmitting visible light is used for the conductive layer 543.

The structure 536 serves as a spacer that prevents the substrate 522 from coming closer to the insulating layer 525 than required. The structure 536 is not necessarily provided.

One of a source and a drain of the transistor 515 is electrically connected to the conductive layer 530 in the light-emitting element 523. For example, the transistor 515 corresponds to the transistor M in FIG. 16.

One of a source and a drain of the transistor 516 is electrically connected to the conductive layer 539 and the conductive layer 543 in the liquid crystal element 524 through a terminal portion 518. That is, the terminal portion 518 electrically connects the conductive layers provided on both surfaces of the insulating layer 525. The transistor 516 corresponds to the transistor SW1 in FIG. 16.

A terminal portion 519 is provided in a region where the substrates 521 and 522 do not overlap with each other. Similarly to the terminal portion 518, the terminal portion 519 electrically connects the conductive layers provided on both surfaces of the insulating layer 525. The terminal portion 519 is electrically connected to a conductive layer obtained by processing the same conductive film as the conductive layer 543. Thus, the terminal portion 519 and the FPC 544 can be electrically connected to each other through a connection layer 545.

A connection portion 547 is provided in part of a region where a bonding layer 542 is provided. In the connection portion 547, the conductive layer obtained by processing the same conductive film as the conductive layer 543 and part of the conductive layer 537 are electrically connected with a connector 548. Accordingly, a signal or a potential input from the FPC 544 can be supplied to the conductive layer 537 through the connector 548.

The structure 536 is provided between the conductive layer 537 and the conductive layer 543. The structure 536 maintains a cell gap of the liquid crystal element 524.

As the conductive layer 543, a metal oxide, a metal nitride, or an oxide such as an oxide semiconductor whose resistance is reduced is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive layer 543.

Note that the structure described in this embodiment can be combined as appropriate with any of the structures described in the other embodiments.

Embodiment 10

In this embodiment, a light-emitting element of one embodiment of the present invention is described. The light-emitting element described in this embodiment has a structure different from that described in Embodiment 2. An element structure and a manufacturing method of the light-emitting element is described with reference to FIGS. 18A and 18B. For the portions similar to those in Embodiment 2, the description of Embodiment 2 can be referred to and description is omitted.

The light-emitting element described in this embodiment has a structure in which an EL layer 3202 including a light-emitting layer 3213 is sandwiched between a pair of electrodes (a cathode 3201 and an anode 3203) formed over a substrate 3200. The EL layer 3202 can be formed by stacking a light-emitting layer, a hole-injection layer, a hole-transport layer, an electron-injection layer, an electron-transport layer, and the like as in the EL layer described in Embodiment 2.

Figure 18A:
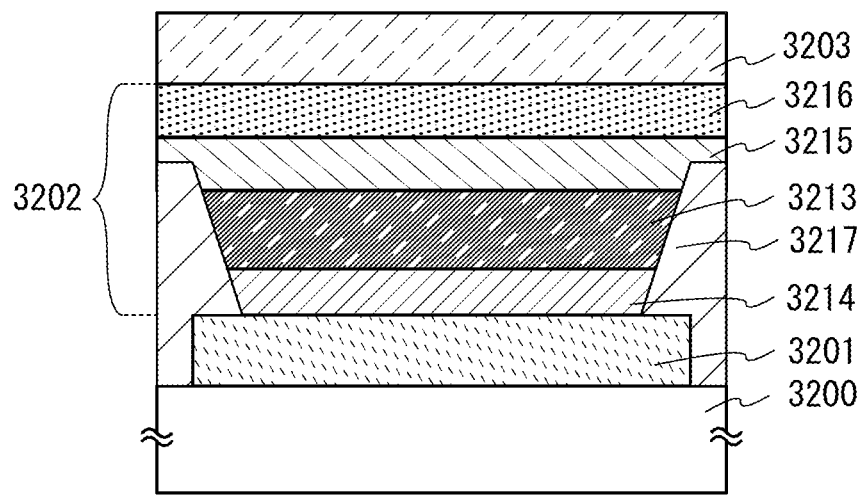
FIGS. 18A and 18B illustrate a light-emitting element.

In this embodiment, as shown in FIG. 18A, description is made on the light-emitting element having a structure in which the EL layer 3202 including an electron-injection layer 3214, the light-emitting layer 3213, a hole-transport layer 3215, and a hole-injection layer 3216 are formed over the cathode 3201 in this order over the substrate 3200 and the anode 3203 is formed over the hole-injection layer 3216. Here, though an electron-transport layer is not provided, the electron-injection layer 3214 can serve as the electron-transport layer with a material having a high electron-transport property.

In the above-described light-emitting element, current flows due to a potential difference applied between the cathode 3201 and the anode 3203, and holes and electrons recombine in the EL layer 3202, whereby light is emitted. Then, this light emission is extracted to the outside through one or both of the cathode 3201 and the anode 3203. Therefore, one or both of the cathode 3201 and the anode 3203 are electrodes having light-transmitting properties; light can be extracted through the electrode having a light-transmitting property.

Figure 18B:
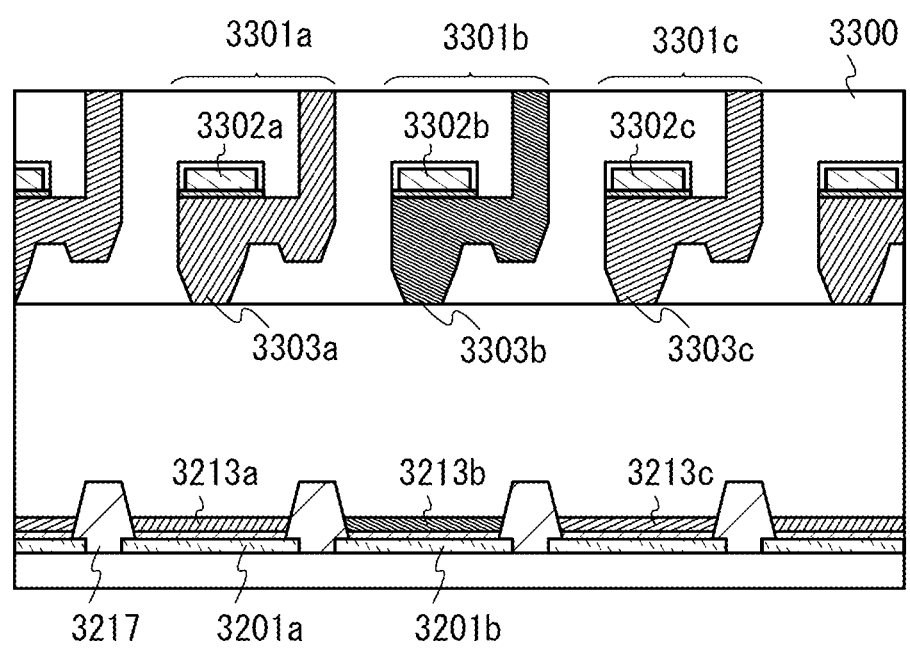

In the light-emitting element described in this embodiment, end portions of the cathode 3201 are covered with insulators 3217 as shown in FIG. 18A. Note that the insulators 3217 are formed so as to fill a space between adjacent cathodes 3201 (e.g., 3201a and 3201b) as shown in FIG. 18B.

As the insulator 3217, an inorganic compound or an organic compound having an insulating property can be used. As the organic compound, a photosensitive resin such as a resist material, e.g., an acrylic resin, a polyimide resin, a fluorine-based resin, or the like can be used. As the inorganic compound, silicon oxide, silicon oxynitride, silicon nitride, or the like can be used, for example. Note that the insulator 3217 preferably has a water-repellent surface. As its treatment method, plasma treatment, chemical treatment (using an alkaline solution or an organic solvent), or the like can be employed.

In this embodiment, the electron-injection layer 3214 formed over the cathode 3201 is formed using a high molecular compound. It is preferable to use a high molecular compound which does not dissolve in the nonaqueous solvent and which has a high electron-transport property. Specifically, the electron-injection layer 3214 is formed using an appropriate combination of any of the materials (including not only a high molecular compound but also an alkali metal, an alkaline earth metal, or a compound thereof) which can be used for the electron-injection layer 115 and electron-transport layer 114 in Embodiment 2. The materials are dissolved in a polar solvent, and the layer is formed by a coating method.

Here, examples of the polar solvent include methanol, ethanol, propanol, isopropanol, butyl alcohol, ethylene glycol, and glycerin.

The light-emitting layer 3213 is formed over the electron-injection layer 3214. The light-emitting layer 3213 is formed by depositing (or applying) ink in which any of the materials (a light-emitting substance) which can be used for the light-emitting layer 3213 in Embodiment 2 are combined as appropriate and dissolved (dispersed) in a nonpolar solvent, by a wet method (an ink-jet method or a printing method). Although the electron-injection layer 3214 is used in common in light-emitting elements of different emission colors, a material corresponding to an emission color is selected for the light-emitting layer 3213. As the nonpolar solvent, an aromatic-based solvent such as toluene or xylene, or a heteroaromatic-based solvent such as pyridine can be used. Alternatively, a solvent such as hexane, 2-methylhexane, cyclohexane, or chloroform can be used.

As shown in FIG. 18B, the ink for forming the light-emitting layer 3213 is applied from a head portion 3300 of an apparatus for applying a solution (hereinafter referred to as solution application apparatus). Note that the head portion 3300 includes a plurality of spraying portions 3301a to 3301c for spraying ink, and piezoelectric elements 3302a to 3302c are provided for the spraying portions 3301a to 3301c. Furthermore, the spraying portions 3301a to 3301c are filled with respective ink 3303a to ink 3303c containing light-emitting substances exhibiting different emission colors.

The ink 3303a to ink 3303c are sprayed from the respective spraying portions 3301a to 3301c, whereby light-emitting layers 3213a to 3213c exhibiting different emission colors are formed.

The hole-transport layer 3215 is formed over the light-emitting layer 3213. The hole-transport layer 3215 can be formed by a combination of any of the materials which can be used for the hole-transport layer 3215 in Embodiment 2. The hole-transport layer 3215 can be formed by a vacuum evaporation method or a coating method. In the case of employing a coating method, the material which is dissolved in a solvent is applied to the light-emitting layer 3213 and the insulator 3217. As a coating method, an ink-jet method, a spin coating method, a printing method, or the like can be used.

The hole-injection layer 3216 is formed over the hole-transport layer 3215. The anode 3203 is formed over the hole-injection layer 3216. They are formed using an appropriate combination of the materials described in Embodiment 2 by a vacuum evaporation method.

The light-emitting element can be formed through the above steps. Note that in the case of using an organometallic complex of one embodiment of the present invention in the light-emitting layer, phosphorescence due to the organometallic complex is obtained. Thus, the light-emitting element can have higher efficiency than a light-emitting element formed using only fluorescent compounds.

The structure described in this embodiment can be used in appropriate combination with any of the structures described in other embodiments.

Example 1

Synthesis Example 1

In this example, a method for synthesizing 9-[4-(3,10-diphenylanthracen-9-yl)phenyl]-9H-carbazole (abbreviation: 2Ph-CzPA) which is an organic compound of one embodiment of the present invention represented by the structural formula (100) in Embodiment 1 is described. The structure of 2Ph-CzPA is shown below.

[Chemical formula 33]

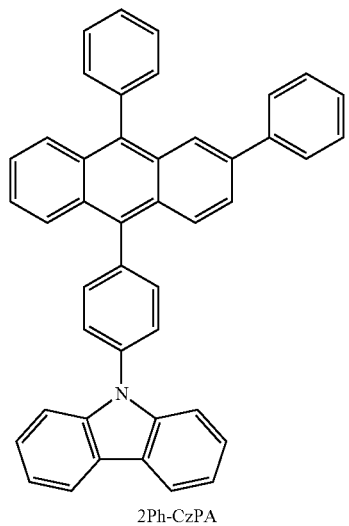

(100)

2Ph-CzPA

Step 1: Synthesis of 2-phenylanthracene

Into a three-neck flask were put 10.67 g (41.5 mmol) of 2-bromoanthracene, 6.07 g (49.8 mmol) of a phenylboronic acid, 20.6 g (149 mmol) of potassium carbonate, 210 mL of toluene, 50 mL of ethanol, and 75 mL of water. This mixture was degassed under reduced pressure, and then the air in the flask was replaced with nitrogen. Then, 93 mg (0.42 mmol) of palladium(II) acetate (abbreviation: Pd(OAc)$_2$) and 253 mg (0.83 mmol) of tris(2-methylphenyl)phosphine were added to the mixture, and this mixture was heated and refluxed for 3 hours. After that, the temperature of the flask was returned to room temperature, and the precipitated solid was separated by filtration. The filtrate was separated into an organic layer and an aqueous layer to give the organic layer. The separated solid was added to the organic layer and dissolved by heating. Then, the resulting solution was filtered through Celite, alumina, and Florisil. The filtrate was concentrated, and the precipitated solid was recrystallized with ethanol. After the cooling, the precipitate was collected by filtration at room temperature, the obtained solid was dried at 75° C. under reduced pressure to give 10.1 g of a target white solid in a yield of 95%. The synthesis scheme of Step 1 is shown in (a-1) below.

[Chemical formula 34]

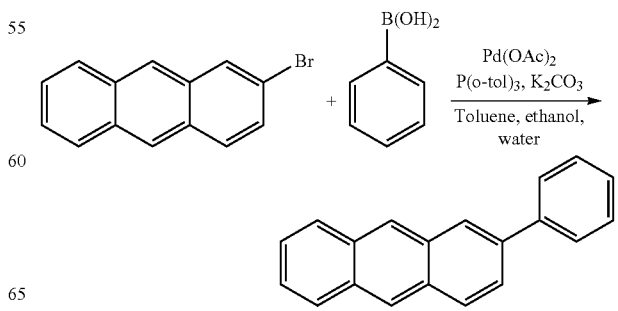

(a-1)

Analysis results by nuclear magnetic resonance spectroscopy ($^1$H-NMR) of the white solid obtained in Step 1 are shown below. These results show that 2-phenylanthracene was synthesized in Step 1.

$^1$H-NMR. δ(CDCl$_3$): 7.37 (td, J=7.0 Hz, 1.5 Hz, 1H), 7.41-7.51 (m, 4H), 7.70-7.78 (m, 3H), 7.95-8.01 (brm, 2H), 8.03 (d, J=8.5 Hz, 1H), 8.18 (s, 1H), 8.41 (s, 1H), 8.44 (s, 1H).

Step 2: Synthesis of 2-phenyl-9-bromoanthracene

Next, 10.0 g (39 mmol) of 2-phenylanthracene was put into a 500 mL three-neck flask, 400 mL of tetrahydrofuran was added thereto, and heating was performed so that 2-phenylanthracene would be dissolved. To this mixed solution was added 7.35 g of N-bromosuccinimide. This solution was heated and refluxed for approximately 20 hours. After the reflux, the solution was cooled down to room temperature and was concentrated. The precipitated solid was slurry-washed with methanol, and then the slurry was filtered. The obtained solid was dried under reduced pressure to give 12.2 g of a target yellow solid in a yield of 93%. The synthesis scheme of Step 2 is shown in (a-2) below.

[Chemical formula 35]

(a-2)

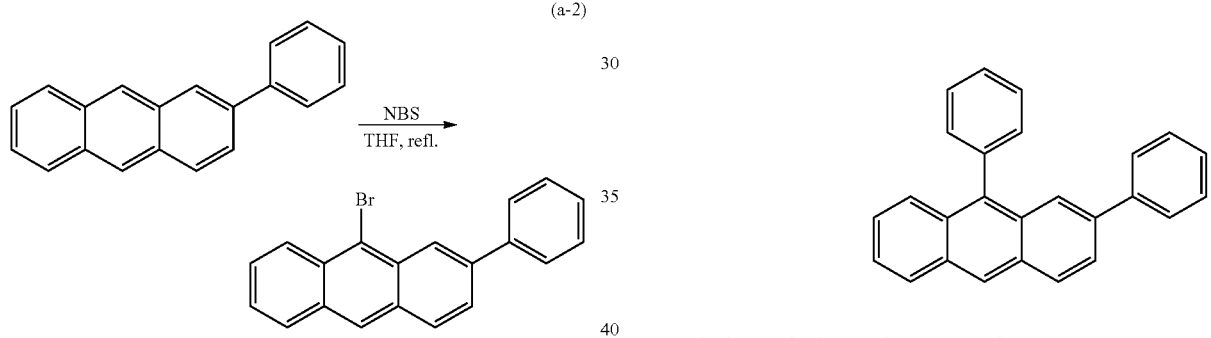

Analysis results by nuclear magnetic resonance spectroscopy ($^1$H-NMR) of the yellow solid obtained in Step 2 are shown below. These results show that 2-phenyl-9-bromoanthracene was synthesized in Step 2.

$^1$H-NMR. δ(CDCl$_3$): 7.42 (t, J=7.5 Hz, 1H), 7.46-7.54 (m, 3H), 7.59 (m, 1H), 7.77 (dd, J=9 Hz, 1.5 Hz, 1H), 7.81 (dd, J=8 Hz, 1.5 Hz, 2H), 7.98 (d, J=9 Hz, 1H), 8.05 (d, J=9 Hz, 1H), 8.42 (s, 1H), 8.51 (d, J=9.5 Hz, 1H), 8.70 (s, 1H).

Step 3: Synthesis of 2,9-diphenylanthracene

Next, 12.1 g (36 mmol) of 2-phenyl-9-bromoanthracene, 5.3 g (44 mmol) of a phenylboronic acid, 18.1 g (131 mmol) of potassium carbonate, 180 mL of toluene, 45 mL of ethanol, and 65 mL of water were put into a 500 mL three-neck flask. This mixture was degassed under reduced pressure, and then the air in the flask was replaced with nitrogen. Then, 82 mg (0.36 mmol) of palladium(II) acetate (abbreviation: Pd(OAc)$_2$) and 221 mg (0.73 mmol) of tris (2-methylphenyl)phosphine were added to the mixture, and this mixture was heated and refluxed for 5 hours. Water and toluene were added to the obtained mixture, and the resulting mixture was separated into an organic layer and an aqueous layer. The aqueous layer was subjected to extraction with toluene. The obtained organic layer and the solution of the extract were combined and washed with water, and magnesium sulfate was added to the solution for drying. This solution was filtered, and the solvent was distilled off. The obtained residue was recrystallized with toluene and ethanol to give 9.6 g of a target yellow solid of 2,9-diphenylanthracene in a yield of 80%. The synthesis scheme of Step 3 is shown in (a-3) below.

[Chemical formula 36]

(a-3)

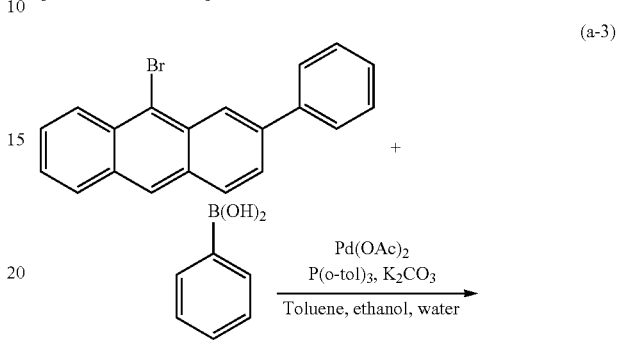

Analysis results by nuclear magnetic resonance spectroscopy ($^1$H-NMR) of the yellow solid obtained in Step 3 are shown below. These results show that an organic compound 2,9-diphenylanthracene was synthesized in Step 3.

$^1$H-NMR. δ(CDCl$_3$): 7.30-7.37 (m, 2H), 7.39-7.48 (m, 5H), 7.50-7.55 (m, 1H), 7.56-7.61 (m, 4H), 7.66 (d, J=8.5 Hz, 1H), 7.75 (dd, J=8.5 Hz, 1.5 Hz, 1H), 7.86 (s, 1H), 8.05 (d, J=8.5 Hz, 1H), 8.13 (d, J=8.5 Hz, 1H), 8.51 (s, 1H).

Step 4: Synthesis of 2,9-diphenyl-10-bromoanthracene

Next, 9.6 g (29 mmol) of 2,9-diphenylanthracene was put into a 500 mL three-neck flask, 145 mL of ethyl acetate was added thereto, and heating was performed so that 2,9-diphenylanthracene would be dissolved. To this mixed solution was added 5.42 g (30 mmol) of N-bromosuccinimide. This solution was heated and refluxed for approximately 20 hours. After the reflux, the solution was cooled down to room temperature and was concentrated. The precipitated solid was slurry-washed with methanol, and then the slurry was filtered. The obtained solid was dried under reduced pressure to give 10.4 g of a target yellow solid in a yield of 87%. The synthesis scheme of Step 4 is shown in (a-4) below.

[Chemical formula 37]

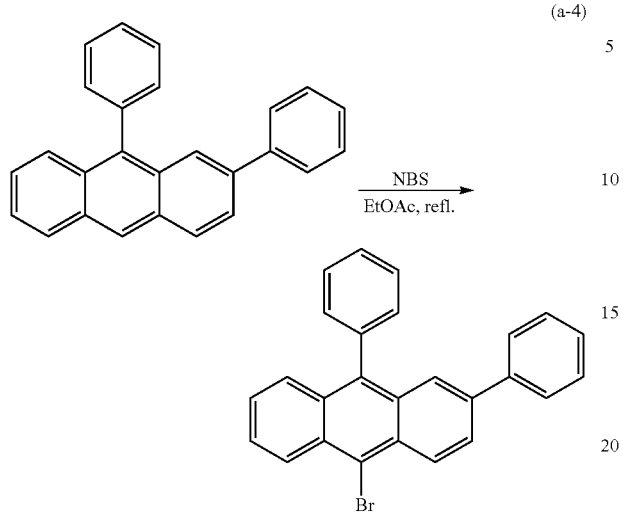

[Chemical formula 38]

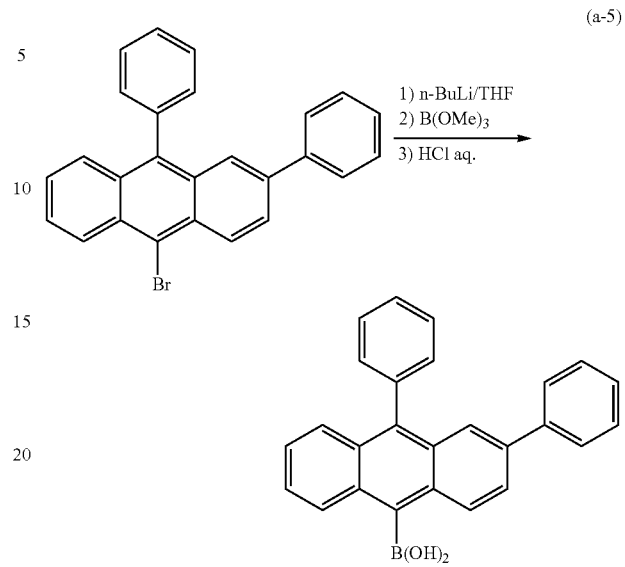

Analysis results by nuclear magnetic resonance spectroscopy ($^1$H-NMR) of the yellow solid obtained in Step 4 are shown below. These results show that an organic compound 2,9-diphenyl-10-bromoanthracene was synthesized in Step 4.

$^1$H-NMR. δ (CDCl$_3$): 7.31-7.45 (m, 6H), 7.53-7.61 (m, 6H), 7.64 (d, J=8.5 Hz, 1H), 7.84 (s, 1H), 7.86 (dd, J=9 Hz, 1.5 Hz, 1H), 8.60 (d, J=9 Hz, 1H), 8.68 (d, J=9 Hz, 1H).

Step 5: Synthesis of 3,10-diphenylanthracen-9-ylboronic Acid

Into a 500 mL flask was put 10.2 g (25 mmol) of 2,9-diphenyl-10-bromoanthracene synthesized in Step 4. The pressure in the flask was reduced, and then the air in the flask was replaced with nitrogen. Then, 120 mL of tetrahydrofuran was added, the mixture was stirred so that 2,9-diphenyl-10-bromoanthracene would be dissolved, and the solution was cooled down to −80° C. After the cooling, 19 mL (1.55 M, 30 mmol) of an n-butyllithium hexane solution was dripped into this solution, and reaction was caused for 2 hours. Into this reaction liquid was dripped 3.5 mL (31 mmol) of trimethylboron acid and reaction was caused for 30 minutes. The temperature of this reaction solution was increased to room temperature, and reaction was continued overnight. To the obtained reaction solution was added 50 mL of a 1 mol/L hydrochloric acid. This mixed solution was separated into an organic layer and an aqueous layer, and the aqueous layer was subjected to extraction with ethyl acetate. The obtained solution of the extract and the organic layer were mixed, neutralized with a saturated aqueous solution of sodium hydrogen carbonate, and then washed with a saturated aqueous solution of sodium chloride. Magnesium sulfate was added to this solution for drying, and filtration was performed. The obtained solution was concentrated, the precipitated solid was slurry-washed with hexane, and then the slurry was filtered. The obtained solid was dried under reduced pressure to give 8.1 g of a target yellow solid in a yield of 87%. The synthesis scheme of Step 5 is shown in (a-5) below.

Analysis results by nuclear magnetic resonance spectroscopy ($^1$H-NMR) of the yellow solid obtained in Step 5 are shown below. These results show that an organic compound 3,10-diphenylanthracen-9-ylboronic acid was synthesized in Step 5.

$^1$H-NMR. δ(CDCl$_3$): 5.25 (s, 2H), 7.30-7.38 (m, 2H), 7.39-7.44 (m, 4H), 7.47-7.51 (m, 1H), 7.52-7.61 (m, 5H), 6.67 (d, J=8.5 Hz, 1H), 7.78 (dd, J=9 Hz, 1.5 Hz, 1H), 7.87 (d, J=1 Hz, 1H), 8.15 (d, J=8.5 Hz, 1H), 8.22 (d, J=8.5 Hz, 1H).

Step 6: Synthesis of 9-(4-bromophenyl)-3,10-diphenylanthracene

Into a round-bottom flask were put 8.1 g (22 mmol) of 3,10-diphenylanthracen-9-ylboronic acid synthesized in Step 5, 7.3 g (26 mmol) of 1-bromo-4-iodobenzene, 8.9 g (65 mmol) of potassium carbonate, 110 mL of toluene, 28 mL of ethanol, and 33 mL of water. This mixture was degassed under reduced pressure, and then the air in the flask was replaced with nitrogen. Then, 97 mg (0.43 mmol) of palladium(II) acetate (abbreviation: Pd(OAc)$_2$) and 226 mg (0.86 mmol) of triphenylphosphine were added to the mixture, and this mixture was heated and refluxed for 5 hours. After that, the temperature of the flask was returned to room temperature, and the obtained mixed solution was separated into an organic layer and an aqueous layer. The obtained organic layer was washed with a saturated aqueous solution of sodium chloride, and filtration was performed. The organic layer was concentrated, and the obtained residue was purified by silica gel column chromatography. The obtained solution was concentrated, and the precipitated solid was recrystallized with ethanol. The solid precipitated at room temperature was collected by filtration, and the obtained residue was dried under reduced pressure to give 8.9 g of a target yellow solid in a yield of 85%. The synthesis scheme of Step 6 is shown in (a-6) below.

[Chemical formula 39]

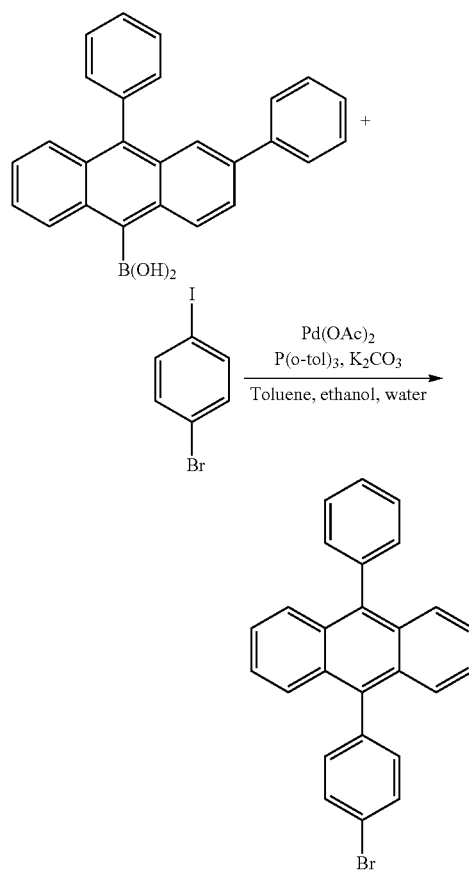

Analysis results by nuclear magnetic resonance spectroscopy ($^1$H-NMR) of the yellow solid obtained in Step 6 are shown below. These results show that an organic compound 9-(4-bromophenyl)-3,10-diphenylanthracene was synthesized in Step 6.

$^1$H-NMR. δ (CDCl$_3$): 7.30-7.43 (m, 7H), 7.50 (d, J=7 Hz, 2H), 7.53-7.57 (m, 3H), 7.59-7.72 (m, 5H), 7.73-7.78 (m, 3H), 7.90 (s, 1H).

Step 7: Synthesis of 9-[4-(3,10-diphenylanthracen-9-yl)phenyl]-9H-carbazole (Abbreviation: 2Ph-CzPA)

Into a 200 mL flask were put 4.3 g (8.9 mmol) of 9-(4-bromophenyl)-3,10-diphenylanthracene, 1.6 g (9.3 mmol) of 9H-carbazole, 2.6 g (27 mmol) of tert-butoxysodium, and 45 mL of mesitylene. This mixture was degassed under reduced pressure, and then the air in the flask was replaced with nitrogen. Then, 32 mg (0.089 mmol) of allylpalladium(II) chloride dimer (abbreviation: [(Allyl)PdCl]$_2$) and 125 mg (0.35 mmol) of di-tert-butyl(1-methyl-2,2-diphenylcyclopropyl)phosphine (abbreviation: cBRIDP) were added, and the mixture was heated and refluxed for 3 hours. The reaction solution was filtered through Celite, alumina, and Florisil. Water was added to this solution, and the obtained mixed solution was separated into an organic layer and an aqueous layer. The obtained organic layer was washed with a saturated aqueous solution of sodium chloride, and dried with magnesium sulfate. Then, filtration was performed. The organic layer was concentrated, and the obtained residue was purified by silica gel column chromatography. The obtained solution was concentrated, and the precipitated solid was recrystallized with ethanol. The solid precipitated at room temperature was collected by filtration, and the obtained residue was dried under reduced pressure to give 4.9 g of a target yellow solid in a yield of 96%. The synthesis scheme of Step 7 is shown in (a-7) below.

[Chemical formula 40]

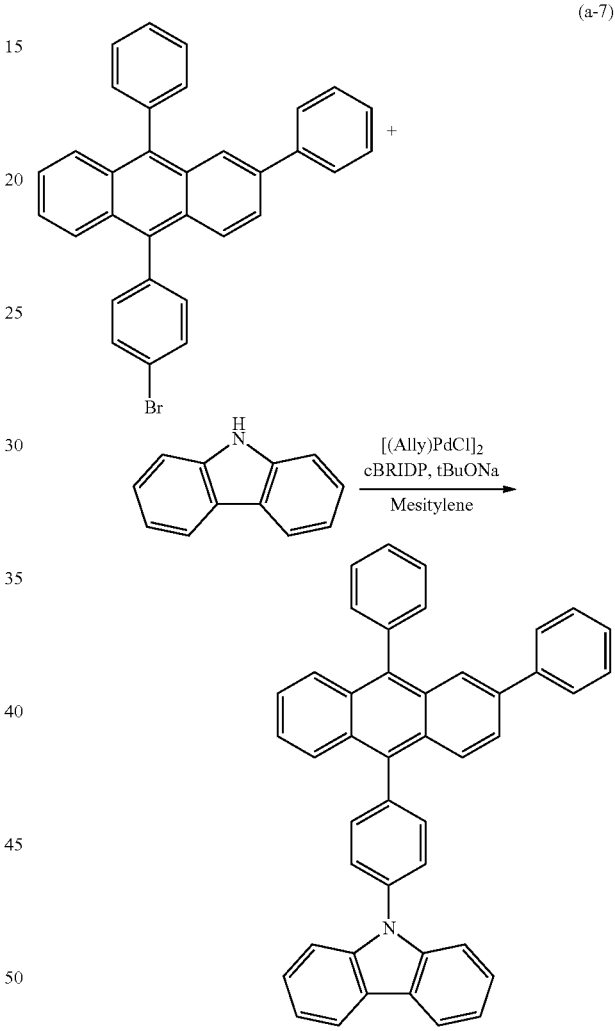

Figure 19:
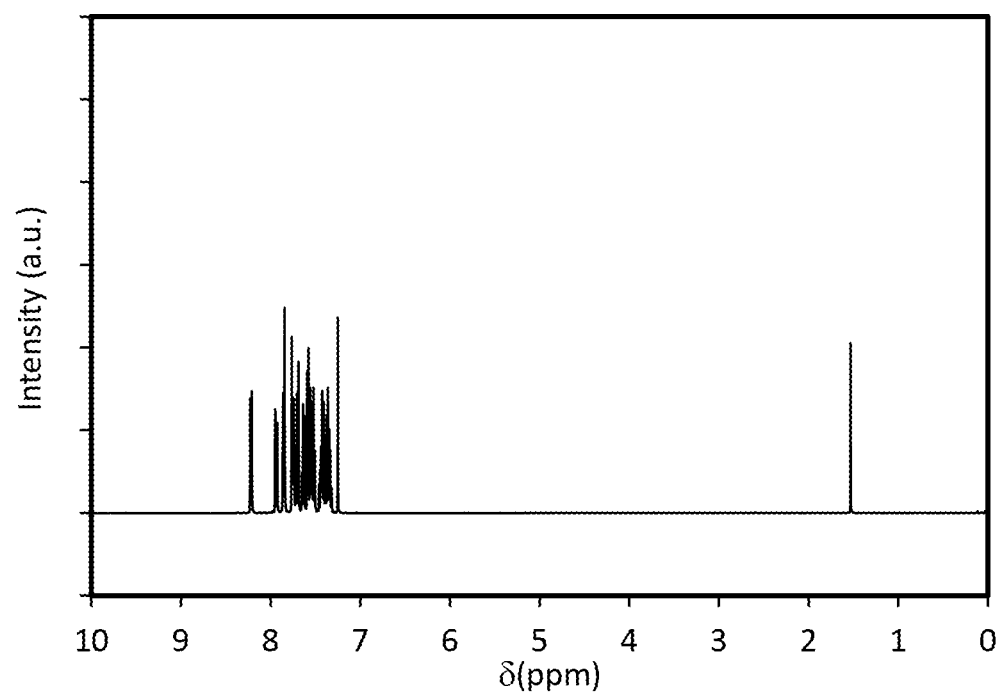
FIG. 19 is a $^1$H-NMR chart of an organic compound represented by the structural formula (100).

Analysis results by nuclear magnetic resonance spectroscopy ($^1$H-NMR) of the yellow solid obtained in Step 7 are shown below. FIG. 19 shows the $^1$H-NMR chart. These results show that the organic compound 2Ph-CzPA was synthesized in this example.

$^1$H-NMR. δ(CDCl$_3$): 7.31-7.47 (m, 7H), 7.49-7.60 (m, 7H), 7.61-7.66 (m, 2H), 7.67-7.77 (m, 64H), 7.82-7.87 (m, 3H), 7.91-7.97 (m, 2H), 8.22 (d, J=7.5 Hz, 2H).

Then, 4.8 g of the obtained solid was purified by a train sublimation method. The purification by sublimation was conducted by heating at 285° C. under a pressure of 3.0 Pa with a flow rate of an argon gas of 15 mL/min. After the purification by sublimation, 4.1 g of a yellow solid was obtained at a collection rate of 86%.

Figure 20:
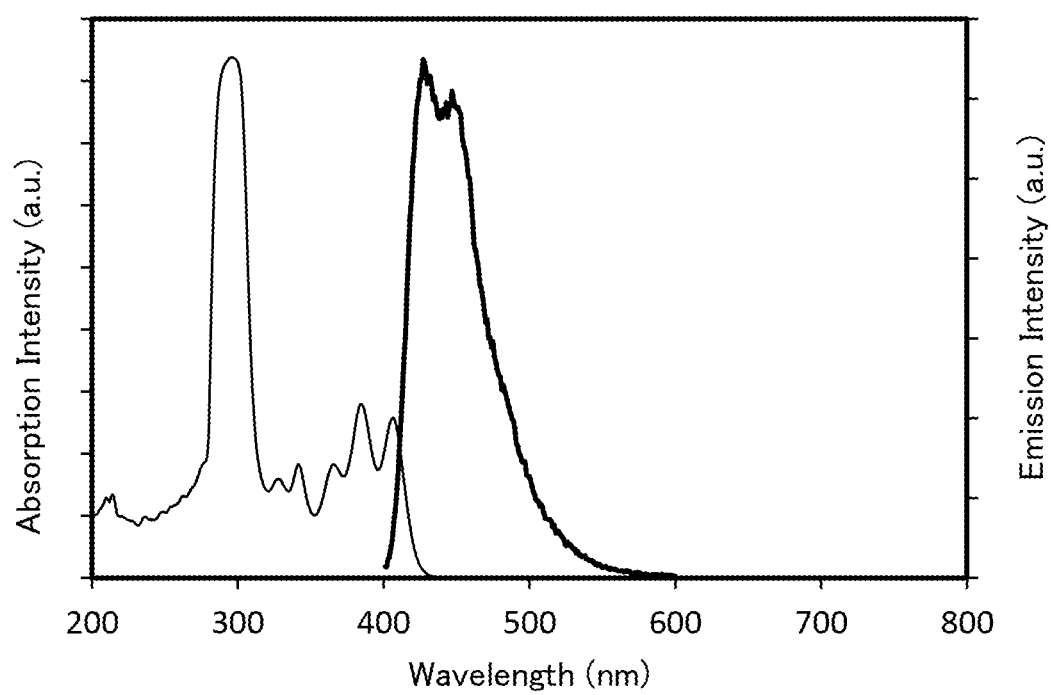
FIG. 20 shows an ultraviolet-visible absorption spectrum and an emission spectrum of the organic compound represented by the structural formula (100).

Next, an ultraviolet-visible absorption spectrum (hereinafter, simply referred to as an absorption spectrum) of a toluene solution of 2Ph-CzPA and an emission spectrum thereof were measured. The measurement of the absorption spectrum was conducted at room temperature, for which an ultraviolet-visible light spectrophotometer (V550 type manufactured by JASCO Corporation) was used and the toluene solution (0.03 mmol/L) was put in a quartz cell. In addition, the measurement of the emission spectrum was conducted at room temperature, for which a fluorescence spectrophotometer (FS920 manufactured by Hamamatsu Photonics K. K.) was used and the toluene solution (0.01 mmol/L) was put in a quartz cell. FIG. 20 shows measurement results of the absorption spectrum and the emission spectrum. The horizontal axis represents wavelength and the vertical axes represent absorbance and emission intensity. In FIG. 20, two solid lines are shown; a thin line represents the absorption spectrum, and a thick line represents the emission spectrum. The absorbance shown in FIG. 20 is a result obtained by subtraction of absorbance of only toluene in a quartz cell from the measured absorbance of the toluene solution (0.03 mmol/L) in a quartz cell.

As shown in FIG. 20, the organic compound 2Ph-CzPA has emission peaks at 427 nm and 447 nm, and bluish purple light emission was observed from the toluene solution.

Next, the organic compound 2Ph-CzPA was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and mass spectrometry (MS) was carried out with Xevo G2 Tof MS manufactured by Waters Corporation. ACQUITY UPLC BEH C8 (2.1×100 mm, 1.7 μm) was used as a column for the LC separation, and the column temperature was set to 40° C. Acetonitrile was used for Mobile Phase A and a 0.1% aqueous solution of formic acid was used for Mobile Phase B. Furthermore, a sample was prepared in such a manner that 2Ph-CzPA was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 572 which underwent the ionization under the above-described conditions was collided with an argon gas in a collision cell to dissociate into product ions. Energy (collision energy) for the collision with argon was set to 70 eV. The measurement mass range was set to m/z (mass-to-charge ratio)=100 to 1200. The detection results of the dissociated product ions by time-of-flight (TOF) MS are shown in FIG. 21.

Figure 21:
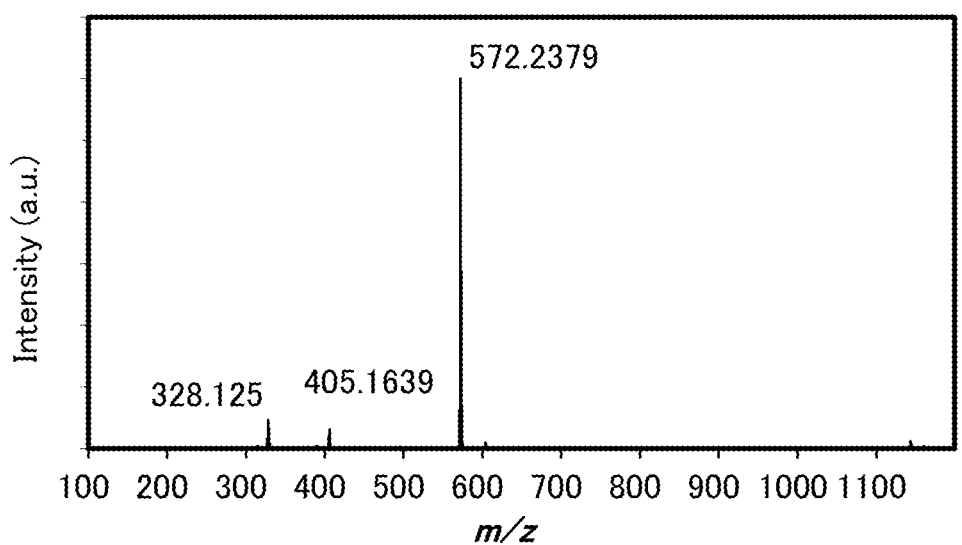
FIG. 21 shows results of LC-MS measurement of the organic compound represented by the structural formula (100).

FIG. 21 shows that product ions of 2Ph-CzPA are mainly detected at m/z of around 572. Note that the result in FIG. 21 shows characteristics derived from 2Ph-CzPA and therefore can be regarded as important data for identifying 2Ph-CzPA contained in a mixture.

Note that a fragment ion at m/z of 406, which was observed in measurement with a collision energy of 70 eV, is probably derived from 2,9,10-triphenylanthracene generated in such a manner that a C—N bond of 2Ph-CzPA was cut. This is one characteristic of 2Ph-CzPA.

Example 2

Synthesis Example 2

In this example, a method for synthesizing 7-[4-(3,10-diphenylanthracen-9-yl)phenyl]dibenzo[c,g]-7H-carbazole (abbreviation: 2Ph-cgDBCzPA) that is an organic compound of one embodiment of the present invention represented by the structural formula (200) in Embodiment 1 is described. The structure of 2Ph-cgDBCzPA is shown below.

[Chemical formula 41]

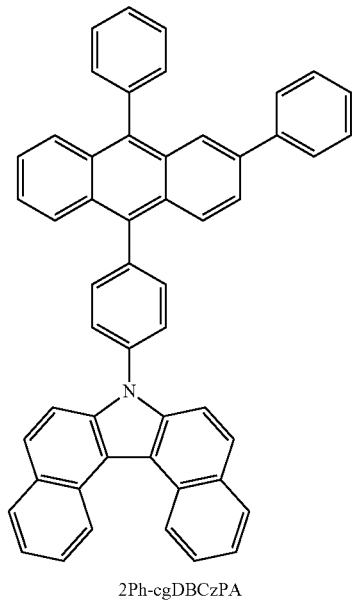

(200)

2Ph-cgDBCzPA

Step 1: Synthesis of 2Ph-cgDBCzPA

Into a 200 mL flask were put 4.3 g (8.9 mmol) of 9-(4-bromophenyl)-3,10-diphenylanthracene (see Step 6 of Example 1), 2.5 g (9.3 mmol) of dibenzo[c,g]-7H-carbazole, 2.6 g (27 mmol) of tert-butoxysodium, and 45 mL of mesitylene. This mixture was degassed under reduced pressure, and then the air in the flask was replaced with nitrogen. Then, 32 mg (0.089 mmol) of allylpalladium(II) chloride dimer (abbreviation: [(Allyl)PdCl]$_2$) and 125 mg (0.35 mmol) of di-tert-butyl(1-methyl-2,2-diphenylcyclopropyl)phosphine (abbreviation: cBRIDP) were added, and the mixture was heated and refluxed for 6 hours. The reaction solution was filtered through Celite, alumina, and Florisil. Water was added to this solution, and the obtained mixed solution was separated into an organic layer and an aqueous layer. The obtained organic layer was washed with a saturated aqueous solution of sodium chloride, and dried with magnesium sulfate. Then, filtration was performed. The organic layer was concentrated, and the obtained residue was purified by silica gel column chromatography. The obtained solution was concentrated, and the precipitated solid was recrystallized with ethanol. The solid precipitated at room temperature was collected by filtration, and the obtained residue was dried under reduced pressure to give 4.8 g of a target yellow solid in a yield of 81%. The synthesis scheme of Step 1 is shown in (b-1) below.

[Chemical formula 42]

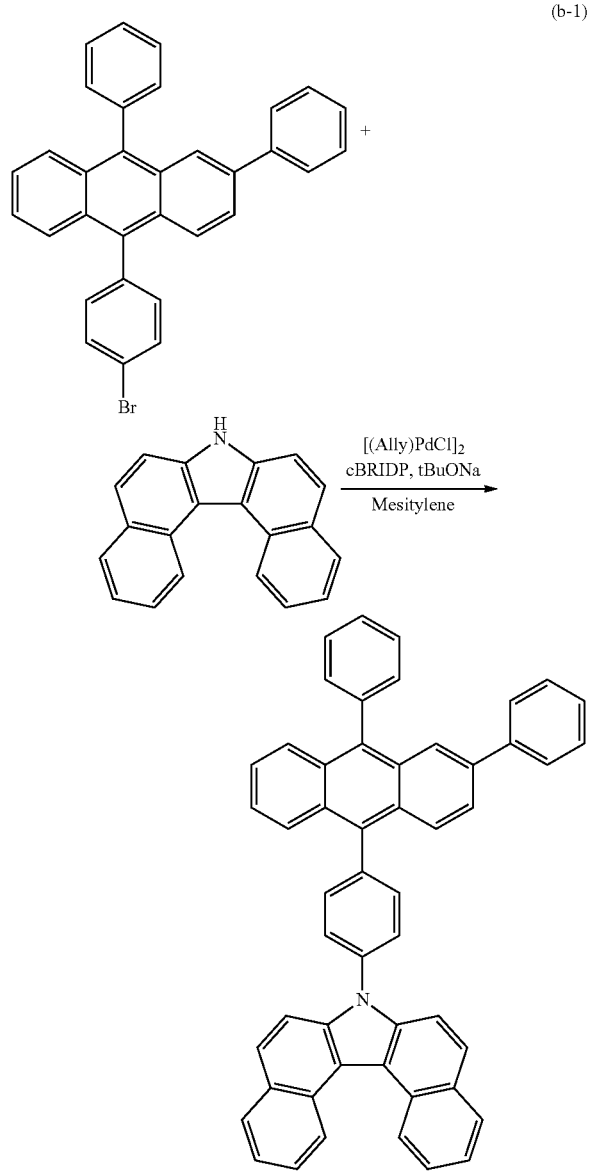

Figure 22:
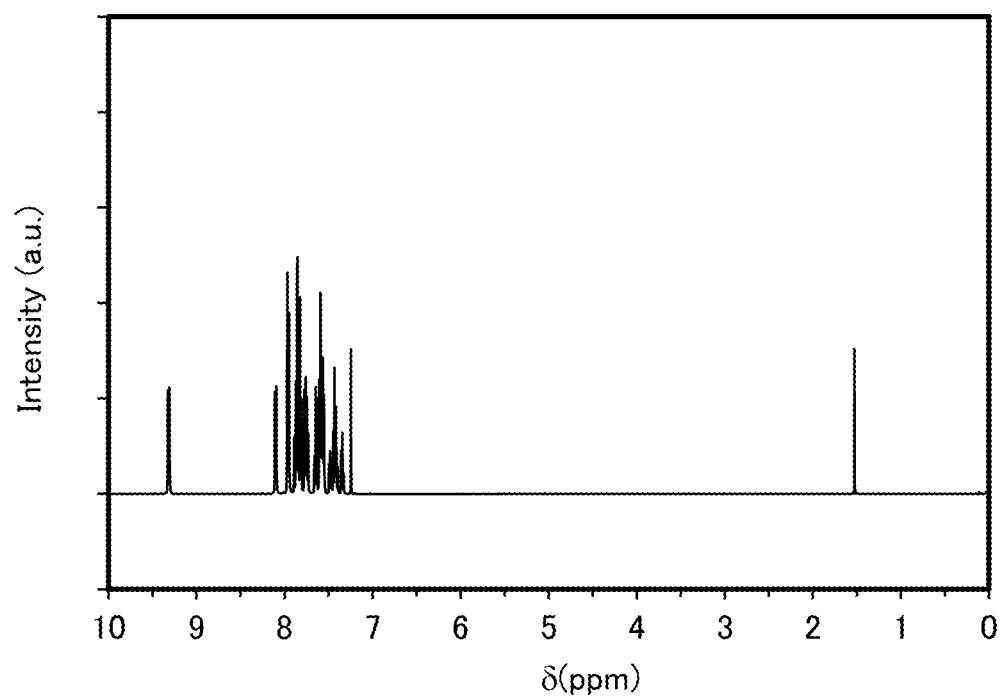
FIG. 22 is a $^1$H-NMR chart of an organic compound represented by the structural formula (200).

Analysis results by nuclear magnetic resonance spectroscopy ($^1$H-NMR) of the yellow solid obtained in Step 1 are shown below. FIG. 22 shows the $^1$H-NMR chart. These results show that the organic compound 2Ph-cgDBCzPA was synthesized in Step 1.

$^1$H-NMR. δ(CDCl$_3$): 7.34 (t, J=7 Hz, 1H), 7.39-7.51 (m, 4H), 7.53-7.61 (m, 7H), 7.62-7.67 (m, 2H), 7.72-7.79 (m, 4H), 7.80-7.90 (m, 7H), 7.93-7.98 (m, 4H), 8.10 (d, J=8 Hz, 2H), 9.32 (d, J=8.5 Hz, 2H).

Then, 4.7 g of the obtained solid was purified by a train sublimation method. The purification by sublimation was conducted by heating at 355° C. under a pressure of 3.0 Pa with a flow rate of an argon gas of 15 mL/min. After the purification by sublimation, 4.1 g of a yellow solid was obtained at a collection rate of 87%.

Figure 23:
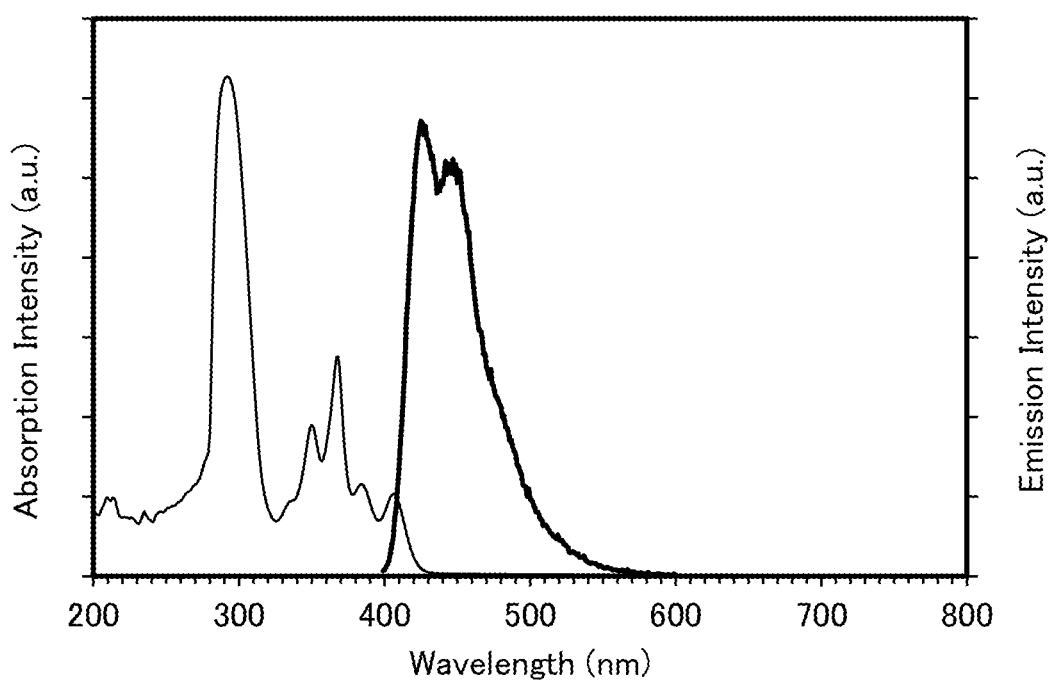
FIG. 23 shows an ultraviolet-visible absorption spectrum and an emission spectrum of the organic compound represented by the structural formula (200).

Next, an ultraviolet-visible absorption spectrum (hereinafter, simply referred to as an absorption spectrum) of a toluene solution of 2Ph-cgDBCzPA and an emission spectrum thereof were measured. The measurement of the absorption spectrum was conducted at room temperature, for which an ultraviolet-visible light spectrophotometer (V550 type manufactured by JASCO Corporation) was used and the toluene solution (0.02 mmol/L) was put in a quartz cell. In addition, the measurement of the emission spectrum was conducted at room temperature, for which a fluorescence spectrophotometer (FS920 manufactured by Hamamatsu Photonics K. K.) was used and the toluene solution (0.01 mmol/L) was put in a quartz cell. FIG. 23 shows measurement results of the absorption spectrum and the emission spectrum. The horizontal axis represents wavelength and the vertical axes represent absorbance and emission intensity. In FIG. 23, two solid lines are shown; a thin line represents the absorption spectrum, and a thick line represents the emission spectrum. The absorbance shown in FIG. 23 is a result obtained by subtraction of absorbance of only toluene in a quartz cell from the measured absorbance of the toluene solution (0.02 mmol/L) in a quartz cell.

As shown in FIG. 23, the organic compound 2Ph-cgDBCzPA has emission peaks at 425 nm and 447 nm, and bluish purple light emission was observed from the toluene solution.

Next, the organic compound 2Ph-cgDBCzPA was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and mass spectrometry (MS) was carried out with Xevo G2 Tof MS manufactured by Waters Corporation. ACQUITY UPLC BEH C8 (2.1×100 mm, 1.7 μm) was used as a column for the LC separation, and the column temperature was set to 40° C. Acetonitrile was used for Mobile Phase A and a 0.1% aqueous solution of formic acid was used for Mobile Phase B. Furthermore, a sample was prepared in such a manner that 2Ph-cgDBCzPA was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 672 which underwent the ionization under the above-described conditions was collided with an argon gas in a collision cell to dissociate into product ions. Energy (collision energy) for the collision with argon was set to 70 eV. The measurement mass range was set to m/z (mass-to-charge ratio)=100 to 1200. The detection results of the dissociated product ions by time-of-flight (TOF) MS are shown in FIG. 24.

Figure 24:
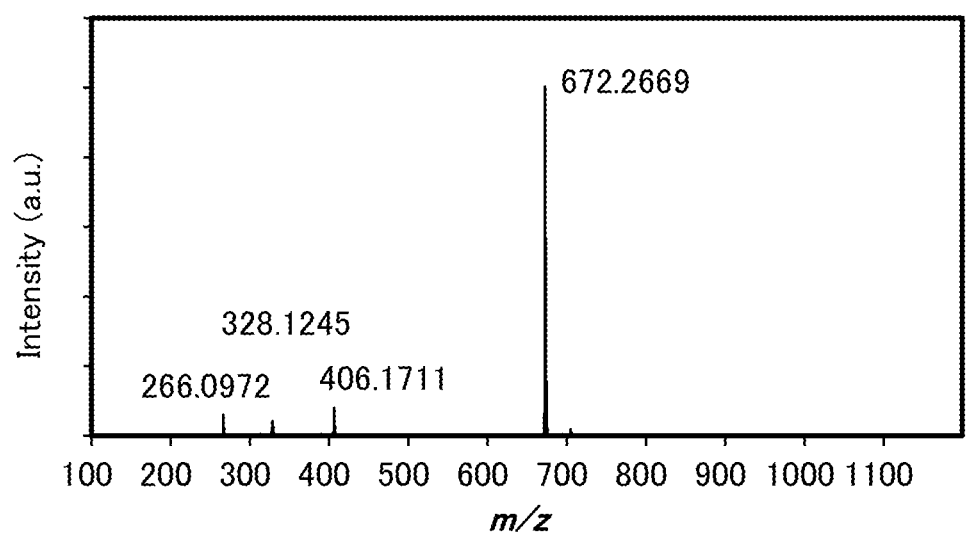
FIG. 24 shows results of LC-MS measurement of the organic compound represented by the structural formula (200).

FIG. 24 shows that product ions of 2Ph-cgDBCzPA are mainly detected at m/z of around 672. Note that the result in FIG. 24 shows characteristics derived from 2Ph-cgDBCzPA and therefore can be regarded as important data for identifying 2Ph-cgDBCzPA contained in a mixture.

Note that a fragment ion at m/z of 406, which was observed in measurement with a collision energy of 70 eV, is probably derived from 2,9,10-triphenylanthracene generated in such a manner that a C—N bond of 2Ph-CzPA was cut, and a fragment ion at m/z of 266 is probably derived from 7H-dibenzo[c,g]carbazole. These data can be regarded as indicating the skeletons included in 2Ph-cgDBCzPA.

Example 3

Figure 25:
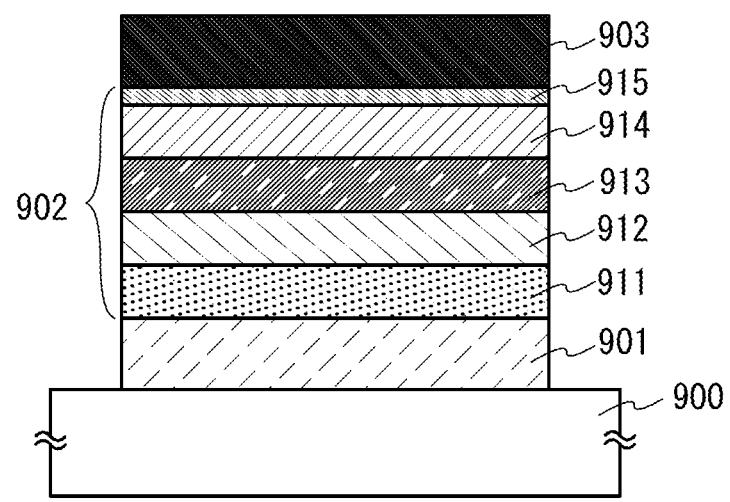
FIG. 25 illustrates a structure of a light-emitting element.
Figure 26:
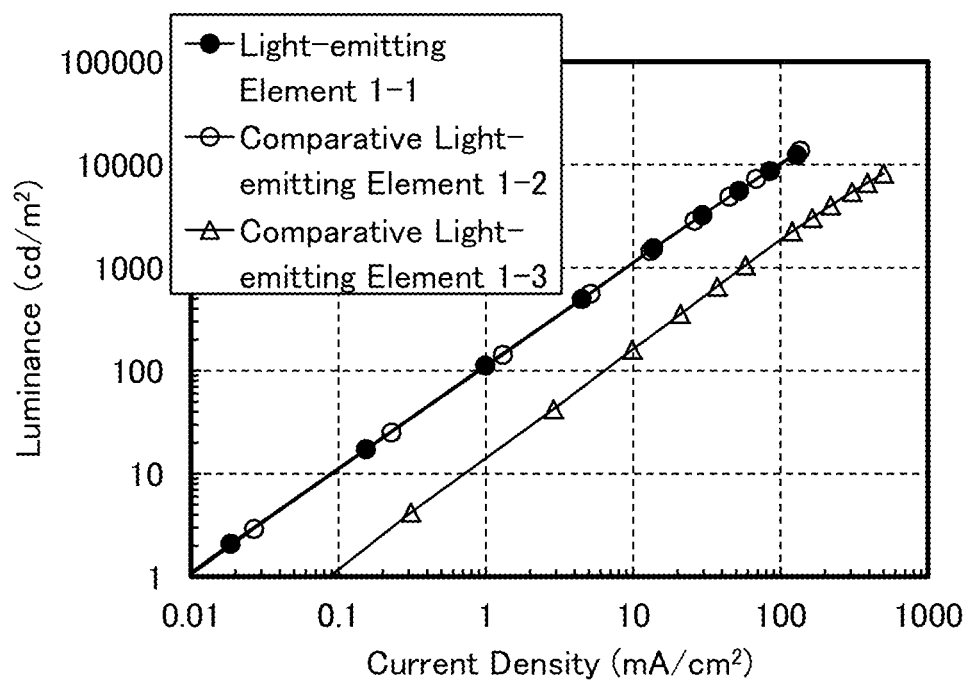
FIG. 26 shows current density-luminance characteristics of a light-emitting element 1-1, a comparative light-emitting element 1-2, and a comparative light-emitting element 1-3.
Figure 27:
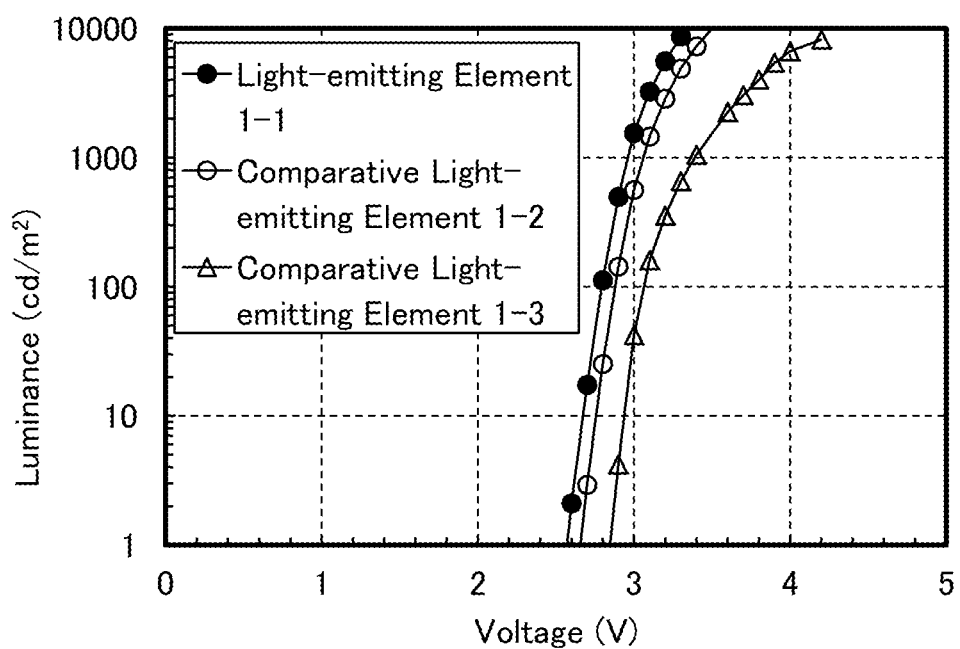
FIG. 27 shows voltage-luminance characteristics of the light-emitting element 1-1, the comparative light-emitting element 1-2, and the comparative light-emitting element 1-3.
Figure 28:
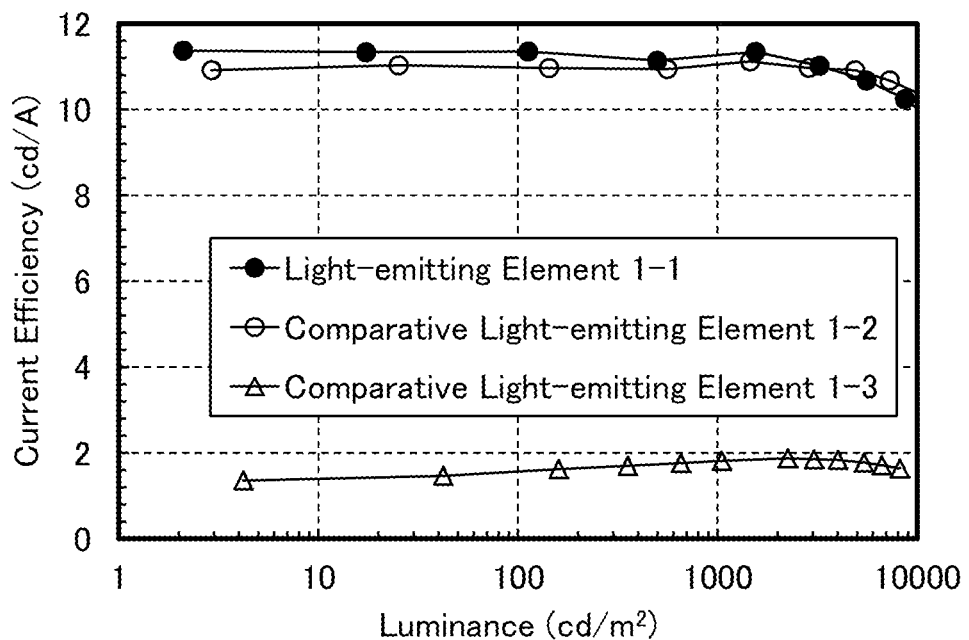
FIG. 28 shows luminance-current efficiency characteristics of the light-emitting element 1-1, the comparative light-emitting element 1-2, and the comparative light-emitting element 1-3.
Figure 29:
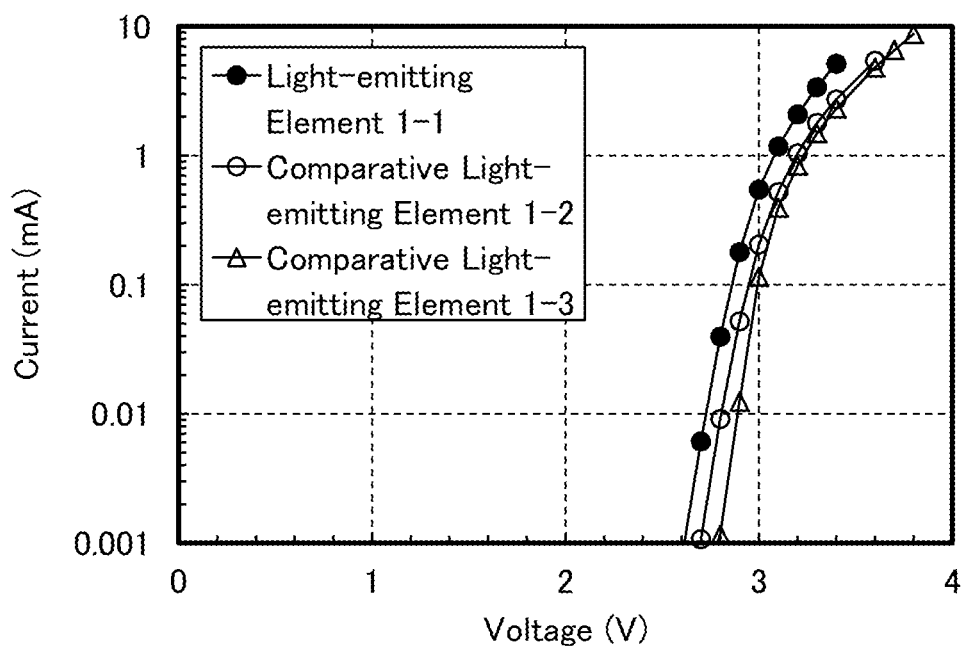
FIG. 29 shows voltage-current characteristics of the light-emitting element 1-1, the comparative light-emitting element 1-2, and the comparative light-emitting element 1-3.

In this example, as a light-emitting element of one embodiment of the present invention, a light-emitting element 1-1 including 2Ph-CzPA whose synthesis method is described in Example 1 as a host material of a light-emitting layer was fabricated. In addition, as comparative light-emitting elements, a comparative light-emitting element 1-2 including CzPA as a host material of a light-emitting layer, and a comparative light-emitting element 1-3 including 2PPA as a host material of a light-emitting layer were fabricated. The measurement results of the characteristics of these light-emitting elements are shown. Note that in this example, the light-emitting element 1-1, the comparative light-emitting element 1-2, and the comparative light-emitting element 1-3 are described with reference to FIG. 25. Chemical formulae of materials used in this example are shown below.

[Chemical formulae 43]

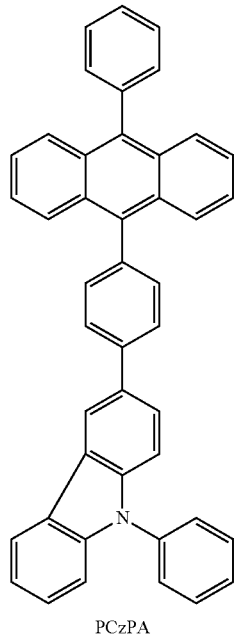

PCzPA

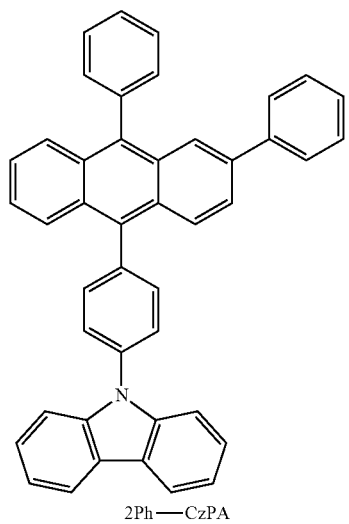

2Ph—CzPA (100)

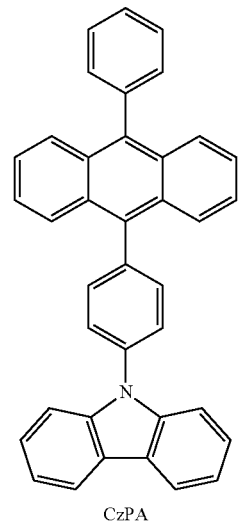

CzPA

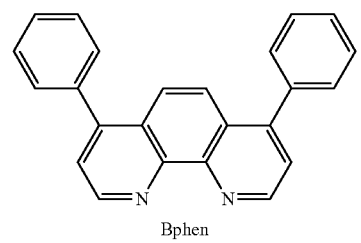

Bphen

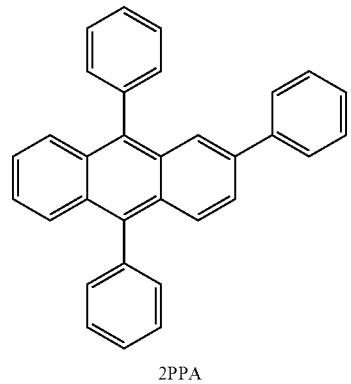

2PPA

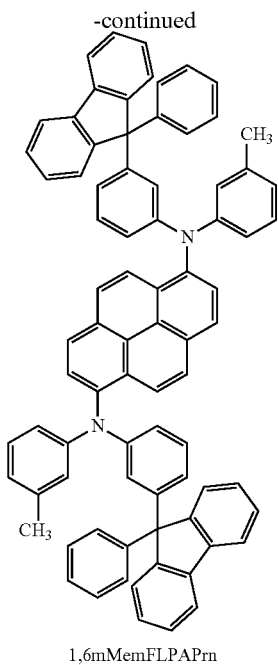

1,6mMemFLPAPrn

<<Fabrication of Light-Emitting Element 1-1, Comparative Light-Emitting Element 1-2, and Comparative Light-Emitting Element 1-3>>

First, indium tin oxide (ITO) containing silicon oxide was deposited over a glass substrate 900 by a sputtering method, whereby a first electrode 901 functioning as an anode was formed. Note that the thickness was set to 70 nm and the electrode area was set to 2 mm×2 mm.

Next, as pretreatment for forming the light-emitting element over the glass substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus. Then, the substrate 900 was cooled down for approximately 30 minutes.

Next, the substrate 900 was fixed to a holder provided in the vacuum evaporation apparatus so that a surface of the substrate over which the first electrode 901 was formed faced downward. In this example, a case is described in which a hole-injection layer 911, a hole-transport layer 912, a light-emitting layer 913, an electron-transport layer 914, and an electron-injection layer 915, which are included in an EL layer 902, were sequentially formed by a vacuum evaporation method.

After reducing the pressure of the vacuum evaporation apparatus to $10^{-4}$ Pa, 9-phenyl-3-[4-(10-phenyl-9-anthryl)phenyl]-9H-carbazole (abbreviation: PCzPA) and molybdenum oxide were deposited by co-evaporation with a mass ratio of PCzPA to molybdenum oxide being 4:2, whereby the hole-injection layer 911 was formed over the first electrode 901. The thickness of the hole-injection layer 911 was set to 10 nm. Note that co-evaporation is an evaporation method in which a plurality of different substances are concurrently vaporized from different evaporation sources.

Next, the hole-transport layer 912 was formed. In the case of each of the light-emitting element 1-1 and the comparative light-emitting element 1-2, PCzPA was deposited to a thickness of 30 nm. In the case of the comparative light-emitting element 1-3, PCzPA was deposited to a thickness of 20 nm.

Next, the light-emitting layer 913 was formed over the hole-transport layer 912. In the case of the light-emitting element 1-1, 9-[4-(3,10-diphenylanthracen-9-yl)phenyl]-9H-carbazole (abbreviation: 2Ph-CzPA) and N,N-bis(3-methylphenyl)-N,N-bis[3-(9-phenyl-9H-fluoren-9-yl)phenyl]-pyrene-1,6-diamine (abbreviation: 1,6mMemFLPAPrn) were deposited to a thickness of 25 nm by co-evaporation with a weight ratio of 2Ph-CzPA to 1,6mMemFLPAPrn being 1:0.03. In the case of the comparative light-emitting element 1-2, 9-[4-(10-phenyl-9-anthracenyl)phenyl]-9H-carbazole (abbreviation: CzPA) and 1,6mMemFLPAPrn were deposited to a thickness of 25 nm by co-evaporation with a weight ratio of CzPA to 1,6mMemFLPAPrn being 1:0.03. In the case of the comparative light-emitting element 1-3, 2,9,10-triphenylanthracene (abbreviation: 2PPA) and 1,6mMemFLPAPrn were deposited to a thickness of 25 nm by co-evaporation with a weight ratio of 2PPA to 1,6mMemFLPAPrn being 1:0.03. Thus, the light-emitting layer 913 was formed.

Next, the electron-transport layer 914 was formed over the light-emitting layer 913. In the case of the light-emitting element 1-1, after 2Ph-CzPA was deposited to a thickness of 10 nm by evaporation, bathophenanthroline (abbreviation: Bphen) was deposited to a thickness of 15 nm by evaporation. In the case of the comparative light-emitting element 1-2, after CzPA was deposited to a thickness of 10 nm by evaporation, Bphen was deposited to a thickness of 15 nm by evaporation. In the case of the comparative light-emitting element 1-3, after 2PPA was deposited to a thickness of 10 nm by evaporation, Bphen was deposited to a thickness of 15 nm by evaporation.

Next, lithium fluoride was deposited by evaporation to a thickness of 1 nm over the electron-transport layer 914, whereby the electron-injection layer 915 was formed.

Finally, aluminum was deposited by evaporation to a thickness of 200 nm over the electron-injection layer 915, whereby a second electrode 903 functioning as a cathode was formed. Thus, each of the light-emitting element 1-1, the comparative light-emitting element 1-2, and the comparative light-emitting element 1-3 was obtained. Note that in all the above evaporation steps, evaporation was performed by a resistance-heating method.

Table 1 shows the element structures of the light-emitting elements fabricated by the above-described method.

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting element 1-1 | ITO (70 nm) | PCzPA:MoOx (4:2 10 nm) | PCzPA (30 nm) | * | 2Ph-CzPA (10 nm) | Bphen (15 nm) | LiF (1 nm) | Al (200 nm) |
| Comparative | ITO | PCzPA:MoOx | PCzPA | ** | CzPA | Bphen | LiF | Al |

TABLE 1-continued

| | First electrode | Hole-injection layer | Hole-transport layer | Light-emitting layer | Electron-transport layer | Electron-injection layer | Second electrode |
|---|---|---|---|---|---|---|---|
| light-emitting element 1-2 | (70 nm) | (4:2 10 nm) | (30 nm) | | (10 nm) | (15 nm) (1 nm) | (200 nm) |
| Comparative light-emitting element 1-3 | ITO (70 nm) | PCzPA:MoOx (4:2 10 nm) | PCzPA (20 nm) | *** | 2PPA (10 nm) | Bphen (15 nm) | LiF (1 nm) | Al (200 nm) |

* 2Ph-CzPA:1,6mMemFLPAPrn (1:0.03 25 nm)
** CzPA:1,6mMemFLPAPrn (1:0.03 25 nm)
*** 2PPA:1,6mMemFLPAPrn (1:0.03 25 nm)

The fabricated light-emitting elements were each sealed in a glove box containing a nitrogen atmosphere so as not to be exposed to the air (specifically, a sealant was applied to surround the elements, and at the time of sealing, UV treatment was performed first and then heat treatment was performed at 80° C. for 1 hour).

<<Operation Characteristics of Light-Emitting Element 1-1, Comparative Light-Emitting Element 1-2, and Comparative Light-Emitting Element 1-3>>

Operation characteristics of the fabricated light-emitting elements were measured. Note that the measurement was carried out at room temperature (under an atmosphere where a temperature was maintained at 25° C.).

FIG. 26, FIG. 27, FIG. 28, and FIG. 29 show current density-luminance characteristics, voltage-luminance characteristics, luminance-current efficiency characteristics, and voltage-current characteristics, respectively, of the light-emitting element 1-1, the comparative light-emitting element 1-2, and the comparative light-emitting element 1-3.

Table 2 shows initial values of main characteristics of the light-emitting elements at around 1000 cd/m$^2$.

The light-emitting element 1-1 (2Ph-CzPA) of one embodiment of the present invention has efficiency as high as the comparative light-emitting element 1-2 (CzPA). This is probably because TTA occurs in 2Ph-CzPA efficiently, which is to be described later.

In contrast, the drive voltage of the light-emitting element 1-1 (2Ph-CzPA) is lower than that of the comparative light-emitting element 1-2 (CzPA). The skeleton of 2Ph-CzPA is a molecular skeleton obtained by combining the skeleton of CzPA with that of 2PPA. However, the drive voltage of the light-emitting element including 2Ph-CzPA is not the average value between the drive voltages of the light-emitting element including CzPA and the light-emitting element including 2PPA; the drive voltage of the light-emitting element including 2Ph-CzPA is lower than the relatively low drive voltage of the light-emitting element including CzPA. This can be said to be an unpredictable and extraordinary effect. From the CV measurement results, the HOMO level of CzPA is −5.79 eV and the LUMO level thereof is −2.73 eV, whereas the HOMO level of 2Ph-CzPA is −5.77 eV and the LUMO level thereof is −2.80 eV. That

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1-1 | 3.0 | 0.55 | 14 | (0.14, 0.17) | 1500 | 11 | 12 | 9.9 |
| Comparative light-emitting element 1-2 | 3.1 | 0.52 | 13 | (0.14, 0.16) | 1500 | 11 | 11 | 10 |
| Comparative light-emitting element 1-3 | 3.4 | 2.3 | 58 | (0.14, 0.11) | 1100 | 1.8 | 1.7 | 2.1 |

Figure 30:
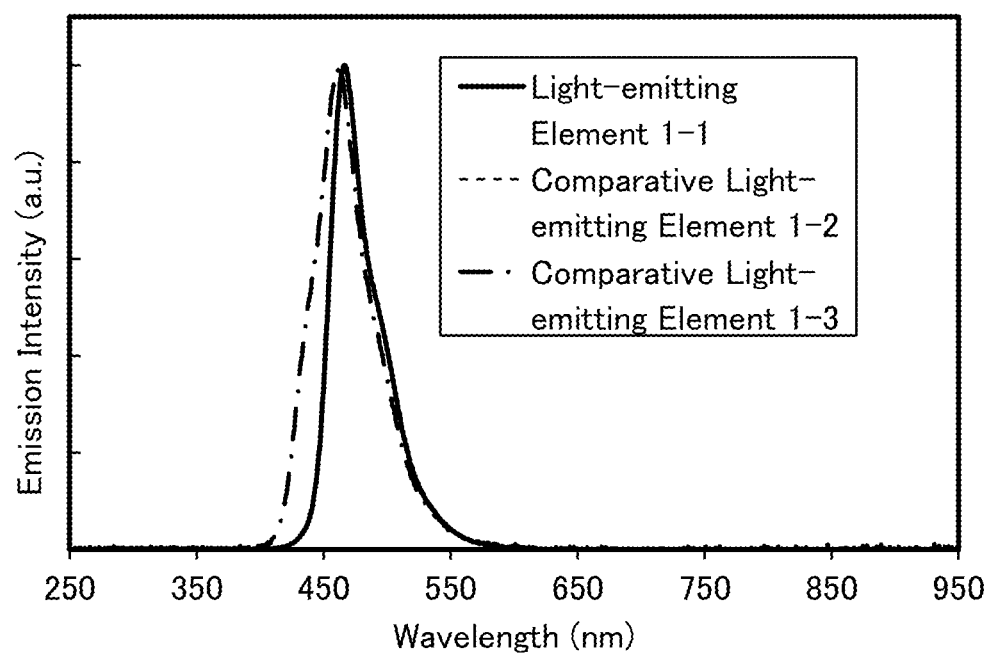
FIG. 30 shows emission spectra of the light-emitting element 1-1, the comparative light-emitting element 1-2, and the comparative light-emitting element 1-3.

FIG. 30 shows emission spectra when a current at a current density of 12.5 mA/cm$^2$ was supplied to the light-emitting elements. In FIG. 30, the emission spectrum of the light-emitting element 1-1 has a peak at around 467 nm, which is presumably derived from blue light emission of 1,6mMemFLPAPrn that is the organic compound used in the EL layer of the light-emitting element 1-1. The spectrum of the comparative light-emitting element 1-2 is similar to that of the light-emitting element 1-1, but the spectrum of the comparative light-emitting element 1-3 has a tail on the short wavelength side. The tail on the short wavelength side is presumably derived from PCzPA used in the hole-transport layer. This indicates that holes are less likely to enter 2PPA from PCzPA. As a result of this, the comparative light-emitting element 1-3 has extremely low drive voltage (current-voltage characteristics) and emission efficiency.

is, it is probable that the gap between the HOMO level and the LUMO level of 2Ph-CzPA is slightly decreased and the drive voltage is correspondingly reduced only when both a carbazole skeleton and a phenyl group bonded to the 3-position of an anthracene skeleton are included.

Figure 31:
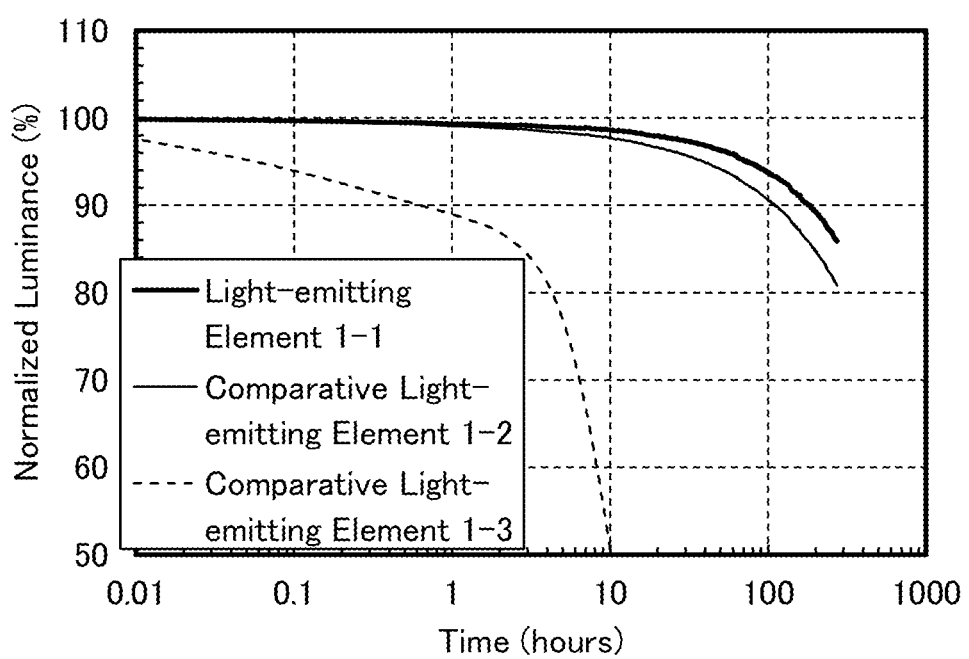
FIG. 31 shows reliability of the light-emitting element 1-1, the comparative light-emitting element 1-2, and the comparative light-emitting element 1-3.
Figure 32:
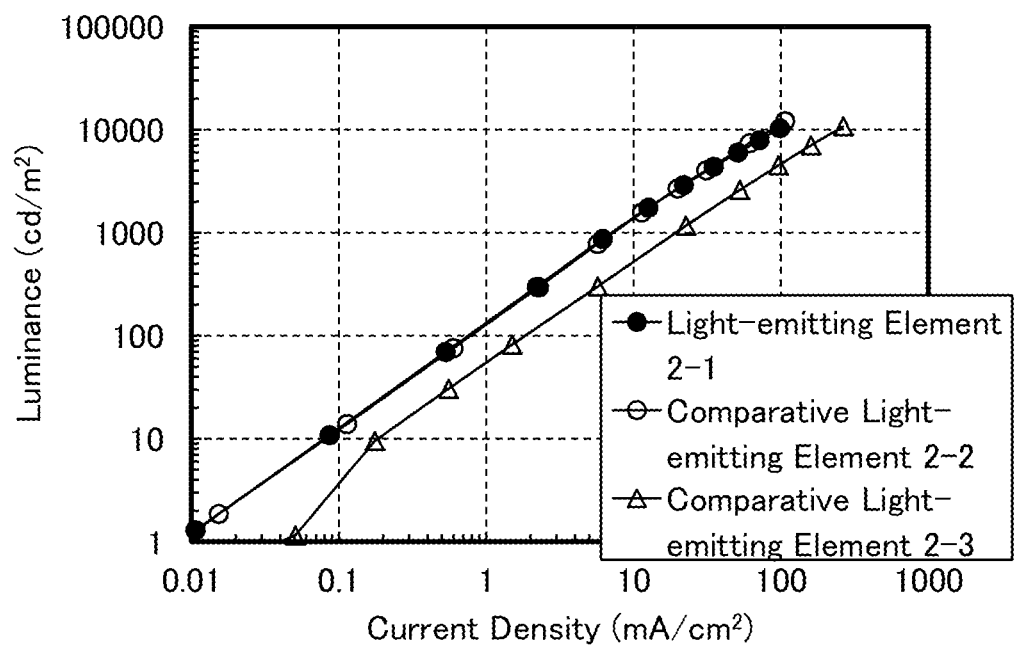
FIG. 32 shows current density-luminance characteristics of a light-emitting element 2-1, a comparative light-emitting element 2-2, and a comparative light-emitting element 2-3.
Figure 33:
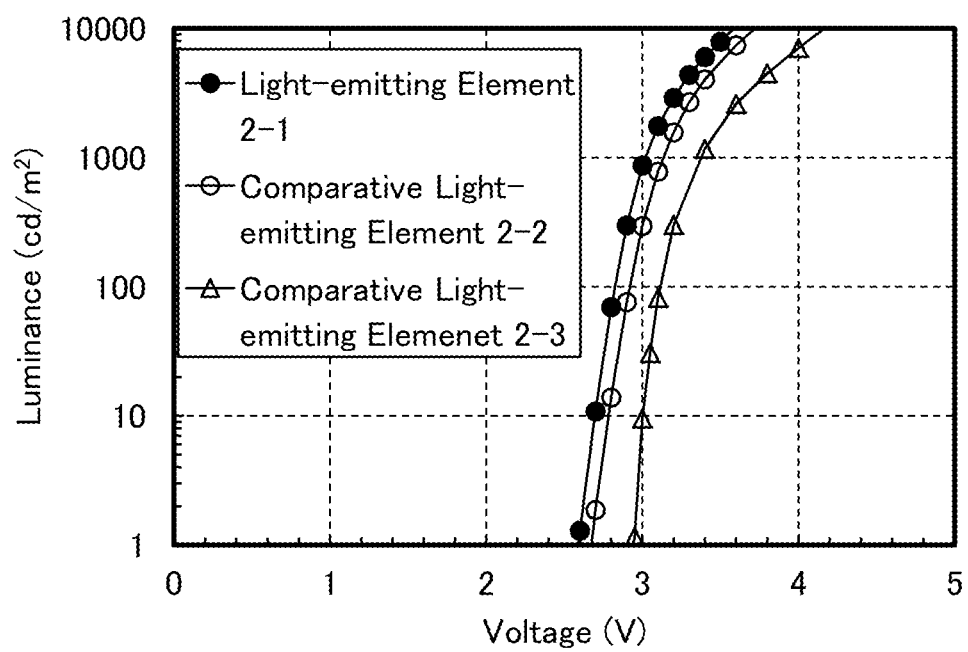
FIG. 33 shows voltage-luminance characteristics of the light-emitting element 2-1, the comparative light-emitting element 2-2, and the comparative light-emitting element 2-3.
Figure 34:
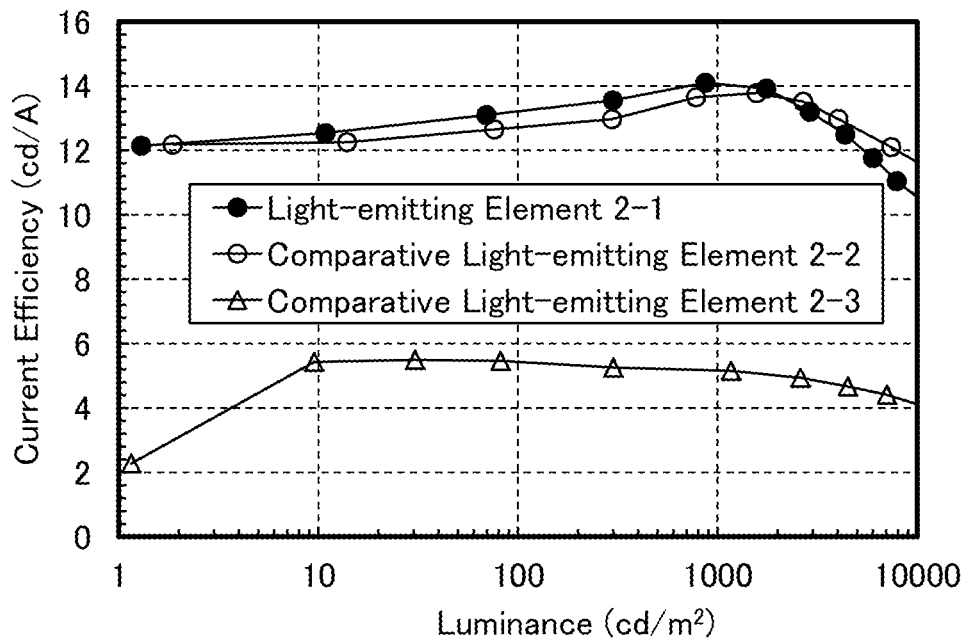
FIG. 34 shows luminance-current efficiency characteristics of the light-emitting element 2-1, the comparative light-emitting element 2-2, and the comparative light-emitting element 2-3.
Figure 35:
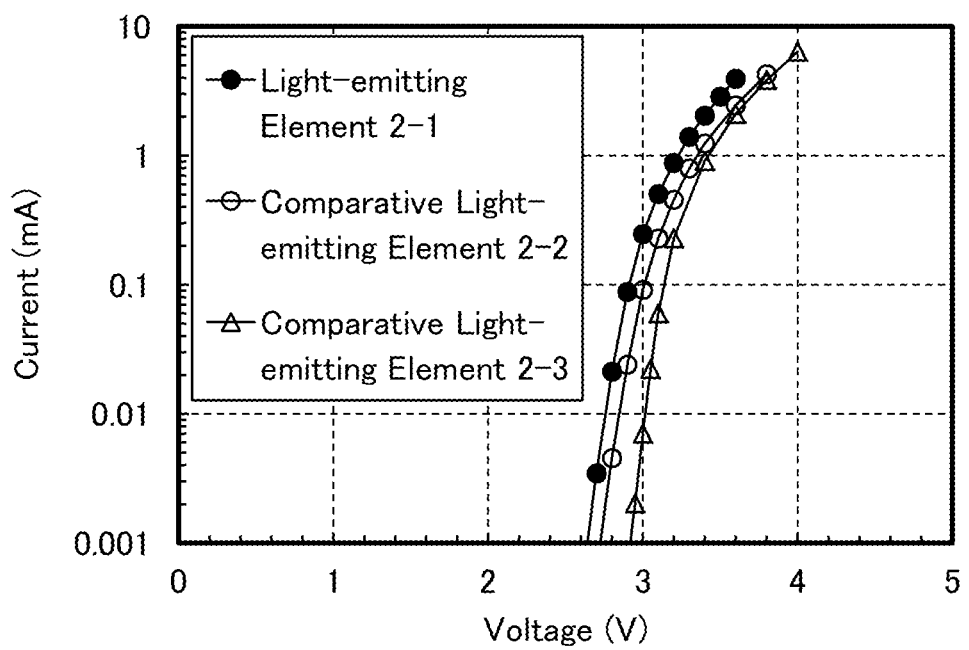
FIG. 35 shows voltage-current characteristics of the light-emitting element 2-1, the comparative light-emitting element 2-2, and the comparative light-emitting element 2-3.

Next, reliability tests were performed on the light-emitting elements. FIG. 31 shows results of the reliability tests. In FIG. 31, the vertical axis represents normalized luminance (%) with an initial luminance of 100%, and the horizontal axis represents driving time (h) of the elements. Note that in the reliability tests, the light-emitting elements were driven under the conditions where the initial luminance was set to 5000 cd/m$^2$ and the current density was constant.

FIG. 31 shows that the comparative light-emitting element 1-3 significantly deteriorates. In contrast, the comparative light-emitting element 1-2 has relatively favorable reliability, and the light-emitting element 1-1 has higher reliability than the comparative light-emitting element 1-2. The skeleton of 2Ph-CzPA is a molecular skeleton obtained by combining the skeleton of CzPA with that of 2PPA. However, the driving lifetime of the light-emitting element including 2Ph-CzPA is not the average value between the driving lifetimes of the light-emitting element including CzPA and the light-emitting element including 2PPA; the driving lifetime of the light-emitting element including 2Ph-CzPA is longer than the relatively long driving lifetime of the light-emitting element including CzPA. This can be said to be an unpredictable and extraordinary effect. This long lifetime is probably because introduction of a phenyl group lowers the LUMO level and a carbazole skeleton receives a hole and stabilizes the morphology of a film at the same time. In other words, the long lifetime of the light-emitting element including 2Ph-CzPA is an indivisible effect of a carbazole skeleton and a phenyl group bonded to the 3-position of an anthracene skeleton.

Example 4

In this example, as a light-emitting element of one embodiment of the present invention, a light-emitting element 2-1 including 2Ph-CzPA whose synthesis method is described in Example 1 as a host material of a light-emitting layer was fabricated. In addition, as comparative light-emitting elements, a comparative light-emitting element 2-2 including CzPA as a host material of a light-emitting layer, and a comparative light-emitting element 2-3 including 2PPA as a host material of a light-emitting layer were fabricated. The measurement results of the characteristics of these light-emitting elements are shown. Note that in this example, the methods for fabricating the light-emitting element 2-1, the comparative light-emitting element 2-2, and the comparative light-emitting element 2-3 were the same as those described in Example 3 except that 3-[4-(9-phenanthryl)-phenyl]-9-phenyl-9H-carbazole (abbreviation: PCPPn) was used instead of PCzPA for the hole-injection layer 911 and the hole-transport layer 912, and the description is omitted here. Chemical formulae of materials used in this example are shown below.

[Chemical formulae 44]

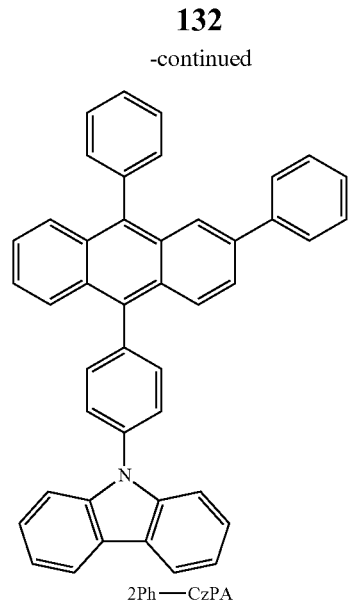

2Ph—CzPA (100)

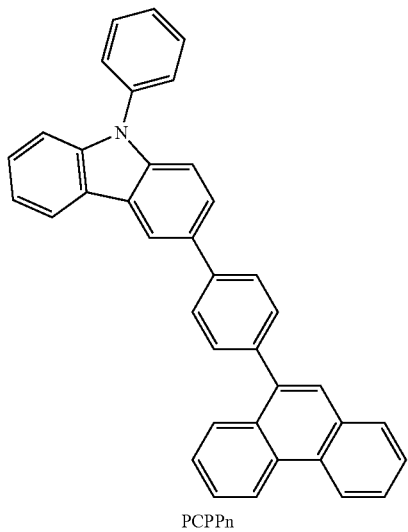

PCPPn

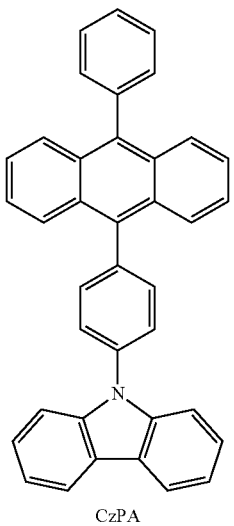

CzPA

133
-continued

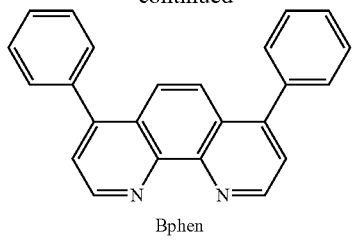

Bphen

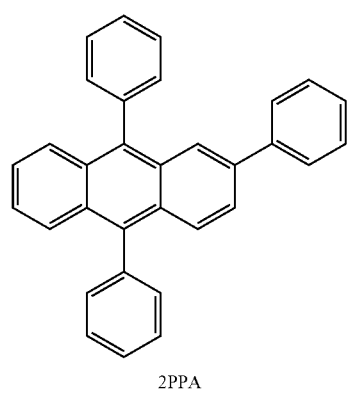

2PPA

134
-continued

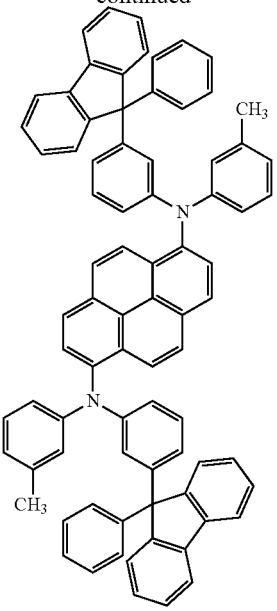

1,6mMemFLPAPrn

<<Fabrication of Light-Emitting Element 2-1, Comparative Light-Emitting Element 2-2, and Comparative Light-Emitting Element 2-3>>

Table 3 shows the element structures of the light-emitting element 2-1, the comparative light-emitting element 2-2, and the comparative light-emitting element 2-3 fabricated in this example.

TABLE 3

| | First electrode | Hole-injection layer | Hole-transport layer | Light-emitting layer | Electron-transport layer | Electron-injection layer | Second electrode |
|---|---|---|---|---|---|---|---|
| Light-emitting element 2-1 | ITO (70 nm) | PCPPn:MoOx (4:2 10 nm) | PCPPn (30 nm) | * | 2Ph-CzPA (10 nm) | Bphen (15 nm) | LiF (1 nm) | Al (200 nm) |
| Comparative light-emitting element 2-2 | ITO (70 nm) | PCPPn:MoOx (4:2 10 nm) | PCPPn (30 nm) | ** | CzPA (10 nm) | Bphen (15 nm) | LiF (1 nm) | Al (200 nm) |
| Comparative light-emitting element 2-3 | ITO (70 nm) | PCPPn:MoOx (4:2 10 nm) | PCPPn (20 nm) | *** | 2PPA (10 nm) | Bphen (15 nm) | LiF (1 nm) | Al (200 nm) |

* 2Ph-CzPA:1,6mMemFLPAPrn (1:0.03 25 nm)
** CzPA:1,6mMemFLPAPrn (1:0.03 25 nm)
*** 2PPA:1,6mMemFLPAPrn (1:0.03 25 nm)

<<Operation Characteristics of Light-Emitting Element 2-1, Comparative Light-Emitting Element 2-2, and Comparative Light-Emitting Element 2-3>>

Operation characteristics of the fabricated light-emitting elements were measured. Note that the measurement was carried out at room temperature (under an atmosphere where a temperature was maintained at 25° C.).

FIG. 32, FIG. 33, FIG. 34, and FIG. 35 show current density-luminance characteristics, voltage-luminance characteristics, luminance-current efficiency characteristics, and voltage-current characteristics, respectively, of the light-emitting element 2-1, the comparative light-emitting element 2-2, and the comparative light-emitting element 2-3.

Table 4 shows initial values of main characteristics of the light-emitting elements at around 1000 cd/m$^2$.

TABLE 4

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 2-1 | 3.0 | 0.25 | 6.2 | (0.14, 0.17) | 870 | 14 | 15 | 12 |
| Comparative light-emitting element 2-2 | 3.1 | 0.23 | 5.7 | (0.14, 0.17) | 780 | 14 | 14 | 12 |
| Comparative light-emitting element 2-3 | 3.4 | 0.91 | 23 | (0.14, 0.14) | 1200 | 5.2 | 4.8 | 5.0 |

Figure 36:
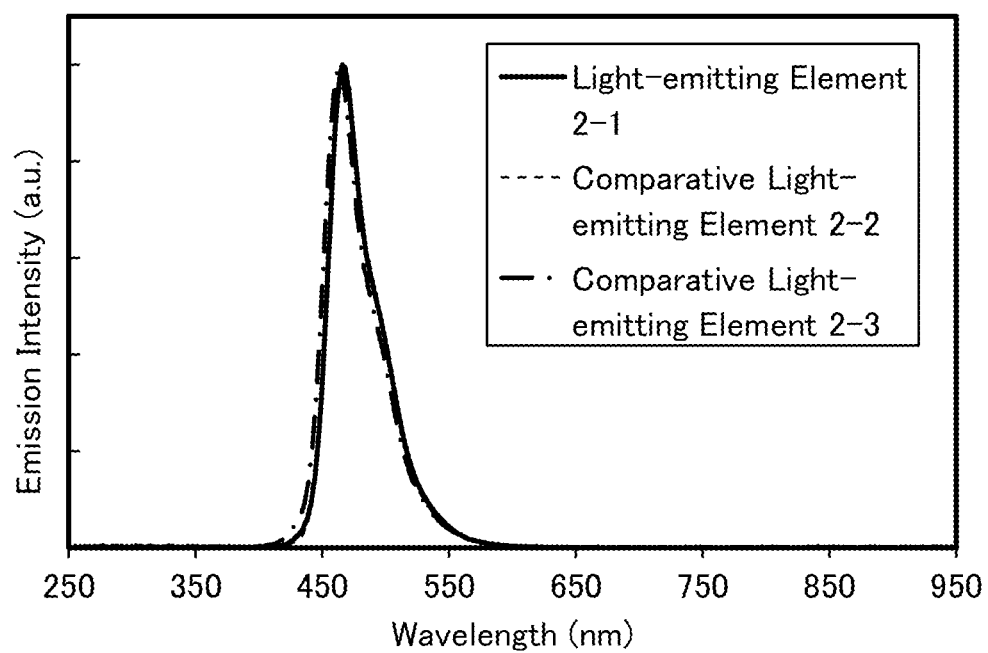
FIG. 36 shows emission spectra of the light-emitting element 2-1, the comparative light-emitting element 2-2, and the comparative light-emitting element 2-3.

FIG. 36 shows emission spectra when a current at a current density of 12.5 mA/cm$^2$ was supplied to the light-emitting elements. In FIG. 36, the emission spectrum of the light-emitting element 2-1 has a peak at around 466 nm, which is presumably derived from blue light emission of 1,6mMemFLPAPrn that is the organic compound used in the EL layer of the light-emitting element 2-1.

Figure 37:
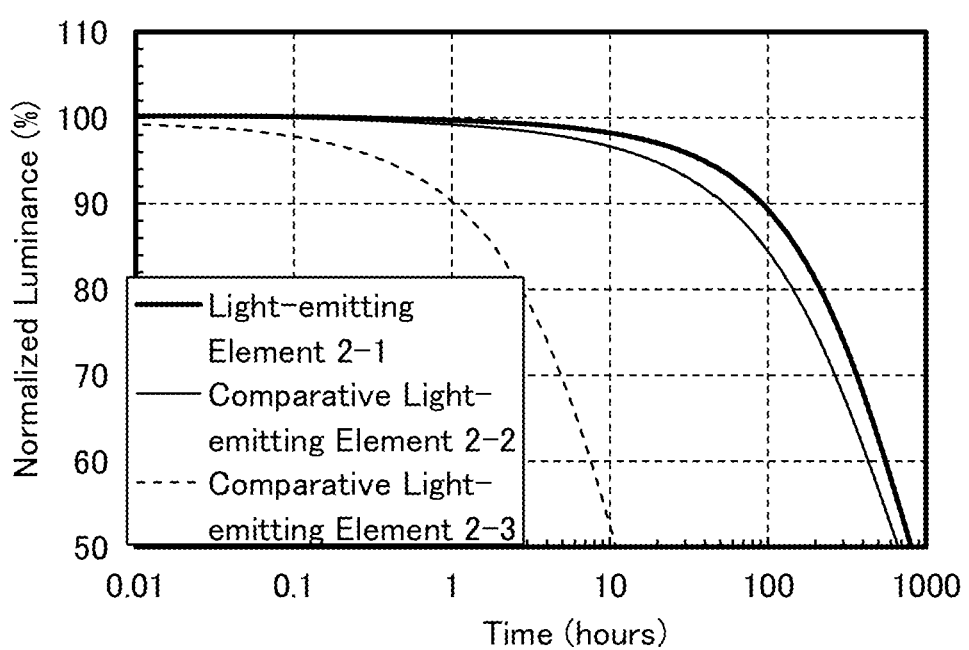
FIG. 37 shows reliability of the light-emitting element 2-1, the comparative light-emitting element 2-2, and the comparative light-emitting element 2-3.
Figure 38:
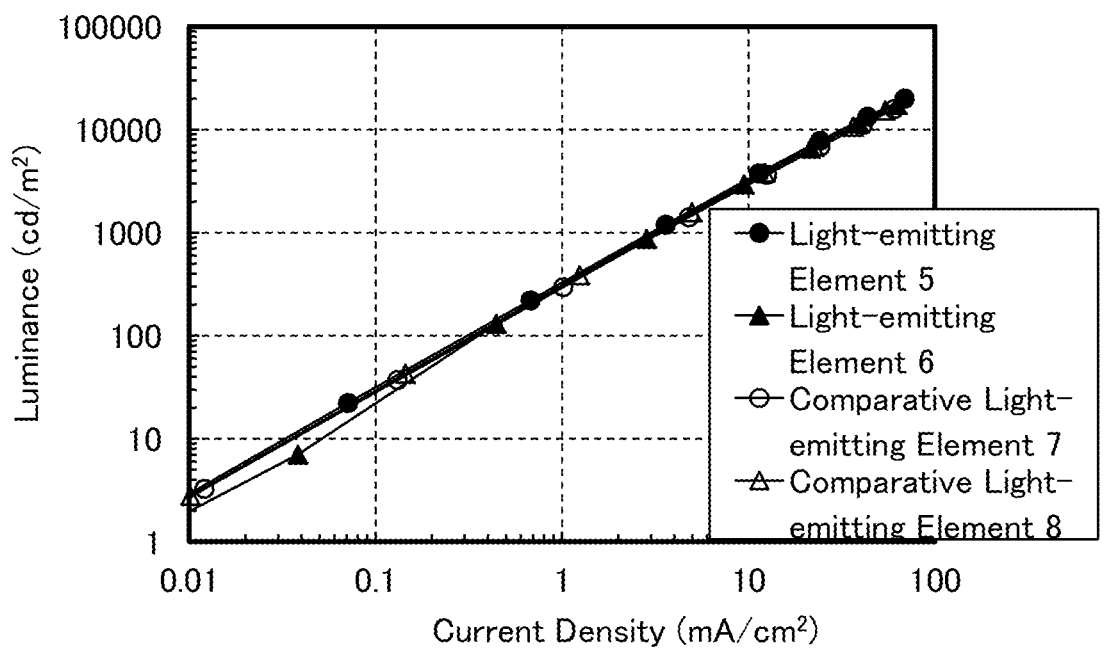
FIG. 38 shows current density-luminance characteristics of a light-emitting element 5, a light-emitting element 6, a comparative light-emitting element 7, and a comparative light-emitting element 8.
Figure 39:
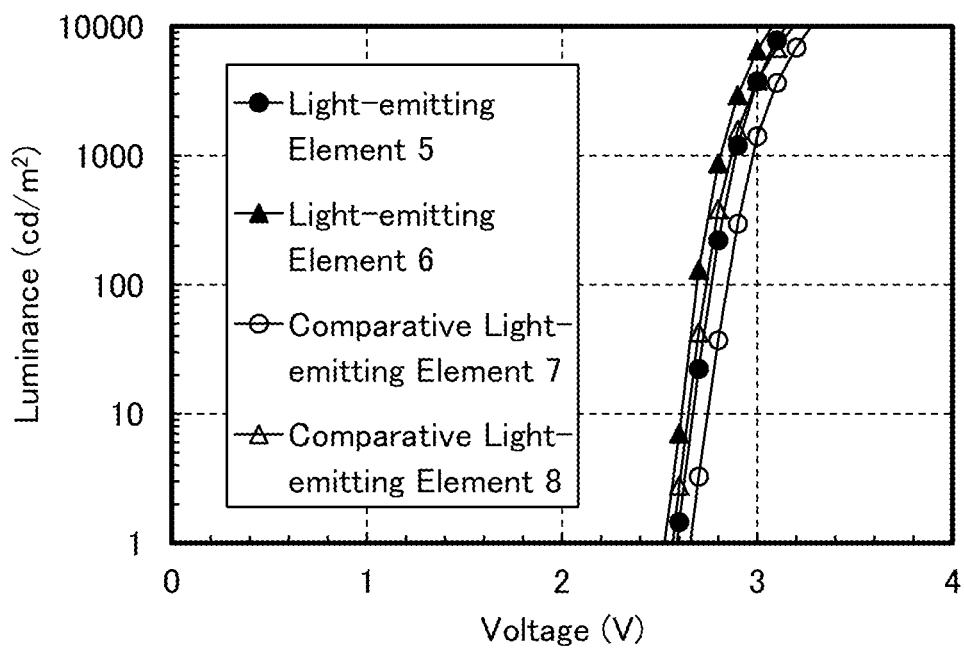
FIG. 39 shows voltage-luminance characteristics of the light-emitting element 5, the light-emitting element 6, the comparative light-emitting element 7, and the comparative light-emitting element 8.
Figure 40:
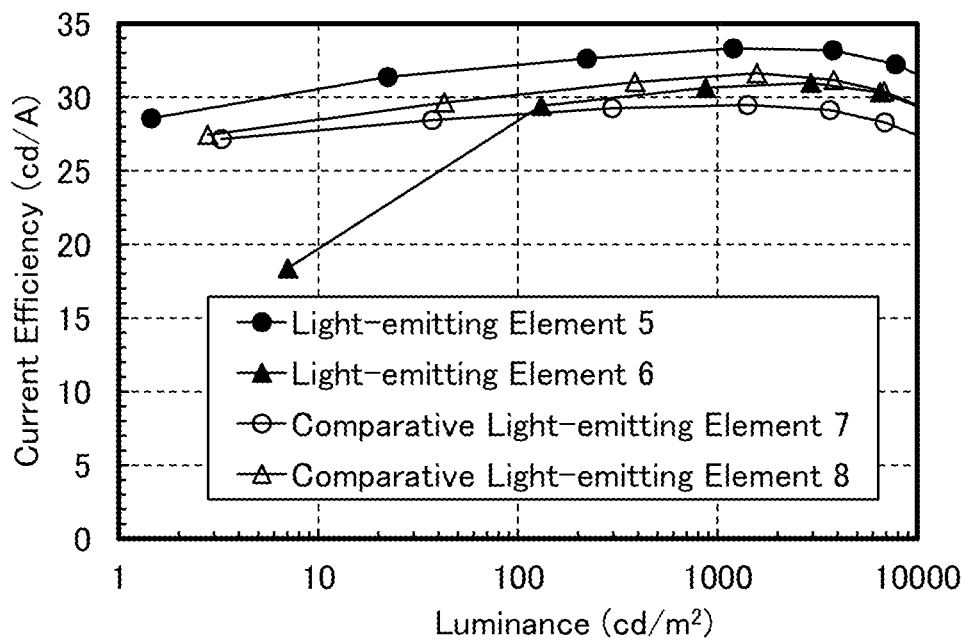
FIG. 40 shows luminance-current efficiency characteristics of the light-emitting element 5, the light-emitting element 6, the comparative light-emitting element 7, and the comparative light-emitting element 8.
Figure 41:
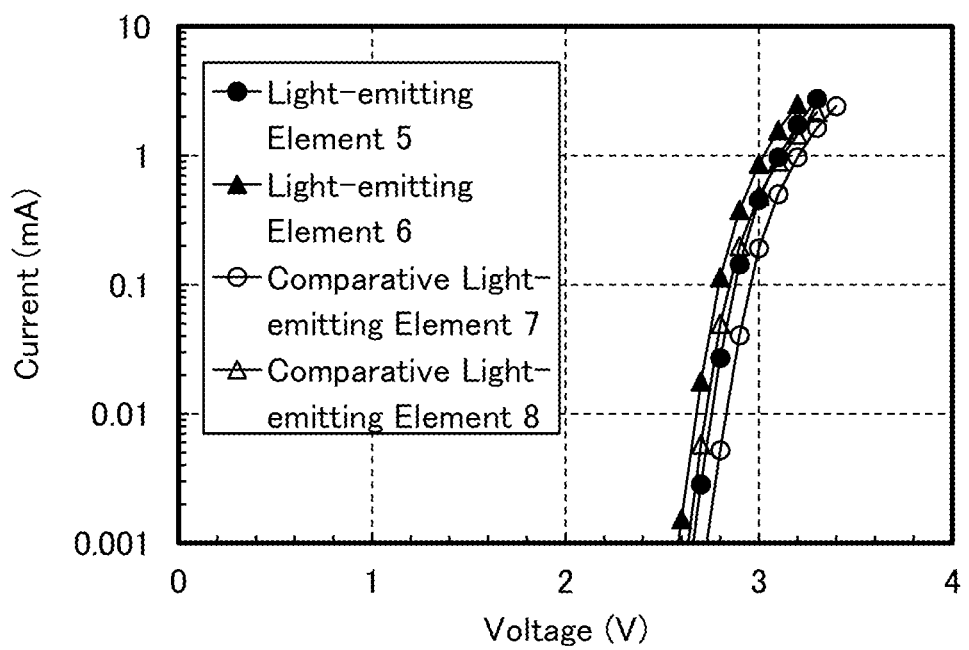
FIG. 41 shows voltage-current characteristics of the light-emitting element 5, the light-emitting element 6, the comparative light-emitting element 7, and the comparative light-emitting element 8.

Next, reliability tests were performed on the light-emitting elements. FIG. 37 shows results of the reliability tests. In FIG. 37, the vertical axis represents normalized luminance (%) with an initial luminance of 100%, and the horizontal axis represents driving time (h) of the elements. Note that in the reliability tests, the light-emitting elements were driven under the conditions where the initial luminance was set to 5000 cd/m$^2$ and the current density was constant.

When the light-emitting element 2-1 is compared with the comparative light-emitting elements, the same tendencies as those in Example 3 are shown as for the emission efficiency, the drive voltage, and the reliability. In other words, even when another compound is used for the hole-transport layer, the use of 2Ph-CzPA as a host can produce the same effects as those described in Example 3. As a result, the light-emitting element 2-1 can achieve efficiency as high as that of the comparative light-emitting element 2-2, and in addition, unpredictably low drive voltage and long lifetime.

Note that PCPPn, which is a material with a high LUMO level, was used for the HTL in fabricating the light-emitting element 2-1, the comparative light-emitting element 2-2, and the comparative light-emitting element 2-3. Owing to its high LUMO level, PCPPn has an electron blocking property. Thus, as compared with PCzPA used for the light-emitting element 1-1, PCPPn prevents electron carriers from moving to the HTL and increases the recombination rate in the light-emitting layer, which contributes to an increase in efficiency of the light-emitting element 2-1.

Example 5

In this example, as light-emitting elements of embodiments of the present invention, a light-emitting element 5 including 2Ph-CzPA whose synthesis method is described in Example 1 as a host material of a light-emitting layer, and a light-emitting element 6 including 2Ph-cgDBCzPA whose synthesis method is described in Example 2 as a host material of a light-emitting layer were fabricated. In addition, as comparative light-emitting elements, a comparative light-emitting element 7 including CzPA as a host material of a light-emitting layer, and a comparative light-emitting element 8 including cgDBCzPA as a host material of a light-emitting layer were fabricated. The measurement results of the characteristics of these light-emitting elements are shown. Note that in this example, the methods for fabricating the light-emitting element 5, the light-emitting element 6, the comparative light-emitting element 7, and the comparative light-emitting element 8 were the same as those described in Example 3 except that N,N'-bis(3-methylphenyl)-N,N'-bis[3-(9-phenyl-9H-fluoren-9-yl)phenyl]-anthracene-9,10-diamine (abbreviation: 9,10mMemFLPA2A) was used as a guest material of the light-emitting layer, and the description is omitted here. Chemical formulae of materials used in this example are shown below.

[Chemical formulae 45]

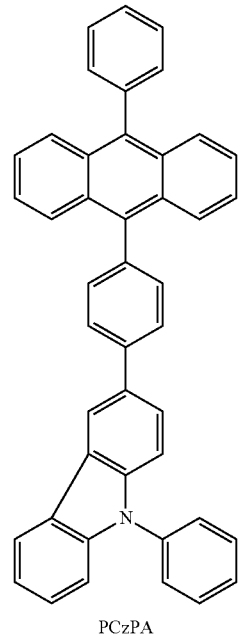

PCzPA

-continued

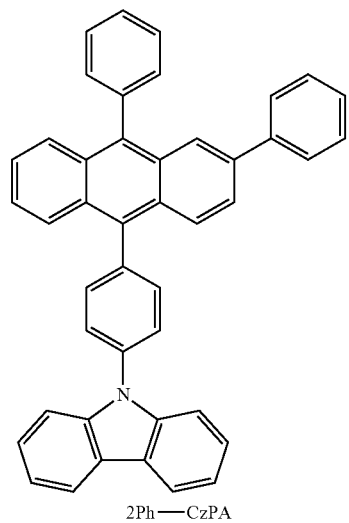
2Ph—CzPA

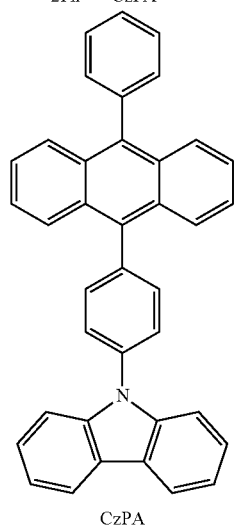
CzPA (200)

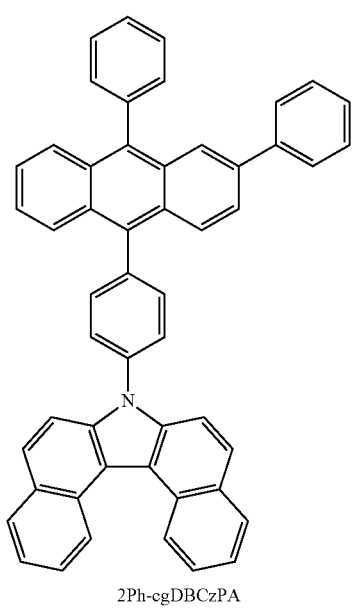
2Ph-cgDBCzPA

-continued (100)

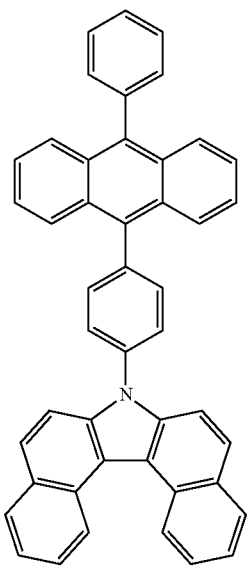
cgDBCzPA

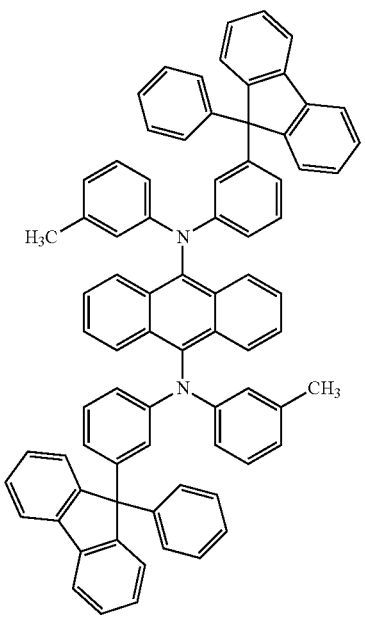
9,10mMemFLPA2A

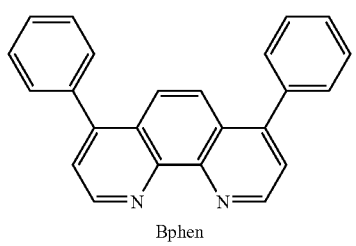
Bphen

<<Fabrication of Light-Emitting Element 5, Light-Emitting Element 6, Comparative Light-Emitting Element 7, and Comparative Light-Emitting Element 8>>

Table 5 shows the element structures of the light-emitting element 5, the light-emitting element 6, the comparative light-emitting element 7, and the comparative light-emitting element 8 fabricated in this example.

TABLE 5

|  | First electrode | Hole-injection layer | Hole-transport layer | Light-emitting layer | Electron-transport layer | Electron-injection layer | Second electrode |
|---|---|---|---|---|---|---|---|
| Light-emitting element 5 | ITO (70 nm) | PCzPA:MoOx (4:2 10 nm) | PCzPA (30 nm) | * | 2Ph-CzPA (10 nm) | Bphen (15 nm) | LiF (1 nm) | Al (200 nm) |
| Light-emitting element 6 | ITO (70 nm) | PCzPA:MoOx (4:2 10 nm) | PCzPA (30 nm) | ** | 2Ph-cgDBCzPA (10 nm) | Bphen (15 nm) | LiF (1 nm) | Al (200 nm) |
| Comparative light-emitting element 7 | ITO (70 nm) | PCzPA:MoOx (4:2 10 nm) | PCzPA (30 nm) | *** | CzPA (10 nm) | Bphen (15 nm) | LiF (1 nm) | Al (200 nm) |
| Comparative light-emitting element 8 | ITO (70 nm) | PCzPA:MoOx (4:2 10 nm) | PCzPA (30 nm) | **** | cgDBCzPA (10 nm) | Bphen (15 nm) | LiF (1 nm) | Al (200 nm) |

* 2Ph-CzPA:9,10mMemFLPA2A (1:0.1 25 nm)
** 2Ph-cgDBCzPA:9,10mMemFLPA2A (1:0.1 25 nm)
*** CzPA:9,10mMemFLPA2A (1:0.1 25 nm)
**** cgDBCzPA:9,10mMemFLPA2A (1:0.1 25 nm)

<<Operation Characteristics of Light-Emitting Element 5, Light-Emitting Element 6, Comparative Light-Emitting Element 7, and Comparative Light-Emitting Element 8>>

Operation characteristics of the light-emitting element 5, the light-emitting element 6, the comparative light-emitting element 7, and the comparative light-emitting element 8 were measured. Note that the measurement was carried out at room temperature (under an atmosphere where a temperature was maintained at 25° C.).

FIG. 38, FIG. 39, FIG. 40, and FIG. 41 show current density-luminance characteristics, voltage-luminance characteristics, luminance-current efficiency characteristics, and voltage-current characteristics, respectively, of the light-emitting element 5, the light-emitting element 6, the comparative light-emitting element 7, and the comparative light-emitting element 8.

Table 6 shows initial values of main characteristics of the light-emitting elements at around 1000 cd/m$^2$.

TABLE 6

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 5 | 2.9 | 0.140 | 3.6 | (0.27, 0.67) | 1200 | 33 | 36 | 9.1 |
| Light-emitting element 6 | 2.8 | 0.110 | 2.8 | (0.27, 0.67) | 870 | 31 | 34 | 8.3 |
| Comparative light-emitting element 7 | 3.0 | 0.19 | 4.8 | (0.26, 0.66) | 1400 | 29 | 31 | 8.2 |
| Comparative light-emitting element 8 | 2.9 | 0.20 | 5.0 | (0.27, 0.67) | 1600 | 32 | 34 | 8.5 |

Figure 42:
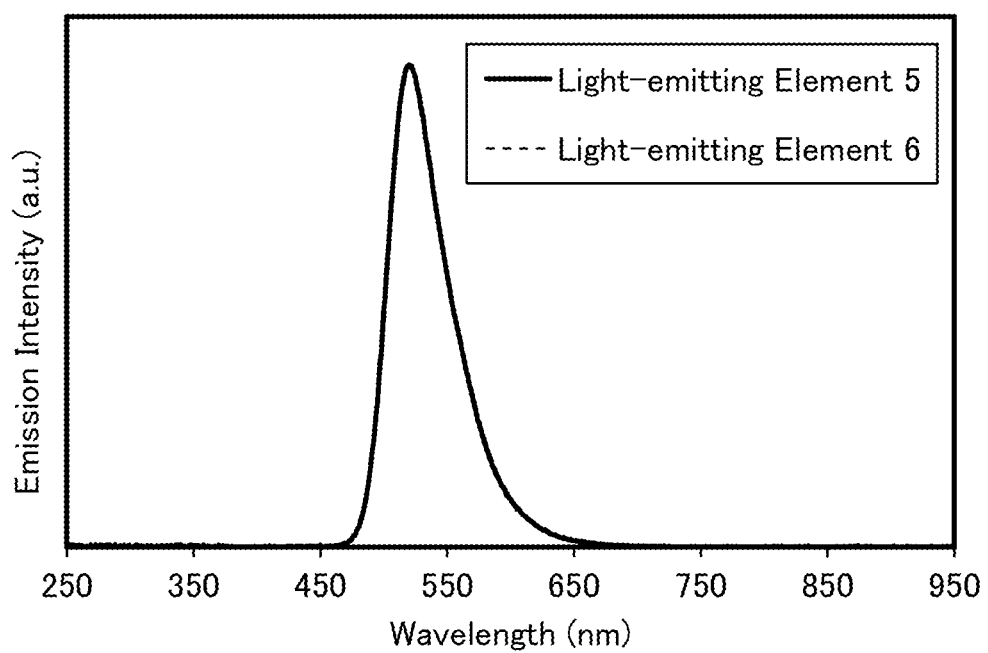
FIG. 42 shows emission spectra of the light-emitting element 5 and the light-emitting element 6.

FIG. 42 shows emission spectra when a current at a current density of 12.5 mA/cm$^2$ was supplied to the light-emitting element 5 and the light-emitting element 6. In FIG. 42, each of the emission spectra of the light-emitting element 5 and the light-emitting element 6 has a peak at around 522 nm, which is presumably derived from green light emission of 9,10mMemFLPA2A that is the organic compound used for the EL layer of each light-emitting element. Although not shown in FIG. 42, the emission spectra of the comparative light-emitting element 7 and the comparative light-emitting element 8 were also derived from 9,10mMemFLPA2A.

What is important is that the drive voltage of the light-emitting element 5 (2Ph-CzPA) is lower than that of the comparative light-emitting element 7 (CzPA). It is demonstrated that the unpredictable effect of 2Ph-CzPA on the drive voltage, which is described in Example 3, is also exhibited even when another light-emitting dopant is used. The emission efficiency of the light-emitting 5 (2Ph-CzPA) is higher than that of the comparative light-emitting element 7 (CzPA). This is presumably because the efficiency of energy transfer to a dopant emitting green light is improved.

It is also notable that the drive voltage of the light-emitting element 6 (2Ph-cgDBCzPA) is lower than that of the comparative light-emitting element 8 (cgDBCzPA). The skeleton of 2Ph-cgDBCzPA is a molecular skeleton obtained by combining the skeleton of cgDBCzPA with that of 2PPA. However, the drive voltage of the light-emitting element including 2Ph-cgDBCzPA is not the average value between the drive voltages of the light-emitting element including 2PPA that has high drive voltage and the light-emitting element including cgDBCzPA; the drive voltage of the light-emitting element including 2Ph-cgDBCzPA is lower than the relatively low drive voltage of the light-emitting element including cgDBCzPA. This can be said to be an unpredictable and extraordinary effect. From the CV measurement results, the HOMO level of cgDBCzPA is −5.69 eV and the LUMO level thereof is −2.74 eV, whereas the HOMO level of 2Ph-cgDBCzPA is −5.70 eV and the LUMO level thereof is −2.81 eV. That is, it is probable that the gap between the HOMO level and the LUMO level of 2Ph-cgDBCzPA is slightly decreased and the drive voltage is correspondingly reduced only when both a carbazole skeleton and a phenyl group bonded to the 3-position of an anthracene skeleton are included. Specifically in this case, an influence on the LUMO level is large. Note that this result demonstrates that the effect of one embodiment of the present invention can also be obtained when a carbazole skeleton includes a condensed ring instead of having a monocyclic structure. In other words, including a carbazole skeleton is essential to the present invention.

Figure 43:
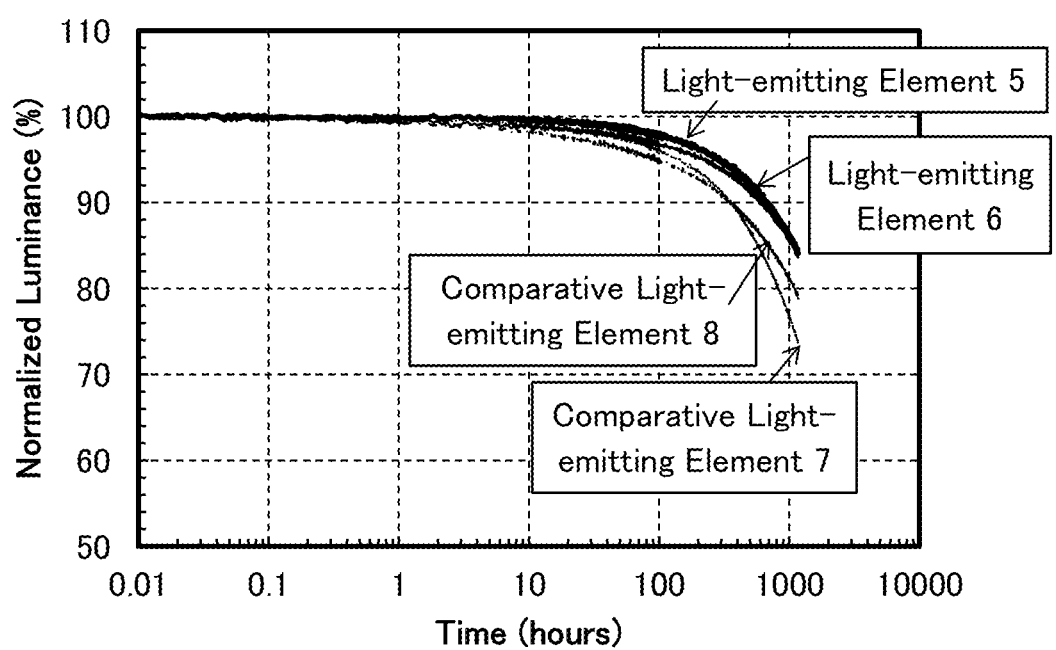
FIG. 43 shows reliability of the light-emitting element 5, the light-emitting element 6, the comparative light-emitting element 7, and the comparative light-emitting element 8.
Figure 44:
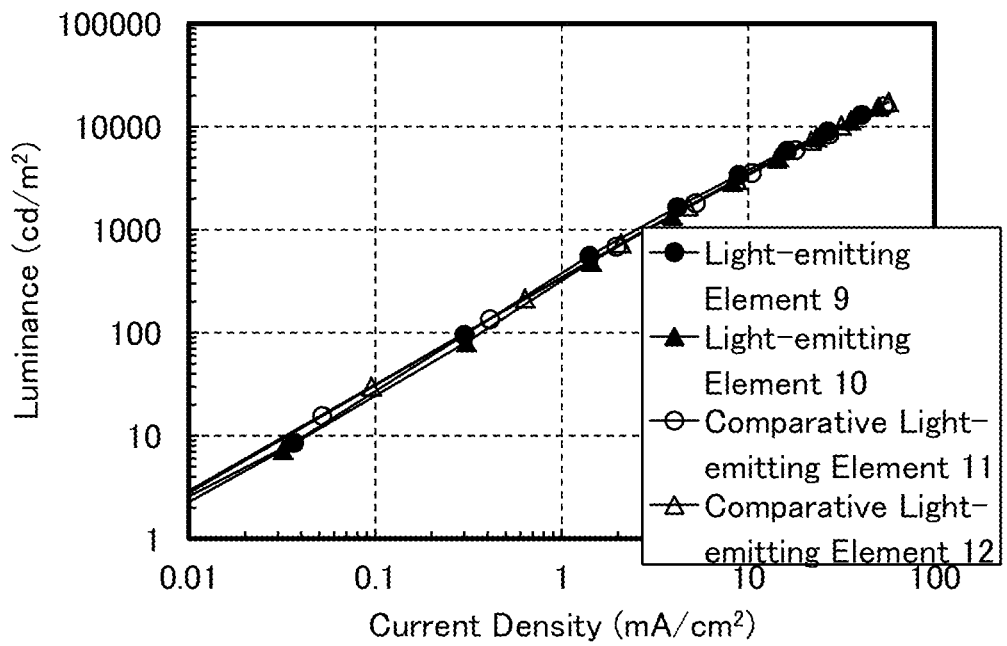
FIG. 44 shows current density-luminance characteristics of a light-emitting element 9, a light-emitting element 10, a comparative light-emitting element 11, and a comparative light-emitting element 12.
Figure 45:
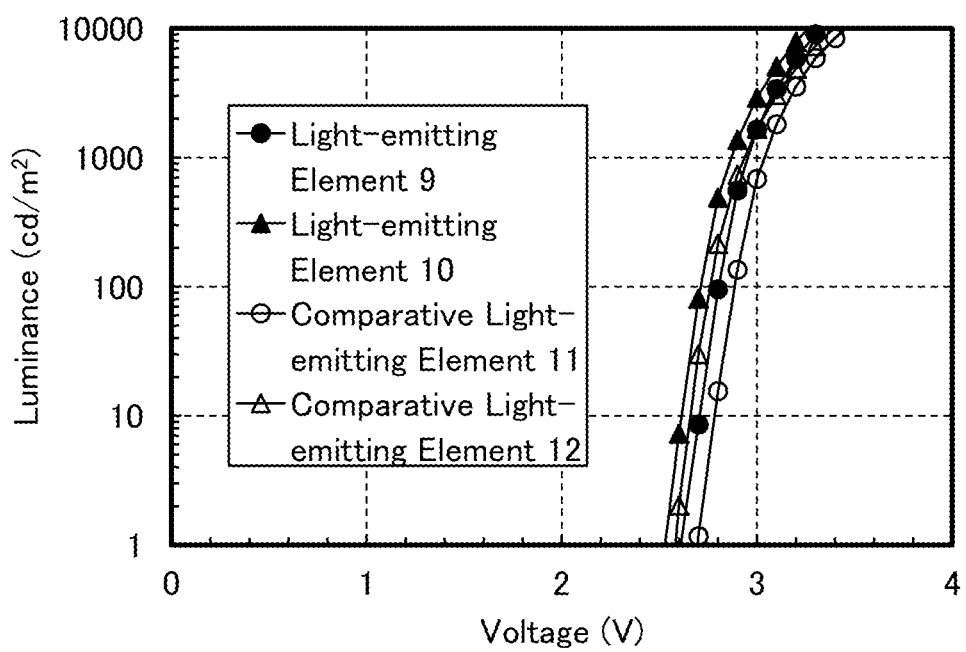
FIG. 45 shows voltage-luminance characteristics of the light-emitting element 9, the light-emitting element 10, the comparative light-emitting element 11, and the comparative light-emitting element 12.
Figure 46:
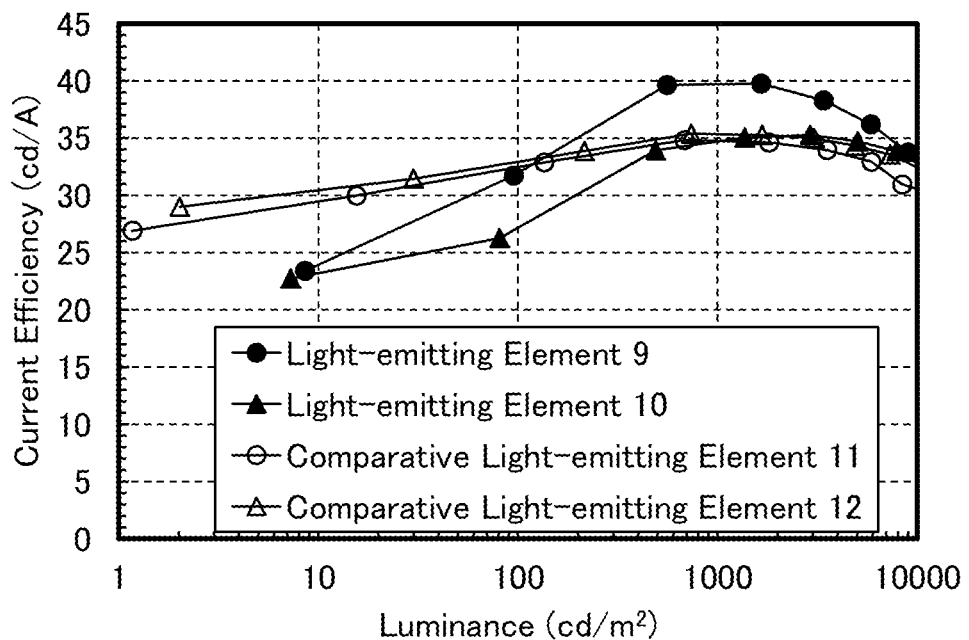
FIG. 46 shows luminance-current efficiency characteristics of the light-emitting element 9, the light-emitting element 10, the comparative light-emitting element 11, and the comparative light-emitting element 12.
Figure 47:
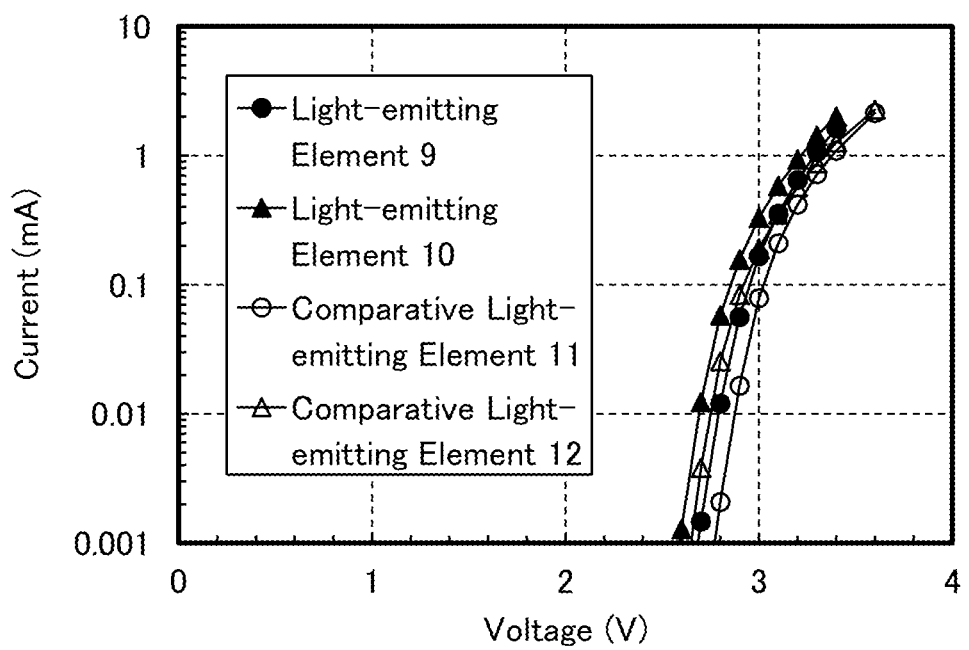
FIG. 47 shows voltage-current characteristics of the light-emitting element 9, the light-emitting element 10, the comparative light-emitting element 11, and the comparative light-emitting element 12.

Next, reliability tests were performed on the light-emitting elements. FIG. 43 shows results of the reliability tests. In FIG. 43, the vertical axis represents normalized luminance (%) with an initial luminance of 100%, and the horizontal axis represents driving time (h) of the elements. Note that in the reliability tests, the light-emitting elements were driven under the conditions where the initial luminance was set to 5000 cd/m² and the current density was constant.

As shown in FIG. 43, the reliability of the light-emitting element 5 is higher than that of the comparative light-emitting element 7. It is demonstrated that the unpredictable effect of 2Ph-CzPA on the driving lifetime, which is described in Example 3, is also exhibited even when another light-emitting dopant is used.

In addition, it is shown that the reliability of the light-emitting element 6 is higher than that of the comparative light-emitting element 8. The skeleton of 2Ph-cgDBCzPA is a molecular skeleton obtained by combining the skeleton of cgDBCzPA with that of 2PPA. However, the driving lifetime of the light-emitting element including 2Ph-cgDBCzPA is not the average value between the drive voltages of the light-emitting element including 2PPA that has extremely short driving lifetime and the light-emitting element including cgDBCzPA; the driving lifetime of 2Ph-cgDBCzPA is longer than the relatively long driving lifetime of the light-emitting element including cgDBCzPA. This can be said to be an unpredictable and extraordinary effect. This long lifetime is probably because introduction of a phenyl group lowers the LUMO level and a carbazole skeleton receives a hole and stabilizes the morphology of a film at the same time. In other words, the long lifetime of the light-emitting element including 2Ph-cgDBCzPA is an indivisible effect of a carbazole skeleton and a phenyl group bonded to the 3-position of an anthracene skeleton. In addition, this result demonstrates that the effect of one embodiment of the present invention can also be obtained when a carbazole skeleton includes a condensed ring instead of having a monocyclic structure. In other words, including a carbazole skeleton is essential to the present invention.

Example 6

In this example, as light-emitting elements of embodiments of the present invention, a light-emitting element 9 including 2Ph-CzPA whose synthesis method is described in Example 1 as a host material of a light-emitting layer, and a light-emitting element 10 including 2Ph-cgDBCzPA whose synthesis method is described in Example 2 as a host material of a light-emitting layer were fabricated. In addition, as comparative light-emitting elements, a comparative light-emitting element 11 including CzPA as a host material of a light-emitting layer, and a comparative light-emitting element 12 including cgDBCzPA as a host material of a light-emitting layer were fabricated. The measurement results of the characteristics of these light-emitting elements are shown. Note that in this example, the methods for fabricating the light-emitting element 9, the light-emitting element 10, the comparative light-emitting element 11, and the comparative light-emitting element 12 were the same as those described in Example 5 except that PCPPn was used for the hole-injection layer and the hole-transport layer instead of PCzPA, and the description is omitted here. Chemical formulae of materials used in this example are shown below.

[Chemical formulae 46]

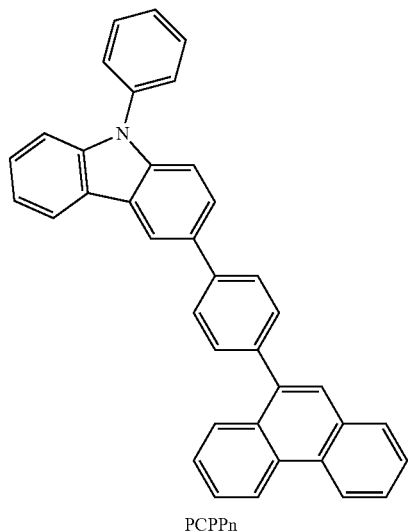

PCPPn

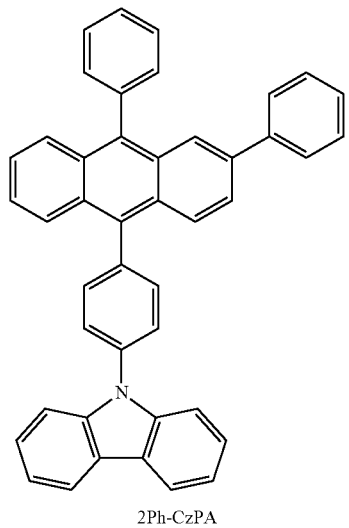

(100)

2Ph-CzPA

-continued

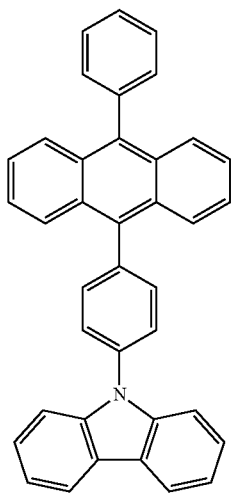
CzPA

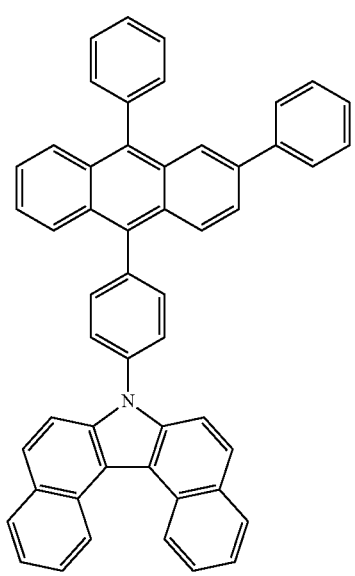
2Ph-cgDBCzPA

-continued

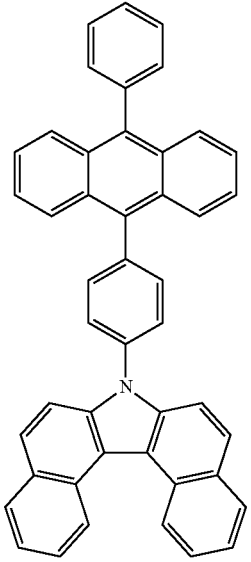
cgDBCzPA

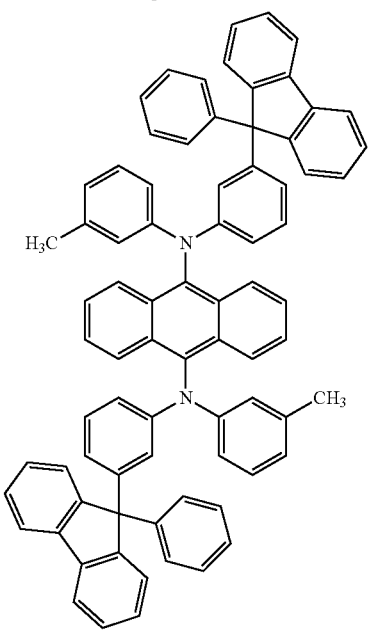
9,10mMemFLPA2A (200)

Bphen

<<Fabrication of Light-Emitting Element 9, Light-Emitting Element 10, Comparative Light-Emitting Element 11, and Comparative Light-Emitting Element 12>>

Table 7 shows the element structures of the light-emitting element 9, the light-emitting element 10, the comparative light-emitting element 11, and the comparative light-emitting element 12 fabricated in this example.

TABLE 7

|  | First electrode | Hole-injection layer | Hole-transport layer | Light-emitting layer | Electron-transport layer | Electron-injection layer | Second electrode |
|---|---|---|---|---|---|---|---|
| Light-emitting element 9 | ITO (70 nm) | PCPPn:MoOx (4:2 10 nm) | PCPPn (30 nm) | * | 2Ph-CzPA (10 nm) | Bphen (15 nm) | LiF (1 nm) | Al (200 nm) |
| Light-emitting element 10 | ITO (70 nm) | PCPPn:MoOx (4:2 10 nm) | PCPPn (30 nm) | ** | 2Ph-cgDBCzPA (10 nm) | Bphen (15 nm) | LiF (1 nm) | Al (200 nm) |
| Comparative light-emitting element 11 | ITO (70 nm) | PCPPn:MoOx (4:2 10 nm) | PCPPn (30 nm) | *** | CzPA (10 nm) | Bphen (15 nm) | LiF (1 nm) | Al (200 nm) |
| Comparative light-emitting element 12 | ITO (70 nm) | PCPPn:MoOx (4:2 10 nm) | PCPPn (30 nm) | **** | cgDBCzPA (10 nm) | Bphen (15 nm) | LiF (1 nm) | Al (200 nm) |

* 2Ph-CzPA:9,10mMemFLPA2A (1:0.1 25 nm)
** 2Ph-cgDBCzPA:9,10mMemFLPA2A (1:0.1 25 nm)
*** CzPA:9,10mMemFLPA2A (1:0.1 25 nm)
**** cgDBCzPA:9,10mMemFLPA2A (1:0.1 25 nm)

<<Operation Characteristics of Light-Emitting Element 9, Light-Emitting Element 10, Comparative Light-Emitting Element 11, and Comparative Light-Emitting Element 12>>

Operation characteristics of the light-emitting element 9, the light-emitting element 10, the comparative light-emitting element 11, and the comparative light-emitting element 12 were measured. Note that the measurement was carried out at room temperature (under an atmosphere where a temperature was maintained at 25° C.).

FIG. 44, FIG. 45, FIG. 46, and FIG. 47 show current density-luminance characteristics, voltage-luminance characteristics, luminance-current efficiency characteristics, and voltage-current characteristics, respectively, of the light-emitting element 9, the light-emitting element 10, the comparative light-emitting element 11, and the comparative light-emitting element 12.

Table 8 shows initial values of main characteristics of the light-emitting elements at around 1000 cd/m$^2$.

Note that in the reliability tests, the light-emitting elements were driven under the conditions where the initial luminance was set to 5000 cd/m$^2$ and the current density was constant.

When the light-emitting element 9 is compared with the comparative light-emitting element 11, the same tendencies as those in Example 5 are shown as for the efficiency, the drive voltage, and the reliability. In other words, even when another compound is used for the hole-transport layer, the use of 2Ph-CzPA as a host can produce the same effects as those described in Example 5. As a result, the light-emitting element 9 can achieve efficiency higher that of the comparative light-emitting element 11, and in addition, unpredictably low drive voltage and long lifetime.

When the light-emitting element 10 is compared with the comparative light-emitting element 12, the same tendencies as those in Example 5 are shown as for the drive voltage and the reliability. In other words, even when another compound is used for the hole-transport layer, the use of 2Ph-cgDBC-

TABLE 8

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 9 | 2.9 | 0.056 | 1.4 | (0.27, 0.66) | 560 | 40 | 43 | 11 |
| Light-emitting element 10 | 2.9 | 0.160 | 3.9 | (0.27, 0.67) | 1400 | 35 | 38 | 9.6 |
| Comparative light-emitting element 11 | 3.0 | 0.079 | 2.0 | (0.26, 0.66) | 680 | 35 | 36 | 9.7 |
| Comparative light-emitting element 12 | 2.9 | 0.083 | 2.1 | (0.27, 0.66) | 740 | 35 | 38 | 9.5 |

Figure 48:
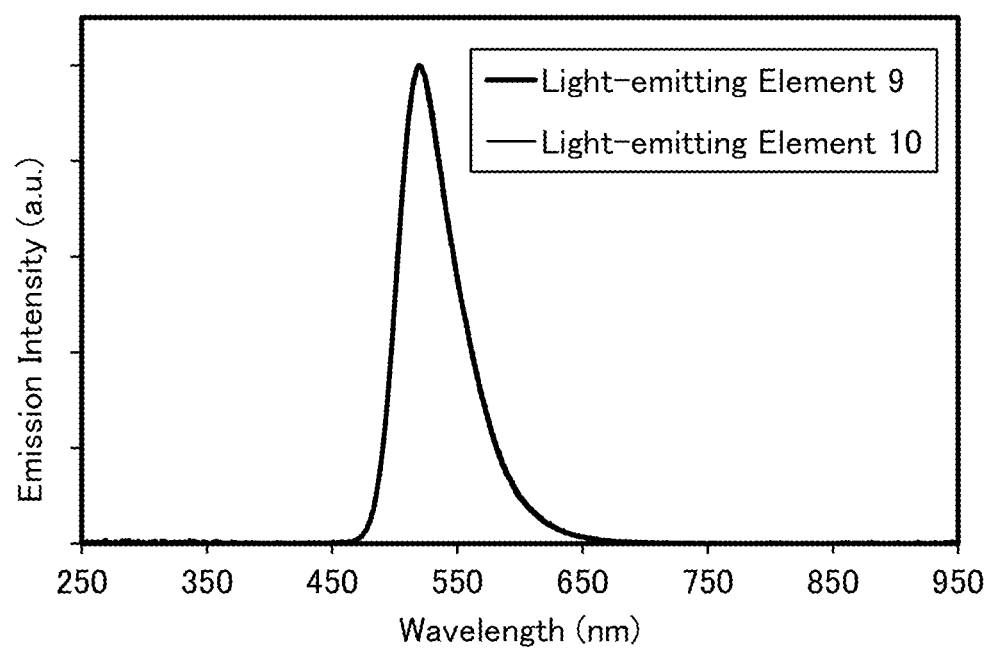
FIG. 48 shows emission spectra of the light-emitting element 9 and the light-emitting element 10.

FIG. 48 shows emission spectra when a current at a current density of 12.5 mA/cm$^2$ was supplied to the light-emitting element 9 and the light-emitting element 10. In FIG. 48, each of the emission spectra of the light-emitting element 9 and the light-emitting element 10 has a peak at around 519 nm, which is presumably derived from green light emission of 9,10mMemFLPA2A that is the organic compound used for the EL layer of each light-emitting element.

Figure 49:
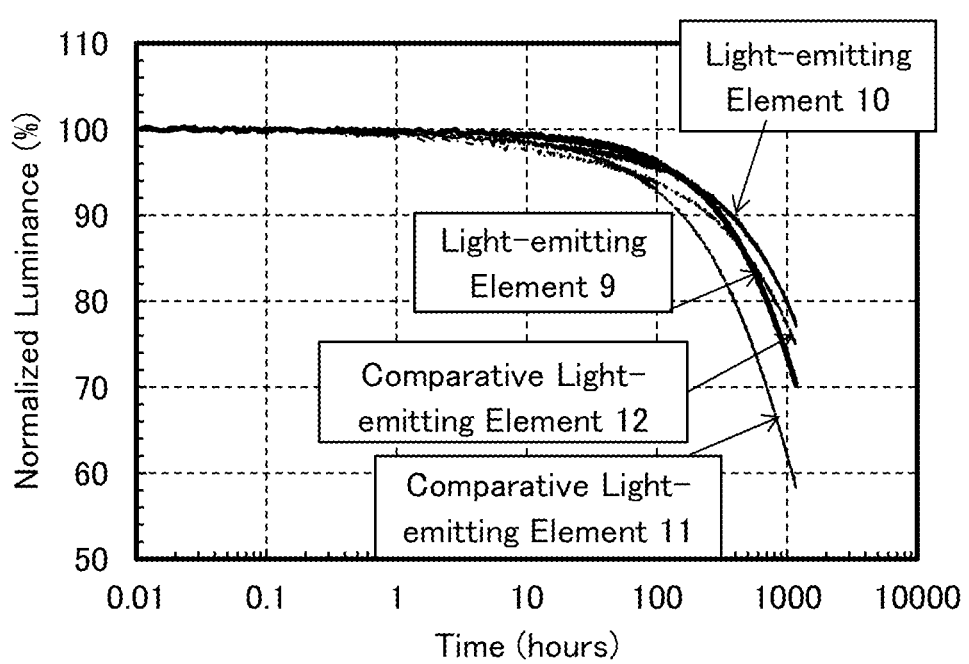
FIG. 49 shows reliability of the light-emitting element 9, the light-emitting element 10, the comparative light-emitting element 11, and the comparative light-emitting element 12.
Figure 50:
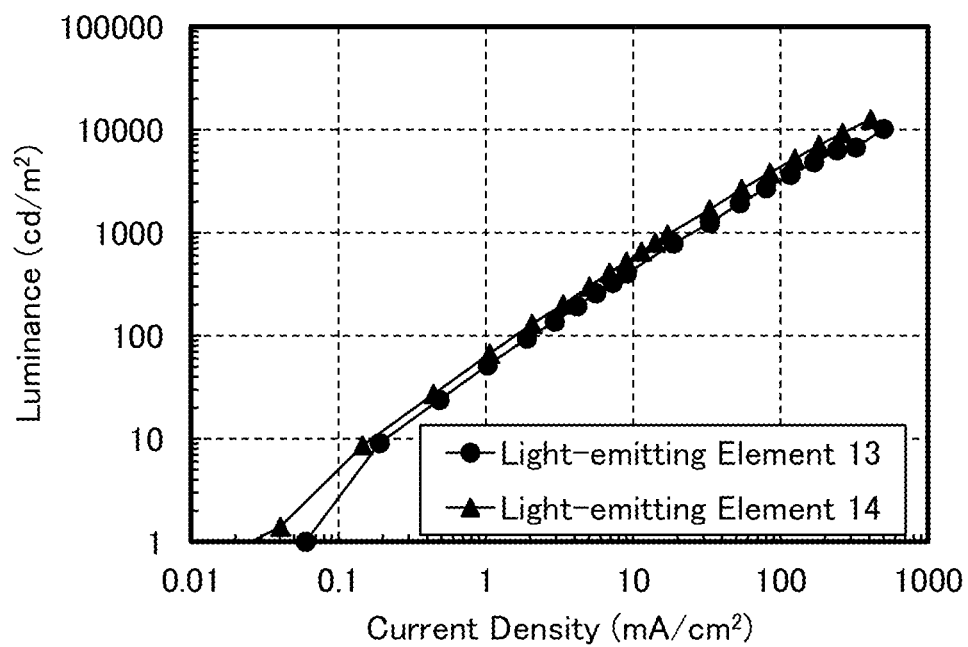
FIG. 50 shows current density-luminance characteristics of a light-emitting element 13 and a light-emitting element 14.
Figure 51:
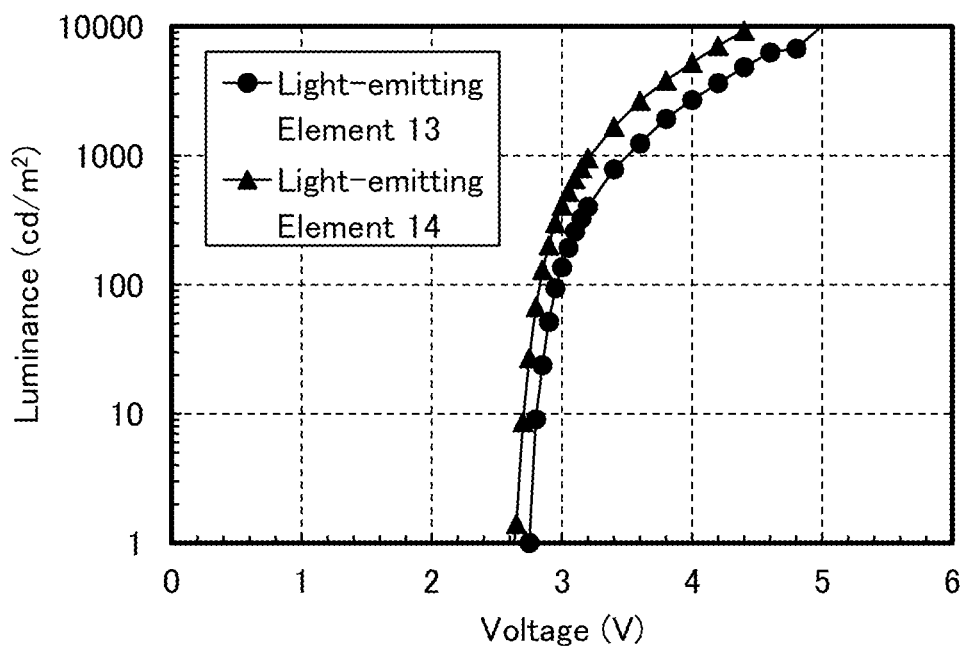
FIG. 51 shows voltage-luminance characteristics of the light-emitting element 13 and the light-emitting element 14.
Figure 52:
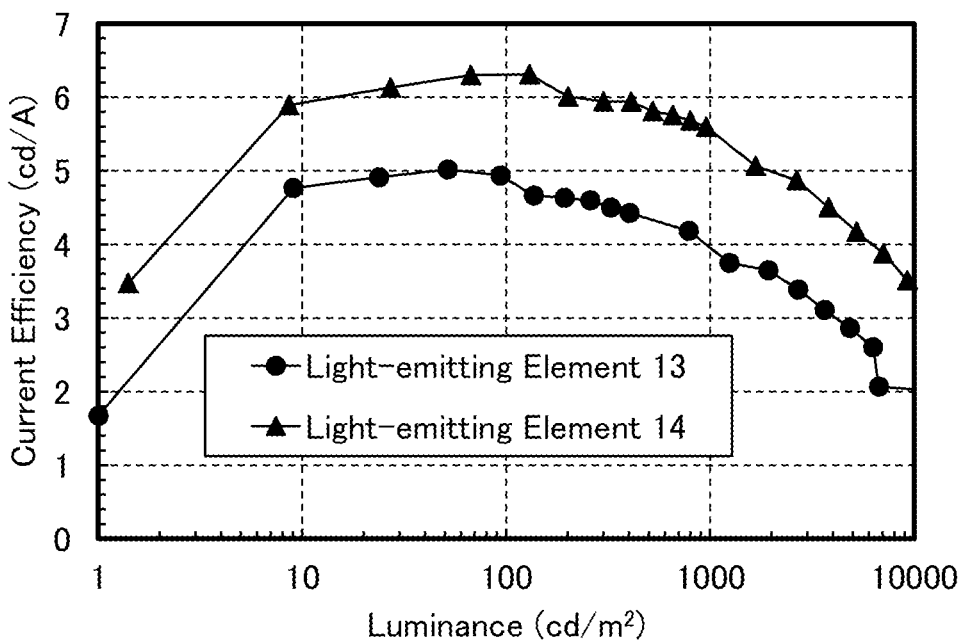
FIG. 52 shows luminance-current efficiency characteristics of the light-emitting element 13 and the light-emitting element 14.
Figure 53:
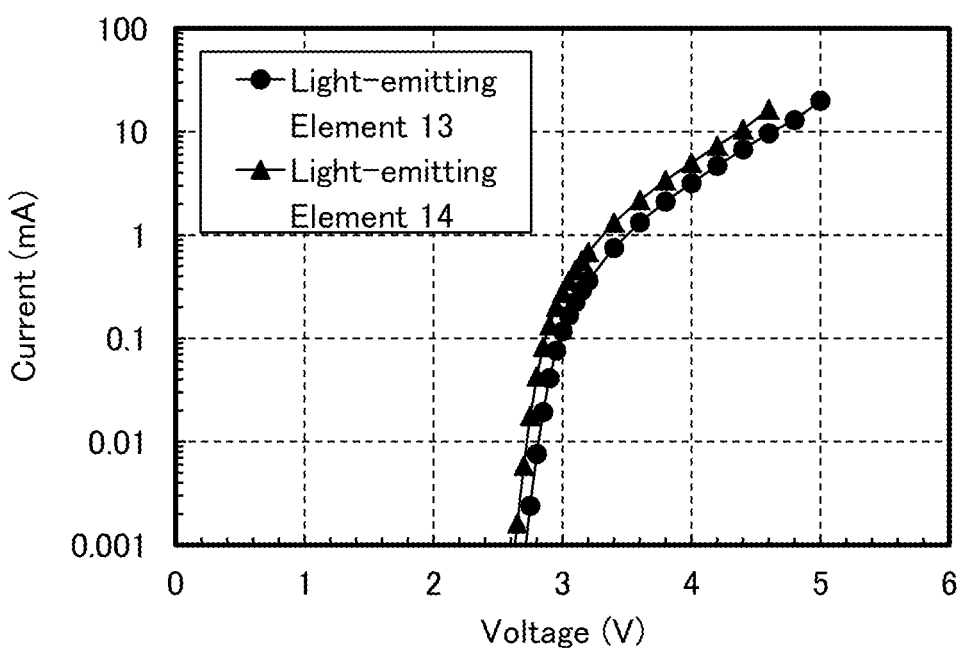
FIG. 53 shows voltage-current characteristics of the light-emitting element 13 and the light-emitting element 14.

Next, reliability tests were performed on the light-emitting elements. FIG. 49 shows results of the reliability tests. In FIG. 49, the vertical axis represents normalized luminance (%) with an initial luminance of 100%, and the horizontal axis represents driving time (h) of the elements.

zPA as a host can produce the same effects as those described in Example 5. As a result, the light-emitting element 10 can achieve efficiency as high as that of the comparative light-emitting element 12, and in addition, unpredictably low drive voltage and long lifetime.

Example 7

In this example, as light-emitting elements of embodiments of the present invention, a light-emitting element 13 including 2Ph-CzPA whose synthesis method is described in Example 1 for a light-emitting layer, and a light-emitting element 14 including 2Ph-cgDBCzPA whose synthesis method is described in Example 2 for a light-emitting layer were fabricated. The measurement results of the characteristics of these light-emitting elements are shown. Note that in this example, the methods for fabricating the light-emitting element 13 and the light-emitting element 14 were the same as those described in Example 4 except that a guest material was omitted from the light-emitting layer and 2,2'-(pyridine-2,6-diyl)bis(4-phenylbenzo[h]quinazoline) (abbreviation: 2,6(P-Bqn)$_2$Py) was used for the electron-transport layer, and the description is omitted here. Chemical formulae of materials used in this example are shown below.

[Chemical formulae 47]

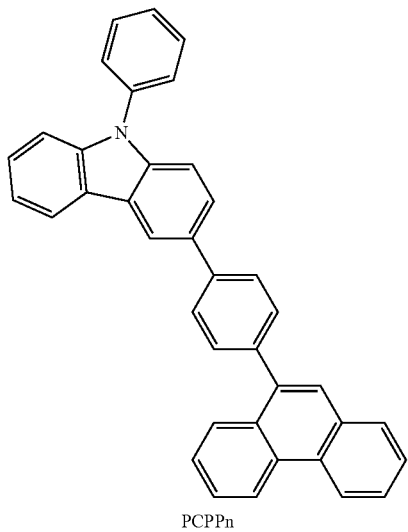

PCPPn

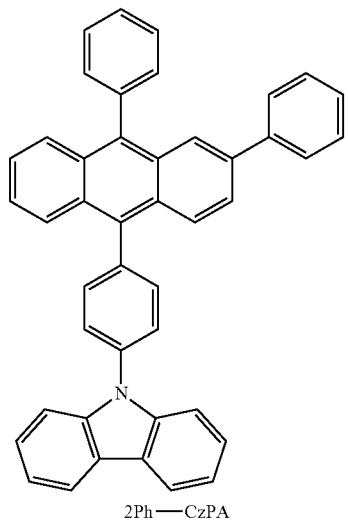

2Ph—CzPA (100)

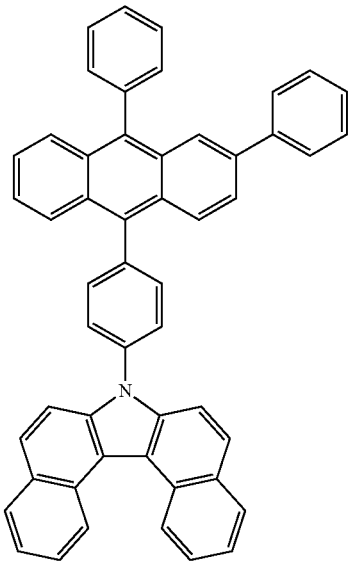

2Ph-cgDBCzPA (200)

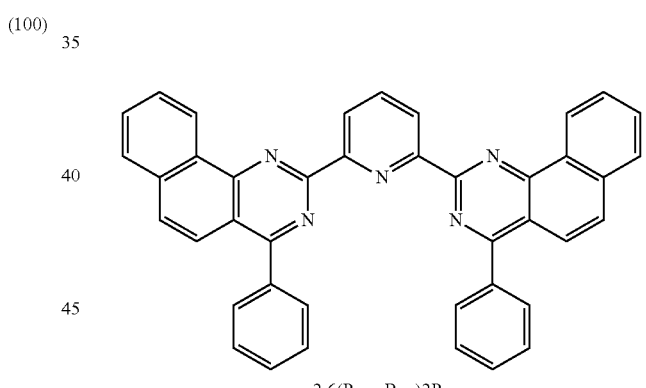

2,6(P—Bqn)2Py

<<Fabrication of Light-Emitting Element 13 and Light-Emitting Element 14>>

Table 9 shows the element structures of the light-emitting element 13 and the light-emitting element 14 fabricated in this example.

TABLE 9

| | First electrode | Hole-injection layer | Hole-transport layer | Light-emitting layer | Electron-transport layer | Electron-injection layer | Second electrode |
|---|---|---|---|---|---|---|---|
| Light-emitting element 13 | ITO (70 nm) | PCPPn:MoO$x$ (4:2 10 nm) | PCPPn (30 nm) | 2Ph-CzPA (25 nm) | 2,6(P-Bqn)2Py (25 nm) | LiF (1 nm) | Al (200 nm) |
| Light-emitting element 14 | ITO (70 nm) | PCPPn:MoO$x$ (4:2 10 nm) | PCPPn (30 nm) | 2Ph-cgDBCzPA (25 nm) | 2,6(P-Bqn)2Py (25 nm) | LiF (1 nm) | Al (200 nm) |

<<Operation Characteristics of Light-Emitting Element 13 and Light-Emitting Element 14>>

Operation characteristics of the light-emitting element 13 and the light-emitting element 14 were measured. Note that the measurement was carried out at room temperature (under an atmosphere where a temperature was maintained at 25° C.).

FIG. 50, FIG. 51, FIG. 52, and FIG. 53 show current density-luminance characteristics, voltage-luminance characteristics, luminance-current efficiency characteristics, and voltage-current characteristics, respectively, of the light-emitting element 13 and the light-emitting element 14.

Table 10 shows initial values of main characteristics of the light-emitting elements at around 1000 cd/m².

TABLE 10

|  | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
| --- | --- | --- | --- | --- | --- | --- | --- | --- |
| Light-emitting element 13 | 3.4 | 0.75 | 19 | (0.14, 0.09) | 780 | 4.2 | 3.9 | 5.8 |
| Light-emitting element 14 | 3.2 | 0.680 | 17 | (0.15, 0.11) | 960 | 5.6 | 5.5 | 6.3 |

Figure 54:
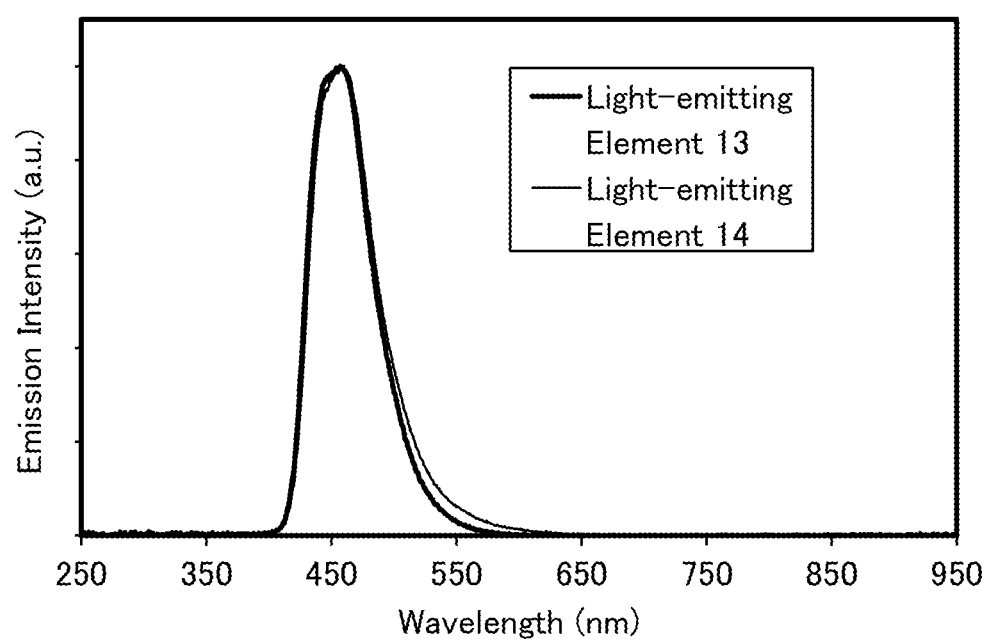
FIG. 54 shows emission spectra of the light-emitting element 13 and the light-emitting element 14.

FIG. 54 shows emission spectra when a current at a current density of 12.5 mA/cm² was supplied to the light-emitting element 13 and the light-emitting element 14. In FIG. 54, each of the emission spectra of the light-emitting element 13 and the light-emitting element 14 has a peak at around 458 nm, which is presumably derived from light emission of 2Ph-CzPA or 2Ph-cgDBCzPA that is the organic compound used for the EL layer of the light-emitting element.

<Delayed Fluorescence Measurement of Light-Emitting Elements>

Next, delayed fluorescence measurement was performed on the light-emitting element 13 and the light-emitting element 14. A picosecond fluorescence lifetime measurement system (manufactured by Hamamatsu Photonics K.K.) was used for the measurement. To measure the lifetimes of fluorescence in the light-emitting elements, a square wave pulse voltage was applied to the light-emitting elements, and time-resolved measurement of light, which was attenuated from the falling of the voltage, was performed using a streak camera. The pulse voltage was applied at a frequency of 10 Hz. By integrating data obtained by repeated measurement, data with a high S/N ratio was obtained. The measurement was performed at room temperature (under an atmosphere where a temperature was maintained at 25° C.).

Figure 55:
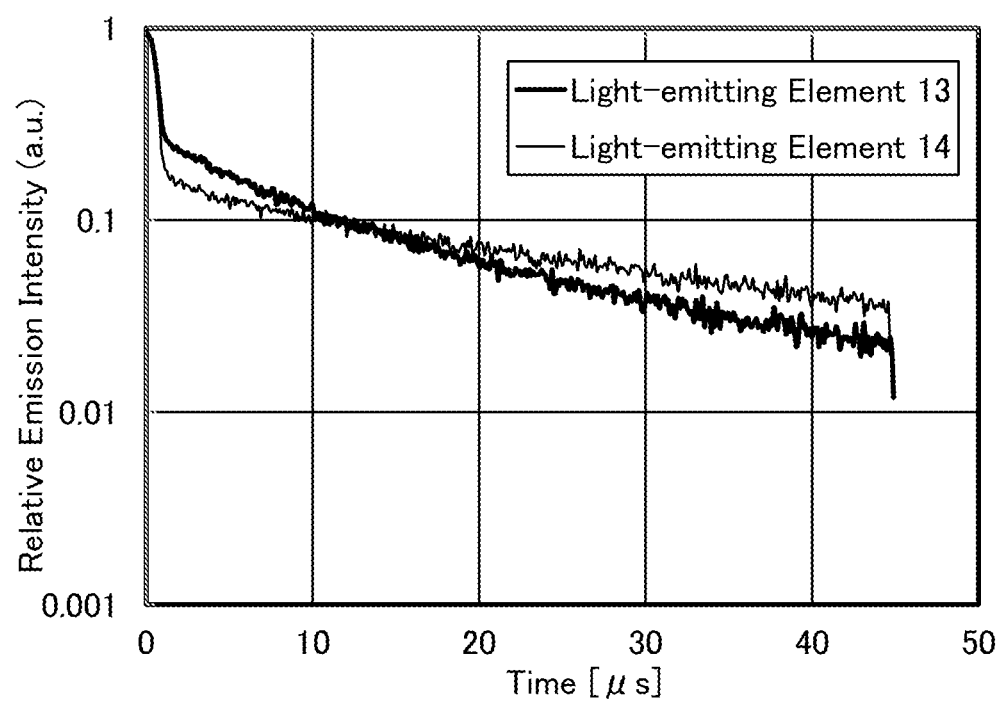
FIG. 55 shows the emission decay curves of the light-emitting element 13 and the light-emitting element 14.

The attenuation curves obtained by the measurement are shown in FIG. 55. In FIG. 55, the horizontal axis represents the time (µs) elapsed after the falling of the pulse voltage and the vertical axis represents the relative emission intensity (arbitrary unit). Fitting of the attenuation curves shown in FIG. 55 was performed using the following formula (1).

[Formula 1]

$$L = \sum_{n=1} A_n \exp\left(-\frac{t}{a_n}\right) \quad (1)$$

In the formula (1), L and t represent normalized emission intensity and elapsed time, respectively.

As the results of the fitting of the attenuation curves in FIG. 55, the fitting was able to be performed when n was 1 and 2. The fitting of the attenuation curves was performed and the proportion of the delayed fluorescence component in the total emission obtained from each of the light-emitting elements was calculated by extrapolation of the fitting curves to t=0. As a result, the proportions of the delayed fluorescence component in the total emission obtained from the light-emitting element 13 and the light-emitting element 14 were calculated to be 27.5% and 17.4%, respectively. In other words, 15% or more of the delayed fluorescence component was observed in each of the light-emitting elements 13 and 14.

The above results show that TTA can occur efficiently in either of the compounds 2Ph-CzPA and 2Ph-cgDBCzPA. This is probably because the oscillator strength of a transition from T1 to Tn of the molecule is increased owing to a phenyl group at the 2-position of an anthracene skeleton. It is thought that an increase in probability of occurrence of TTA in a host material and transfer of a large amount of singlet excitation energy generated due to TTA to a dopant are effective in increasing the efficiency of a fluorescent light-emitting element. An increase in probability of transition from T1 to Tn of a host molecule contributes greatly to an increase in the probability of occurrence of TTA in a host material. An increase in the oscillator strength of a transition from T1 to Tn in the molecule is thought to contribute greatly to the increase in probability of the transition. It is demonstrated by calculation that introduction of a phenyl group so as to bond to the 2-position of an anthracene skeleton increases the oscillator strength of transition from T1 to Tn.

As described above, TTA can occur efficiently in the compounds of embodiments of the present invention. Therefore, as described in Examples 3 to 6, when used as a host of a fluorescent dopant, each of the compounds can realize a highly efficient fluorescent element.

Example 8

Synthesis Example 3

In this example, a method for synthesizing 9-[4-(3,10-diphenylanthracen-9-yl)phenyl]-3-phenyl-9H-carbazole (abbreviation: 2Ph-CzPAP) which is an organic compound of one embodiment of the present invention represented by the structural formula (103) in Embodiment 1 is described. The structure of 2Ph-CzPAP is shown below.

[Chemical formula 48]

(103)

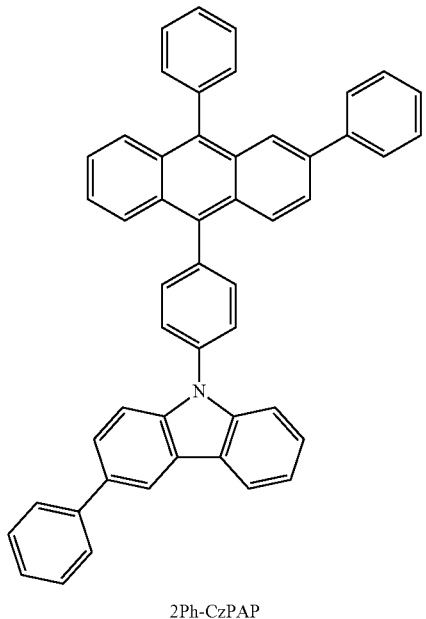

2Ph-CzPAP

Step 1: Synthesis of 3-phenyl-9H-carbazole

Into a 300 mL flask were put 12.3 g (50 mmol) of 3-bromo-9H-carbazole, 6.71 g (55 mmol) of phenylboronic acid, 22.8 g (165 mmol) of potassium carbonate, 100 mL of toluene, 25 mL of ethanol, and 82 mL of tap water. This mixture was degassed under reduced pressure, and then the air in the flask was replaced with nitrogen. To this mixture were added 112 mg (0.50 mmol) of palladium acetate and 304 mg (1.0 mmol) of tris(ortho-tolyl)phosphine. This mixture was heated and refluxed for approximately 4 hours for reaction.

After cooled down to room temperature, the reaction liquid was separated into an organic layer and an aqueous layer. The obtained organic layer was washed with a saturated aqueous solution of sodium chloride. Magnesium sulfate was added to this solution for drying, and filtration was performed. This solution was concentrated, and the obtained mixture was purified by silica gel column chromatography. The obtained solution was concentrated, and the obtained mixture was recrystallized with ethanol. The precipitated solid was collected by filtration at room temperature, and the obtained residue was dried under reduced pressure to give 11.1 g of a target white solid in a yield of 91%. The synthesis scheme of Step 1 is shown in (c-1) below.

[Chemical formula 49]

(c-1)

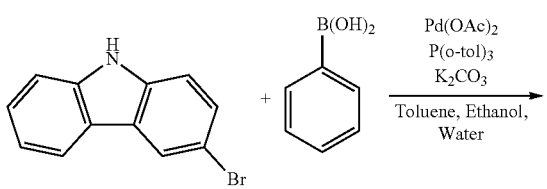

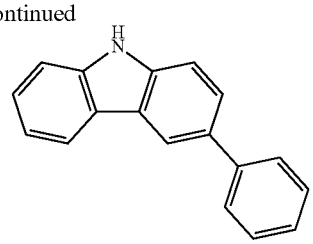

Analysis results by nuclear magnetic resonance spectroscopy ($^1$H-NMR) of the white solid obtained in Step 1 are shown below. These results show that the organic compound 3-phenyl-9H-carbazole was synthesized in this example.

$^1$H-NMR. δ(CDCl$_3$): 8.29 (d, J=1.5 Hz, 1H), 8.13 (d, J=7.5 Hz, 1H), 8.07-8.10 (brs, 1H), 7.71 (dd, J=1.0 Hz, 8.5 Hz, 2H), 7.67 (dd, J=1.5 Hz, 8.0 Hz, 1H), 7.41-7.51 (m, 5H), 7.34 (td, J=8.0 Hz, 1.0 Hz, 1H), 7.26 (td, J=7.0 Hz, 1.5 Hz, 1H).

Step 2: Synthesis of 2Ph-CzPAP

Into a 200 mL flask were put 4.85 g (10.0 mmol) of 9-(4-bromophenyl)-3,10-diphenylanthracene (see Step 6 of Example 1), 2.55 g (10.5 mmol) of 3-phenyl-9H-carbazole, 2.88 g (30.0 mmol) of tert-butoxysodium, and 50 mL of mesitylene. This mixture was degassed under reduced pressure, and then the air in the flask was replaced with nitrogen. Then, 37 mg (0.10 mmol) of allylpalladium(II) chloride dimer (abbreviation: [(Allyl)PdCl]$_2$) and 141 mg (0.40 mmol) of di-tert-butyl(1-methyl-2,2-diphenylcyclopropyl)phosphine (abbreviation: cBRIDP) were added, and the mixture was heated and refluxed for 11 hours.

The reaction solution was filtered through Celite, alumina, and Florisil, and washed with hot toluene. The solution was concentrated, and the obtained residue was purified by silica gel column chromatography. The obtained solution was concentrated, and the mixture was recrystallized with toluene and ethanol. The solid precipitated at room temperature was collected by filtration, and the obtained residue was dried under reduced pressure to give 5.9 g of a target yellow solid in a yield of 91%. The synthesis scheme of Step 2 is shown in (c-2) below.

[Chemical formula 50]

(c-2)

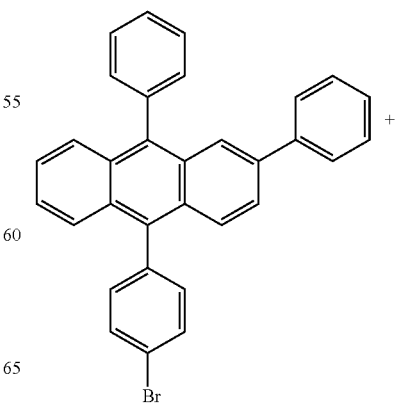

153
-continued

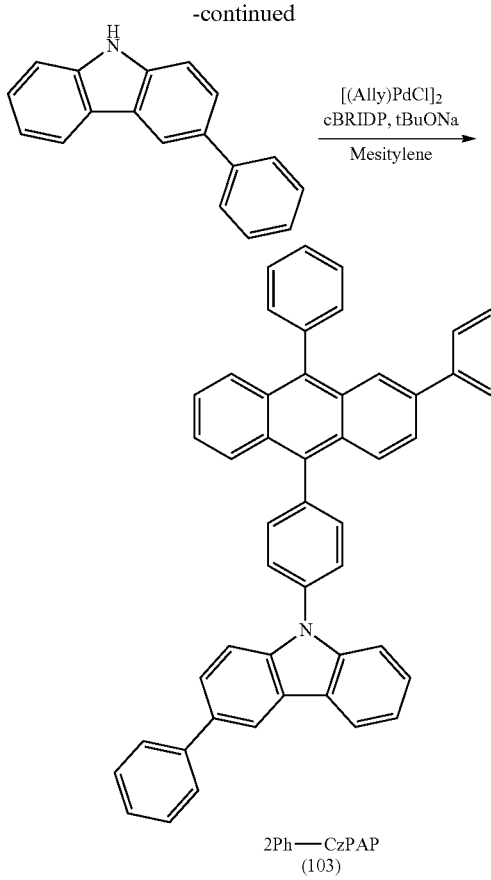

2Ph—CzPAP
(103)

Figure 56:
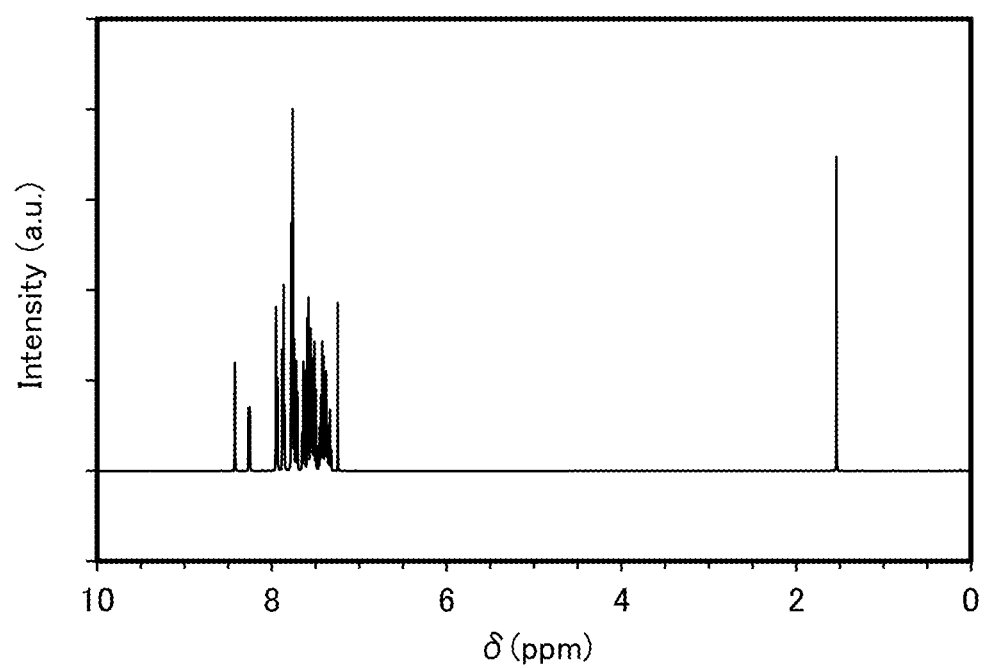
FIG. 56 is a $^1$H-NMR chart of an organic compound represented by the structural formula (103).

Analysis results by nuclear magnetic resonance spectroscopy ($^1$H-NMR) of the yellow solid obtained in Step 2 are shown below. FIG. 56 shows the $^1$H-NMR chart. These results show that 2Ph-CzPAP which is the organic compound of one embodiment of the present invention represented by the above structural formula was synthesized in this example.

$^1$H-NMR. δ(CDCl$_3$): 8.42 (s, 1H), 8.26 (d, J=7.5 Hz, 1H), 7.95 (s, 1H), 7.94 (d, J=9.0 Hz, 1H), 7.85-7.89 (m, 3H), 7.70-7.79 (m, 9H), 7.62-7.66 (m, 2H), 7.49-7.60 (m, 8H), 7.31-7.47 (m, 7H).

Then, 3.0 g of the obtained solid was purified by a train sublimation method. The purification by sublimation was conducted by heating at 315° C. under a pressure of 3.2 Pa with a flow rate of an argon gas of 12 mL/min. After the purification by sublimation, 2.4 g of a yellow solid was obtained at a collection rate of 78%.

Figure 57:
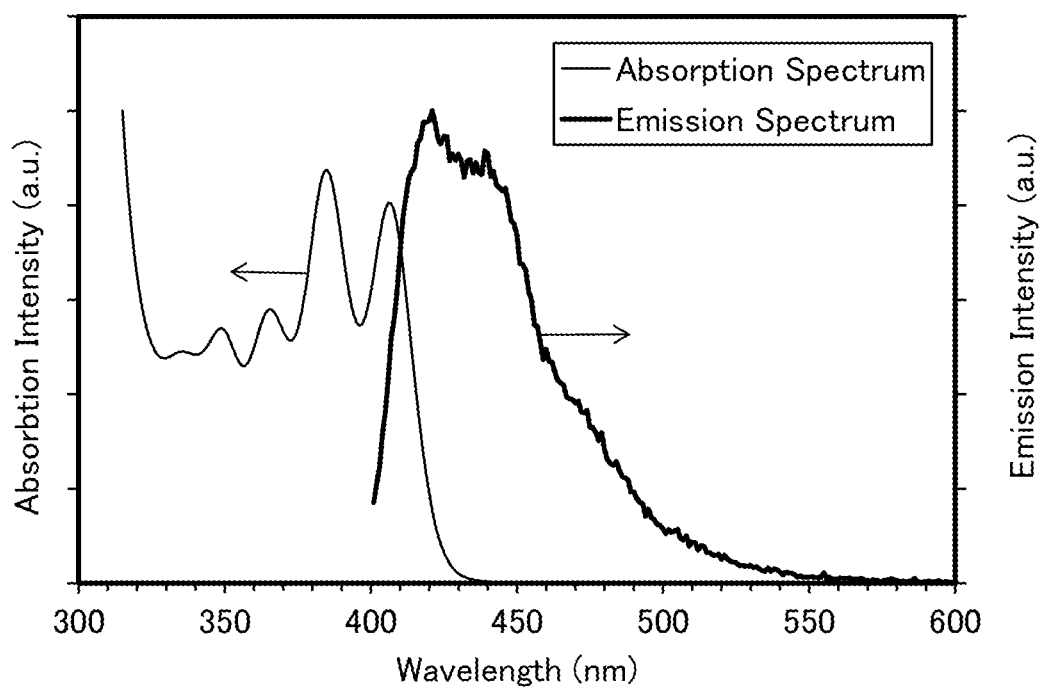
FIG. 57 shows an ultraviolet-visible absorption spectrum and an emission spectrum of the organic compound represented by the structural formula (103).

Next, an ultraviolet-visible absorption spectrum (hereinafter, simply referred to as an absorption spectrum) of a toluene solution of 2Ph-CzPAP and an emission spectrum thereof were measured. Since the measurement methods are similar to those of Example 1, the description is omitted. FIG. 57 shows measurement results of the absorption spectrum and the emission spectrum. The horizontal axis represents wavelength and the vertical axes represent absorbance and emission intensity. In FIG. 57, two solid lines are shown; a thin line represents the absorption spectrum, and a thick line represents the emission spectrum. The absorbance shown in FIG. 57 is a result obtained by subtraction of absorbance of only toluene in a quartz cell from the measured absorbance of the toluene solution (0.02 mmol/L) in a quartz cell.

154

Example 9

Synthesis Example 4

In this example, a method for synthesizing 9-[4-(3,10-diphenylanthracen-9-yl)phenyl]-2-phenyl-9H-carbazole (abbreviation: 2Ph-CzPAP-02) which is an organic compound of one embodiment of the present invention represented by the structural formula (102) in Embodiment 1 is described. The structure of 2Ph-CzPAP-02 is shown below.

[Chemical formula 51]

(102)

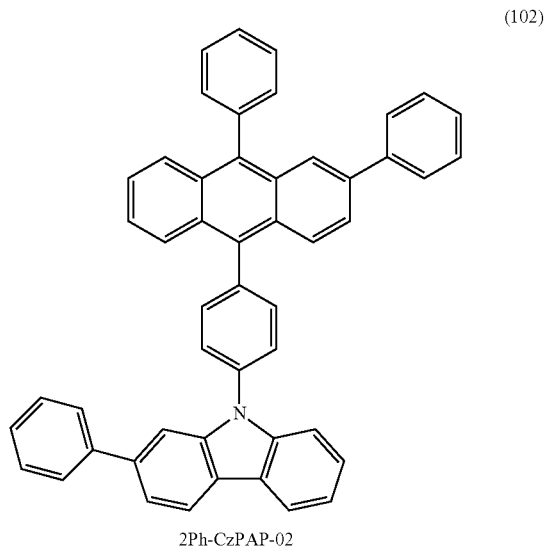

2Ph-CzPAP-02

Step 1: Synthesis of 2-phenyl-9H-carbazole

Into a 300 mL flask were put 12.1 g (50 mmol) of 2-bromo-9H-carbazole, 6.71 g (55 mmol) of phenylboronic acid, 22.8 g (165 mmol) of potassium carbonate, 100 mL of toluene, 25 mL of ethanol, and 82 mL of tap water. This mixture was degassed under reduced pressure, and then the air in the flask was replaced with nitrogen. To this mixture were added 112 mg (0.50 mmol) of palladium acetate and 304 mg (1.0 mmol) of tris(ortho-tolyl)phosphine. This mixture was heated and refluxed for approximately 6 hours for reaction.

After cooled down to room temperature, the reaction liquid was separated into an organic layer and an aqueous layer. The obtained organic layer was washed with a saturated aqueous solution of sodium chloride. Magnesium sulfate was added to this solution for drying, and filtration was performed. This solution was concentrated, and the obtained mixture was purified by silica gel column chromatography. The obtained solution was concentrated, and the obtained mixture was recrystallized with ethanol. The precipitated solid was collected by filtration at room temperature, and the obtained residue was dried under reduced pressure to give 8.6 g of a target white solid in a yield of 71%. The synthesis scheme of Step 1 is shown in (d-1) below.

[Chemical formula 52]

(d-1)

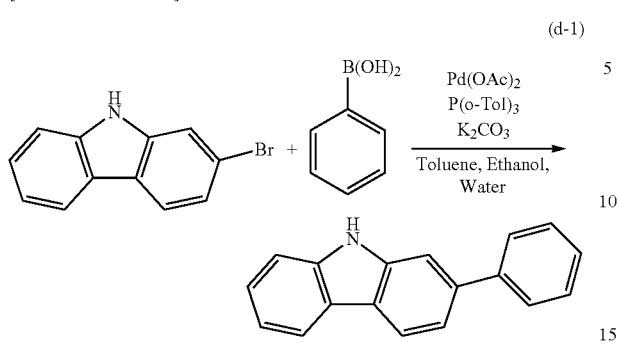

Analysis results by nuclear magnetic resonance spectroscopy (¹H-NMR) of the white solid obtained in Step 1 are shown below. These results show that the organic compound 2-phenyl-9H-carbazole was synthesized in Step 1.

¹H-NMR. δ(CDCl₃): 8.11 (d, J=8 Hz, 1H), 8.08 (d, J=8 Hz, 1H), 8.03 (brs, 1H), 7.66-7.70 (m, 2H), 7.61-7.63 (m, 1H), 7.39-7.50 (m, 5H), 7.32-7.37 (m, 1H), 7.24 (td, J=5.5 Hz, 2.5 Hz, 1H).

Step 2: Synthesis of 2Ph-CzPAP-02

Into a 200 mL flask were put 4.4 g (9.0 mmol) of 9-(4-bromophenyl)-3,10-diphenylanthracene (see Step 6 of Example 1), 2.3 g (9.45 mmol) of 2-phenyl-9H-carbazole, 2.6 g (27 mmol) of tert-butoxysodium, and 45 mL of mesitylene. This mixture was degassed under reduced pressure, and then the air in the flask was replaced with nitrogen. Then, 33 mg (0.09 mmol) of allylpalladium(II) chloride dimer (abbreviation: [(Allyl)PdCl]₂) and 127 mg (0.36 mmol) of di-tert-butyl(1-methyl-2,2-diphenylcyclopropyl) phosphine (abbreviation: cBRIDP) were added, and the mixture was heated and refluxed for approximately 9 hours.

The reaction solution was filtered through Celite, alumina, and Florisil. The filtrate was concentrated, and a toluene solution was added for dissolving. This solution was purified by silica gel column chromatography. The obtained solution was concentrated, and the precipitated solid was recrystallized with toluene and ethanol. The solid precipitated at room temperature was collected by filtration, and the obtained residue was dried under reduced pressure to give 5.3 g of a target yellow solid in a yield of 91%. The synthesis scheme of Step 2 is shown in (d-2) below.

[Chemical formula 53]

(d-2)

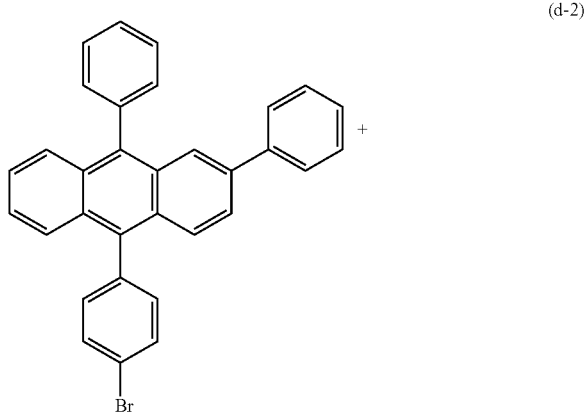

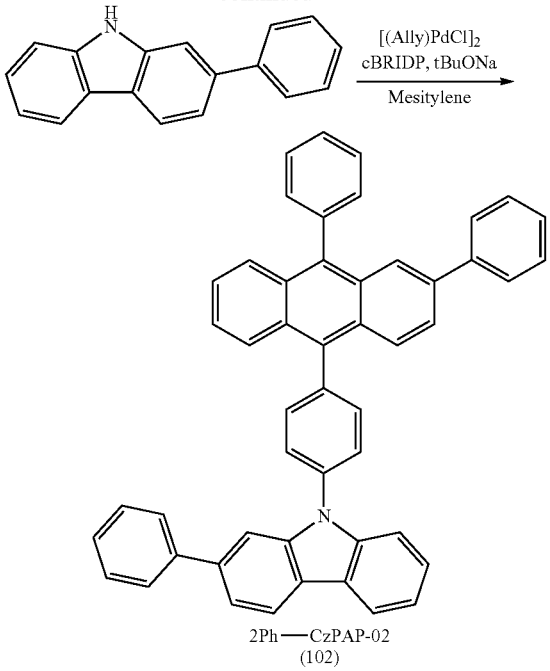

2Ph—CzPAP-02
(102)

Figure 58:
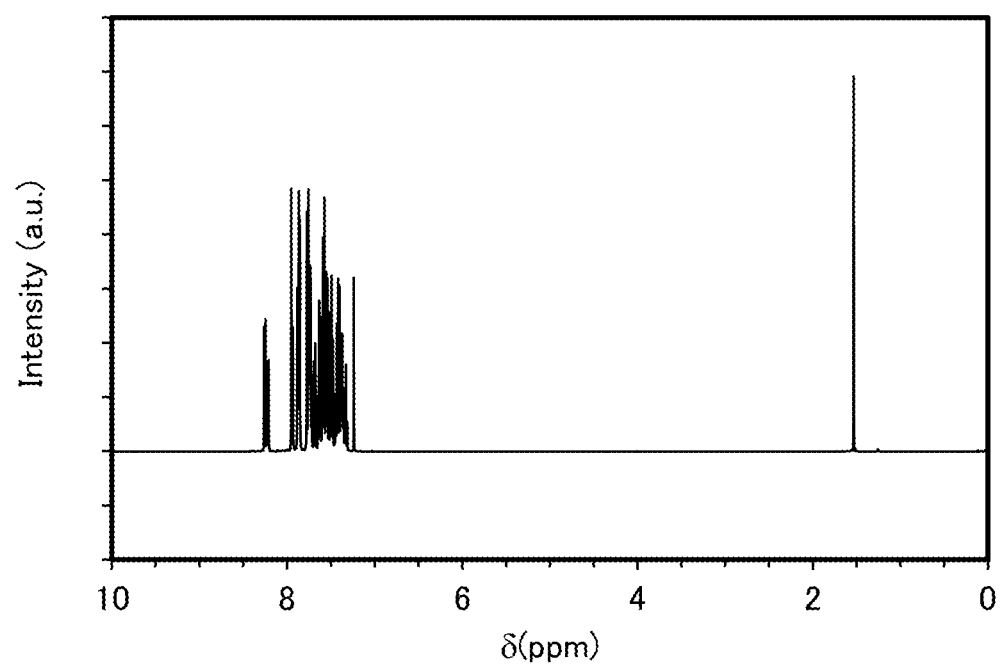
FIG. 58 is a $^1$H-NMR chart of an organic compound represented by the structural formula (102).

Analysis results by nuclear magnetic resonance spectroscopy (¹H-NMR) of the yellow solid obtained in Step 2 are shown below. FIG. 58 shows the ¹H-NMR chart. These results show that 2Ph-CzPAP-02 which is the organic compound of one embodiment of the present invention represented by the above structural formula was synthesized in this example.

¹H-NMR. δ(CDCl₃): 8.26 (d, J=8 Hz, 1H), 8.22 (d, J=7.5 Hz, 1H), 7.95 (s, 1H), 7.94 (d, J=7.5 Hz, 1H), 7.84-7.89 (m, 4H), 7.71-7.78 (m, 6H), 7.68 (d, J=9 Hz, 1H), 7.31-7.66 (m, 18H).

Then, 2.8 g of the obtained solid was purified by a train sublimation method. The purification by sublimation was conducted by heating at 315° C. under a pressure of 3.0 Pa with a flow rate of an argon gas of 13 mL/min. After the purification by sublimation, 2.4 g of a yellow solid was obtained at a collection rate of 84%.

Figure 59:
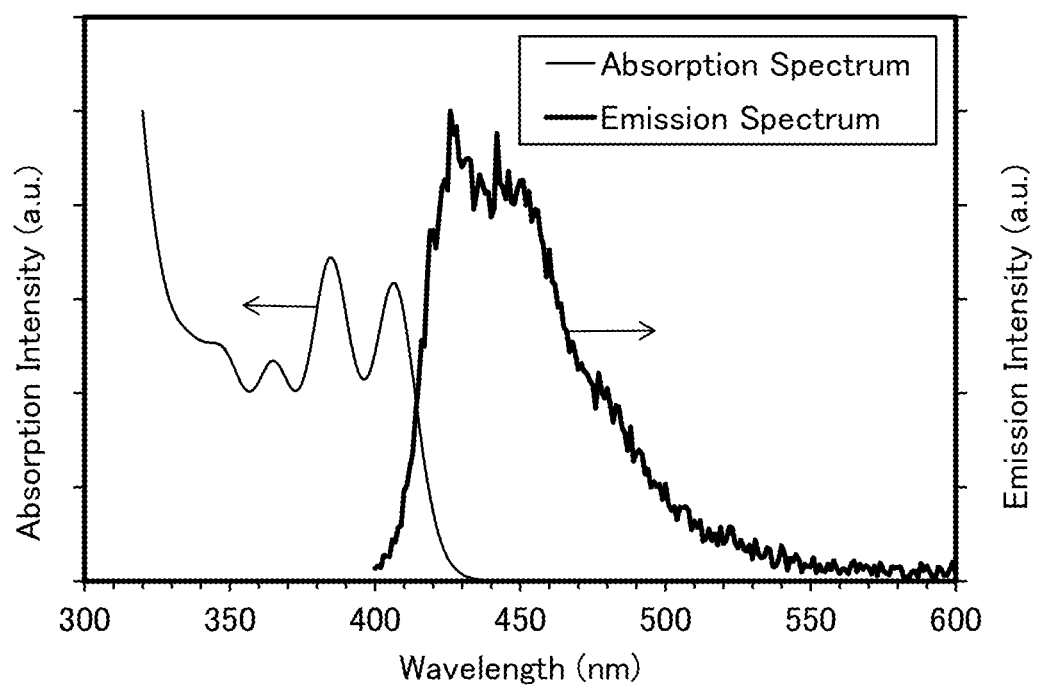
FIG. 59 shows an ultraviolet-visible absorption spectrum and an emission spectrum of the organic compound represented by the structural formula (102).

Next, an ultraviolet-visible absorption spectrum (hereinafter, simply referred to as an absorption spectrum) of a toluene solution of 2Ph-CzPAP-02 and an emission spectrum thereof were measured. Since the measurement methods are similar to those of Example 1, the description is omitted. FIG. 59 shows measurement results of the absorption spectrum and the emission spectrum. The horizontal axis represents wavelength and the vertical axes represent absorbance and emission intensity. In FIG. 59, two solid lines are shown; a thin line represents the absorption spectrum, and a thick line represents the emission spectrum. The absorbance shown in FIG. 59 is a result obtained by subtraction of absorbance of only toluene in a quartz cell from the measured absorbance of the toluene solution (0.02 mmol/L) in a quartz cell.

Example 10

Synthesis Example 5

In this example, a method for synthesizing 9-[4-(3,10-diphenylanthracen-9-yl)phenyl]-4-phenyl-9H-carbazole (abbreviation: 2Ph-CzPAP-03) which is an organic compound of one embodiment of the present invention represented by the structural formula (104) in Embodiment 1 is described. The structure of 2Ph-CzPAP-03 is shown below.

[Chemical formula 54]

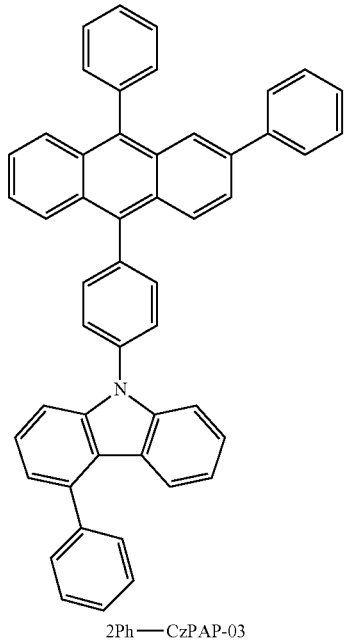

(104)

2Ph—CzPAP-03

Step 1: Synthesis of 4-phenyl-9H-carbazole

Into a 300 mL flask were put 12.3 g (50 mmol) of 4-bromo-9H-carbazole, 6.71 g (55 mmol) of phenylboronic acid, 22.8 g (165 mmol) of potassium carbonate, 100 mL of toluene, 25 mL of ethanol, and 82 mL of tap water. This mixture was degassed under reduced pressure, and then the air in the flask was replaced with nitrogen. To this mixture were added 112 mg (0.50 mmol) of palladium acetate and 304 mg (1.0 mmol) of tris(ortho-tolyl)phosphine. This mixture was heated and refluxed for approximately 8 hours for reaction.

After cooled down to room temperature, the reaction liquid was separated into an organic layer and an aqueous layer. The obtained organic layer was washed with a saturated aqueous solution of sodium chloride. Magnesium sulfate was added to this solution for drying, and filtration was performed. This solution was concentrated, and the obtained mixture was purified by silica gel column chromatography. The obtained solution was concentrated, and the obtained mixture was recrystallized with ethanol. The precipitated solid was collected by filtration at room temperature, and the obtained residue was dried under reduced pressure to give 7.7 g of a target white solid in a yield of 63%. The synthesis scheme of Step 1 is shown in (e-1) below.

[Chemical formula 55]

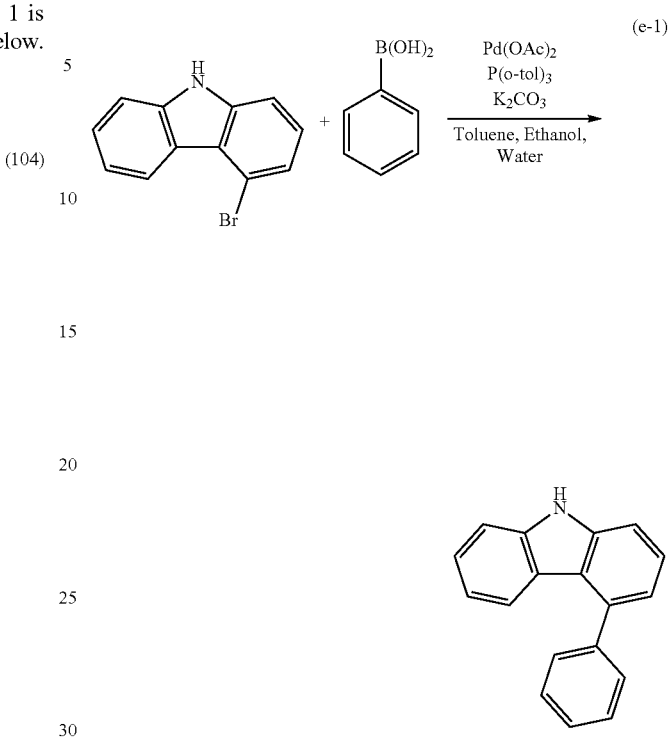

(e-1)

Analysis results by nuclear magnetic resonance spectroscopy ($^1$H-NMR) of the white solid obtained in Step 1 are shown below. These results show that the organic compound 4-phenyl-9H-carbazole was synthesized in Step 1.

$^1$H-NMR. δ(CDCl$_3$): 8.14 (brs, 1H), 7.61-7.65 (m, 2H), 7.50-7.55 (m, 2H), 7.38-7.49 (m, 5H), 7.32-7.38 (m, 1H), 7.11 (dd, J=1 Hz, 6.5 Hz, 1H), 6.95-7.00 (m, 1H).

Step 2: Synthesis of 2Ph-CzPAP-03

Into a 200 mL flask were put 4.4 g (9.0 mmol) of 9-(4-bromophenyl)-3,10-diphenylanthracene (see Step 6 of Example 1), 2.3 g (9.45 mmol) of 4-phenyl-9H-carbazole, 2.6 g (27 mmol) of tert-butoxysodium, and 45 mL of mesitylene. This mixture was degassed under reduced pressure, and then the air in the flask was replaced with nitrogen. Then, 33 mg (0.09 mmol) of allylpalladium(II) chloride dimer (abbreviation: [(Allyl)PdCl]$_2$) and 127 mg (0.36 mmol) of di-tert-butyl(1-methyl-2,2-diphenylcyclopropyl)phosphine (abbreviation: cBRIDP) were added, and the mixture was heated and refluxed for approximately 11 hours.

The reaction solution was filtered through Celite, alumina, and Florisil. The organic layer was concentrated, and the obtained residue was purified by silica gel column chromatography. The obtained solution was concentrated, and the precipitated solid was recrystallized with toluene and ethanol. The solid precipitated at room temperature was collected by filtration, and the obtained residue was dried under reduced pressure to give 3.0 g of a target yellow solid in a yield of 51%. The synthesis scheme of Step 2 is shown in (e-2) below.

[Chemical formula 56]

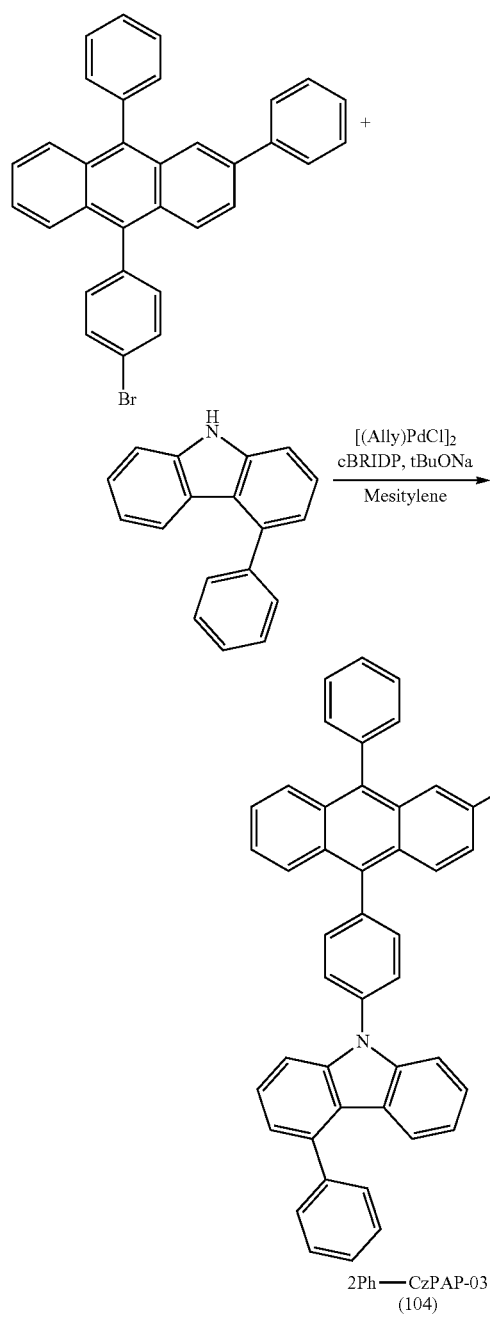

Figure 60:
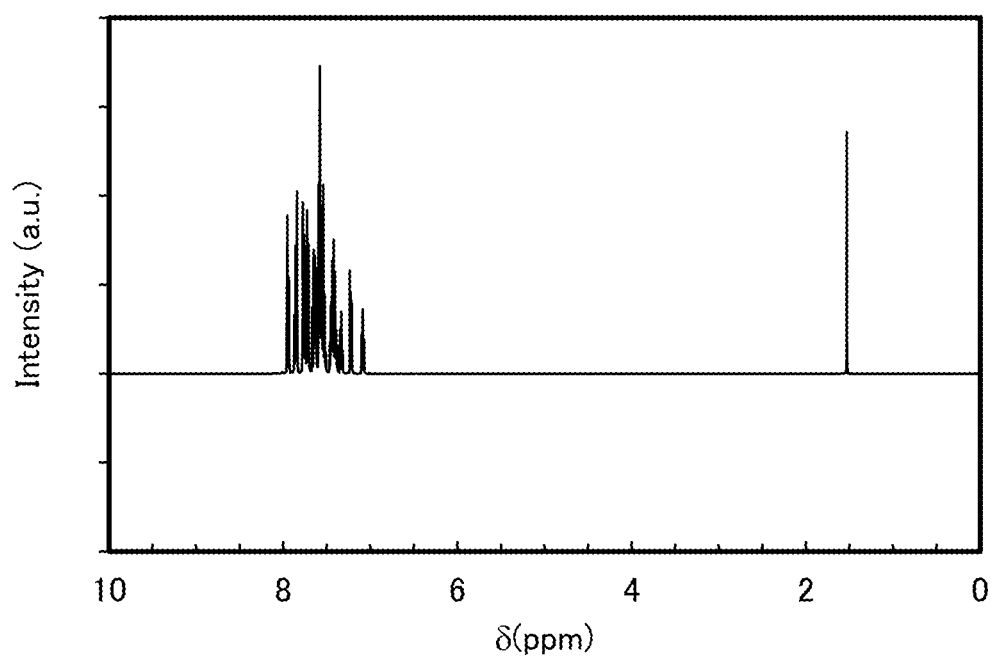
FIG. 60 is a ¹H-NMR chart of an organic compound represented by the structural formula (104).

Analysis results by nuclear magnetic resonance spectroscopy (¹H-NMR) of the yellow solid obtained in Step 2 are shown below. FIG. 60 shows the ¹H-NMR chart. These results show that 2Ph-CzPAP-03 which is the organic compound of one embodiment of the present invention represented by the above structural formula was synthesized in this example.

¹H-NMR. δ(CDCl$_3$): 7.95 (s, 1H), 7.95 (d, J=11.5 Hz, 1H), 7.83-7.88 (m, 3H), 7.70-7.79 (m, 6H), 7.61-7.68 (m, 4H), 7.50-7.60 (m, 10H), 7.37-7.47 (m, 5H), 7.31-7.36 (m, 1H), 7.22 (d, J=6 Hz, 1H), 7.09 (t, J=7 Hz, 1H).

Then, 5.0 g of the obtained solid was purified by a train sublimation method. The purification by sublimation was conducted by heating at 320° C. under a pressure of 3.0 Pa with a flow rate of an argon gas of 13 mL/min. After the purification by sublimation, 4.5 g of a yellow solid was obtained at a collection rate of 91%.

Figure 61:
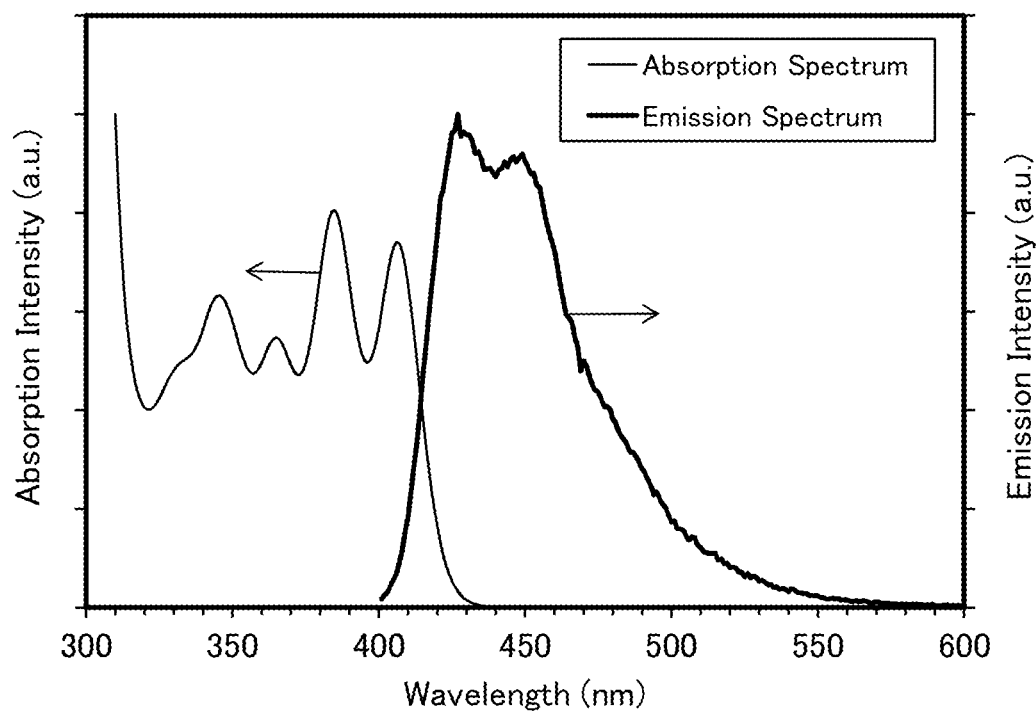
FIG. 61 shows an ultraviolet-visible absorption spectrum and an emission spectrum of the organic compound represented by the structural formula (104).
Figure 62:
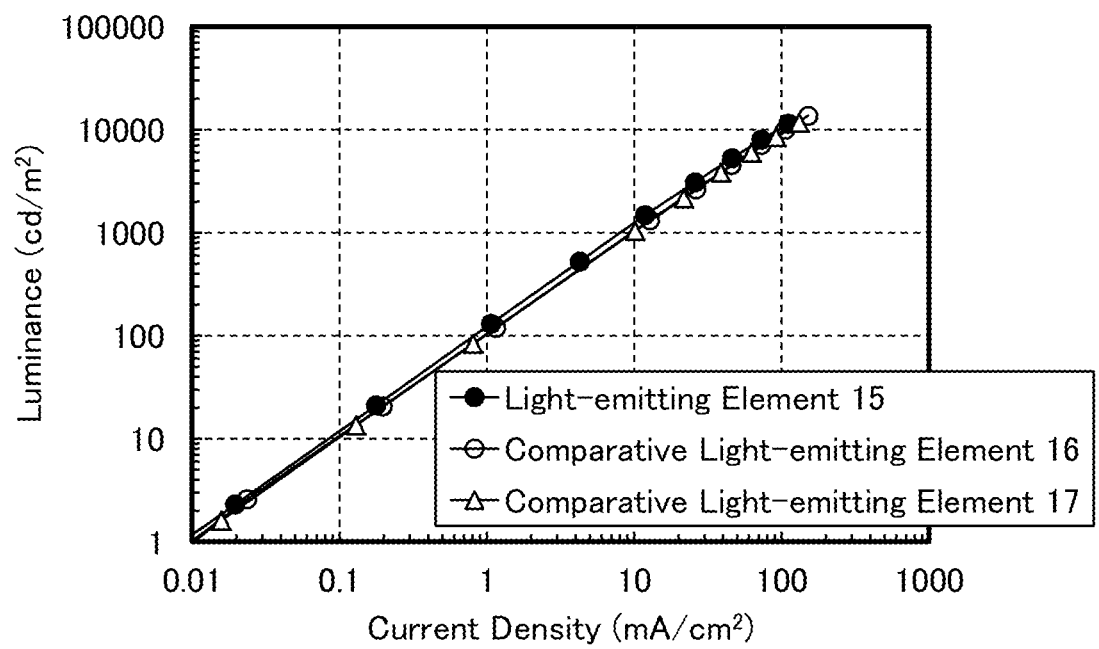
FIG. 62 shows current density-luminance characteristics of a light-emitting element 15, a comparative light-emitting element 16, and a comparative light-emitting element 17.
Figure 63:
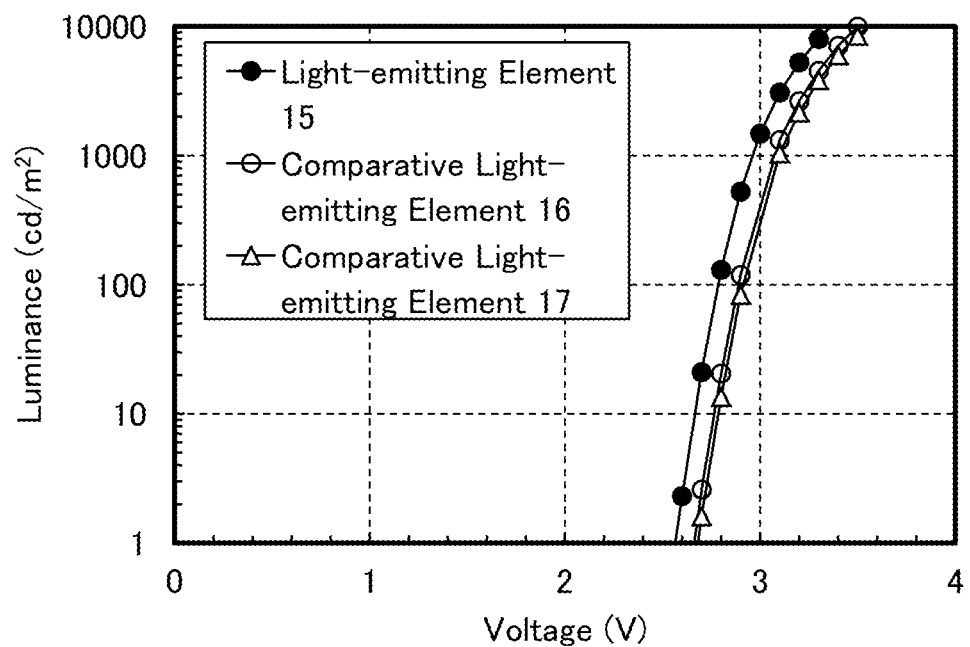
FIG. 63 shows voltage-luminance characteristics of the light-emitting element 15, the comparative light-emitting element 16, and the comparative light-emitting element 17.
Figure 64:
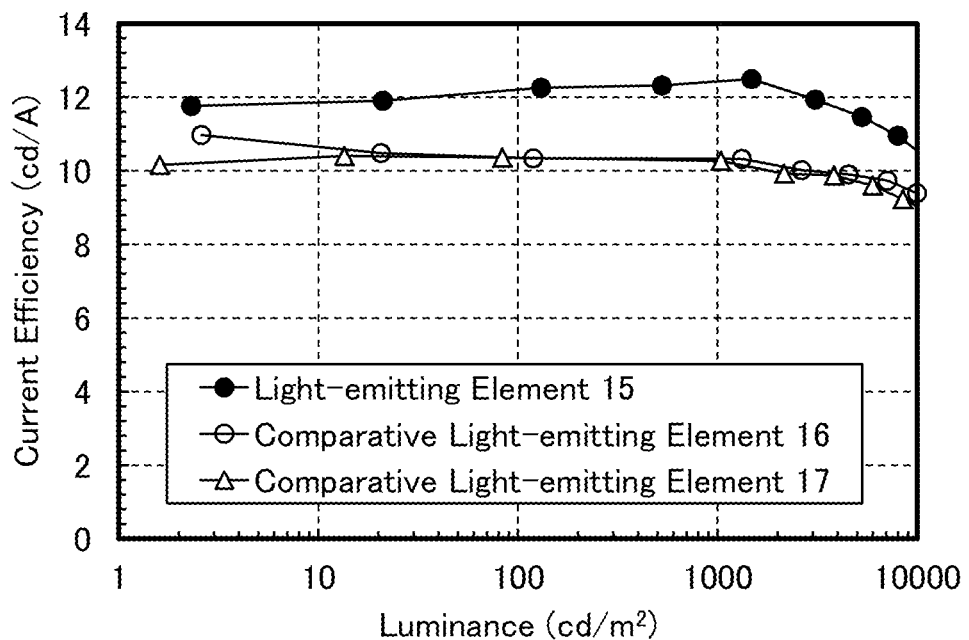
FIG. 64 shows luminance-current efficiency characteristics of the light-emitting element 15, the comparative light-emitting element 16, and the comparative light-emitting element 17.
Figure 65:
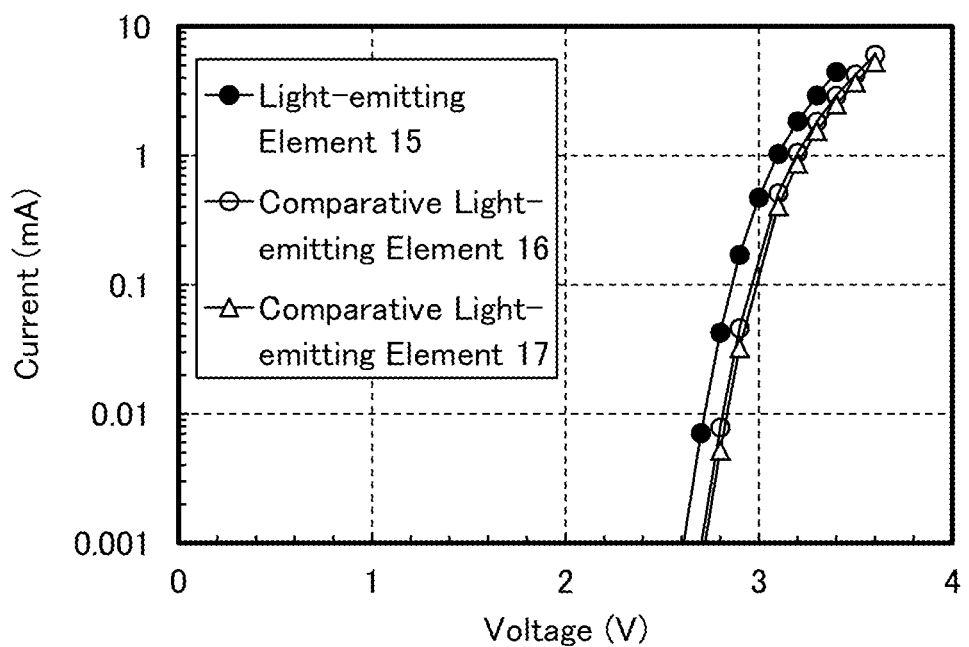
FIG. 65 shows voltage-current characteristics of the light-emitting element 15, the comparative light-emitting element 16, and the comparative light-emitting element 17.

Next, an ultraviolet-visible absorption spectrum (hereinafter, simply referred to as an absorption spectrum) of a toluene solution of 2Ph-CzPAP-03 and an emission spectrum thereof were measured. Since the measurement methods are similar to those of Example 1, the description is omitted. FIG. 61 shows measurement results of the absorption spectrum and the emission spectrum. The horizontal axis represents wavelength and the vertical axes represent absorbance and emission intensity. In FIG. 61, two solid lines are shown; a thin line represents the absorption spectrum, and a thick line represents the emission spectrum. The absorbance shown in FIG. 61 is a result obtained by subtraction of absorbance of only toluene in a quartz cell from the measured absorbance of the toluene solution (0.02 mmol/L) in a quartz cell.

Example 11

In this example, as a light-emitting element of one embodiment of the present invention, a light-emitting element 15 including 2Ph-CzPAP-02 whose synthesis method is described in Example 9 as a host material of a light-emitting layer was fabricated. In addition, as comparative light-emitting elements, a comparative light-emitting element 16 including CzPA as a host material of a light-emitting layer and a comparative light-emitting element 17 including 2-phenyl-9-[4-(10-phenyl-9-anthryl)phenyl]-9H-carbazole (abbreviation: CzPAPII) as a host material of a light-emitting layer were fabricated. The measurement results of the characteristics of these light-emitting elements are shown. Note that other examples can be referred to for the methods for fabricating the light-emitting element 15, the comparative light-emitting element 16, and the comparative light-emitting element 17 in this example, and the description is omitted here. Chemical formulae of materials used in this example are shown below.

[Chemical formula 57]

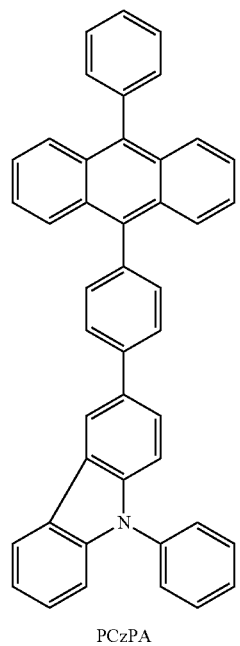

PCzPA

-continued

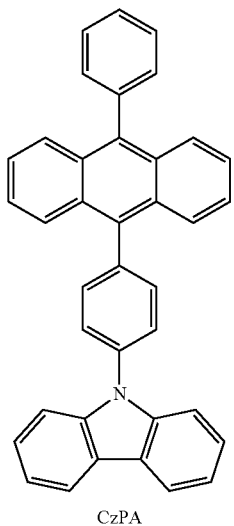
CzPA

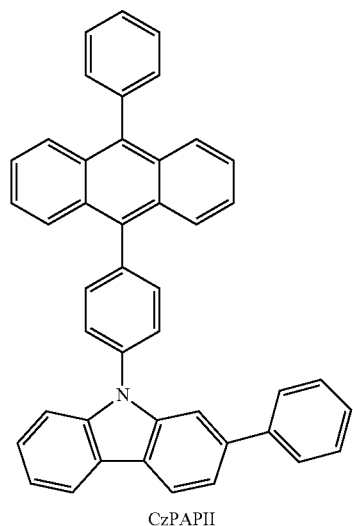
CzPAPII (102)

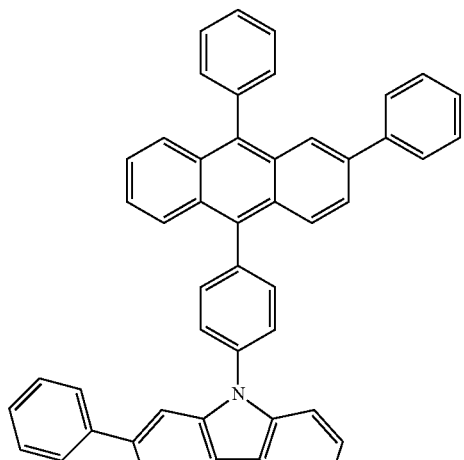
2Ph-CzPAP-02

-continued

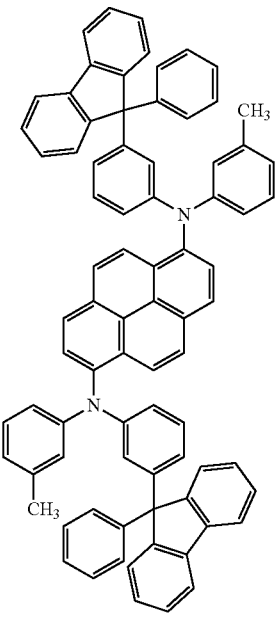
1,6mMemFLPAPrn

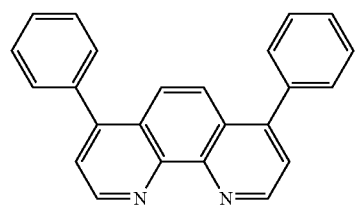
BPhen

<<Fabrication of Light-Emitting Element 15, Comparative Light-Emitting Element 16, and Comparative Light-Emitting Element 17>>

Table 11 shows the element structures of the light-emitting element 15, the comparative light-emitting element 16, and the comparative light-emitting element 17 fabricated in this example.

TABLE 11

| | First electrode | Hole-injection layer | Hole-transport layer | Light-emitting layer | Electron-transport layer | Electron-injection layer | Second electrode |
|---|---|---|---|---|---|---|---|
| Light-emitting element 15 | ITO (70 nm) | PCzPA:MoOx (4:2 10 nm) | PCzPA (30 nm) | * | 2Ph-CzPAP-02 (10 nm) | Bphen (15 nm) | LiF (1 nm) | Al (200 nm) |
| Comparative light-emitting element 16 | ITO (70 nm) | PCzPA:MoOx (4:2 10 nm) | PCzPA (30 nm) | ** | CzPA (10 nm) | Bphen (15 nm) | LiF (1 nm) | Al (200 nm) |
| Comparative light-emitting element 17 | ITO (70 nm) | PCzPA:MoOx (4:2 10 nm) | PCzPA (30 nm) | *** | CzPAPII (10 nm) | Bphen (15 nm) | LiF (1 nm) | Al (200 nm) |

\* 2Ph-CzPAP-02:1,6mMemFLPAPrn (1:0.03 25 nm)
\*\* CzPA:1,6mMemFLPAPrn (1:0.03 25 nm)
\*\*\* CzPAPII:1,6mMemFLPAPrn (1:0.03 25 nm)

<<Operation Characteristics of Light-Emitting Element 15, Comparative Light-Emitting Element 16, and Comparative Light-Emitting Element 17>>

Operation characteristics of the light-emitting element 15, the comparative light-emitting element 16, and the comparative light-emitting element 17 were measured. Note that the measurement was carried out at room temperature (under an atmosphere where a temperature was maintained at 25° C.).

FIG. 62, FIG. 63, FIG. 64, and FIG. 65 show current density-luminance characteristics, voltage-luminance characteristics, luminance-current efficiency characteristics, and voltage-current characteristics, respectively, of the light-emitting element 15, the comparative light-emitting element 16, and the comparative light-emitting element 17.

Table 12 shows initial values of main characteristics of the light-emitting elements at around 1000 cd/m$^2$.

The efficiency, the drive voltage, and the reliability of the light-emitting element 15 are more favorable than those of the comparative light-emitting element 16. The structure of 2Ph-CzPAP-02 used for the light-emitting element 15 is different from that of CzPA used for the comparative light-emitting 16 in that a phenyl group is introduced so as to bond to an anthryl group. An anthryl group is a skeleton that determines the HOMO levels and the LUMO levels of these molecules; thus, introduction of a phenyl group so as to bond to an anthryl group can make the HOMO level of 2Ph-CzPAP-02 high. The HOMO level of 2Ph-CzPAP-02 in which a phenyl group is introduced so as to bond to an anthryl group is higher than those of CzPA and CzPAPII. Accordingly, a carrier injection barrier to a light-emitting

TABLE 12

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 15 | 2.9 | 0.17 | 4.3 | (0.14, 0.20) | 530 | 12 | 13 | 9.2 |
| Comparative light-emitting element 16 | 3.1 | 0.51 | 13 | (0.14, 0.15) | 1300 | 10 | 10 | 9.2 |
| Comparative light-emitting element 17 | 3.1 | 0.40 | 10 | (0.14, 0.15) | 1000 | 10 | 10 | 9 |

Figure 66:
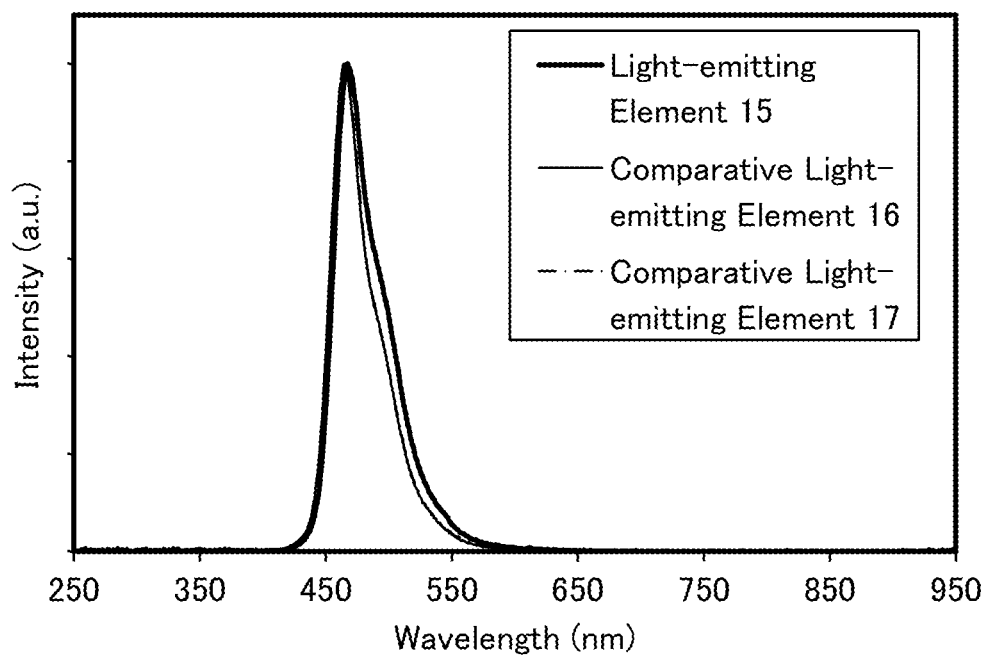
FIG. 66 shows emission spectra of the light-emitting element 15, the comparative light-emitting element 16, and the comparative light-emitting element 17.

FIG. 66 shows emission spectra when a current at a current density of 12.5 mA/cm$^2$ was supplied to the light-emitting element 15, the comparative light-emitting element 16, and the comparative light-emitting element 17. In FIG. 66, each of the emission spectra of the light-emitting element 15, the comparative light-emitting element 16, and the comparative light-emitting element 17 has a peak at around 466 nm, which is presumably derived from blue light emission of 1,6mMemFLPAPrn that is the organic compound used for the EL layer of each light-emitting element.

Figure 67:
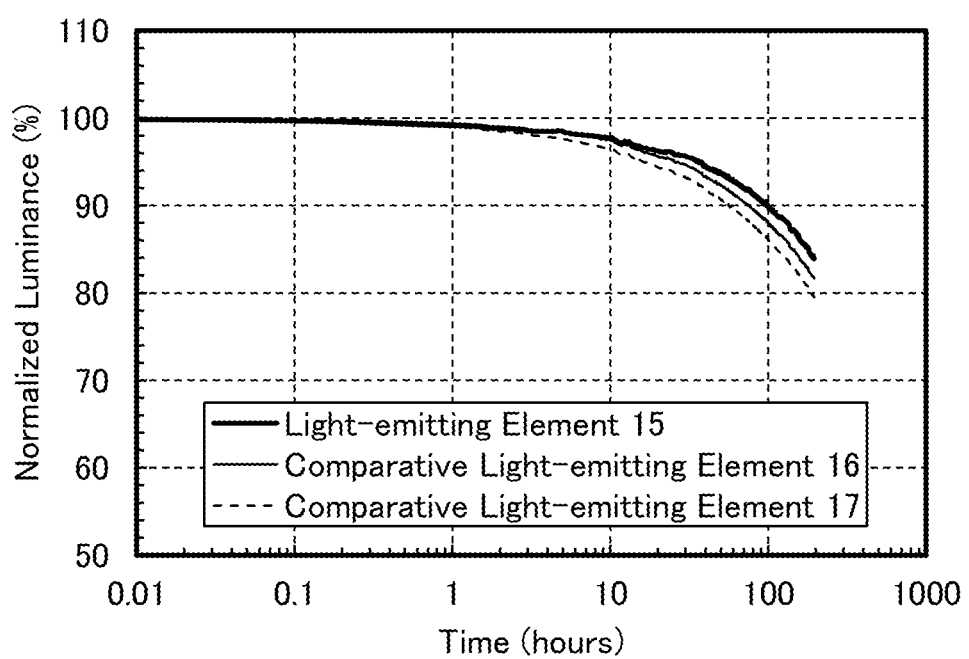
FIG. 67 shows reliability of the light-emitting element 15, the comparative light-emitting element 16, and the comparative light-emitting element 17.

Next, reliability tests were performed on the light-emitting elements. FIG. 67 shows results of the reliability tests. In FIG. 67, the vertical axis represents normalized luminance (%) with an initial luminance of 100%, and the horizontal axis represents driving time (h) of the elements. Note that in the reliability tests, the light-emitting elements were driven under the conditions where the initial current density was set to 50 mA/cm$^2$ and the current density was constant.

layer can be small with the use of 2Ph-CzPAP-02, whereby the drive voltage of the light-emitting element 15 is decreased.

The efficiency, the drive voltage, and the reliability of the light-emitting element 15 are more favorable than those of the comparative light-emitting element 17. Both 2Ph-CzPAP-02 used for the light-emitting element 15 and CzPAPII used for the comparative light-emitting element 17 have a structure in which a phenyl group is introduced so as to bond to a carbazolyl group. However, a carbazolyl group does not dominantly affect determination of the HOMO levels and the LUMO levels of these molecules. Thus, the HOMO levels and the LUMO levels were not influenced by this introduction of a phenyl group, and the drive voltages of the light-emitting elements were not changed.

Accordingly, an organic compound in which a substituent that makes the HOMO level high and the LUMO level low, such as a phenyl group, is introduced so as to bond to a group that determines the HOMO level and the LUMO level of a molecule is used for a light-emitting layer of a light-emitting element, whereby the drive voltage of the light-emitting element can be reduced.

In comparison between the comparative light-emitting element 16 and the comparative light-emitting element 17, although a phenyl group is introduced so as to bond to a carbazolyl group of CzPA, an improvement in the efficiency and a reduction in the drive voltage are not achieved, and these characteristics of CzPA are the same as those of CzPAPII. Moreover, the reliability of the comparative light-emitting element 17 is lower than that of the comparative light-emitting element 16, which is probably due to the structure of CzPAPII in which a phenyl group is introduced so as to bond to a carbazolyl group of CzPA. However, although 2Ph-CzPAP-02 has a structure in which a phenyl group is introduced so as to bond to a carbazolyl group, the reliability of the light-emitting element 15 is improved. This is because of the structure of 2Ph-CzPAP-02 in which a phenyl group is introduced so as to bond to an anthryl group. As described above, although the same structure is included, whether characteristics are improved or not depends on molecular modification, which is unpredictable.

Reference Synthesis Example

A method for synthesizing N,N'-bis(3-methylphenyl)-N,N'-bis[3-(9-phenyl-9H-fluoren-9-yl)phenyl]-anthracene-9,10-diamine (abbreviation: 9,10mMemFLPA2A) used in the above examples in this specification is described below. The structure of 9,10mMemFLPA2A is shown below.

[Chemical formula 58]

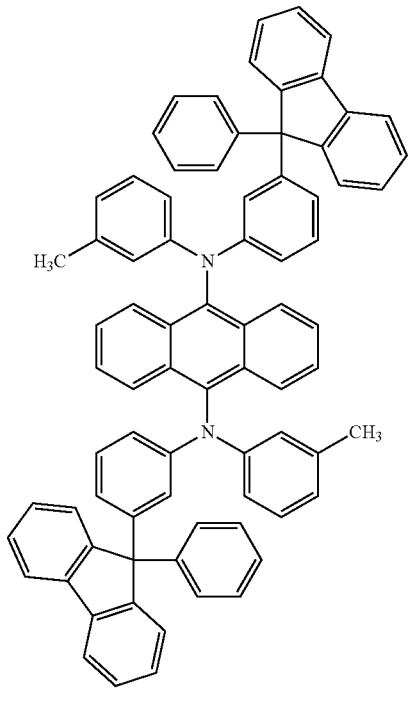

9,10mMemFLPA2A

In a 100 mL three-neck flask were put 0.5 g (1.4 mmol) of 9,10-dibromoanthracene, 1.3 g (3.0 mmol) of 3-methylphenyl-3-(9-phenyl-9H-fluoren-9-yl)phenylamine, and 0.4 g (4.4 mmol) of sodium tert-butoxide. The air in the flask was replaced with nitrogen.

To this mixture were added 14.7 mL of toluene and 0.2 mL of a 10% hexane solution of tri(tert-butyl)phosphine. The temperature of this mixture was set to 80° C., 62.9 mg (0.1 mmol) of bis(dibenzylideneacetone)palladium(0) and 0.2 mL of a 10% hexane solution of tri(tert-butyl)phosphine were added to the mixture, and stirring was performed for 11.8 hours. After the stirring, toluene was added to the mixture, and heating was performed. While being hot, the mixture was suction-filtered through Florisil, Celite, and alumina to give a filtrate.

The obtained filtrate was concentrated to give a solid, which was then purified by silica gel column chromatography (a developing solvent in which the ratio of hexane to toluene was 3:2) to give a yellow solid. The obtained yellow solid was recrystallized with toluene to give 1.0 g of a target yellow solid in a yield of 66%.

By a train sublimation method, 1.0 g of the obtained yellow solid was purified. In the purification by sublimation, the solid was heated at 315° C. at a pressure of $2.5 \times 10^{-2}$ Pa without an argon gas stream. After the purification by sublimation, 0.8 g of a target yellow solid was obtained at a collection rate of 82%. The synthesis scheme of the above synthesis method is shown in (f-1) below.

[Chemical formula 59]

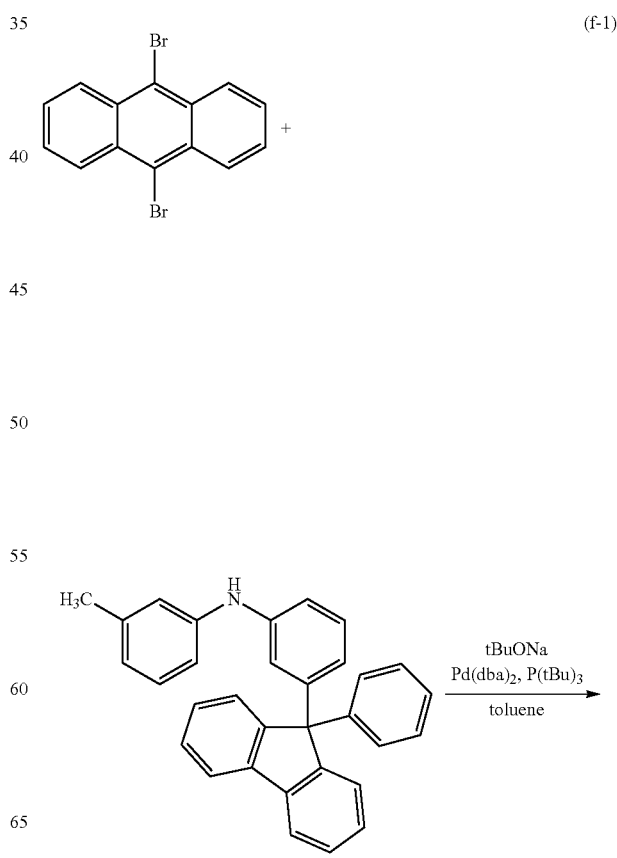

(f-1)

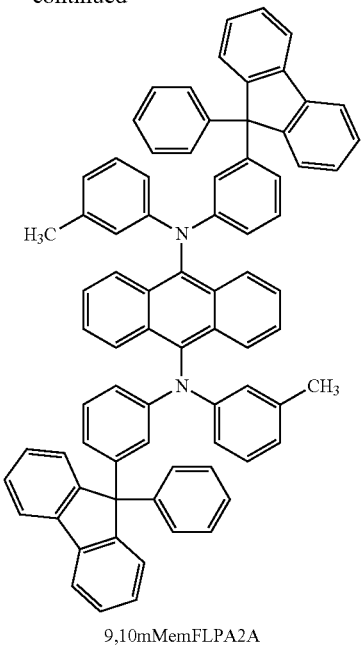

9,10mMemFLPA2A

Analysis results by nuclear magnetic resonance spectroscopy ($^1$H-NMR) of the yellow solid obtained by the above synthesis method are shown below. These results show that the organic compound 9,10mMemFLPA2A was synthesized.

$^1$H-NMR. (CDCl$_3$, 300 MHz): δ=2.22 (s, 3H), 2.24 (s, 3H), 6.41-6.67 (m, 7H), 6.80-7.35 (m, 33H), 7.49 (t, J=1.8 Hz, 1H), 7.53 (t, J=1.8 Hz, 1H), 7.73 (d, J=7.2 Hz, 4H), 8.08-8.12 (m, 4H).

This application is based on Japanese Patent Application serial no. 2016-035629 filed with Japan Patent Office on Feb. 26, 2016, the entire contents of which are hereby incorporated by reference.

What is claimed is:

1. An organic compound represented by a general formula (G1):

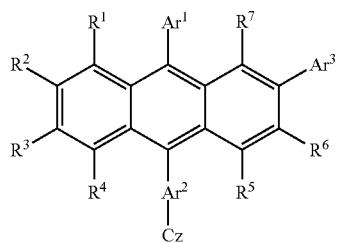

wherein Ar$^1$ and Ar$^3$ each independently represent a substituted or unsubstituted aryl group having 6 to 30 carbon atoms,
wherein Ar$^2$ represents a substituted or unsubstituted arylene group having 6 to 14 carbon atoms,
wherein Cz represents a substituted or unsubstituted heterocyclic group comprising a carbazole skeleton directly bonded to the Ar$^2$, and includes an aromatic ring fused to the carbazole skeleton, and
wherein R$^1$ to R$^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms.

2. The organic compound according to claim 1, wherein the Ar$^2$ represents a substituted or unsubstituted phenylene group.

3. A light-emitting element comprising the organic compound according to claim 1.

4. A light-emitting element comprising an EL layer between a pair of electrodes,
wherein the EL layer comprises the organic compound according to claim 1.

5. A light-emitting element comprising an EL layer between a pair of electrodes,
wherein the EL layer comprises a light-emitting layer, and
wherein the light-emitting layer comprises the organic compound according to claim 1.

6. A light-emitting device comprising:
the light-emitting element according to claim 3; and
at least one of a transistor and a substrate.

7. An electronic device comprising:
the light-emitting device according to claim 6; and
at least one of a microphone, a camera, an operation button, an external connection portion, and a speaker.

8. A lighting device comprising:
the light-emitting element according to claim 3; and
at least one of a housing, a sealing substrate with unevenness, and a diffusion plate.

9. An organic compound represented by a general formula (G2):

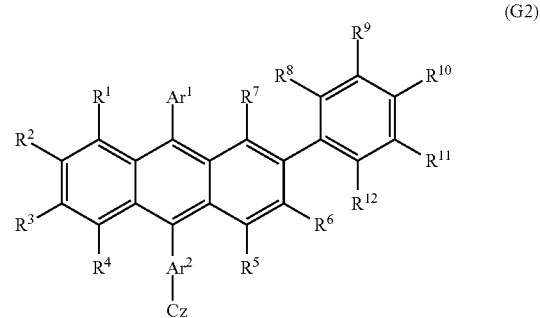

wherein Ar$^1$ represents a substituted or unsubstituted aryl group having 6 to 30 carbon atoms,
wherein Ar$^2$ represents a substituted or unsubstituted arylene group having 6 to 14 carbon atoms,
wherein Cz represents a substituted or unsubstituted heterocyclic group comprising a carbazole skeleton directly bonded to the Ar$^2$, and includes an aromatic ring fused to the carbazole skeleton,
wherein R$^1$ to R$^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms, and
wherein R$^8$ to R$^{12}$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

10. The organic compound according to claim 9, wherein any adjacent substituents among the $R^8$ to the $R^{12}$ are bonded to each other to form a ring.

11. The organic compound according to claim 9, wherein the $Ar^2$ represents a substituted or unsubstituted phenylene group.

12. A light-emitting element comprising the organic compound according to claim 9.

13. A light-emitting element comprising an EL layer between a pair of electrodes,
wherein the EL layer comprises the organic compound according to claim 9.

14. A light-emitting element comprising an EL layer between a pair of electrodes,
wherein the EL layer comprises a light-emitting layer, and
wherein the light-emitting layer comprises the organic compound according to claim 9.

15. A light-emitting device comprising:
the light-emitting element according to claim 12; and
at least one of a transistor and a substrate.

16. An electronic device comprising:
the light-emitting device according to claim 15; and
at least one of a microphone, a camera, an operation button, an external connection portion, and a speaker.

17. A lighting device comprising:
the light-emitting element according to claim 12; and
at least one of a housing, a sealing substrate with unevenness, and a diffusion plate.

18. An organic compound represented by a general formula (G3):

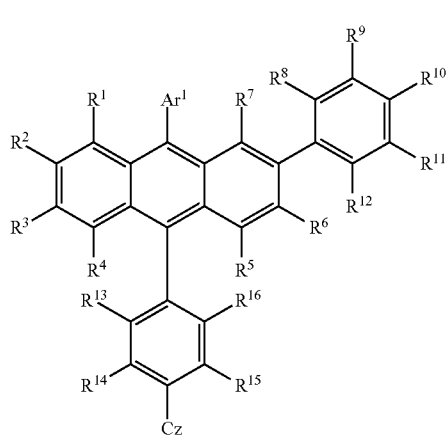

(G3)

wherein $Ar^1$ represents a substituted or unsubstituted aryl group having 6 to 30 carbon atoms,
wherein Cz represents a substituted or unsubstituted heterocyclic group comprising a carbazole skeleton, and includes an aromatic ring fused to the carbazole skeleton,
wherein $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms, and
wherein $R^8$ to $R^{16}$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

19. The organic compound according to claim 18, wherein any adjacent substituents among the $R^8$ to the $R^{16}$ are bonded to each other to form a ring.

20. A light-emitting element comprising the organic compound according to claim 18.

21. A light-emitting element comprising an EL layer between a pair of electrodes,
wherein the EL layer comprises the organic compound according to claim 18.

22. A light-emitting element comprising an EL layer between a pair of electrodes,
wherein the EL layer comprises a light-emitting layer, and
wherein the light-emitting layer comprises the organic compound according to claim 18.

23. A light-emitting device comprising:
the light-emitting element according to claim 20; and
at least one of a transistor and a substrate.

24. An electronic device comprising:
the light-emitting device according to claim 23; and
at least one of a microphone, a camera, an operation button, an external connection portion, and a speaker.

25. A lighting device comprising:
the light-emitting element according to claim 20; and
at least one of a housing, a sealing substrate with unevenness, and a diffusion plate.

26. An organic compound represented by a general formula (G5):

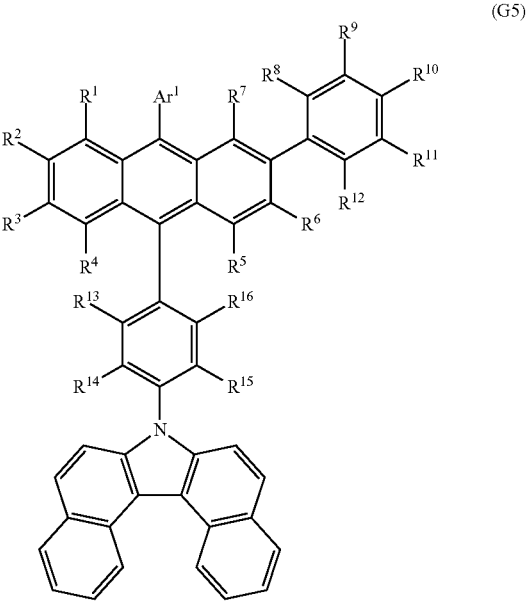

(G5)

wherein Ar¹ represents a substituted or unsubstituted aryl group having 6 to 30 carbon atoms, wherein $R^1$ to $R^7$ each independently represent any of hydrogen, a substituted or unsubstituted alkyl group having 1 to 6 carbon atoms, a substituted or unsubstituted aryl group having 6 to 14 carbon atoms, and a substituted or unsubstituted heteroaryl group having 3 to 12 carbon atoms, and wherein $R^8$ to $R^{16}$ each independently represent any of hydrogen, an alkyl group having 1 to 6 carbon atoms, an alkoxy group having 1 to 6 carbon atoms, a hydroxyl group, sulfanyl group, a substituted or unsubstituted arylamino group having 6 to 12 carbon atoms, a vinyl group, a substituted or unsubstituted aryl group having 6 to 13 carbon atoms, and a substituted or unsubstituted heteroaryl group having 3 to 12 carbon atoms.

27. The organic compound according to claim 26, wherein any adjacent substituents among the $R^8$ to the $R^{16}$ are bonded to each other to form a ring.

28. A light-emitting element comprising the organic compound according to claim 26.

29. A light-emitting element comprising an EL layer between a pair of electrodes,
wherein the EL layer comprises the organic compound according to claim 26.

30. A light-emitting element comprising an EL layer between a pair of electrodes,
wherein the EL layer comprises a light-emitting layer, and
wherein the light-emitting layer comprises the organic compound according to claim 26.

31. A light-emitting device comprising:
the light-emitting element according to claim 28; and
at least one of a transistor and a substrate.

32. An electronic device comprising:
the light-emitting device according to claim 31; and
at least one of a microphone, a camera, an operation button, an external connection portion, and a speaker.

33. A lighting device comprising:
the light-emitting element according to claim 28; and
at least one of a housing, a sealing substrate with unevenness, and a diffusion plate.

34. An organic compound represented by a structural formula (200):

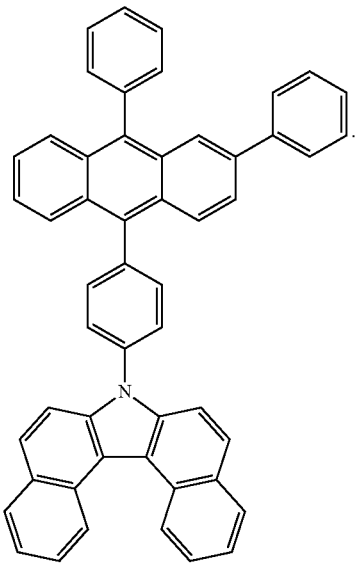

(200)

35. A light-emitting element comprising the organic compound according to claim 34.

36. A light-emitting element comprising an EL layer between a pair of electrodes,
wherein the EL layer comprises the organic compound according to claim 34.

37. A light-emitting element comprising an EL layer between a pair of electrodes,
wherein the EL layer comprises a light-emitting layer, and
wherein the light-emitting layer comprises the organic compound according to claim 34.

38. A light-emitting device comprising:
the light-emitting element according to claim 37; and
at least one of a transistor and a substrate.

39. An electronic device comprising:
the light-emitting device according to claim 38; and
at least one of a microphone, a camera, an operation button, an external connection portion, and a speaker.

40. A lighting device comprising:
the light-emitting element according to claim 37; and
at least one of a housing, a sealing substrate with unevenness, and a diffusion plate.

* * * * *